US010907178B2

(12) United States Patent
Bernate et al.

(10) Patent No.: US 10,907,178 B2
(45) Date of Patent: *Feb. 2, 2021

(54) AUTOMATED CELL PROCESSING METHODS, MODULES, INSTRUMENTS, AND SYSTEMS COMPRISING FLOW-THROUGH ELECTROPORATION DEVICES

(71) Applicant: Inscripta, Inc., Boulder, CO (US)

(72) Inventors: Jorge Bernate, Boulder, CO (US); Don Masquelier, Boulder, CO (US); Phillip Belgrader, Pleasanton, CA (US); Kevin Ness, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 123 days.

This patent is subject to a terminal disclaimer.

(21) Appl. No.: 16/426,310

(22) Filed: May 30, 2019

(65) Prior Publication Data

US 2019/0284579 A1 Sep. 19, 2019

Related U.S. Application Data

(63) Continuation of application No. 16/147,865, filed on Sep. 30, 2018, now Pat. No. 10,323,258.

(60) Provisional application No. 62/566,374, filed on Sep. 30, 2017, provisional application No. 62/566,375, filed on Sep. 30, 2017, provisional application No. (Continued)

(51) Int. Cl.
*C12M 3/00* (2006.01)
*C12M 1/00* (2006.01)
*B01L 3/00* (2006.01)
*C12N 15/87* (2006.01)

*C12M 1/42* (2006.01)
*C12N 15/70* (2006.01)
(Continued)

(52) U.S. Cl.
CPC ............. *C12N 15/87* (2013.01); *C12M 23/44* (2013.01); *C12M 35/02* (2013.01); *C12M 41/48* (2013.01); *C12N 15/70* (2013.01); *C12N 15/81* (2013.01)

(58) Field of Classification Search
CPC ....... C12M 35/00; C12M 35/02; C12M 35/04
See application file for complete search history.

(56) References Cited

U.S. PATENT DOCUMENTS 4,833,080 A 5/1989 Brent et al.
4,959,317 A 9/1990 Sauer et al.
(Continued)

FOREIGN PATENT DOCUMENTS

EP 2240238 10/2010
EP 2395087 12/2011
(Continued)

OTHER PUBLICATIONS

International Search Report and Written Opinion for International Application No. PCT/US2018/53608, dated Dec. 13, 2018, p. 1-9.
(Continued)

*Primary Examiner* — Nathan A Bowers
(74) *Attorney, Agent, or Firm* — Sarah Brashears; Dianna L. DeVore

(57) ABSTRACT

In an illustrative embodiment, automated multi-module cell editing instruments comprising one or more flow-through electroporation devices or modules are provided to automate genome editing in live cells.

20 Claims, 52 Drawing Sheets

Related U.S. Application Data

62/566,688, filed on Oct. 2, 2017, provisional application No. 62/567,697, filed on Oct. 3, 2017, provisional application No. 62/620,370, filed on Jan. 22, 2018, provisional application No. 62/649,731, filed on Mar. 29, 2018, provisional application No. 62/671,385, filed on May 14, 2018, provisional application No. 62/648,130, filed on Mar. 26, 2018, provisional application No. 62/657,651, filed on Apr. 13, 2018, provisional application No. 62/657,654, filed on Apr. 13, 2018, provisional application No. 62/689,068, filed on Jun. 23, 2018.

(51) Int. Cl.
*C12N 15/81* (2006.01)
*C12M 1/36* (2006.01)

(56) References Cited

U.S. PATENT DOCUMENTS

| | | |
|---|---|---|
| 5,464,764 A | 11/1995 | Capecchi et al. |
| 5,487,992 A | 1/1996 | Capecchi et al. |
| 5,627,059 A | 5/1997 | Capecchi et al. |
| 5,631,153 A | 5/1997 | Capecchi et al. |
| 5,654,182 A | 8/1997 | Wahl et al. |
| 5,677,177 A | 10/1997 | Wahl et al. |
| 5,885,836 A | 3/1999 | Wahl et al. |
| 5,888,732 A | 3/1999 | Hartley et al. |
| 6,074,605 A | 6/2000 | Meserol et al. |
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,361,427 B2 | 6/2016 | Hillson |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,017,760 B2 | 7/2018 | Gill et al. |
| 2002/0155616 A1* | 10/2002 | Hiramatsu .......... B01L 3/545 436/165 |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0224192 A1 | 10/2006 | Dimmer et al. |
| 2006/0269446 A1* | 11/2006 | Gilbert .......... B01L 3/502776 422/400 |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2008/0195020 A1* | 8/2008 | Cabuz .......... A61B 5/150221 604/4.01 |
| 2010/0076057 A1 | 3/2010 | Sontheimer et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2012/0184025 A1* | 7/2012 | Kawata .......... G01N 35/04 435/287.2 |
| 2013/0005025 A1 | 1/2013 | Church et al. |
| 2013/0196441 A1 | 8/2013 | Rubinsky et al. |
| 2014/0121728 A1 | 5/2014 | Dhillon et al. |
| 2014/0350456 A1 | 11/2014 | Caccia |
| 2015/0136604 A1* | 5/2015 | Nielsen .......... B01L 7/52 204/453 |
| 2015/0191719 A1 | 7/2015 | Hudson et al. |
| 2015/0297887 A1 | 10/2015 | Dhillon et al. |
| 2016/0272961 A1 | 9/2016 | Lee |
| 2016/0281047 A1 | 9/2016 | Chen et al. |
| 2016/0298074 A1 | 10/2016 | Dai |
| 2016/0367991 A1 | 12/2016 | Petersen et al. |
| 2017/0029805 A1 | 2/2017 | Li et al. |
| 2017/0218355 A1 | 8/2017 | Buie et al. |
| 2017/0283761 A1 | 10/2017 | Corso |
| 2017/0307606 A1 | 10/2017 | Hallock |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0112235 A1 | 4/2018 | Li et al. |
| 2018/0169148 A1 | 6/2018 | Adair et al. |
| 2018/0179485 A1 | 6/2018 | Borenstein et al. |
| 2019/0017072 A1 | 1/2019 | Ditommaso et al. |

FOREIGN PATENT DOCUMENTS

| | | |
|---|---|---|
| EP | 3030652 | 6/2016 |
| EP | 1766004 | 8/2016 |
| EP | 2459696 | 11/2017 |
| WO | WO 2003/057819 | 7/2001 |
| WO | WO 2003/087341 | 10/2003 |
| WO | WO 2009/091578 | 7/2009 |
| WO | WO 2010079430 | 7/2010 |
| WO | WO 2011/072246 | 6/2011 |
| WO | WO 2013/176772 | 11/2013 |
| WO | WO 201/5021270 | 2/2015 |
| WO | WO 2016/003485 | 1/2016 |
| WO | WO 2016/145290 | 9/2016 |
| WO | WO 2017/078631 | 5/2017 |
| WO | WO 2018/015544 | 1/2018 |
| WO | WO 2018/191715 | 10/2018 |

OTHER PUBLICATIONS

International Search Report and Written Opinion for International Application No. PCT/US2018/053670, dated Jan. 3, 2019, p. 1-13.
International Search Report and Written Opinion for International Application No. PCT/US2018/53671, dated Sep. 26, 2018, p. 1-12.
International Search Report and Written Opinion for International Application No. PCT/US2018/040519, dated Sep. 26, 2018, p. 1-8.

(56) References Cited

OTHER PUBLICATIONS

First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Eklund, et al., "Altered target site specificity variants of the I-Ppol His-Cys bis homing endonuclease" Nucleic Acids Research, 35(17):5839-50 (2007).
Garst, et al., "Genome-wide mapping of mutations at single-nucleotide resolution for protein, metabolic and genome engineering", Nature Biotechnology, 35(1):48-59 (2017).
Boles, et al., "Digital-to-biological converter for on-demand production of biologics", Nature Biotechnology, doi:10.1038/nbt.3859 (May 29, 2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Pines, et al., "Codon Compression Algorithms for Saturation Mutagenesis", ACS Synthetic Biology, 4:604-14 (2015).
Verwaal, et al., "CRISPR/Cpfl enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).

Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1):81-9 (2009).
Lefevre et al., "Alanine-stretch scanning mutagenesis: a simple and efficient method to probe protein structure and function," Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).

* cited by examiner

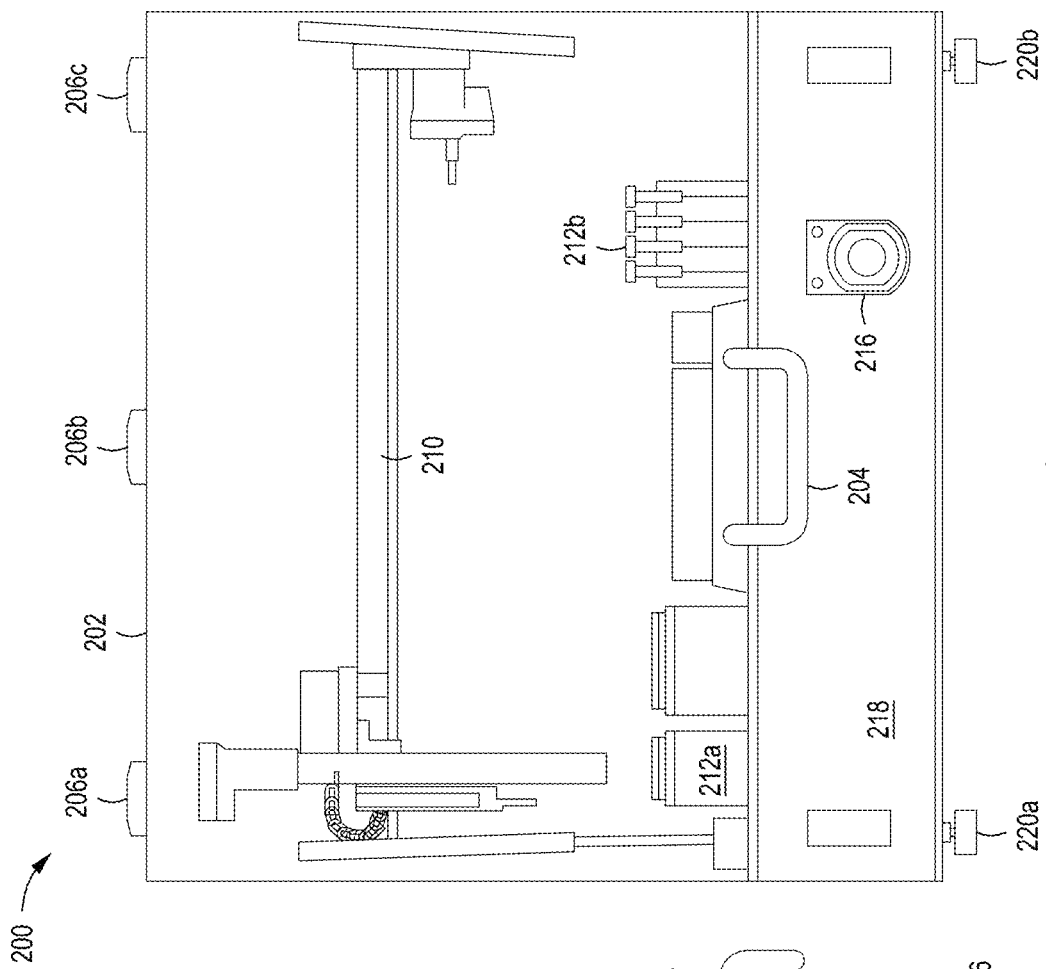
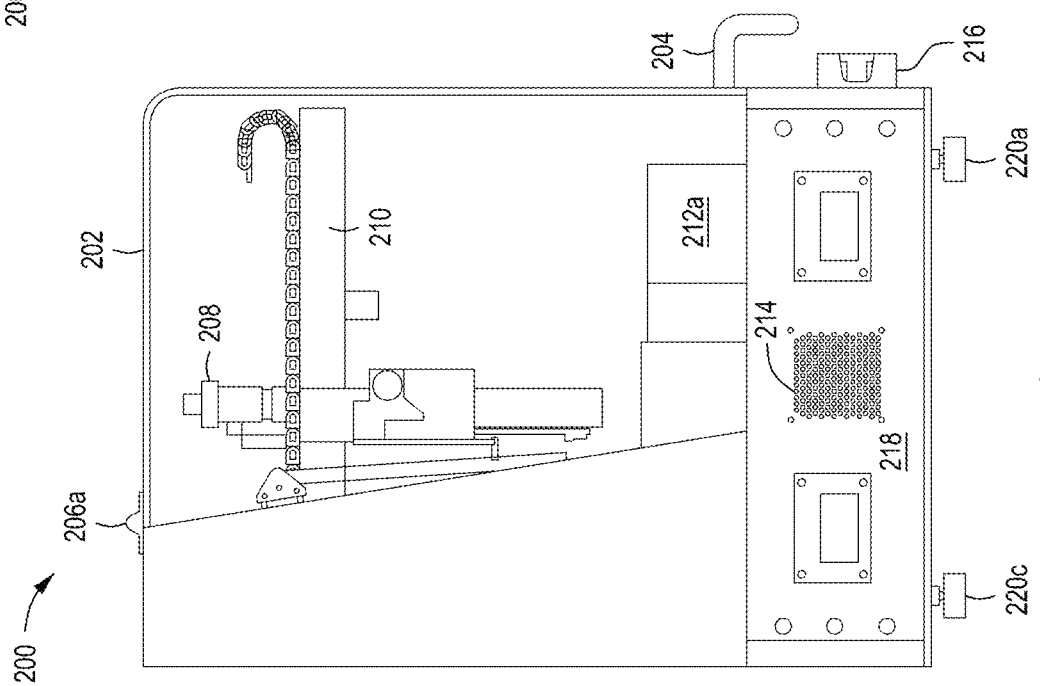

AUTOMATED CELL PROCESSING METHODS, MODULES, INSTRUMENTS, AND SYSTEMS COMPRISING FLOW-THROUGH ELECTROPORATION DEVICES

RELATED APPLICATIONS

This application is a continuation of U.S. patent application Ser. No. 16/147,865, entitled "Automated Cell Processing Methods, Modules, Instruments, and Systems Comprising Flow-through Electroporation Devices," filed Sep. 30, 2018, which claims priority to U.S. Patent Application Ser. No. 62/566,374, entitled "Electroporation Device," filed Sep. 30, 2017; U.S. Patent Application Ser. No. 62/566,375, entitled "Electroporation Device," filed Sep. 30, 2017; U.S. Patent Application Ser. No. 62/566,688, entitled "Introduction of Exogenous Materials into Cells," filed Oct. 2, 2017; U.S. Patent Application Ser. No. 62/567,697, entitled "Automated Nucleic Acid Assembly and Introduction of Nucleic Acids into Cells," filed Oct. 3, 2017; U.S. Patent Application Ser. No. 62/620,370, entitled "Automated Filtration and Manipulation of Viable Cells," filed Jan. 22, 2018; U.S. Patent Application Ser. No. 62/649,731, entitled "Automated Control of Cell Growth Rates for Induction and Transformation," filed Mar. 29, 2018; U.S. Patent Application Ser. No. 62/671,385, entitled "Automated Control of Cell Growth Rates for Induction and Transformation," filed May 14, 2018; U.S. Patent Application Ser. No. 62/648,130, entitled "Genomic Editing in Automated Systems," filed Mar. 26, 2018; U.S. Patent Application Ser. No. 62/657,651, entitled "Combination Reagent Cartridge and Electroporation Device," filed Apr. 13, 2018; U.S. Patent Application Ser. No. 62/657,654, entitled "Automated Cell Processing Systems Comprising Cartridges," filed Apr. 13, 2018; and U.S. Patent Application Ser. No. 62/689,068, entitled "Nucleic Acid Purification Protocol for Use in Automated Cell Processing Systems," filed Jun. 20, 2018. All above identified applications are hereby incorporated by reference in their entireties for all purposes.

BACKGROUND

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genome editing with engineered nucleases is a method in which changes to nucleic acids are made in the genome of a living organism. Certain nucleases create site-specific double-strand breaks at target regions in the genome, which can be repaired by nonhomologous end-joining or homologous recombination, resulting in targeted edits. These methods, however, have not been compatible with automation due to low efficiencies and challenges with cell transformation, growth measurement, and cell selection. Moreover, traditional benchtop devices do not necessarily scale and integrate well into an automated, modular instrument or system. Methods and instruments to create edited cell populations thus remain cumbersome—including methods and instruments for automated cell transformation—and the challenges of introducing multiple rounds of edits using recursive techniques has limited the nature and complexity of the cell populations that can be created.

There is thus a need for automated instruments, systems and methods for introducing assembled nucleic acids and other biological molecules into living cells in an automated fashion where the edited cells may be used for further experimentation outside of the automated instrument.

SUMMARY OF ILLUSTRATIVE EMBODIMENTS

In certain embodiments, automated modules, instruments, systems and methods are used for nuclease-directed genome editing of one or more target genomic regions in multiple cells, the methods being performed in automated multi-module cell editing instruments. These methods can be used to generate libraries of living cells of interest with desired genomic changes. The automated methods carried out using the automated multi-module cell editing instruments described herein may employ a variety of nuclease-directed genome editing techniques, and can be used with or without use of one or more selectable markers.

The present disclosure thus provides, in selected embodiments, modules, instruments, and systems for automated multi-module cell editing, including nuclease-directed genome editing. In particular, the instruments and systems comprise a flow-through electroporation (FTEP) device for transforming the cells to be edited. Other specific embodiments of the automated multi-module cell editing instruments of the disclosure are designed for recursive genome editing, e.g., sequentially introducing multiple edits into genomes inside one or more cells of a cell population through two or more editing operations.

Thus, provided herein are embodiments of an automated multi-module cell editing instrument comprising: a housing configured to contain all or some of the modules; a receptacle configured to receive cells; one or more receptacles configured to receive nucleic acids; a transformation module configured to introduce the nucleic acids into the cells wherein the transformation module comprises one or more FTEP devices; a recovery module configured to allow the cells to recover after cell transformation in the transformation module; an editing module configured to allow the nucleic acids transformed into the cells to edit nucleic acids in the cells; and a processor configured to operate the automated multi-module cell editing instrument based on user input and/or selection of an appropriate controller script.

In some embodiments, the automated multi-module cell editing instruments comprise a flow-through electroporation (FTEP) device for introducing an exogenous material into cells in a fluid, where the FTEP device comprises: one or more inlets and inlet channels for introducing a fluid comprising cells and exogenous material into the FTEP device; an outlet and an outlet channel for removing a fluid comprising transformed cells and exogenous material from the FTEP device; a flow channel intersecting and positioned between a first inlet channel and the outlet channel, wherein the flow channel decreases in width between the first inlet channel and the center of the flow channel and the outlet channel and the center of the flow channel; and two or more electrodes positioned in the flow channel between the intersection of the flow channel with the first inlet channel and the intersection of the flow channel with the outlet channel, wherein the electrodes are in fluid communication with fluid in the flow channel but are not in the direct flow path of the cells in the flow channel, and wherein the electrodes apply one or more electric pulses to the cells in the fluid as they pass through the flow channel, thereby introducing the exogenous material into the cells in the fluid.

In some aspects of this embodiment, the two electrodes in the FTEP device are located from 0.5 mm to 10 mm apart, or from 1 mm to 8 mm apart, or from 3 mm and 7 mm apart, or from 4 mm to 6 mm apart.

In other embodiments, the automated multi-module cell editing instruments comprise a flow-through electroporation (FTEP) device for introducing an exogenous material into cells in a fluid, where the FTEP device comprises: at least one inlet and at least one inlet channel for introducing a fluid comprising cells and exogenous material to the FTEP device; an outlet and an outlet channel for removing transformed cells and exogenous material from the FTEP device; a flow channel positioned between a first inlet channel and the outlet channel, wherein the flow channel intersects with the first inlet channel and the outlet channel and wherein a portion of the flow channel narrows between the inlet channel intersection and the outlet channel intersection; and an electrode positioned on either side of the flow channel and in direct contact with the fluid in the flow channel, the electrodes defining the narrowed portion of the flow channel, and wherein the electrodes apply one or more electric pulses to the cells in the fluid as they pass through the flow channel, thereby introducing the exogenous material into the cells in the fluid.

In some aspects of this embodiment, the electrodes are positioned on either side of the flow channel, are in direct contact with the fluid in the flow channel and define the decrease in width of the flow channel. In some configurations of this aspect, the electrodes are between 10 µm to 5 mm apart, or between 25 µm to 2 mm apart.

In some aspects of these embodiments, the FTEP device is between 3 cm to 15 cm in length, or between 4 cm to 12 cm in length, or from 4.5 cm to 10 cm in length, or from 5 cm to 8 cm in length. In some aspects of these embodiments, this embodiment of the FTEP device is between 0.5 cm to 5 cm in width, or from 0.75 cm to 3 cm in width, or from 1 cm to 2.5 cm in width, or from 1 cm to 1.5 cm in width. In some aspects of these embodiments, the narrowest part of the channel width in the FTEP device is from 10 µM to 5 mm such that whatever cell type is being transformed will not be physically contorted or "squeezed" by features of the FTEP device.

Also in some aspects of these embodiments, the flow rate in the FTEP ranges from 0.1 ml to 5 ml per minute, or from 0.5 ml to 3 ml per minute, or from 1 ml to 2.5 ml per minute. In some aspects of these embodiments the electrodes are configured to deliver 1-25 Kv/cm, or 10-20 Kv/cm.

In some aspects of these embodiments, the FTEP device further comprises one or more filters between the one or more inlet channels and the outlet channel. In some aspects, there are two filters, one between the inlet channel and the narrowed portion of the flow channel, and one between the narrowed portion of the flow channel and the outlet channel. In some aspects of these embodiments, the filters are graduated in pore size with the larger pores proximal to the inlet chamber or outlet chamber, and the small pores proximal to the narrowed portion of the flow channel. In some aspects, the small pores are the same size or larger than the size of the narrowed portion of the flow channel. In some aspects of these embodiments, the filter is formed separately from the body of the FTEP device and placed into the FTEP device as it is being assembled. Alternatively, in some aspects of these embodiments, the filter may be formed as part of and integral to the body of the FTEP device.

In some aspects of these embodiments, the FTEP device further comprises a reservoir connected to the inlet for introducing the cells in fluid into the FTEP device and a reservoir connected to the outlet for removing transformed cells from the FTEP device, and in some aspects, the FTEP device comprises two inlets and two inlet channels and further comprises a reservoir connected to a second inlet for introducing the exogenous material into the FTEP device. In some aspects the FTEP device comprises a reservoir connected to the inlet for introducing both the cells in fluid and the exogenous material into the FTEP device and a reservoir connected to the outlet for removing transformed cells from the FTEP device In some aspects of these embodiments, the reservoirs coupled to the inlet(s) and outlet range in volume from 100 µL to 10 ml, or from 0.5 ml to 7 ml, or from 1 ml to 5 ml.

In some aspects of these embodiments, the FTEP devices can provide a cell transformation rate of $10^3$ to $10^{12}$ cells per minute, or $10^4$ to $10^{10}$ per minute, or $10^5$ to $10^9$ per minute, or $10^6$ to $10^8$ per minute. Typically, $10^8$ yeast cells may be transformed per minute, and $10^{10}$-$10^{11}$ bacterial cells may be transformed per minute. In some aspects of these embodiments, the transformation of cells results in at least 90% viable cells, or 95% viable cells, and up to 99% viable cells.

In some aspects of these embodiments, the FTEP device is manufactured by injection molding from crystal styrene, cyclo-olefin polymer, or cyclo-olefin co-polymer, and in some aspects of this embodiment the electrodes are fabricated from stainless steel. In some aspects of these embodiments, the FTEP devices are fabricated as multiple FTEP devices in parallel on a single substrate where the FTEP devices are then separated for use.

In some embodiments of the automated multi-module cell processing system of which the FTEP is a part, the nucleic acids in the one or more receptacles comprise a vector backbone and an editing cassette (e.g., an oligonucleotide designed to direct nuclease-directed editing upon expression in the cell), and the automated multi-module cell editing instrument further comprises a nucleic acid assembly module. In some aspects, the nucleic acid assembly module comprises a magnet, and in some aspects, the nucleic acid assembly module is configured to perform nucleic acid assembly using a single, isothermal reaction. In other aspects, the nucleic acid assembly module is configured to perform an amplification and/or ligation method. In some aspects, the nucleic acid assembly module also comprises means for isolating, washing, concentrating, diluting and/or resuspending the assembled nucleic acids.

In some embodiments of the automated multi-module cell editing instrument of which the FTEP is a part, the editing module and the recovery module are combined.

In some embodiments, the automated multi-module cell editing instrument comprising the FTEP may further comprise a growth module configured to grow the cells, and in some implementations, the growth module measures optical density of the growing cells, either continuously or at intervals. In some implementations, a processor controlling the instrument is configured to adjust growth conditions in the growth module such that the cells reach a target optical density at a time requested by a user. Further, in some embodiments, the user may be updated regarding growth process, e.g. through a user interface of the automated multi-module cell editing instrument or through a portable computing device application in communication with the automated multi-module cell editing instrument.

In some embodiments, the automated multi-module cell editing instrument comprising the FTEP also comprises a reagent cartridge with one or more receptacles configured to receive cells and one or more receptacles configured to receive nucleic acids. In some embodiments, the automated multi-module cell editing instrument comprising the FTEP also comprises a reagent cartridge with one or more receptacles configured to receive both cells and nucleic acids. Further, the reagent cartridge may also contain some or all reagents required for cell editing. In some implementations, the reagents contained within the reagent cartridge are locatable by a script read by the processor, and in some implementations, the reagent cartridge includes reagents and is provided in a kit. In some embodiments, the FTEP device (e.g., transformation module) is contained within the reagent cartridge.

Some embodiments of the automated multi-module cell editing instrument further comprise a filtration module configured to exchange the liquid medium in which the cells are suspended and/or concentrate the cells. In specific aspects, the filtration system can also be used to render the cells electrocompetent.

In other embodiments, an automated multi-module cell editing instrument is provided, where the automated multi-module cell editing instrument comprises a housing configured to house some or all of the modules; a receptacle configured to receive cells; at least one receptacle configured to receive a vector backbone and an editing cassette; a nucleic acid assembly module configured to a) assemble the vector backbone and editing cassette, and b) de-salt assembled nucleic acids after assembly; a growth module configured to grow the cells and measure optical density (OD) of the cells; a filtration module configured to concentrate the cells and render the cells electrocompetent; a transformation module comprising an FTEP device to introduce the assembled nucleic acids into the cells; a combination recovery and editing module configured to allow the cells to recover after electroporation in the transformation module and to allow the assembled nucleic acids to edit nucleic acids in the cells; and a processor configured to operate the automated multi-module cell editing instrument based on user input and/or selection of an appropriate controller script.

In some implementations, the FTEP device is provided as part of a reagent cartridge, which also comprises a plurality of reagent reservoirs and a script readable by a processor for dispensing reagents located in the plurality of reagent reservoirs and controlling the flow-through electroporation device.

In some aspects, the growth module includes a temperature-controlled rotating growth vial, a motor assembly to spin the vial, a spectrophotometer for measuring, e.g., OD in the vial, and a processor to accept input from a user and control the growth rate of the cells. The growth module may automatically measure the OD of the growing cells in the rotating growth vial continuously or at set intervals, and control the growth of the cells to a target OD and a target time as specified by the user. That is, the methods and devices described herein provide a feedback loop that monitors cell growth in real time, and adjusts parameters (e.g., the temperature of the rotating growth vial) in real time to reach the target OD at a target time specified by a user.

Systems for using the automated multi-module cell editing instrument to implement genomic editing operations within cells are also provided. These systems optionally include one or more interfaces between the instrument and other devices or receptacles for cell preparation, nucleic acid preparation, selection of edited cell populations, functional analysis of edited cell populations, storage of edited cell populations, and the like.

In addition, methods for using the automated multi-module cell editing instrument containing an FTEP device are provided. In some methods, electrocompetent cells are provided directly to the instrument and transferred to a transformation module. In some methods, cells are transferred to a growth module, where they are grown to a desired optical density. The cells are then transferred from the growth vial to a filtration module where they are concentrated and optionally rendered electrocompetent. The cells are then transferred to a the FTEP device.

In some aspects, assembled nucleic acids for transformation are provided directly to the instrument, and transferred to a transformation module. In some aspects, nucleic acids, such as a vector backbone and one or more oligonucleotide editing cassettes, are transferred to a nucleic acid assembly module either simultaneously or sequentially with the cell introduction or preparation. In this aspect, nucleic acids are assembled, de-salted (e.g., through a liquid exchange or osmosis), and transferred to an FTEP device to be electroporated into the electrocompetent cells. Electroporation (e.g., transformation or transfection) takes place in the FTEP device, then the transformed cells are transferred to a recovery/editing module that optionally includes selection of the cells containing the one or more genomic edits. After recovery, editing, and/or selection, the cells may be retrieved and used directly for research or stored for further research, or subjected to another round (or multiple rounds) of genomic editing by repeating the editing steps within the instrument.

Also provided are cell libraries created using an automated multi-module cell editing instrument, where the instrument comprises: a housing; a receptacle configured to receive cells and one or more rationally-designed nucleic acids comprising sequences to facilitate nuclease-directed genome editing events in the cells; an FTEP device for introduction of the nucleic acid(s) into the cells; an editing module for allowing the nuclease-directed genome editing events to occur in the cells, and a processor configured to operate the automated multi-module cell editing instrument based on user input, wherein the nuclease-directed genome editing events created by the automated instrument result in a cell library comprising individual cells with rationally-designed edits.

In some aspects, the cell library created using the instruments and methods of the disclosure comprises a saturation mutagenesis cell library. In some aspects, the cell library created using the instruments and methods of the disclosure comprises a promoter swap cell library. In other aspects, the cell library created using the instruments and methods of the disclosure comprises a terminator swap cell library. In yet other aspects, the cell library created using the instruments and methods of the disclosure comprises a single nucleotide polymorphism (SNP) swap cell library. In yet other aspects, the cell library created using the instruments and methods of the disclosure comprises a promoter swap cell library. In some implementations, the library created using the instruments and methods of the disclosure comprises at least 100,000 edited cells, and in yet other implementations, the library created using the instruments and methods of the disclosure comprises at least 1,000,000 edited cells. In some implementations, the nuclease-directed genome editing is RGN-directed genome editing. In a preferred aspect, the instrument is configured for using an inducible nuclease or guide nucleic acid. The nuclease may be, e.g., chemically induced, virally induced, light induced, temperature induced, or heat induced.

In some embodiments that involve recursive editing, the automated multi-module cell editing instruments of the disclosure introduce two or more genome edits into cells, with a single genome edit added to the genomes of the cell population for each cycle. Alternatively, some aspects the automated multi-module cell editing instruments of the present disclosure are useful for providing two or more edits per cell in a cell population per cycle, three or more edits per cell in a cell population, five or more edits per cell in a population, or 10 or more edits per cell in a single cycle for a cell population. In either scenario, one or more sequential cycles of editing may be performed.

In specific embodiments, the automated multi-module cell editing instrument is able to provide an editing efficiency of at least 10% of the cells introduced to the editing module per cycle, preferably an editing efficiency of at least 20% of the cells introduced to the editing module per cycle, more preferably an editing efficiency of at least 25% of the cells introduced to the editing module per cycle, still more preferably an editing efficiency of at least 30% of the cells introduced to the editing module automated multi-module cell editing instrument per cycle, yet more preferably an editing efficiency of at least 40% of the cells introduced to the editing module per cycle and even more preferably 50%, 60%, 70%, 80%, 90% or more of the cells introduced to the editing module per cycle.

Other features, advantages, and aspects will be described below in more detail.

BRIEF DESCRIPTION OF THE DRAWINGS

The accompanying drawings, which are incorporated into and constitute a part of the specification, illustrate one or more embodiments and, together with the description, explain these embodiments. The accompanying drawings have not necessarily been drawn to scale. Any dimensions illustrated in the accompanying graphs and figures are for illustration purposes only and may or may not represent actual or preferred values or dimensions. Where applicable, some or all features may not be illustrated to assist in the description of underlying features. In the drawings:

FIGS. 2A and 2B depict side and front views of the automated multi-module cell editing instrument of FIGS. 1A and 1B.

It should be understood that the drawings are not necessarily to scale, and that like reference numbers refer to like features.

DETAILED DESCRIPTION OF ILLUSTRATIVE EMBODIMENTS

Figure 1A:
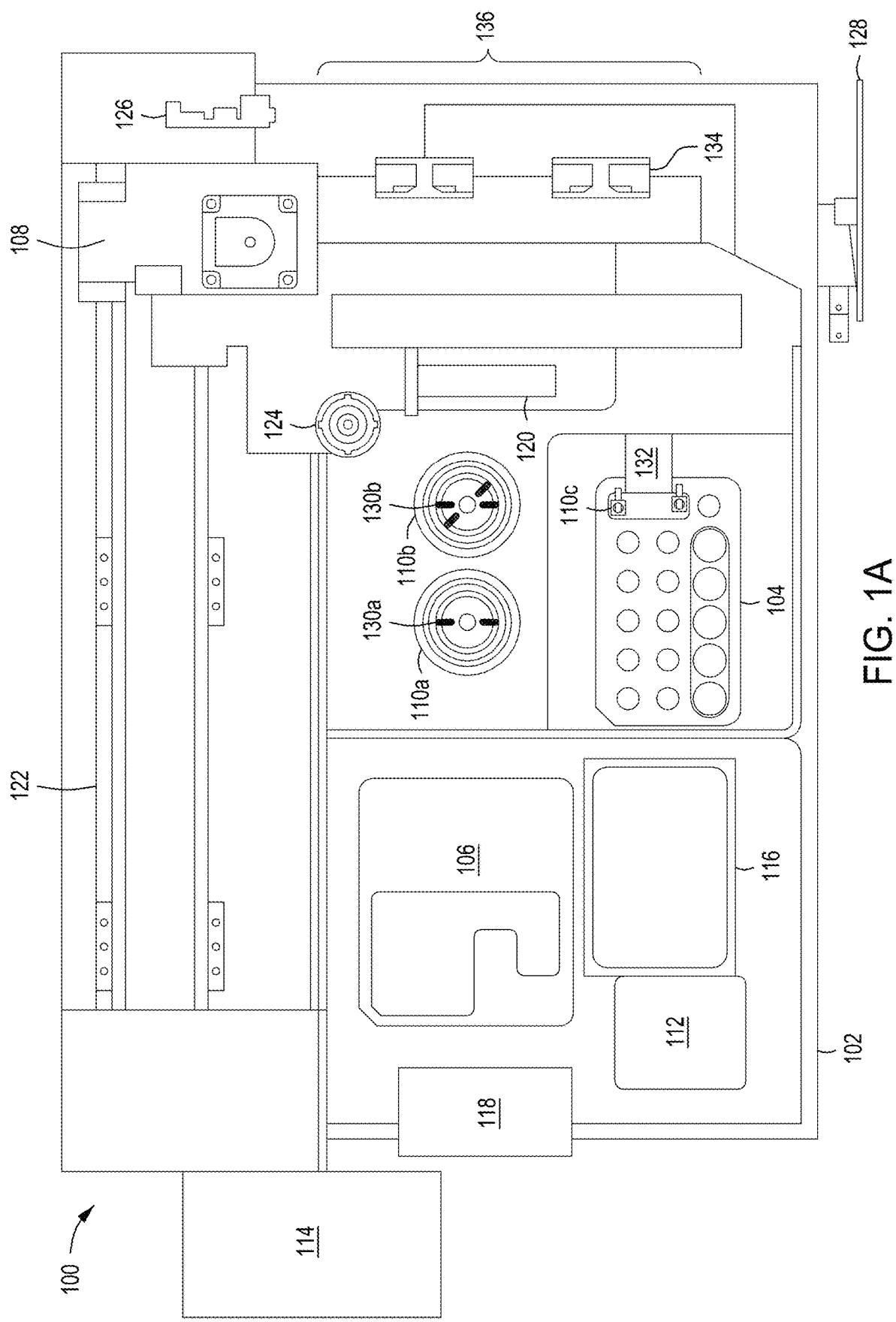
FIGS. 1A and 1B depict plan and perspective views of an example embodiment of an automated multi-module cell editing instrument for the multiplexed genome editing of multiple cells using a replaceable cartridge(s) as a part of the instrument.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include synthesis, assembly, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* 3$^{rd}$ Ed., W. H. Freeman Pub., New York, N.Y.; Berg et al. (2002) *Biochemistry*, 5$^{th}$ Ed., W.H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. CRISPR-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes.

Note that as used herein and in the appended claims, the singular forms "a," "an," and "the" include plural referents unless the context clearly dictates otherwise. Thus, for example, reference to "an oligo" refers to one or more oligos that serve the same function, to "the methods" includes reference to equivalent steps and methods known to those skilled in the art, and so forth. That is, unless expressly specified otherwise, as used herein the words "a," "an," "the" carry the meaning of "one or more." Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this disclosure belongs.

All publications (including patents, published applications, and non-patent literature) mentioned herein are incorporated by reference for all purposes, including but not limited to the purpose of describing and disclosing devices, systems, and methods that may be used or modified in connection with the presently described methods, modules, instruments, and systems.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment.

Further, the particular features, structures or characteristics may be combined in any suitable manner in one or more embodiments. Further, it is intended that embodiments of the disclosed subject matter cover modifications and variations thereof.

Introduction and Overview

In selected embodiments, the automated multi-module cell editing instruments and systems comprising FTEP devices described herein can be used in multiplexed genome editing in living cells, as well as in methods for constructing libraries of edited cell populations. The automated multi-module cell editing instruments disclosed herein can be used for a variety of genome editing techniques, and in particular with nuclease-directed genome editing techniques. The automated multi-module cell editing instruments of the disclosure provide novel methods and modules for introducing nucleic acid sequences into live cells to target genomic sites. The methods include constructing libraries comprising various classes of genomic edits to coding regions, non-coding regions, or both. The automated multi-module cell editing instruments are particularly suited to introducing genome edits to multiple cells in a single cycle, thereby generating libraries of cells having one or more genome edits in an automated, multiplexed fashion. The automated multi-module cell editing instruments are also suited to introduce two or more edits, e.g., edits to different target genomic sites in individual cells of a cell population.

Whether one or many, the genome edits are preferably rationally-designed edits; that is, nucleic acids that are designed and created to introduce specific edits to target regions within a cell's genome. The sequences used to facilitate genome-editing events include sequences that assist in guiding nuclease cleavage, introducing a genome edit to a region of interest, and/or both. The sequences may also include an edit to a region of the cell's genome to allow the specific rationally-designed edit in the cell's genome to be tracked. Such methods of introducing edits into cells are taught, e.g., in U.S. Pat. No. 9,982,278, entitled "CRISPR enabled multiplexed genome engineering," and U.S. Pat. Nos. 10,017,760, 10,017,760, entitled "Methods for generating barcoded combinatorial libraries."

Nuclease-Directed Genome Editing

In selected embodiments, the automated multi-module cell editing instruments comprising the FTEP devices described herein utilize a nuclease-directed genome editing system. Multiple different nuclease-based systems exist for editing an organism's genome, and each can be used in either single editing systems, sequential editing systems (e.g., using different nuclease-directed systems sequentially to provide two or more genome edits in a cell) and/or recursive editing systems, (e.g. utilizing a single nuclease-directed system to introduce two or more genome edits in a cell). Exemplary nuclease-directed genome editing systems are described herein, although a person of skill in the art would recognize upon reading the present disclosure that other enzyme-directed editing systems are also supported by the automated multi-module cell editing instruments and FTEP devices of the illustrative embodiments. That is, it should be noted that the automated instruments and systems as set forth herein can use the introduced nucleases to cleave the genome and introduce an edit into a target genomic region.

In particular aspects of the illustrative embodiments, the nuclease editing system is an inducible system that allows control of the timing of the editing. The inducible system may include inducible expression of the nuclease, inducible expression of the editing cassette(s), or both. The ability to modulate nuclease activity can reduce off-target cleavage and facilitate precise genome engineering. Further, inducible systems are useful when selecting for edited cells as described in U.S. Ser. Nos. 62/718,449 filed 14 Aug. 2018; and 62/724,851, filed 30 Aug. 2018, both of which are incorporated by reference in their entirety.

In certain aspects, cleavage by a nuclease can be also be used in the automated multi-module cell editing instruments described and claimed to select cells with a genomic edit at a target region. For example, cells that have been subjected to a genomic edit using an RNA-directed nuclease that removes a particular nuclease recognition site or nuclease recognition site can be selected using the automated multi-module cell editing instruments and systems of the illustrative embodiments by exposing the cells to a nuclease following such edit. The DNA in the cells without the genome edit will be cleaved and subsequently will have limited growth and/or perish, whereas the cells that received the genome edit removing the nuclease recognition site will not be affected by the subsequent exposure to the nuclease.

The promoters driving transcription of one or more components of the nucleic acid-guided nuclease editing system (e.g., one or both of the nuclease and guide nucleic acid) may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

The cells that can be transformed or transfected using the FTEP devices and edited using the automated multi-module cell editing instruments include any prokaryotic, archaeal or eukaryotic cell. For example, prokaryotic cells for use with the present illustrative embodiments can be gram positive bacterial cells, e.g., *Bacillus subtilis*, or gram negative bacterial cells, e.g., *E. coli* cells. Eukaryotic cells for use with the automated multi-module cell editing instruments of the illustrative embodiments include any plant cells and any animal cells, e.g. fungal cells, insect cells, amphibian cells, nematode cells, or mammalian cells.

In selected embodiments, the automated multi-module cell editing instruments described herein perform zinc-finger nuclease genome editing. Zinc-finger nucleases (ZFNs) are artificial restriction enzymes generated by fusing a zinc finger DNA-binding domain to a DNA-cleavage domain. Zinc finger domains can be engineered to target-specific regions in an organism's genome. (Urnov et al., Nature Reviews Genetics, 11:636-646 (2010); International Patent Application Publication WO 2003/087341 A2 to Carroll et al., entitled "Targeted Chromosomal Mutagenesis Using Zinc Finger Nucleases," filed Jan. 22, 2003). Using the endogenous DNA repair machinery of an organism, ZFNs can be used to precisely alter a target region of the genome. ZFNs can be used to disable dominant mutations in heterozygous individuals by producing double-strand breaks ("DSBs") in the DNA in the mutant allele, which will, in the absence of a homologous template, be repaired by non-homologous end-joining (NHEJ). NHEJ repairs DSBs by joining the two ends together and usually produces no mutations, provided that the cut is clean and uncomplicated. (Durai et al., Zinc finger nucleases: custom-designed molecular scissors for genome engineering of plant and mammalian cells, Nucleic Acids Res., 33(18):5978-90 (2005)). This repair mechanism can be used to induce errors in the genome via indels or chromosomal rearrangement, often rendering the gene products coded at that location non-functional.

Multiple pairs of ZFNs can also be used to completely remove entire large segments of genomic sequence (Lee et al., Genome Res., 20 (1): 81-9 (2009); and US Patent Application Publication 2011/0082093 A1 to Gregory et al. entitled "Methods and Compositions for Treating Trinucleotide Repeat Disorders," filed Jul. 28, 2010). Expanded CAG/CTG repeat tracts are the genetic basis for more than a dozen inherited neurological disorders including Huntington's disease, myotonic dystrophy, and several spinocerebellar ataxias. It has been demonstrated in human cells that ZFNs can direct DSBs to CAG repeats and shrink the repeat from long pathological lengths to short, less toxic lengths (Mittelman, et al., Zinc-finger directed double-strand breaks within CAG repeat tracts promote repeat instability in human cells, PNAS USA, 106 (24): 9607-12 (2009); and US Patent Application Publication 2013/0253040 A1 to Miller et al. entitled "Methods and Compositions for Treating Huntington's Disease," filed Feb. 28, 2013).

In another embodiment, the automated multi-module cell editing modules, instruments, and systems described herein perform meganuclease genome editing. Meganucleases were identified in the 1990s, and subsequent work has shown that they are particularly promising tools for genome editing, as they are able to efficiently induce homologous recombination, generate mutations in coding or non-coding regions of the genome, and alter reading frames of the coding regions of genomes. (See, e.g., Epinat, et al., Nucleic Acids Research, 31(11): 2952-62 (2003); and U.S. Pat. No. 8,921,332 to Choulika et al. entitled "Chromosomal Modification Involving the Induction of Double-stranded DNA Cleavage and Homologous Recombination at the Cleavage Site," issued Dec. 30, 2014.) The high specificity of meganucleases gives them a high degree of precision and much lower cell toxicity than other naturally occurring restriction enzymes.

In yet another embodiment, the automated multi-module cell editing modules, instruments and systems described herein perform transcription activator-like effector nuclease editing. Transcription activator-like effector nucleases (TALENs) are restriction enzymes that can be engineered to cut specific sequences of DNA. They are made by fusing a TAL effector DNA-binding domain to a DNA cleavage domain (a nuclease which cuts DNA strands). Transcription activator-like effector nucleases (TALENs) can be engineered to bind to practically any desired DNA sequence, so when combined with a nuclease, DNA can be cut at specific locations. (See, e.g., Miller, et al., Nature Biotechnology, 29 (2): 143-8 (2011); Boch, Nature Biotech., 29(2): 135-6 (2011); International Patent Application Publication WO 2010/079430 A1 to Bonas et al. entitled "Modular DNA-binding Domains and Methods of Use," filed Jan. 12, 2010; International Patent Application Publication WO 2011/072246 A2 to Voytas et al. entitled "TAL Effector-Mediated DNA Modification," filed Dec. 10, 2010).

Alternatively, DNA can be introduced into a genome in the presence of exogenous double-stranded DNA fragments using homology dependent repair (HDR). The dependency of HDR on a homologous sequence to repair DSBs can be exploited by inserting a desired sequence within a sequence that is homologous to the flanking sequences of a DSB which, when used as a template by HDR system, leads to the creation of the desired change within the genomic region of interest.

Like ZFNs, TALENs can edit genomes by inducing DSBs. The TALEN-created site-specific DSBs at target regions are repaired through NHEJ or HDR, resulting in targeted genome edits. TALENs can be used to introduce indels, rearrangements, or to introduce DNA into a genome through NHEJ in the presence of exogenous double-stranded DNA fragments.

In other embodiments, the genome editing of the automated multi-module cell editing instruments of the illustrative embodiments utilize clustered regularly interspaced short palindromic repeats (CRISPR) techniques, in which RNA-guided nucleases (RGNs) are used to edit specific target regions in an organism's genome. By delivering the RGN complexed with a synthetic guide RNA (gRNA) into a cell, the cell's genome can be cut at a desired location, allowing edits to the target region of the genome. The guide RNA helps the RGN proteins recognize and cut the DNA of the target genome region. By manipulating the nucleotide sequence of the guide RNA, the RGN system may be programmed to target any DNA sequence for cleavage.

The RGN system used with the automated multi-module cell editing instruments of the illustrative embodiments can perform genome editing using any RNA-guided nuclease system with the ability to both cut and paste at a desired target genomic region. In certain aspects, the RNA-guided nuclease system may use two separate RNA molecules as a gRNA, e.g., a CRISPR RNA (crRNA) and trans-activating CRISPR RNA (tracrRNA). In other aspects, the gRNA may be a single gRNA that includes both the crRNA and tracrRNA sequences.

In certain aspects, the genome editing both introduces a desired DNA change to a target region and removes the proto-spacer motif (PAM) region from the target region, thus precluding any additional editing of the genome at that target region, e.g., upon exposure to a RNA-guided nuclease complexed with a synthetic gRNA complementary to the target region. (See, e.g., U.S. Pat. Nos. 9,982,278 and 10,017,760 both of which are incorporated herein in their entirety.) In this aspect, a first editing event can be, e.g., an RGN-directed editing event or a homologous recombination event, and cells having the desired edit can be selected using an RGN complexed with a synthetic gRNA complementary to the target region. Cells that did not undergo the first editing event will be cut, and thus will not continue to be viable under appropriate selection criteria. The cells containing the desired mutation will not be cut, as they will no longer contain the necessary PAM site, and will continue to grow and propagate in the automated multi-module cell editing instrument.

When an RGN system is used for selection, it is primarily the cutting activity that is needed; thus the RNA-guided nuclease protein system can either be the same as used for editing, or may be a RGN system that is efficient in cutting using a particular PAM site, but not necessarily efficient in editing at the site. One important aspect of the nuclease used for selection is the recognition of the PAM site that is replaced using the editing approach of the previous genome editing operation.

In yet another embodiment, the genome editing of the automated multi-module cell editing instruments of the illustrative embodiments can utilize homologous recombination methods including the cre-lox technique and the FRET technique. Site-specific homologous recombination differs from general homologous recombination in that short specific DNA sequences, which are required for the recombinase recognition, are the only sites at which recombination occurs. Site-specific recombination requires specialized recombinases to recognize the sites and catalyze the recombination at these sites. A number of bacteriophage- and yeast-derived site-specific recombination systems, each comprising a recombinase and specific cognate sites, have been shown to work in eukaryotic cells for the purpose of DNA integration and are therefore applicable for use in the present invention, and these include the bacteriophage P1 Cre/lox, yeast FLP-FRT system, and the Dre system of the tyrosine family of site-specific recombinases. Such systems and methods of use are described, for example, in U.S. Pat. Nos. 7,422,889; 7,112,715; 6,956,146; 6,774,279; 5,677,177; 5,885,836; 5,654,182; and 4,959,317, which are incorporated herein by reference to teach methods of using such recombinases. Other systems of the tyrosine family such as bacteriophage lambda Int integrase, HK2022 integrase, and in addition systems belonging to the separate serine family of recombinases such as bacteriophage phiC31, R4Tp901 integrases are known to work in mammalian cells using their respective recombination sites, and are also applicable for use in the present invention. Exemplary methodologies for homologous recombination are described in U.S. Pat. Nos. 6,689,610; 6,204,061; 5,631,153; 5,627,059; 5,487,992; and 5,464,764, each of which is incorporated by reference in its entirety.

Instrument Architecture

Figure 1B:
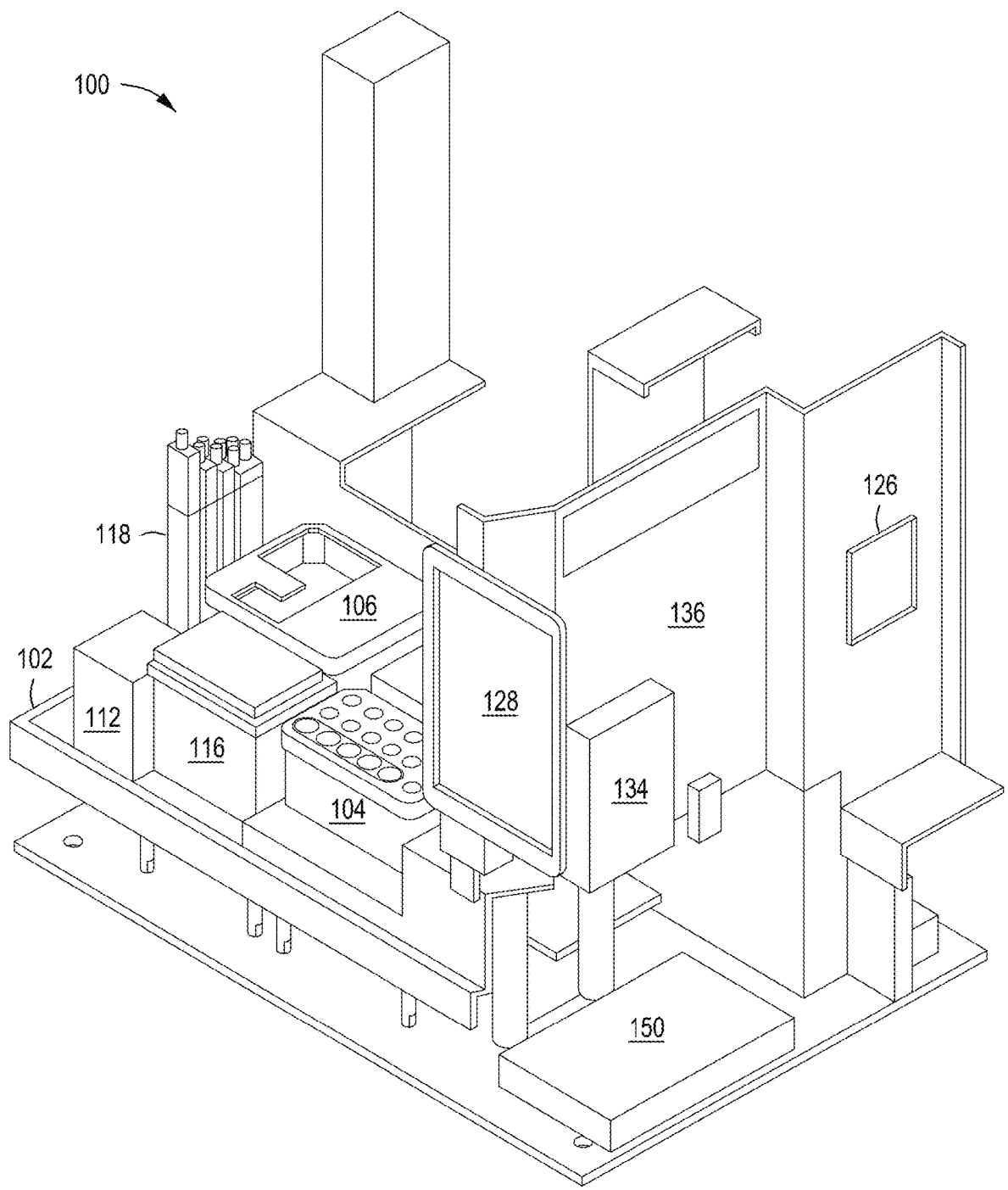

FIGS. 1A and 1B depict one example of an automated multi-module cell editing instrument 100 utilizing cartridge-based source materials (e.g., reagents, enzymes, nucleic acids, wash solutions, etc.). The instrument 100, for example, may be designed as a desktop instrument for use within a laboratory environment. The instrument 100 may incorporate a mixture of reusable and disposable elements for performing various staged operations in conducting automated genome cleavage and/or editing in cells. Cartridge-based source materials, for example, may be positioned in designated areas on a deck 102 of the instrument 100 for access by a robotic handling instrument 108. As illustrated in FIG. 1B, the deck 102 may include a protection sink such that contaminants spilling, dripping, or overflowing from any of the modules of the instrument 100 are contained within a lip of the protection sink.

Turning to FIG. 1A, the instrument 100, in some implementations, includes a reagent cartridge 104 for introducing DNA samples and other source materials to the instrument 100, an FTEP device 110c (here as a part of reagent cartridge 104), a wash cartridge 106 for introducing eluent and other source materials to the instrument 100, and a robotic handling system 108 for moving materials between modules (for example, modules 110a, 110b, and 110c) cartridge receptacles (for example, receptacles of cartridges 104 and 106), and storage units (e.g., units 112, 114, 116, and 118) of the instrument 100 to perform automated genome cleavage and/or editing. Upon completion of processing of a cell supply, in some embodiments, cell output may be transferred by the robot handling instrument 108 to a storage unit or receptacle placed in, e.g., reagent cartridge 104 or wash cartridge 106 for temporary storage and later retrieval.

The robotic handling system 108, for example, may include an air displacement pump 120 to transfer liquids from the various reagent reservoirs of the cartridges 104, 106 to the various modules 110a-110c and to the storage units (112, 114, 116 or 118). In other embodiments, the robotic handling system 108 may include a pick and place head (not illustrated) to transfer containers of source materials (e.g., tubes or vials) from the reagent cartridge 104 and/or the wash cartridge 106 to the various modules 110a-110c. In some embodiments, one or more cameras or other optical sensors (not shown) confirm proper movement and position of the robotic handling apparatus along gantry 122.

In some embodiments, the robotic handling system 108 uses disposable transfer tips provided in a transfer tip supply 116 (e.g., pipette tip rack) to transfer source materials, reagents (e.g., nucleic acids, enzymes, buffers), and cells within the instrument 100. Used transfer tips, for example, may be discarded in a solid waste unit 112. In some implementations, the solid waste unit 112 contains a kicker to remove tubes, tips, vials, and/or filters from the pick and place head of robotic handling system 108. For example, as illustrated the robotic handling system 108 includes a filter pickup head 124.

Figure 18:
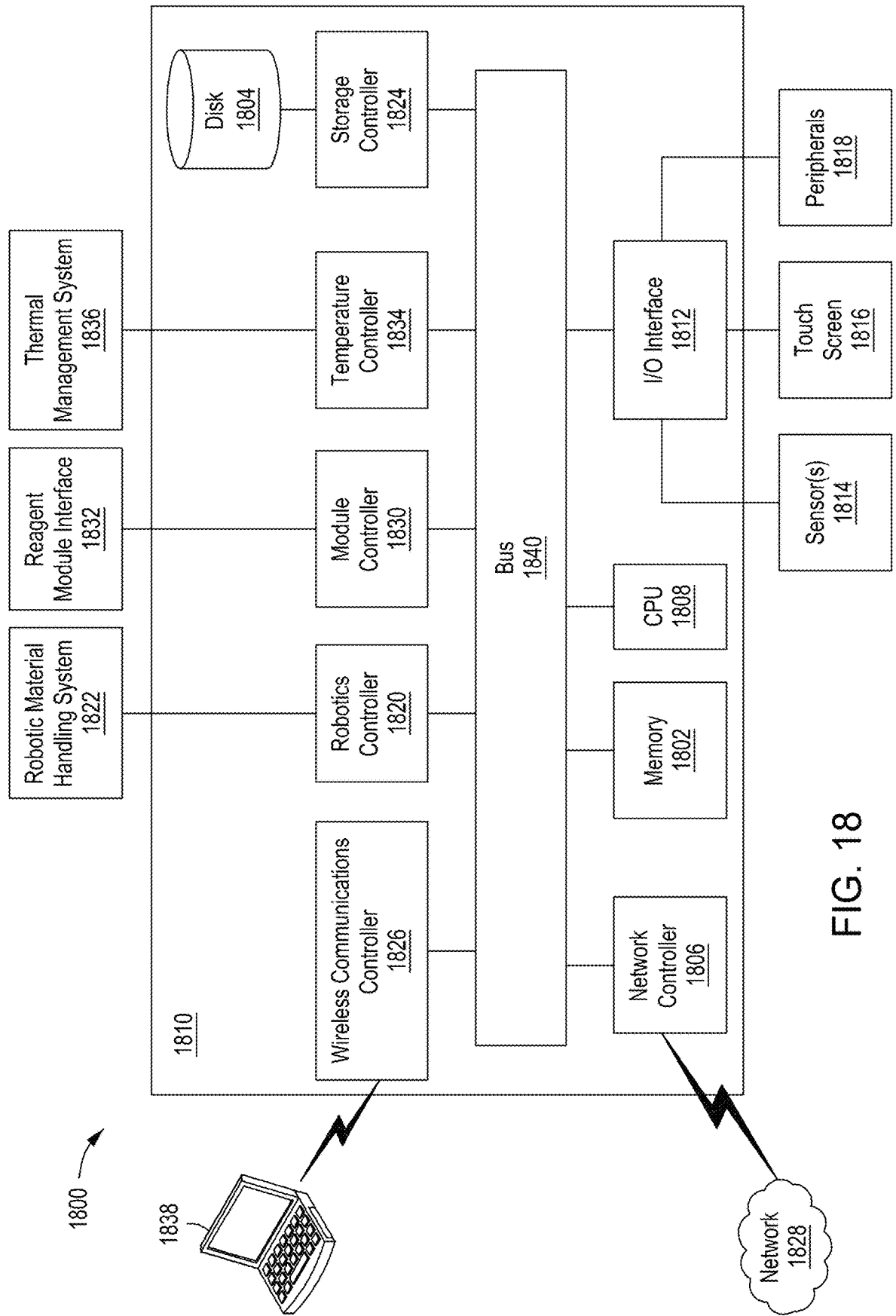
FIG. 18 is an example control system for use in an automated multi-module cell editing instrument.

In some implementations, the instrument 100 is controlled by a processing system 126 such as the processing system 1810 of FIG. 18. The processing system 126 may be configured to operate the instrument 100 based on user input. For example, user input may be received by the instrument 100 through a touch screen control display 128. The processing system 126 may control the timing, duration, temperature and other operations of the various modules 110a-110c of the instrument 100. Turning to FIG. 1B, the processing system 126 may be connected to a power source 150 for the operation of the instrument 100.

Returning to FIG. 1A, the reagent cartridge 104, as illustrated, includes sixteen reservoirs (a matrix of 5×3 reservoirs, plus an additional reservoir) and a flow-through FTEP device 110c (e.g., transformation modules as described in detail below in relation to FIGS. 4A-4I, 5A-5G, 6, 7A-7E, 8A-8U, 9A-9C and 10A-10G). The wash cartridge 106 may be configured to accommodate large tubes or reservoirs to store, for example, wash solutions, or solutions that are used often throughout an iterative process. Further, in some embodiments the wash cartridge 106 may include a number of smaller tubes, vials, or reservoirs to retain smaller volumes of, e.g., source media as well as a receptacle or repository for edited cells. For example, the wash cartridge 106 may be configured to remain in place when two or more reagent cartridges 104 are sequentially used and replaced. Although the reagent cartridge 104 and wash cartridge 106 are shown in FIG. 1A as separate cartridges, in other embodiments, the contents of the wash cartridge 106 may be incorporated into the reagent cartridge 104. In further embodiments, three or more cartridges may be loaded into the automated multi-module cell editing instrument 100. In certain embodiments, the reagent cartridge 104, wash cartridge 106, and other components of the modules 110a-110c in the automated multi-module cell editing instrument 100 are packaged together in a kit.

The wash and reagent cartridges 104, 106, in some implementations, are disposable kits provided for use in the automated multi-module cell editing instrument 100. For example, the user may open and position each of the reagent cartridge 104 and the wash cartridge 106 within a chassis of the automated multi-module cell editing instrument prior to activating cell processing. Example chassis are discussed in further detail below in relation to FIGS. 2A through 2D.

Components of the cartridges 104, 106, in some implementations, are marked with machine-readable indicia, such as bar codes, for recognition by the robotic handling system 108. For example, the robotic handling system 108 may scan containers within each of the cartridges 104, 106 to confirm contents. In other implementations, machine-readable indicia may be marked upon each cartridge 104, 106, and the processing system of the automated multi-module cell editing instrument 100 may identify a stored materials map based upon the machine-readable indicia. (See, e.g., element 1112 of FIG. 11B and element 1130 of FIG. 11D.)

Figure 11A:
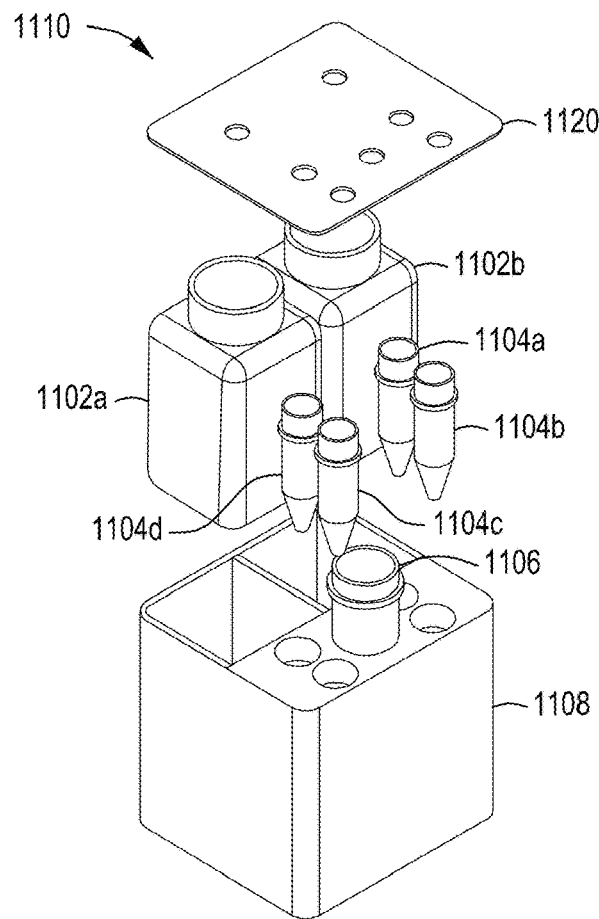
FIGS. 11A-11B depict an exploded view and a top view, respectively, of an example wash cartridge for use in an automated multi-module cell editing instrument.
Figure 11B:
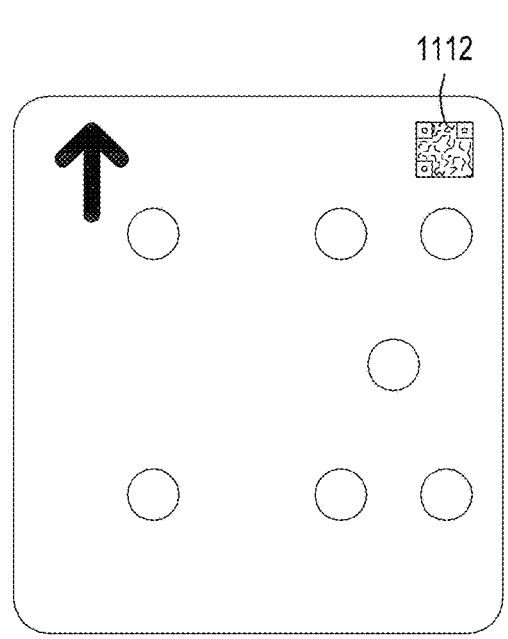

In some embodiments, the wash cartridge 106 (FIG. 1A) is in some embodiments a wash cartridge such as that illustrated in FIGS. 11A-11B. The cartridge 1100 includes a pair of containers 1102 a, b, a set of four small tubes 1104 a, b, c, d, and a larger tube 1106 held in a cartridge body 1108. One or more of the containers 1102 a, b, and tubes 1104 a, b, c, d and 1106, in some embodiments, is sealed with a pierceable foil for access by an automated liquid handling system, such as a sipper or pipettor. In other embodiments, one or more of the containers 1102 a, b, and tubes 1104 a, b, c, d, and 1106 includes a sealable access gasket. The top of one or more of the containers 1102 a, b, and tubes 1104 a, b, c, d, and 1106, in some embodiments, is marked with machine-readable indicia (not illustrated) for automated identification of the contents.

In some embodiments, containers 1102 a, b contain wash solutions. The wash solution may be a same or different wash solutions. In some examples, wash solutions may contain, e.g., buffer, buffer and 10% glycerol, 80% ethanol.

In some implementations, a cover 1120 secures the containers 1102 a, b and tubes 1104 a, b, c, d and 1106 within the cartridge body 1108. Turning to FIG. 11B, the cover 1120 may include apertures for access to each of the containers 1102 a, b and tubes 1104 a, b, c, d and 1106. Further, the cover 1120 may include machine-readable indicia 1112 for identifying the type of cartridge (e.g., accessing a map of the cartridge contents). Alternatively, apertures may be marked separately with the individual contents.

Figure 11C:
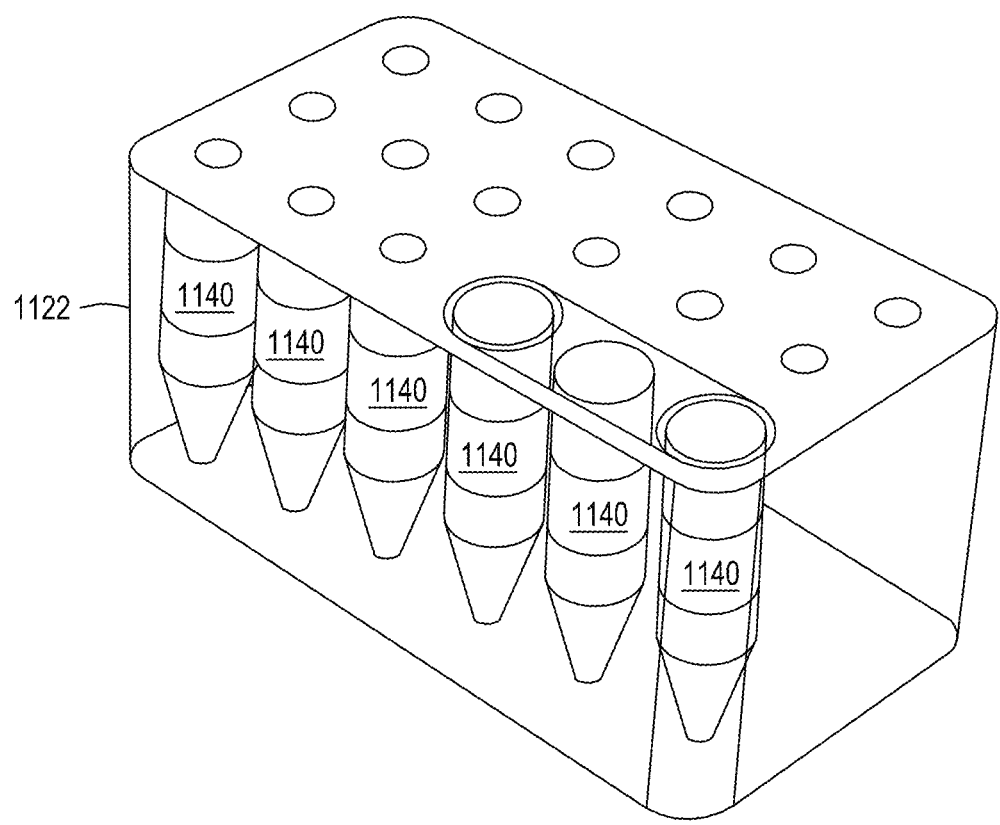
FIGS. 11C-11E depict an example reagent cartridge for use in an automated multi-module cell editing instrument.

In some embodiments, the reagent cartridge 104 of FIG. 1A is a reagent cartridge such as that illustrated in FIG. 11C. FIG. 11C shows a reagent cartridge 1122 including a set of eighteen tubes or vials 1140; however, the embodiment shown in FIG. 11C does not include an FTEP device. Looking at FIG. 11E, reagent cartridge includes sixteen tubes or vials 1126 *a-p* and an FTEP device 1124, held in a cartridge body 1122. One or more of the tubes or vials 1140 (FIG. 11C) or 1126 *a-p* (FIG. 11E), in some embodiments, is sealed with pierceable foil for access by an automated liquid handling system, such as a sipper or pipettor. In other embodiments such as that shown in FIG. 11E, one or more of the tubes or vials 1126*a*-1126*p* includes a sealable access gasket. The top of each of the small tubes or vials 1126*a*-1126*p*, in some embodiments, is marked with machine-readable indicia (not illustrated) for automated identification of the contents. The machine-readable indicia may include a bar code, QR code, or other machine-readable coding. Other automated means for identifying a particular container can include color coding, symbol recognition (e.g., text, image, icon, etc.), and/or shape recognition (e.g., a relative shape of the container). Rather than being marked upon the vessel itself, in some embodiments, an upper surface of the cartridge body and/or the cartridge cover may contain machine-readable indicia for identifying contents. The small tubes or vials may each be of a same size. Alternatively, multiple volumes of tubes or vials may be provided in the reagent cartridge 1120. In an illustrative example, each tube or vial may be designed to hold between 2 and 20 mL, between 4 and 10 mL, or about 5 mL. In some embodiments where only small volumes of some reagents are required, tube inserts may be used to accommodate small (e.g., microfuge) tubes in a larger receptacle.

In an illustrative example, the tubes or vials 1126*a*-1126*p* may each hold one the following materials: a vector backbone, oligonucleotides, reagents for nucleic acid assembly, a user-supplied cell sample, an inducer agent, magnetic beads in buffer, ethanol, an antibiotic for cell selection, reagents for eluting cells and nucleic acids, an oil overlay, other reagents, and cell growth and/or recovery media.

Figure 11D:
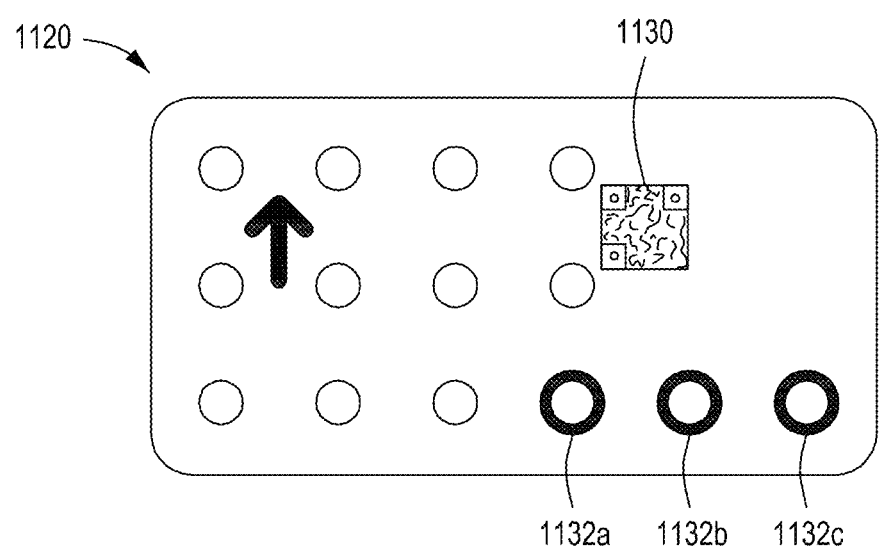

In some implementations, a cover 1120 as seen in FIG. 11D secures the tubes or vials 1140 within the cartridge body 1122 of FIG. 11C. Turning to FIG. 11D, the cover 1120 may include apertures for access to each of the small tubes or vials 1126. Three large apertures 1132 are outlined in a bold band to indicate positions to add user-supplied materials. The user-supplied materials, for example, may include a vector backbone, oligonucleotides, and a cell sample. Further, the cover 1120 may include machine-readable indicia 1130 for identifying the type of cartridge (e.g., accessing a map of the cartridge contents). Alternatively, each aperture may be marked separately with the individual contents. In some implementations, to ensure positioning of user-supplied materials, the vials or tubes provided for filling in the lab environment may have unique shapes or sizes such that the cell sample vial or tube only fits in the cell sample aperture, the oligonucleotides vial or tube only fits in the oligonucleotides aperture, and so on.

Turning back to FIG. 1A, also illustrated is the robotic handling system 108 including the gantry 122. In some examples, the robotic handling system 108 may include an automated liquid handling system such as those manufactured by Tecan Group Ltd. of Mannedorf, Switzerland, Hamilton Company of Reno, Nev. (see, e.g., WO2018015544A1 to Ott, entitled "Pipetting device, fluid processing system and method for operating a fluid processing system"), or Beckman Coulter, Inc. of Fort Collins, Colo. (see, e.g., US20160018427A1 to Striebl et al., entitled "Methods and systems for tube inspection and liquid level detection"). The robotic handling system 108 may include an air displacement pipettor 120. The reagent cartridges 104, 106 allow for particularly easy integration with the liquid handling instrumentation of the robotic handling system 108 such as air displacement pipettor 120. In some embodiments, only the air displacement pipettor 120 is moved by the gantry 122 and the various modules 110*a*-110*c* and cartridges 104, 106 remain stationary. Pipette tips may be provided in a pipette transfer tip supply 116 for use with the air displacement pipettor 120.

In some embodiments, an automated mechanical motion system (actuator) (not shown) additionally supplies XY axis motion control or XYZ axis motion control to one or more modules 110*a*-110*c* and/or cartridges 104, 106 of the automated multi-module cell editing instrument 100. Used pipette tips, for example, may be placed by the robotic handling system in a waste repository 112. For example, an active module may be raised to come into contact-accessible positioning with the robotic handling system or, conversely, lowered after use to avoid impact with the robotic handling system as the robotic handling system is moving materials to other modules within the automated multi-module cell editing instrument 100.

The automated multi-module cell editing instrument 100, in some implementations, includes the FTEP device 110*c* (e.g., transformation or transfection module) included in the reagent cartridge 104. A flow-through electroporation connection bridge 132, for example, is engaged with the flow-through electroporation device after the cells and nucleic acids are transferred into the device via an input channel. The bridge 132 provides both a liquid-tight seal and an electrical connection to the electrodes, as well as control for conducting electroporation within the FTEP device 110*c*. For example, the electroporation connection bridge 132 may be connected to FTEP controls 134 within an electronics rack 136 of the automated multi-module cell editing instrument 100.

In some implementations, the automated multi-module cell editing instrument 100 includes dual cell growth modules 110*a*, 110*b*. The cell growth modules 110*a*, 110*b*, as illustrated each include a rotating cell growth vial 130*a*, 130*b*. At least one of the cell growth modules 110*a*, 110*b* may additionally include an integrated filtration module (not illustrated). In alternative embodiments, a filtration module or a cell wash and concentration module may instead be separate from cell growth modules 110*a*, 110*b* (e.g., as described in relation to cell growth module 1710*a* and filtration module 1710*b* of FIGS. 17A and 17B). The cell growth modules 110*a*, 110*b*, for example, may each include the features and functionalities discussed in relation to the cell growth module 1300 of FIGS. 13A-C.

A filtration portion of one or both of the cell growth modules 110*a*, 110*b*, in some embodiments, uses replaceable filters stored in a filter cassette 118. For example, the robotic handling system may include the filter pick-up head 124 to pick up and engage filters for use with one or both of the cell growth modules 110*a*, 110*b*. The filter pick-up head transfers a filter to the growth module, pipettes up the cells from the growth module, then washes and renders the cells electrocompetent. The medium from the cells, and the wash fluids are disposed in waste module 114.

In some implementations, automated multi-module cell editing instrument 100 includes a nucleic acid assembly and purification function (e.g., nucleic acid assembly module) for combining materials provided in the reagent cartridge 104 into an assembled nucleic acid for cell editing. Further, a desalting or purification operation purifies the assembled nucleic acids and de-salts the buffer such that the nucleic acids are more efficiently electroporated into the cells. The nucleic acid assembly and purification feature may include a reaction chamber or tube receptacle (not shown) and a magnet (not shown).

Although the example instrument 100 is illustrated as including a particular arrangement of modules 110, this implementation is for illustrative purposes only. For example, in other embodiments, more or fewer modules 110 may be included within the instrument 100, and different modules may be included such as, e.g., a module for cell fusion to produce hybridomas and/or a module for expression and/or protein production. Further, certain modules may be replicated within certain embodiments, such as the duplicate cell growth modules 110a, 110b of FIG. 1A.

In some embodiments, the cells are modified prior to introduction onto the automated multi-module cell editing instrument. For example, bacterial cells of interest may harbor a λ red system to facilitate genome repair, and/or the cells may harbor an antibiotic resistance gene, so they may be selected easily. FIGS. 2A through 2D illustrate example chassis 200 and 230 for use in desktop versions of an automated multi-module cell editing instrument. For example, the chassis 200 and 230 may have a width of about 24-48 inches, a height of about 24-48 inches and a depth of about 24-48 inches. Each of the chassis 200 and 230 may be designed to hold multiple modules and disposable supplies used in automated cell processing. Further, each chassis 200 and 230 may mount a robotic handling system for moving materials between modules.

FIGS. 2A and 2B depict a first example chassis 200 of an automated multi-module cell editing instrument. As illustrated, the chassis 200 includes a cover 202 having a handle 204 and hinges 206a-206c for lifting the cover 202 and accessing an interior of the chassis 200. A cooling grate 214 may allow for air flow via an internal fan (not shown). Further, the chassis 200 is lifted by adjustable feet 220. The feet 220a-220c, for example, may provide additional air flow beneath the chassis 200. A control button 216, in some embodiments, allows for single-button automated start and/or stop of cell processing within the chassis 200.

Inside the chassis 200, in some implementations, a robotic handling system 208 is disposed along a gantry 210 above materials cartridges 212a, 212b. Control circuitry, liquid handling tubes, air pump controls, valves, thermal units (e.g., heating and cooling units) and other control mechanisms, in some embodiments, are disposed below a deck of the chassis 200, in a control box region 218.

Although not illustrated, in some embodiments a display screen may be positioned upon a front face of the chassis 200, for example covering a portion of the cover 202. The display screen may provide information to the user regarding a processing status of the automated multi-module cell editing instrument. In another example, the display screen may accept inputs from the user for conducting the cell processing.

Figure 2D:
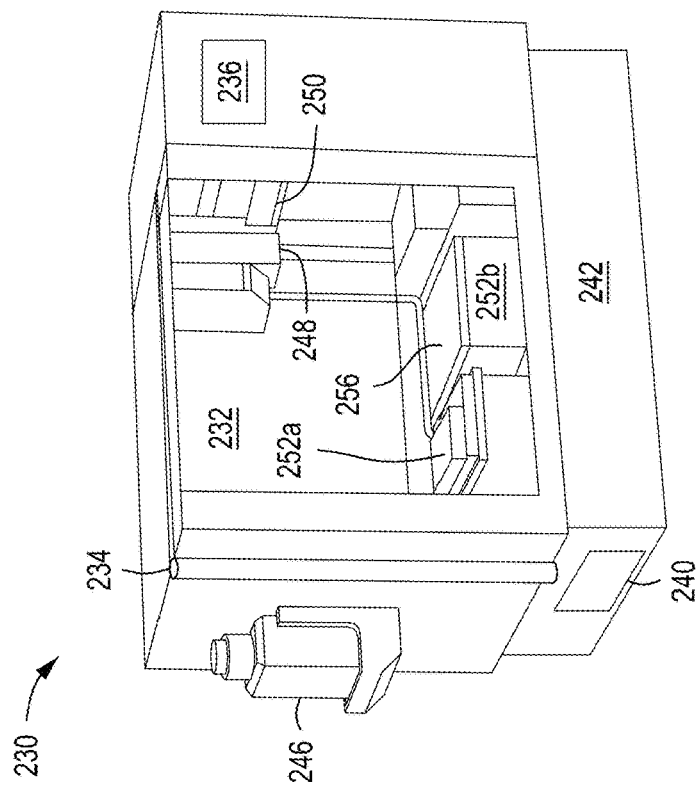
FIGS. 2C and 2D depict a second example chassis of an automated multi-module cell editing instrument.
Figure 2C:
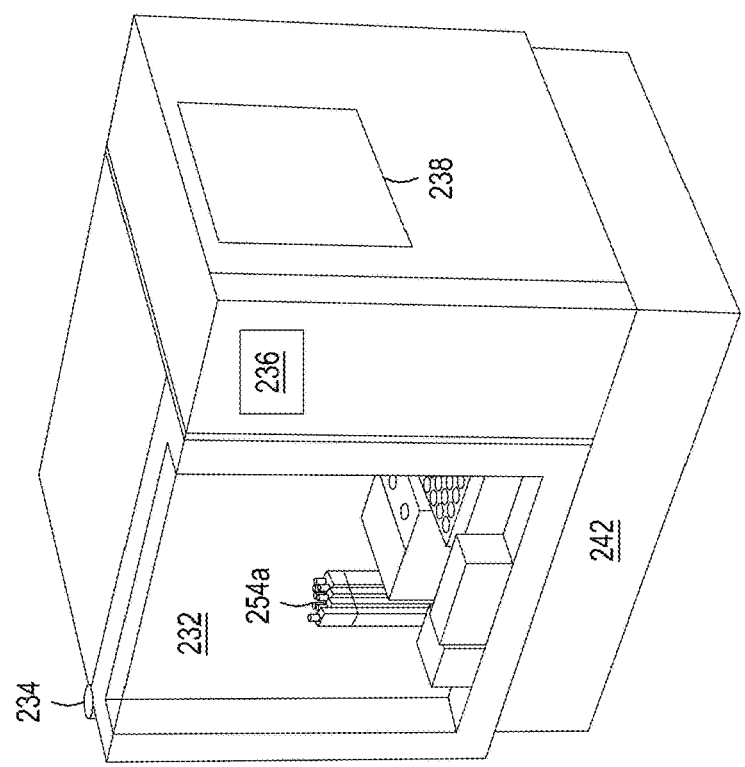

FIGS. 2C and 2D depict a second example chassis 230 of an automated multi-module cell editing instrument. The chassis 230, as illustrated, includes a transparent door 232 with a hinge 234. For example, the door may swing to the left of the page to provide access to a work area of the chassis. The user, for example, may open the transparent door 232 to load supplies, such as reagent cartridges and wash cartridges, into the chassis 230.

In some embodiments, a front face of the chassis 230 further includes a display (e.g., touch screen display device) 236 illustrated to the right of the door 232. The display 236 may provide information to the user regarding a processing status of the automated multi-module cell editing instrument. In another example, the display 236 may accept inputs from the user, e.g., for pausing or conducting the cell processing.

An air grate 238 on a right face of the chassis 230 may provide for air flow within a work area (e.g., above the deck) of the chassis 230 (e.g., above a deck). A second air grate 240 on a left of the chassis 230 may provide for air flow within a control box region 242 (e.g., below the deck) of the chassis 230. Although not illustrated, in some embodiments, feet such as the feet 220a-220c of the chassis 200 may raise the chassis 230 above a work surface, providing for further air flow.

Inside the chassis 230, in some implementations, a robotic handling system 248 is disposed along a gantry 250 above cartridges 252a, 252b, material supplies 254a, 254b (e.g., pipette tips and filters), and modules (e.g., dual growth vials, FTEP device, nucleic acid assembly module (not shown)). Control circuitry, liquid handling tubes, air pump controls, valves, and other control mechanisms, in some embodiments, are disposed below a deck of the chassis 230, in the control box region 242.

In some embodiments, a liquid waste unit 246 is mounted to the left exterior wall of the chassis 230. The liquid waste unit 246, for example, may be mounted externally to the chassis 230 to avoid potential contamination and to ensure prompt emptying and replacement of the liquid waste unit 246.

Nucleic Acid Assembly Module

Certain embodiments of the automated multi-module cell editing instruments of the present disclosure include a nucleic acid assembly module instrument. The nucleic acid assembly module is configured to accept and assemble the nucleic acids necessary to facilitate the desired genome editing events. The nucleic acid assembly module may also be configured to accept the appropriate vector backbone for vector assembly and subsequent electroporation into the cells of interest.

In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that include one or more free ends, no free ends (e.g. circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Additional vectors include fosmids, phagemids, and synthetic chromosomes.

Recombinant expression vectors can include a nucleic acid in a form suitable for transformation, and for some nucleic acid sequences, translation and expression of the nucleic acid in a host cell, which means that the recombinant expression vectors include one or more regulatory elements—which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g. in an in vitro transcription/translation system or in a host cell when the vector is introduced into the host cell). Appropriate recombination and cloning methods are disclosed in U.S. patent application Ser. No. 10/815,730, entitled "Recombinational Cloning Using Nucleic Acids Having Recombination Sites" published Sep. 2, 2004 as US 2004-0171156 A1, the contents of which are herein incorporated by reference in their entirety for all purposes.

In some embodiments, a regulatory element is operably linked to one or more elements of a targetable nuclease system so as to drive transcription, and for some nucleic acid sequences, translation and expression of the one or more components of the targetable nuclease system.

In addition, the polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably liked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated multi-module cell editing instruments include, but are not limited to, those assembly methods that use restriction endonucleases, including PCR, BioBrick assembly (U.S. Pat. No. 9,361,427 to Hillson entitled "Scar-less Multi-part DNA Assembly Design," issued Jun. 7, 2016), Type IIS cloning (e.g., GoldenGate assembly; European Patent Application Publication EP 2 395 087 A1 to Weber et al. entitled "System and Method of Modular Cloning," filed Jul. 6, 2010), and Ligase Cycling Reaction (de Kok S, ACS Synth Biol., 3(2):97-106 (2014); Engler, et al., PLoS One, 3(11):e3647 (2008); U.S. Pat. No. 6,143,527 to Pachuk et al. entitled "Chain Reaction Cloning Using a Bridging Oligonucleotide and DNA Ligase," issued Nov. 7, 2000). In other embodiments, the nucleic acid assembly techniques performed by the disclosed automated multi-module cell editing instruments are based on overlaps between adjacent parts of the nucleic acids, such as Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244-51 (2009); U.S. Pat. No. 5,888,732 to Hartley et al., entitled "Recombinational Cloning Using Engineered Recombination Sites," issued Mar. 30, 1999; U.S. Pat. No. 6,277,608 to Hartley et al. entitled "Recominational Cloning Using Nucleic Acids Having Recombination Sites," issued Aug. 21, 2001), and topoisomerase-mediated cloning (Udo, PLoS One, 10(9):e0139349 (2015); U.S. Pat. No. 6,916,632 B2 to Chestnut et al. entitled "Methods and Reagents for Molecular Cloning," issued Jul. 12, 2005). These and other nucleic acid assembly techniques are described, e.g., in Sands and Brent, Curr Protoc Mol Biol., 113:3.26.1-3.26.20 (2016); Casini et al., Nat Rev Mol Cell Biol., (9):568-76 (2015); Patron, Curr Opinion Plant Biol., 19:14-9 (2014)).

The nucleic acid assembly module is temperature controlled depending upon the type of nucleic acid assembly used in the automated multi-module cell editing instrument. For example, when PCR is utilized in the nucleic acid assembly module, the module will have a thermocycling capability allowing the temperatures to cycle between denaturation, annealing and extension. When single temperature assembly methods are utilized in the nucleic acid assembly module, the module will have the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated multi-module cell editing instrument.

Figure 3:
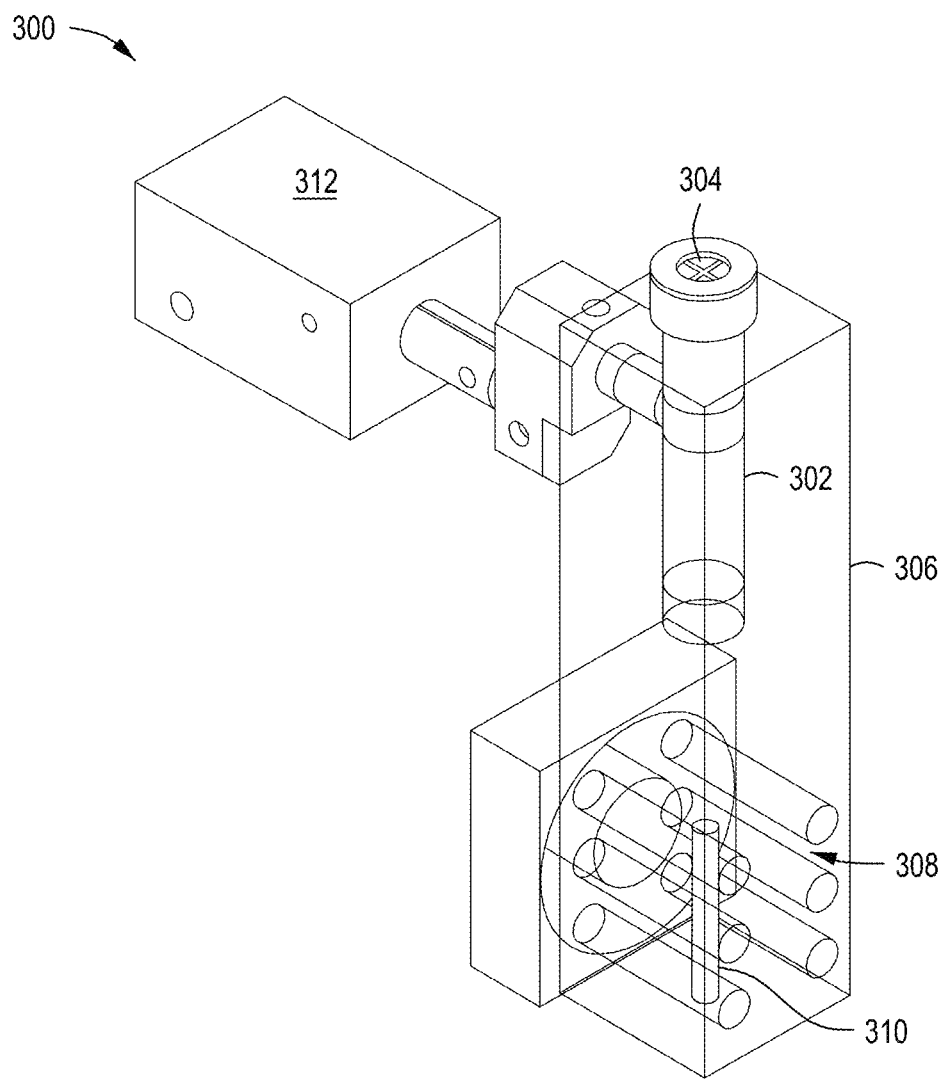
FIG. 3 depicts an example combination nucleic acid assembly module and purification module for use in an automated multi-module cell editing instrument.

In one embodiment, the nucleic acid assembly module is a module to perform assembly using a single, isothermal reaction, such as that illustrated in FIG. 3. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes—an exonuclease, a polymerase, and a ligase-along with buffer components. Because the process is isothermal and can be performed in a 1-step or 2-step method using a single reaction vessel, isothermal assembly reactions are ideal for use in an automated multi-module cell editing instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

FIG. 3 illustrates an example nucleic acid assembly module 300 with integrated purification. The nucleic acid assembly module 300 includes a chamber 302 having an access gasket 304 for transferring liquids to and from the nucleic acid assembly module 300 (e.g., via a pipette or sipper). In some embodiments, the access gasket 304 is connected to a replaceable vial which is positioned within the chamber 302. For example, a user or robotic manipulation system may place the vial within the nucleic acid assembly module 300 for processing.

The chamber 302 shares a housing 306 with a resistive heater 308. Once a sample has been introduced to the chamber 302 of the nucleic acid assembly module 300, the resistive heater 308 may be used to heat the contents of the chamber 302 to a desired temperature. Thermal ramping may be set based upon the contents of the chamber 302 (e.g., the materials supplied through the access gasket 304 via pipettor or sipper unit of the robotic manipulation system). The processing system of the automated multi-module cell editing instrument may determine the target temperature and thermal ramping plan. The thermal ramping and target temperature may be controlled through monitoring a thermal sensor such as a thermistor 310 included within the housing 306. In a particular embodiment, the resistive heater 308 is designed to maintain a temperature within the housing 306 of between 20° and 80° C., between 25° and 75° C., between 37° and 65° C., between 40° and 60° C., between 45 and 55° C. or preferably about 50° C.

Purification Module

In some embodiments, when a nucleic acid assembly module is included in the automated multi-module cell editing instrument, the instrument also can include a purification module to remove unwanted components of the nucleic acid assembly mixture (e.g., salts, minerals) and, in certain embodiments, concentrate the assembled nucleic acids. Examples of methods for exchanging the liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc.

In one aspect, the purification module provides filtration, e.g., ultrafiltration. For example, a range of microconcentrators fitted with anisotropic, hydrophilic-generated cellulose membranes of varying porosities is available. In another example, the purification and concentration involves contacting a liquid sample including the assembled nucleic acids and an ionic salt with an ion exchanger including an insoluble phosphate salt, removing the liquid, and eluting the nucleic acid from the ion exchanger.

In a specific aspect of the purification module, SPRI beads can be used where 0.6-2.0× volumes of SPRI beads can be added to the nucleic acid assembly. The nucleic acid assembly product becomes bound to the SPRI beads, and the SPRI beads are pelleted by automatically positioning a magnet close to the tube, vessel, or chamber harboring the pellet. For example, 0.6-2.0× volumes of SPRI beads can be added to the nucleic acid assembly. The SPRI beads, for example, may be washed with ethanol, and the bound nucleic acid assembly product is eluted. e.g., in water, Tris buffer, or 10% glycerol.

In a specific aspect, a magnet is coupled to a linear actuator that positions the magnet. In some implementations, the nucleic acid assembly module is a combination assembly and purification module designed for integrated assembly and purification. For example, as discussed above in relation to the nucleic acid assembly module depicted in FIG. 3, once sufficient time has elapsed for the nucleic acid assembly reaction to take place, the contents of the chamber 302 (e.g., the nucleic acid assembly reagents and nucleic acids), in some embodiments, are combined with magnetic beads (not shown) to activate the purification process. The SPRI beads in buffer are delivered to the contents of the nucleic acid assembly module, for example, by a robotic handling system. Thereafter, a solenoid 312, in some embodiments, is actuated by a magnet to excite the magnetic beads contained within the chamber 302. The solenoid, in a particular example, may impart between a 2 pound magnetic pull force and a 5 pound pull force, or approximately a 4 pound magnetic pull force to the magnetic beads within the chamber 302. The contents of the chamber 302 may be incubated for sufficient time for the assembled vector and oligonucleotides to bind to the magnetic beads.

After binding, in some implementations, the bound nucleic acid assembly mix (e.g., nucleic acid assembly reagents+assembled vector and oligonucleotides) is removed from the nucleic acid assembly module and the nucleic acids attached to the beads are washed one to several times with 80% ethanol. Once washed, the nucleic acids attached to the beads are eluted into buffer and are transferred to the transformation module. That is, in some embodiments, the nucleic acid assembly module and purification module are combined.

In some implementations, a vial is locked in position in the chamber 302 for processing. For example, a user may press the vial beyond a detent in the chamber 302 designed to retain the vial upon engagement with a pipettor or sipper. In another example, the user may twist the vial into position, thus engaging a protrusion to a corresponding channel and barring upward movement. A position sensor (not illustrated) may ensure retraction of the vial. The position sensor, in a particular embodiment, is a magnetic sensor detecting engagement between a portion of the chamber 302 and the vial. In other embodiments, the position sensor is an optical sensor detecting presence of the vial at a retracted position. In embodiments using a channel and protrusion, a mechanic switch pressed down by the protrusion may detect engagement of the vial Growth Module As the nucleic acids are being assembled, the cells may be grown in preparation for editing. Cell growth can be monitored by optical density (e.g., at OD 600 nm) that is measured in a growth module, and a feedback loop is used to adjust the cell growth so as to reach a target OD at a target time. Other measures of cell density and physiological state that can be measured include but are not limited to, pH, dissolved oxygen, released enzymes, acoustic properties, and electrical properties.

In some aspects, the growth module includes a culture tube in a shaker or vortexer that is interrogated by a spectrophotometer or fluorimeter. The shaker or vortexer can heat or cool the cells and cell growth is monitored by real-time absorbance or fluorescence measurements. In one aspect, the cells are grown at 25° C.-40° C. to an OD600 absorbance of 1-10 ODs. The cells may also be grown at temperature ranges from 25° C.-35° C., 25° C.-30° C., 30° C.-40° C., 30° C.-35° C., 35° C.-40° C., 40° C.-50° C., 40° C.-45° C. or 44° C.-50° C. In another aspect, the cells are induced by heating at 42° C.-50° C. or by adding an inducing agent. The cells may also be induced by heating at ranges from 42° C.-46° C., 42° C.-44° C., 44° C.-46° C., 44° C.-48° C., 46° C.-48° C., 46° C.-50° C., or 48° C.-50° C. In some aspects, the cells are cooled to 0° C.-10° C. after induction. The cells may also be cooled to temperature ranges of 0° C.-5° C., 0° C.-2° C., 2° C.-4° C., 4° C.-6° C., 6° C.-8° C., 8° C.-10° C., or 5° C.-10° C. after induction.

Figure 13A:
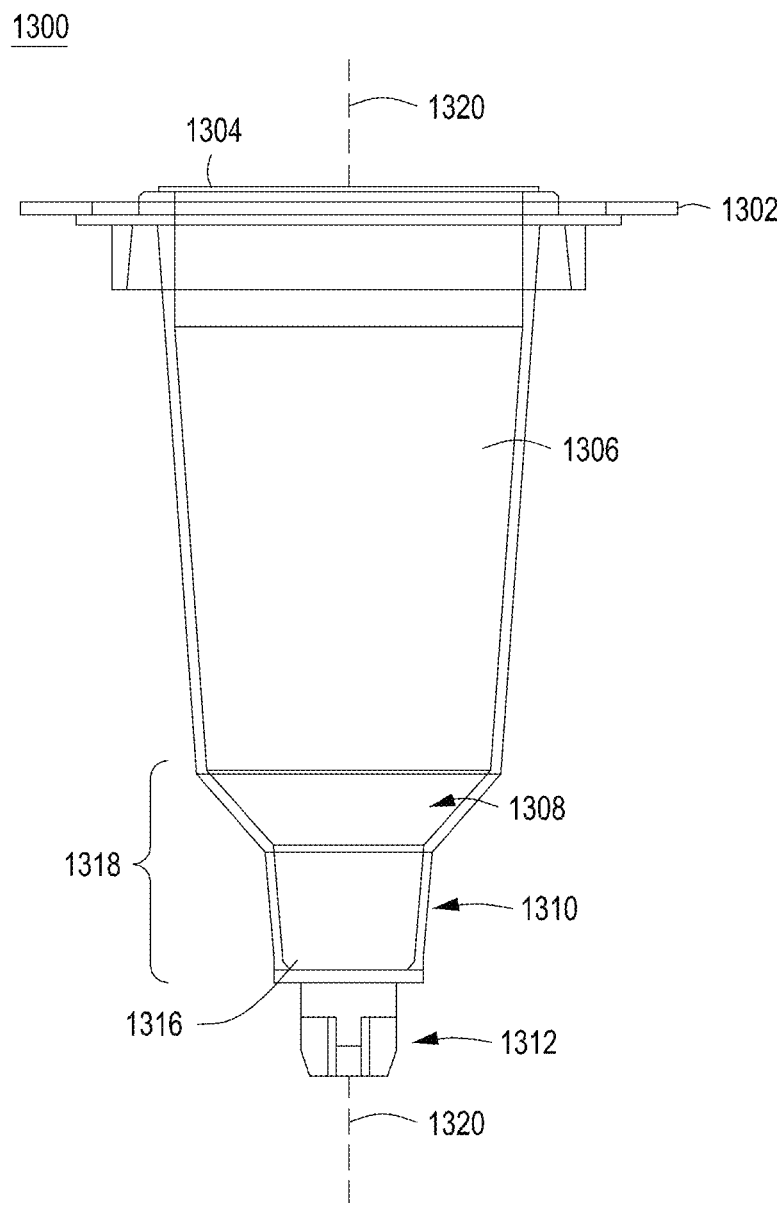
FIGS. 13A-13C depict example cell growth module components for use in an automated multi-module cell editing instrument.
Figure 13B:
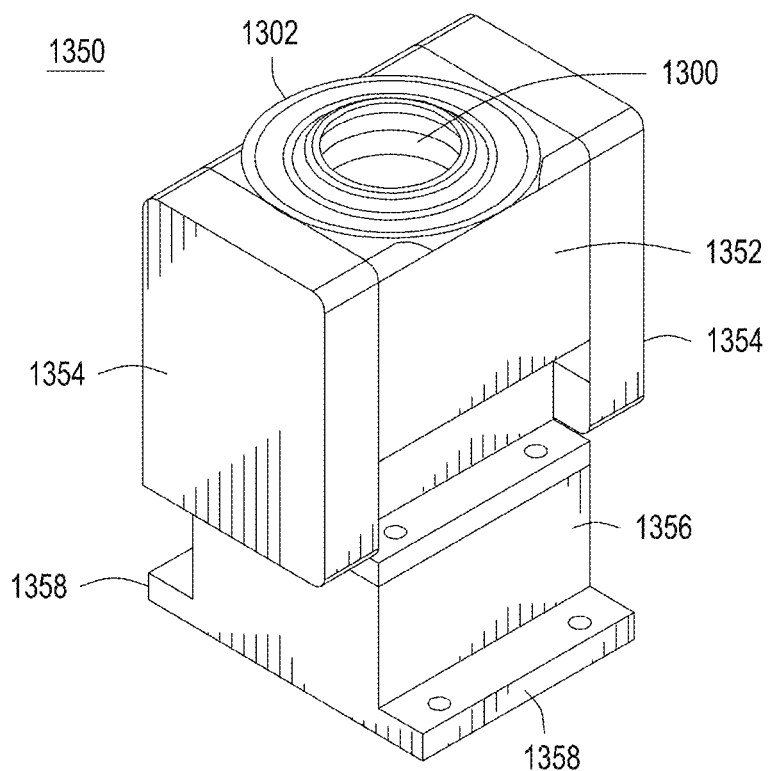
Figure 13C:
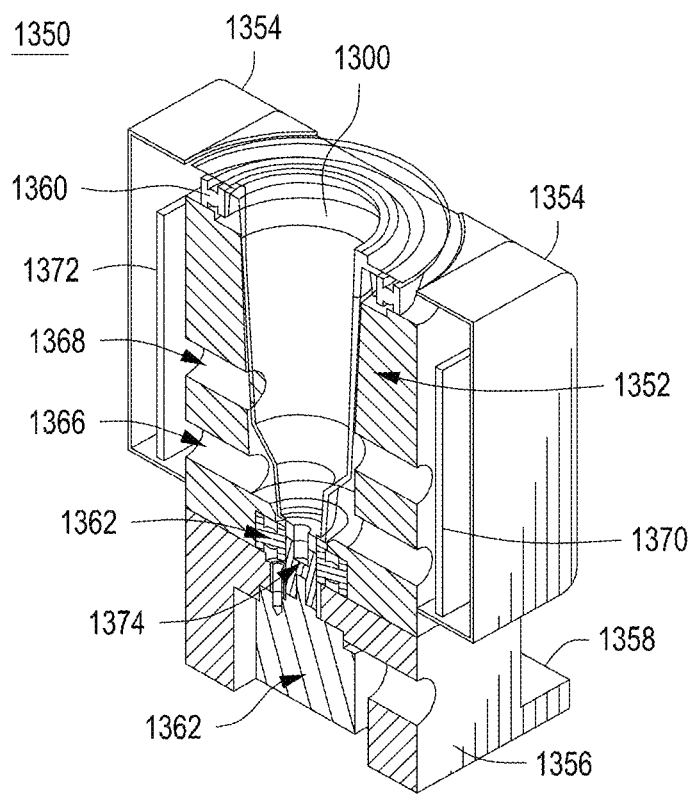

FIG. 13A shows one embodiment of a rotating growth vial 1300 for use with a cell growth device, such as cell growth device 1350 illustrated in FIGS. 13B-C. The rotating growth vial 1300, in some implementations, is a transparent container having an open end 1304 for receiving liquid media and cells, a central vial region 1306 that defines the primary container for growing cells, a tapered-to-narrowed region 1318 defining at least one light path 1308, 1310, a closed end 1316, and a drive engagement mechanism 1312. The rotating growth vial 1300 may have a central longitudinal axis 1320 around which the vial 1300 rotates, and the light paths 1308, 1310 may be generally perpendicular to the longitudinal axis of the vial. In some examples, first light path 1310 may be positioned in the lower narrowed portion of the tapered-to-narrowed region 1318. The drive engagement mechanism 1312, in some implementations, engages with a drive mechanism (e.g., actuator, motor (not shown)) to rotate the vial 1300. The actuator may include a drive shaft 1374 for a drive motor (not shown).

In some embodiments, the rotating growth vial 1300 includes a second light path 1308, for example, in the upper tapered region of the tapered-to-narrowed region 1318. In some examples, the walls defining the upper tapered region of the tapered-to-narrowed region 1318 for the second light path 1308 may be disposed at a wider angle relative to the longitudinal axis 1320 than the walls defining the lower narrowed portion of the tapered-to-narrowed region 1310 for the first light path 1310. Both light paths 1308, 1310, for example, may be positioned in a region of the rotating growth vial 1300 that is constantly filled with the cell culture (cells+growth media), and is not affected by the rotational speed of the growth vial 1300. As illustrated, the second light path 1308 is shorter than the first light path 1310 allowing for sensitive measurement of optical density (OD) values when the OD values of the cell culture in the vial are at a high level (e.g., later in the cell growth process), whereas the first light path 1310 allows for sensitive measurement of OD values when the OD values of the cell culture in the vial are at a lower level (e.g., earlier in the cell growth process).

The rotating growth vial 1300 may be reusable, or preferably, the rotating growth vial is consumable. In some embodiments, the rotating growth vial 1300 is consumable and can be presented to the user pre-filled with growth medium, where the vial 1300 is sealed at the open end 1304 with a foil seal. A medium-filled rotating growth vial packaged in such a manner may be part of a kit for use with a stand-alone cell growth device or with a cell growth module that is part of an automated multi-module cell editing instrument. To introduce cells into the vial, a user need only pipette up a desired volume of cells and use the pipette tip to punch through the foil seal of the vial 1300. Alternatively, of course, an automated instrument may transfer cells from, e.g., a reagent cartridge, to the growth vial. The growth medium may be provided in the growth vial or may also be transferred from a reagent cartridge to the growth vial before the addition of cells. Open end 1304 may include an extended lip 1302 to overlap and engage with the cell growth device 1350 (FIG. 13B). In automated instruments, the rotating growth vial 1300 may be tagged with a barcode or other identifying means that can be read by a scanner or camera that is part of the processing system 1810 as illustrated in FIG. 18.

In some implementations, the volume of the rotating growth vial 1300 and the volume of the cell culture (including growth medium) may vary greatly, but the volume of the rotating growth vial 1300 should be large enough for the cell culture in the growth vial 1300 to get proper aeration while the vial 1300 is rotating. In practice, the volume of the rotating growth vial 1300 may range from 1-250 ml, 2-100 ml, from 5-80 ml, 10-50 ml, or from 12-35 ml. Likewise, the volume of the cell culture (cells+growth media) should be appropriate to allow proper aeration in the rotating growth vial 1300. Thus, the volume of the cell culture should be approximately 10-85% of the volume of the growth vial 800, or 15-80% of the volume of the growth vial, or 20-70%, 30-60%, or 40-50% of the volume of the growth vial. In one example, for a 35 ml growth vial 1300, the volume of the cell culture would be from about 4 ml to about 27 ml.

The rotating growth vial 1300, in some embodiments, is fabricated from a bio-compatible transparent material, or at least the portion of the vial 1300 including the light path(s) is transparent. Additionally, material from which the rotating growth vial 1300 is fabricated should be able to be cooled to about 0° C. or lower and heated to about 75° C. or higher, such as about 2° C. or to about 70° C., about 4° C. or to about 60° C., or about 4° C. or to about 55° C. to accommodate both temperature-based cell assays and long-term storage at low temperatures. Further, the material that is used to fabricate the vial is preferably able to withstand temperatures up to 55° C. without deformation while spinning. Suitable materials include glass, polyvinyl chloride, polyethylene, polyamide, polyethylene, polypropylene, polycarbonate, poly(methyl methacrylate) (PMMA), polysulfone, polyurethane, and co-polymers of these and other polymers. Preferred materials include polypropylene, polycarbonate, or polystyrene. In some embodiments, the rotating growth vial 800 is inexpensively fabricated by, e.g., injection molding or extrusion.

FIGS. 13 B-C illustrate views of an example cell growth device 1350 that receives the rotating growth vial 1300. In some embodiments, the cell growth device 1350 rotates to heat or cool the cells or cell growth within the vial 1300 to a predetermined temperature range. In some implementations, the rotating growth vial 1300 can be positioned inside a main housing 1352 with the extended lip 1302 of the vial 1300 extending past an upper surface of the main housing 1352. In some aspects, the extended lip 1302 provides a grasping surface for a user inserting or withdrawing the vial 1300 from the main housing 1352 of the device 1350. Additionally, when fully inserted into the main housing 1352, a lower surface of the extended lip 1302 abuts an upper surface of the main housing 1352. In some examples, the main housing 1352 of the cell growth device 1350 is sized such that outer surfaces of the rotating growth vial 1300 abut inner surfaces of the main housing 1352 thereby securing the vial 1300 within the main housing 1352. In some implementations, the cell growth device 1350 can include end housings 1354 disposed on each side of the main housing 1354 and a lower housing 1356 disposed at a lower end of the main housing 1352. In some examples, the lower housing 1356 may include flanges 1358 that can be used to attach the cell growth device 1350 to a temperature control (e.g, heating/cooling) mechanism or other structure such as a chassis of an automated cell processing system.

As shown in FIG. 13C, the cell growth device 1350, in some implementations, can include an upper bearing 1360 and lower bearing 1362 positioned in main housing 1352 that support the vertical load of a rotating growth vial 1300 that has been inserted into the main housing 1352. In some examples, the cell growth device 1350 may also include a primary optical port 1366 and a secondary optical port 1368 that are aligned with the first light path 1310 and second light path 1308 of the vial 1300 when inserted into the main housing 1352. In some examples, the primary and secondary optical ports 1366, 1368 are gaps, openings, or portions of the main housing constructed from transparent materials that allow light to pass through the vial 1300 to perform cell growth OD measurements. In addition to the optical ports 1366, 1368, the cell growth device 1350 may include an emission board 1370 that provides one or more illumination sources for the light path(s), and detector board 1372 to detect the light after the light travels through the cell culture liquid in the rotating growth vial 1300. In one example, the illumination sources disposed on the emission board 1370 may include light emission diodes (LEDs) or photodiodes that provide illumination at one or more target wavelengths commensurate with the growth media typically used in cell culture (whether, e.g., mammalian cells, bacterial cells, animal cells, yeast cells).

In some implementations, the emission board 1370 and/or detector board 1372 are communicatively coupled through a wired or wireless connection to a processing system (e.g., processing system 126, 1720, 1810) that controls the wavelength of light output by the emission board 1370 and receives and processes the illumination sensed at the detector board 1372. The remotely controllable emission board 1370 and detector board 1372, in some aspects, provide for conducting automated OD measurements during the course of cell growth. For example, the processing system 126, 1720 may control the periodicity with which OD measurements are performed, which may be at predetermined intervals or in response to a user request Further, the processing system 126, 1720 can use the sensor data received from the detector board 1372 to perform real-time OD measurements and adjust cell growth conditions (e.g., temperature, speed/direction of rotation).

In some embodiments, the lower housing 1356 may contain a drive motor (not shown) that generates rotational motion that causes the rotating growth vial 1300 to spin within the cell growth device 1350. In some implementations, the drive motor may include a drive shaft 1374 that engages a lower end of the rotating growth vial 1300. The drive motor that generates rotational motion for the rotating growth vial 1300, in some embodiments, is a brushless DC type drive motor with built-in drive controls that can be configured to maintain a constant revolution per minute (RPM) between 0 and about 3000 RPM. Alternatively, other motor types such as a stepper, servo, or brushed DC motors can be used. Optionally, the drive motor may also have direction control to allow reversing of the rotational direction, and a tachometer to sense and report actual RPM. In other examples, the drive motor can generate oscillating motion by reversing the direction of rotation at a predetermined frequency. In one example, the vial 1300 is rotated in each direction for one second at a speed of 350 RPM. The drive motor, in some implementations, is communicatively coupled through a wired or wireless communication network to a processing system (e.g., processing system 126, 1720) that is configured to control the operation of the drive motor, which can include executing protocols programmed into the processor and/or provided by user input, for example as described in relation to module controller 1830 of FIG. 18. For example, and the drive motor can be configured to vary the speed and/or rotational direction of the vial 1300 to cause axial precession of the cell culture thereby enhancing mixing in order to prevent cell aggregation and increase aeration. In some examples, the speed or direction of rotation of the drive motor may be varied based on optical density sensor data received from the detector board 1372.

In some embodiments, main housing 1352, end housings 1354 and lower housing 1356 of the cell growth device 1350 may be fabricated from a robust material including aluminum, stainless steel, and other thermally conductive materials, including plastics. These structures or portions thereof can be created through various techniques, e.g., metal fabrication, injection molding, creation of structural layers that are fused, etc. While in some examples the rotating growth vial 1300 is reusable, in other embodiments, the vial 1300 is preferably is consumable. The other components of the cell growth device 1350, in some aspects, are preferably reusable and can function as a stand-alone benchtop device or as a module in an automated multi-module cell editing instrument.

In some implementations, the processing system that is communicatively coupled to the cell growth module may be programmed with information to be used as a "blank" or control for the growing cell culture. A "blank" or control, in some examples, is a vessel containing cell growth medium only, which yields 100% transmittance and 0 OD, while the cell samples deflect light rays and will have a lower percentage transmittance and higher OD. As the cells grow in the media and become denser, transmittance decreases and OD increases. The processor of the cell growth module, in some implementations, may be programmed to use wavelength values for blanks commensurate with the growth media typically used in cell culture (whether, e.g., mammalian cells, bacterial cells, animal cells, yeast cells). Alternatively, a second spectrophotometer and vessel may be included in the cell growth module, where the second spectrophotometer is used to read a blank at designated intervals.

To reduce background of cells that have not received a genome edit, the growth module may also allow a selection process to enrich for the edited cells. For example, the introduced nucleic acid can include a gene, which confers antibiotic resistance or another selectable marker. Alternating the introduction of selectable markers for sequential rounds of editing can also eliminate the background of unedited cells and allow multiple cycles of the automated multi-module cell editing instrument to select for cells having sequential genome edits.

Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, and chloramphenicol-resistance gene. In some embodiments, removing dead cell background is aided using lytic enhancers such as detergents, osmotic stress, temperature, enzymes, proteases, bacteriophage, reducing agents, or chaotropes. In other embodiments, cell removal and/or media exchange is used to reduce dead cell background.

Cell Wash and/or Concentration Module

The cell wash and/or concentration module can utilize any method for exchanging the liquids in the automated multi-module cell processing instrument, and may concentrate the cells or allow them to remain in essentially the same or greater volume of liquid as used in the nucleic acid assembly module. Further, in some aspects, the processes performed in the cell wash module also render the cells electrocompetent, by, e.g., use of glycerol in the wash.

Numerous different methods can be used to wash the cells, including density gradient purification, dialysis, ion exchange columns, filtration, centrifugation, dilution, and the use of beads for purification.

In some aspects, the cell wash and/or concentration module utilizes a centrifugation device. In other aspects, the cell wash and/or concentration module utilizes a filtration module. In yet other aspects, beads are coupled to moieties that bind to the cell surface. These moieties include but are not limited to antibodies, lectins, wheat germ agglutinin, mutated lysozymes, and ligands.

In other aspects, the cells are engineered to be magnetized, allowing magnets to pellet the cells after wash steps. The mechanism of cell magnetization can include but is not limited to ferritin protein expression.

Figure 12A:
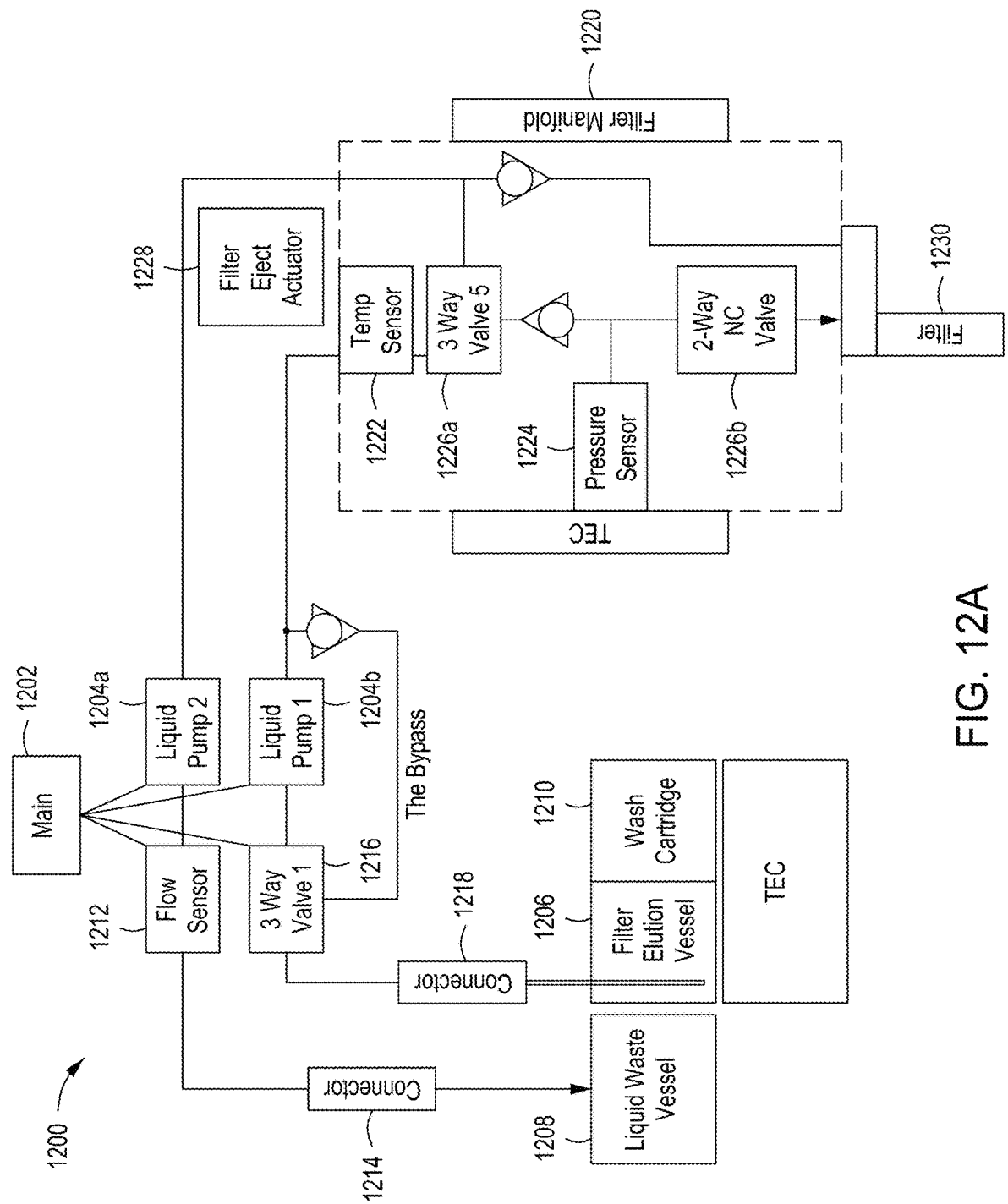
FIGS. 12A-12C provide a functional block diagram and two perspective views of an example filtration module for use in an automated multi-module cell editing instrument.

The cell wash and/or concentration module, in some implementations, is a filtration module. Turning to FIG. 12A, a block diagram illustrates example functional units of a filtration module 1200. In some implementations, a main control 1202 of the filtration module 1200 includes a first liquid pump 1204 b to intake wash fluid 1206 and a second liquid pump 1204 a to remove liquid waste to a liquid waste unit 1208 (e.g., such as the liquid waste unit 114 of FIG. 1A or liquid waste unit 1728 of FIGS. 17A and 17B). A flow sensor 1212 may be disposed on a connector 1214 to the liquid waste unit 1208 to monitor release of liquid waste from the filtration module. A valve 1216 (a three-way valve as illustrated) may be disposed on a connector 1218 to the wash fluid 1206 in wash cartridge 1210 to selectively connect the wash fluid 1206 and the filtration module 1200.

The filtration module 1200, in some implementations, includes a filter manifold 1220 for filtering and concentrating a cell sample. The filter manifold 1220 may include one or more temperature sensor(s) 1222 and pressure sensor (s) 1224 to monitor flow and temperature of the wash fluid and/or liquid waste. The sensors 1222, 1224, in some embodiments, are monitored and analyzed by a processing system of the automated multi-mode cell processing system, such as the processing system 1810 of FIG. 18. The filter manifold 1220 may include one or more valves 1226 and 1126 b for directing flow of the wash fluid and/or liquid waste. The processing system of the automated multi-mode cell processing instrument, for example, may actuate the valves according to a set of instructions for directing filtration by the filtration module 1200.

The filtration module 1200 includes at least one filter 1230. Examples of filters suitable for use in the filtration module 1200 include membrane filters, ceramic filters and metal filters. The filter may be used in any shape; the filter may for example be cylindrical or essentially flat. The filter selected for a given operation or a given workflow, in some embodiments, depends upon the type of workflow (e.g., bacterial, yeast, viral, etc.) or the volumes of materials being processed. For example, while flat filters are relatively low cost and commonly used, filters with a greater surface area, such as cylindrical filters, may accept higher flow rates. In another example, hollow filters may demonstrate lower recovery rates when processing small volumes of sample (e.g., less than about 10 ml). For example, for use with bacteria, it may be preferable that the filter used is a membrane filter, particularly a hollow fiber filter. With the term "hollow fiber" is meant a tubular membrane. The internal diameter of the tube, in some examples, is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules having hollow fibers are commercially available from various companies, including G.E. Life Sciences (Marlborough, Mass.) and InnovaPrep (Drexel, Mo.) (see, e.g., US20110061474A1 to Page et al., entitled "Liquid to Liquid Biological Particle Concentrator with Disposable Fluid Path").

In some implementations, the filtration module 1200 includes a filter ejection means 1228 (e.g., actuator) to eject a filter 1230 post use. For example, a user or the robotic handling system may push the filter 1230 into position for use such that the filter is retained by the filter manifold 1220 during filtration. After filtration to remove the used filter 1230, the filter ejection actuator 1228 may eject the filter 1230, releasing the filter 1230 such that the user or the robotic handling system may remove the used filter 1230 from the filtration module 1200. The used filter 1230, in some examples, may be disposed within the solid waste unit 112 of FIGS. 1A-1B, solid waste unit 1718 of FIGS. 17A and 17B, or returned to a filter cartridge 1240, as illustrated in FIG. 12D.

Figure 12D:
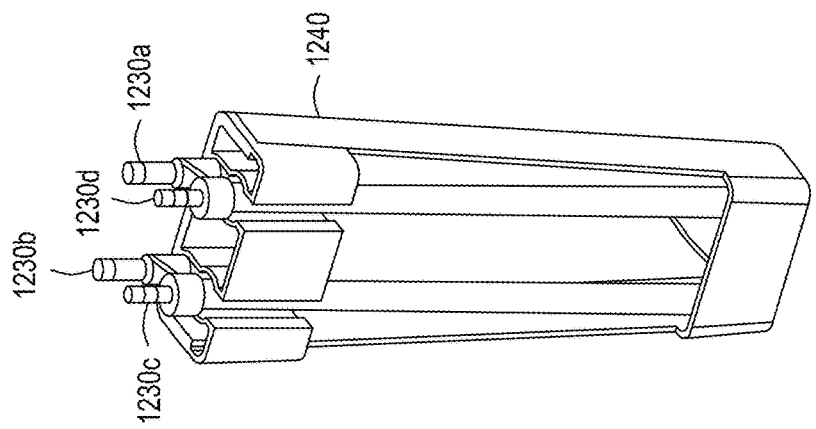
FIG. 12D is a perspective view of an example filter cartridge for use in an automated multi-module cell editing instrument.
Figure 17A:
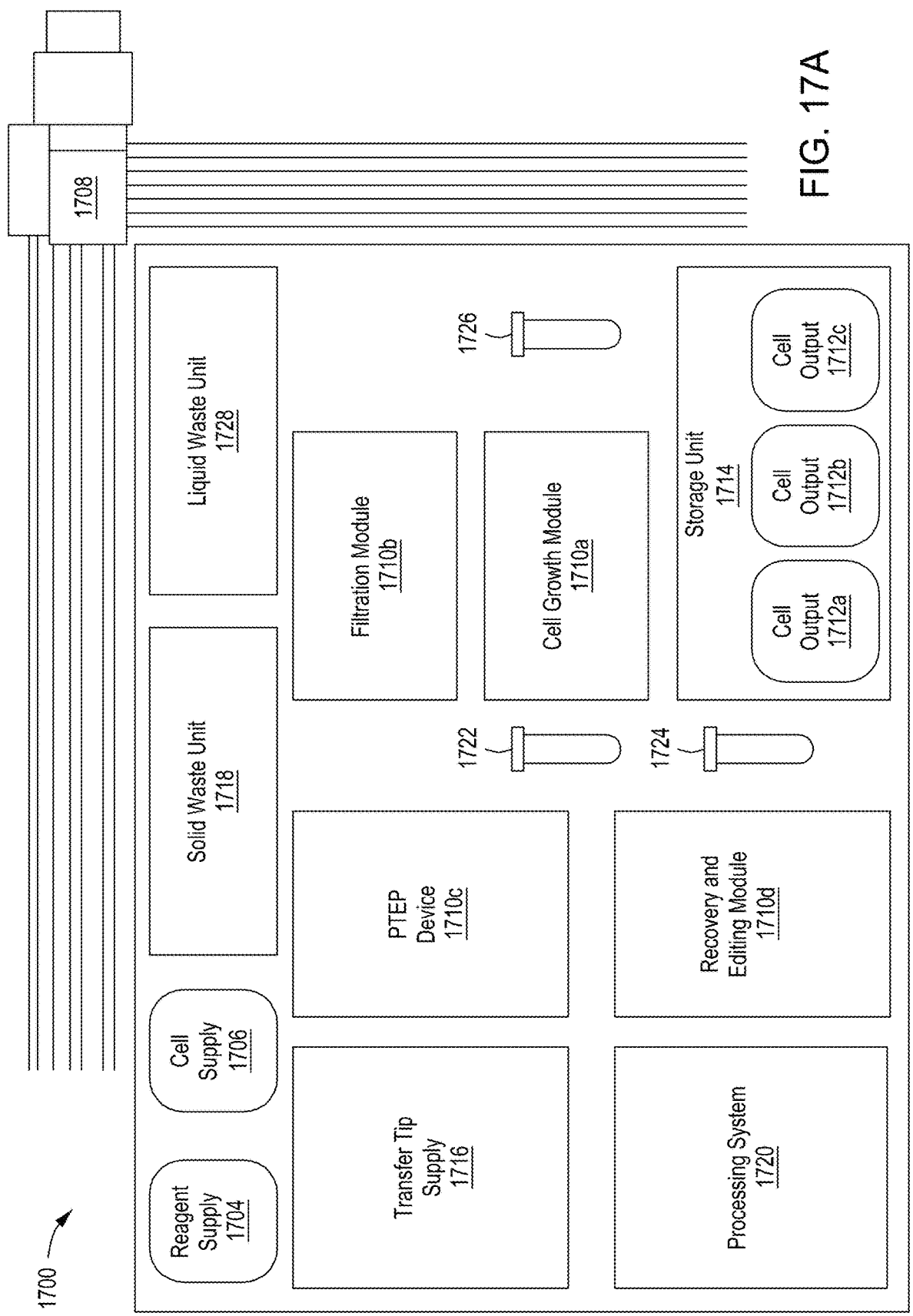
FIG. 17A is a functional block system diagram of another example embodiment of an automated multi-module cell editing instrument for the multiplexed genome editing of multiple cells.
Figure 17B:
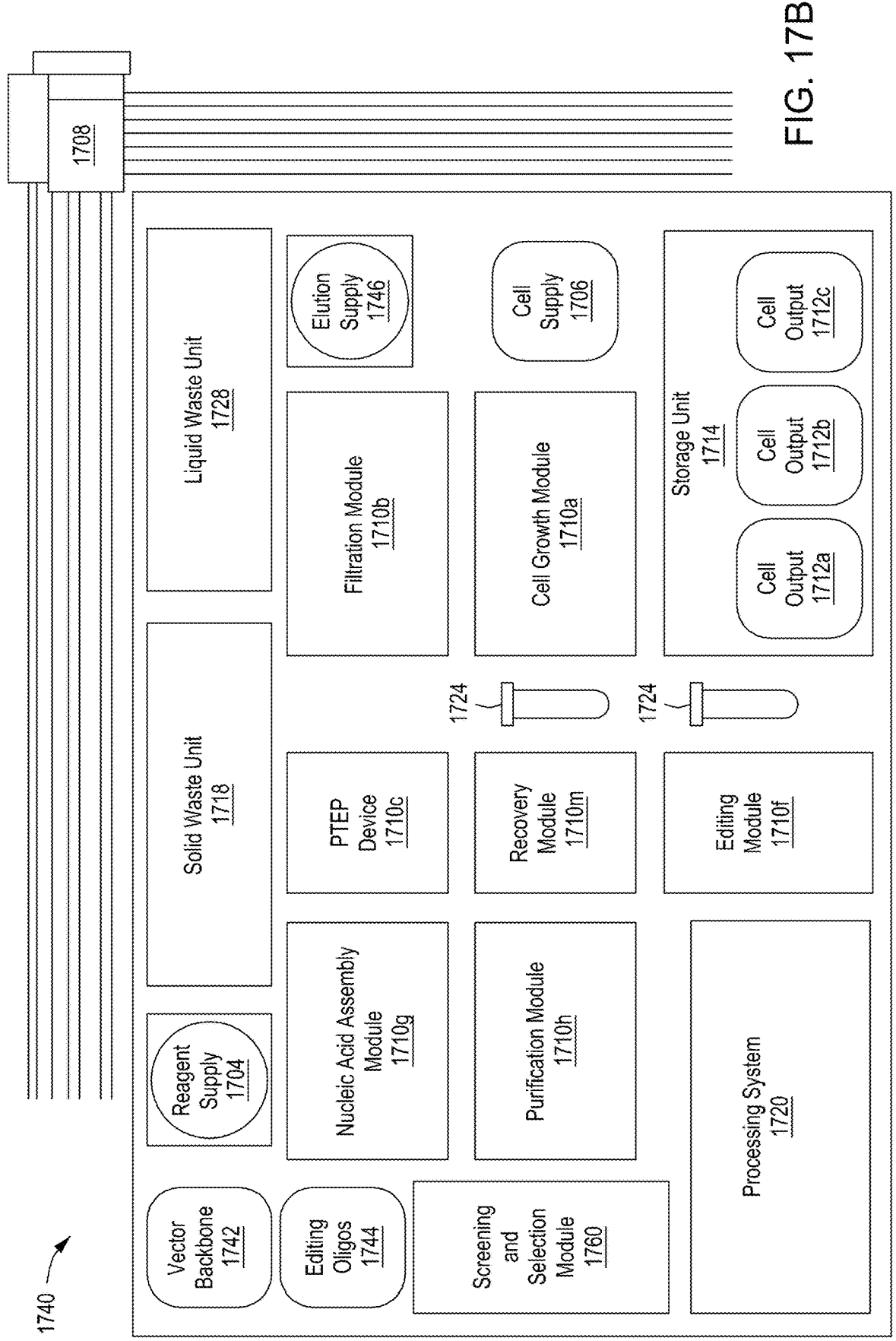
FIG. 17B is a functional block system diagram of yet another example embodiment of an automated multi-module cell editing instrument for the recursive, multiplexed genome editing of multiple cells.

Turning to FIG. 12D, in some implementations, filters 1230 a, b, c, d provided in the filter cartridge 1240 disposed within the chassis of the automated multi-module cell editing instrument are transported to the filtration module 1200 by a robotic handling system (e.g., the robotic handling system 108 described in relation to FIGS. 1A and 1B, or robotic handling system 1708 of FIGS. 17A and 17B) and positioned within the filtration module 1200 prior to use.

The filtration module 1200, in some implementations, requires periodic cleaning. For example, the processing system may alert a user when cleaning is required through the user interface of the automated multi-module cell editing instrument and/or through a wireless messaging means (e.g., text message, email, and/or personal computing device application). A decontamination filter, for example, may be loaded into the filtration module 1200 and the filtration module 1200 may be cleaned with a wash solution and/or alcohol mixture.

In some implementations, the filtration module 1200 is in fluid connection with a wash cartridge 1210 (such as the wash cartridge 1100 of FIG. 11A) containing the wash fluid 1206 via the connector 1218. For example, upon positioning by the user of the wash cartridge 1210 within the chassis of the automated multi-module cell editing instrument, the connector 1218 may mate with a bottom inlet of the wash cartridge 1210, creating a liquid passage between the wash fluid 1206 and the filtration module 1200.

Figure 12C:
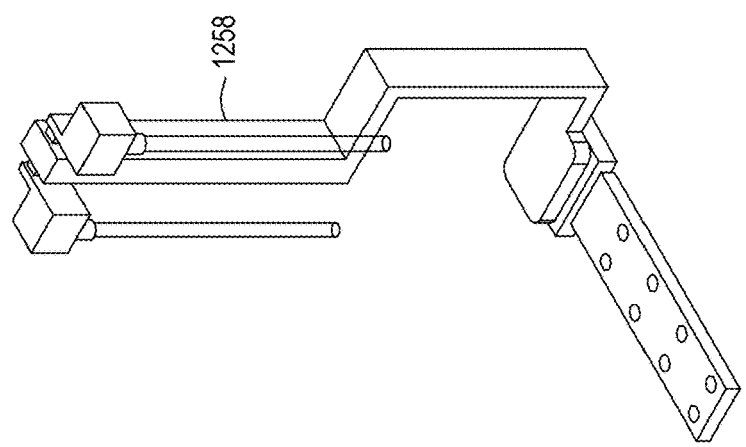
Figure 12B:
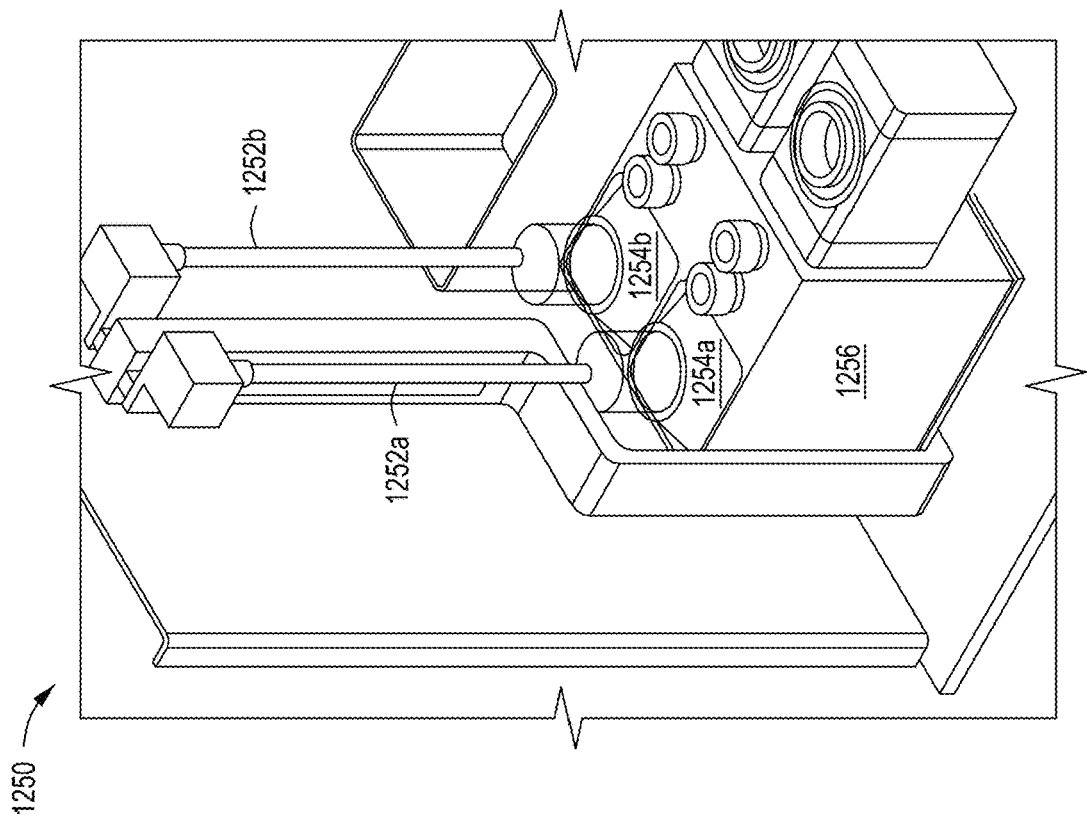

Turning to FIGS. 12B and 12C, in some implementations, a dual filter filtration module 1250 includes dual filters 1252a and 1252b disposed over dual wash reservoirs 1254a and 1254b. In an example, each filter may be a hollow core fiber filter having 0.45 um pores and greater than 85 cm$^2$ area. The wash reservoirs 1254a and 1254b, in some examples, may be 50 mL, 100 mL, or over 200 mL in volume. In some embodiments, the wash reservoirs 1254a and 1254b are disposed in a wash cartridge 1256, such as the wash or reagent cartridge 1100 of FIG. 11A.

The processing system of the automated multi-module cell editing instrument, in some implementations, controls actuation of the dual filters 1252a and 1252b in an X (horizontal) and Z (vertical) direction to position the filters 1252a, 1252b in the wash reservoirs 1254a and 1254b. In a particular example, the dual filters 1252a and 1252b may be move in concert along the X axis but have independent Z axis range of motion.

As illustrated, the dual filters 1252a and 1252b of the filtration module 1250 are connected to a slender arm body 1258. In some embodiments, any pumps and valves of the filtration module 1250 may be disposed remotely from the body 1258 (e.g., within a floor of the chassis of the automated multi-module cell editing instrument). In this manner, the filtration module 1250 may replace much bulkier conventional commercial filtration modules.

Further, in some embodiments, the filtration module 1250 is in liquid communication with a waste purge system designed to release liquid waste into a liquid waste storage unit, such as the liquid waste vessel 1208 of FIG. 12A or the liquid waste storage unit 114 of FIG. 1A or 1728 of FIGS. 17A and 17B.

FTEP Module

The FTEP (transformation) module may implement any cell transformation or transfection techniques routinely performed by electroporation. Electroporation is a widely-used method for permeabilization of cell membranes that works by temporarily generating pores in the cell membranes with electrical stimulation. The applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. The cells and material to be electroporated into the cells (collectively "the cell sample") is then placed in a cuvette embedded with two flat electrodes for an electrical discharge. For example, Bio-Rad (Hercules, Calif.) makes the GENE PULSER XCELL™ line of products to electroporate cells in cuvettes. Traditionally, electroporation requires high field strength.

Generally speaking, microfluidic electroporation—using cell suspension volumes of less than approximately 20 ml and as low as 1 µl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit FTEP device configurations; and integrated, automated multi-module cell editing and analysis.

The present disclosure provides electroporation devices, modules, and methods that achieve high efficiency cell electroporation with low toxicity where the electroporation devices and systems can be integrated with other automated cell processing tools. Further, the electroporation device of the disclosure allows for multiplexing where two to many electroporation units are constructed and used in parallel, and allows for particularly easy integration with robotic liquid handling instrumentation. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

During the electroporation process, it is important to use voltage sufficient for achieving electroporation of material into the cells, but not too much voltage as too much voltage will decrease cell viability. For example, to electroporate a suspension of a human cell line, 200 volts is needed for a 0.2 ml sample in a 4 mm-gap cuvette with exponential discharge from a capacitor of about 1000 g. However, if the same 0.2 ml cell suspension is placed in a longer container with 2 cm electrode distance (5 times of cuvette gap distance), the voltage required would be 1000 volts, but a capacitor of only 40 µF (1/25 of 1000 µF) is needed because the electric energy from a capacitor follows the equation of:

$$E=0.5U^2C$$

where E is electric energy, U is voltage and C is capacitance. Therefore a high voltage pulse generator is actually easy to manufacture because it needs a much smaller capacitor to store a similar amount of energy. Similarly, it would not be difficult to generate other wave forms of higher voltages.

The electroporation devices of the disclosure can allow for a high rate of cell transformation in a relatively short amount of time. The rate of cell transformation is dependent on the cell type and the number of cells being transformed. For example, for $E.\ coli$, the electroporation devices can provide a cell transformation rate of $10^3$ to $10^{12}$ cells per second, $10^4$ to $10^{10}$ per second, $10^5$ to $10^9$ per second, or $10^6$ to $10^8$ per second. Typically, $10^8$ yeast cells may be transformed per minute, and $10^{10}$-$10^{12}$ bacterial cells may be transformed per minute. The electroporation devices also allow transformation of batches of cells ranging from 1 cell to $10^{12}$ cells in a single transformation procedure using parallel devices.

Figure 4A:
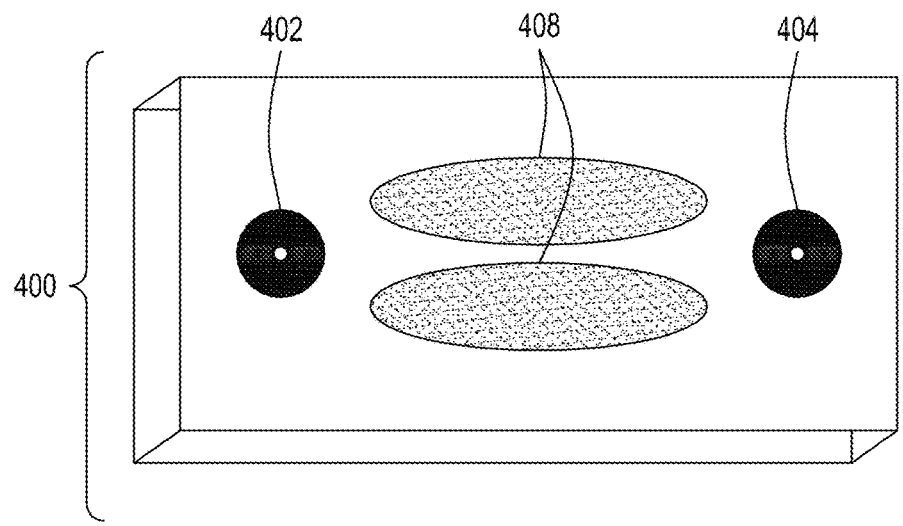
FIG. 4A is an illustration of a top view of one embodiment of the FTEP devices of the disclosure.
Figure 4B:
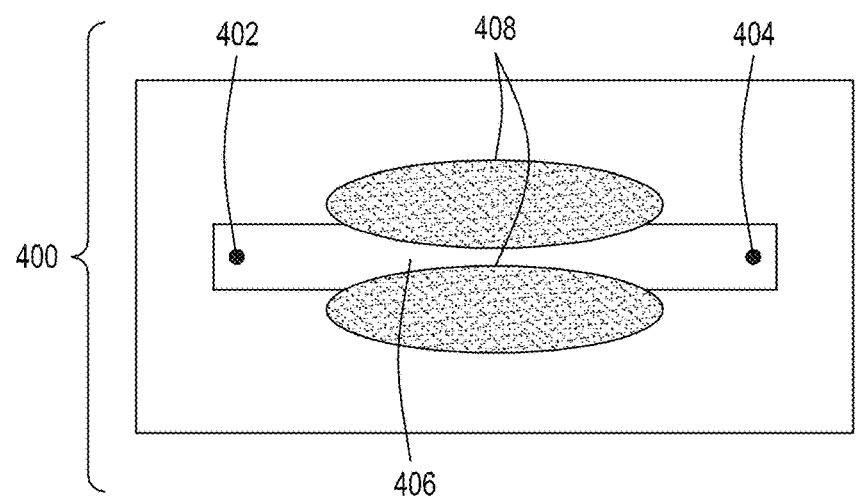
FIG. 4B is an illustration of the top view of a cross section of the embodiment of the device shown in FIG. 4A.
Figure 4C:
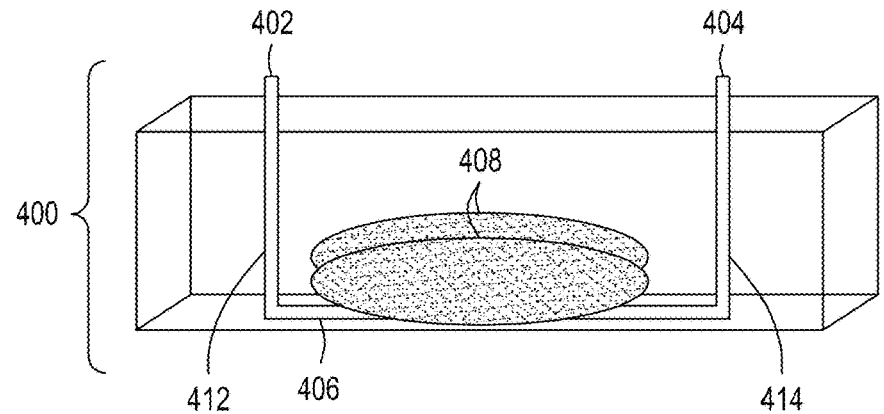
FIG. 4C is an illustration of a side view of a cross section of the embodiment of the device shown in FIGS. 4A and 4B.

One embodiment of the FTEP device described herein is illustrated in FIGS. 4A-4C. FIG. 4A shows a planar top view of an FTEP device 400 having an inlet 402 for introducing a fluid containing cells and exogenous material to be delivered to the cells into the FTEP device 400 and an outlet 404 for removing the transformed cells following electroporation. Oval electrodes 408 are positioned so as to define a center portion of the flow channel (not shown) where the channel narrows based on the curvature of the electrodes. FIG. 4B shows a cutaway view from the top of the device 400, with the inlet 402, outlet 404, and electrodes 408 positioned with respect to a flow channel 406. Note that the electrodes 408 define a narrowing of flow channel 406. FIG. 4C shows a side cutaway view of the device 400 with the inlet 402 and inlet channel 412, and outlet 404 and outlet channel 414. The electrodes 408 are oval in shape and positioned so that they define a narrowed portion of the flow channel 406.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes (and, e.g., bottom sealing film) later added to form the FTEP unit (see, FIG. 10F (i)). Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture. (See, e.g., FIG. 9A.)

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 408 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

Additionally, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, in the embodiments shown in FIGS. 4A-4I, 5A-5H, 6, and 7A-7E where the electrodes form a portion of the wall of the flow channel where the flow channel decreases in width, the distance between the electrodes in the flow channel may be between 10 μm and 5 mm, or between 25 μm and 3 mm, or between 50 μm and 2 mm, or between 75 μm and 1 mm. In other embodiments such as those depicted in FIGS. 8A-8U, 9A-9C, and 10A-10D where the electrodes are positioned on either end of the channel narrowing, the distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is typically wide enough so that at least two cells can fit in the narrowed portion side-by-side. For example, a typical bacterial cell is 1 μm in diameter; thus, the narrowed portion of the flow channel of the FTEP device used to transform such bacterial cells will be at least 2 μm wide. In another example, if a mammalian cell is approximately 50 μm in diameter, the narrowed portion of the flow channel of the FTEP device used to transform such mammalian cells will be at least 100 μm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 μL to 10 mL, or from 500 μL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 μm are preferred. In another embodiment of the invention, the flow-through electroporation device comprises at least one additional electrode which applies a ground potential to the FTEP device.

The electrodes are configured to deliver 1-25 Kv/cm, or 5-20 Kv/cm, or 10-20 Kv/cm. The further apart the electrodes are, the more voltage needs to be supplied; in addition, the voltage delivered of course depends on the types of cells being porated, the medium in which the cells are suspended, the size of the electroporation channel, and the length and diameter of the electrodes. There are many different pulse forms that may be employed with the FTEP device, including exponential decay waves, square or rectangular waves, arbitrary wave forms, or a selected combination of wave forms. One type of common pulse form is the exponential decay wave, typically made by discharging a loaded capacitor to the cell sample. The exponential decay wave can be made less steep by linking an inductor to the cell sample so that the initial peak current can be attenuated. When multiple waveforms in a specified sequence are used, they can be in the same direction (direct current) or different directions (alternating current). Using alternating current can be beneficial in that two topical surfaces of a cell instead of just one can be used for molecular transport, and alternating current can prevent electrolysis. The pulse generator can be controlled by a digital or analog panel. In some embodiments, square wave forms are preferred, and in other embodiments, an initial wave spike before the square wave is preferred.

The FTEP device may be configured to electroporate cell sample volumes between 1 μl to 5 ml, 10 μl to 2 ml, 25 μl to 1 ml, or 50 μl to 750 μl. The medium or buffer used to suspend the cells and material (reagent) to be electroporated into the cells for the electroporation process may be any suitable medium or buffer, such as MEM, DMEM, IMDM, RPMI, Hanks', PBS and Ringer's solution, where the media may be provided in a reagent cartridge as part of a kit. Further, because the cells must be made electrocompetent prior to transformation or transfection, the buffer also may comprise glycerol or sorbitol, and may also comprise a surfactant. For electroporation of most eukaryotic cells the medium or buffer usually contains salts to maintain a proper osmotic pressure. The salts in the medium or buffer also render the medium conductive. For electroporation of very small prokaryotic cells such as bacteria, sometimes water or 10% glycerol is used as a low conductance medium to allow a very high electric field strength. In that case, the charged molecules to be delivered still render water-based medium more conductive than the lipid-based cell membranes and the medium may still be roughly considered as conductive particularly in comparison to cell membranes.

The compound to be electroporated into the cells can be any compound known in the art to be useful for electroporation, such as nucleic acids, oligonucleotides, polynucleotides, DNA, RNA, peptides, proteins and small molecules like hormones, cytokines, chemokines, drugs, or drug precursors. In the nucleic acid-guided nuclease editing embodiments, the compounds electroporated into the cells are nucleic acids and proteins.

Figure 4D:
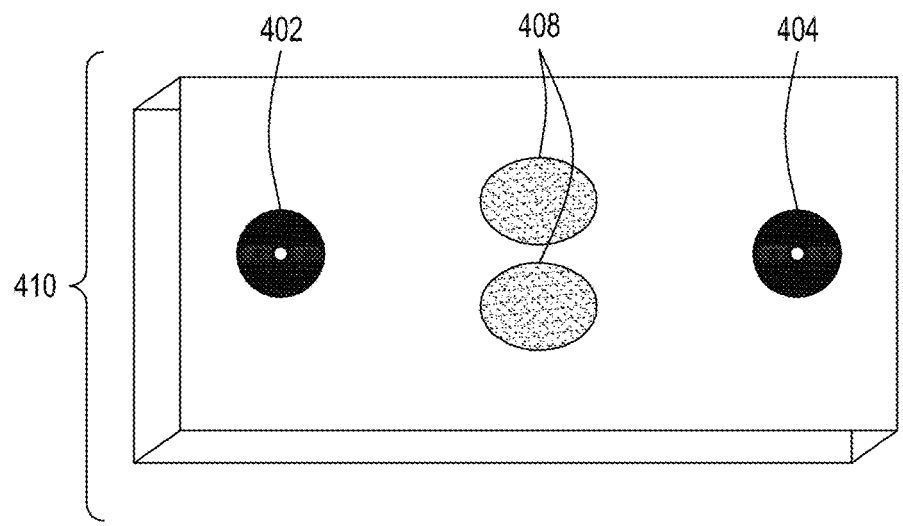
FIG. 4D is an illustration of a top view of another embodiment of the FTEP devices of the disclosure.
Figure 4E:
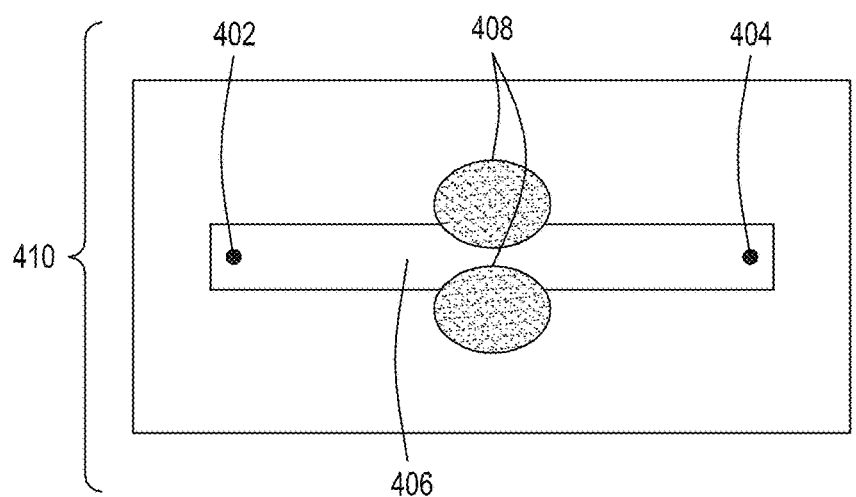
FIG. 4E is an illustration of the top view of a cross section of the embodiment of the device shown in FIG. 4D.
Figure 4F:
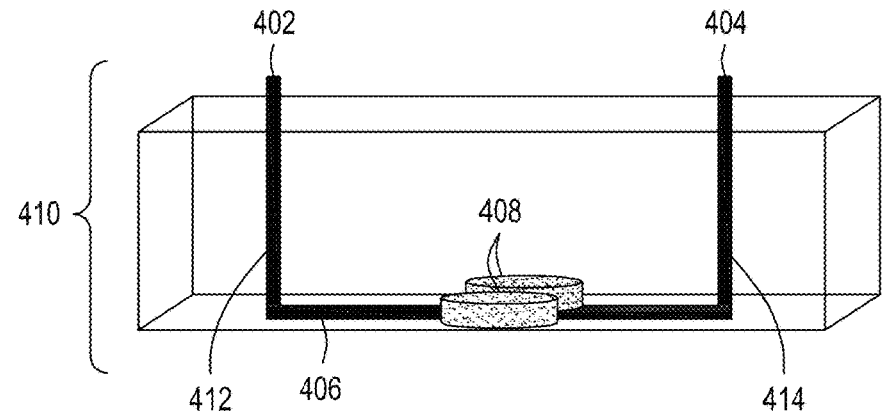
FIG. 4F is an illustration of a side view of a cross section of the embodiment of the device shown in FIGS. 4D and 4E.

Another embodiment of the FTEP devices described herein is illustrated in FIGS. 4D-4F. FIG. 4D shows a top planar view of an FTEP device 410 having an inlet 402 for introducing a fluid containing cells and exogenous material into the FTEP device 410 and an outlet 404 for removing the transformed cells following electroporation. Cylindrical electrodes 408 are positioned so as to define a center portion of the flow channel (not shown) where the flow channel narrows as a result of the curvature of the electrodes. FIG. 4E shows a cutaway view from the top of the FTEP device 410, with the inlet 402, outlet 404, and electrodes 408 positioned with respect to a flow channel 406. Again, note that the electrodes 408 define a narrowed portion or region of flow channel 406. FIG. 4F shows a side cutaway view of FTEP device 410 with the inlet 402 and inlet channel 412, and outlet 404 and outlet channel 414. The electrodes 408 are cylindrical and positioned in the flow channel 406 defining a narrowed portion of the flow channel 406.

Figure 4G:
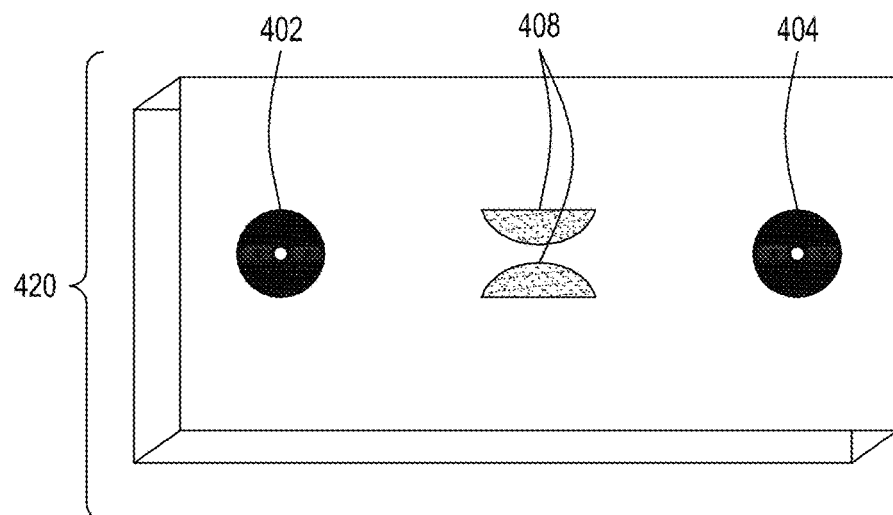
FIG. 4G is an illustration of a top view of yet another embodiment of the FTEP devices of the disclosure.
Figure 4H:
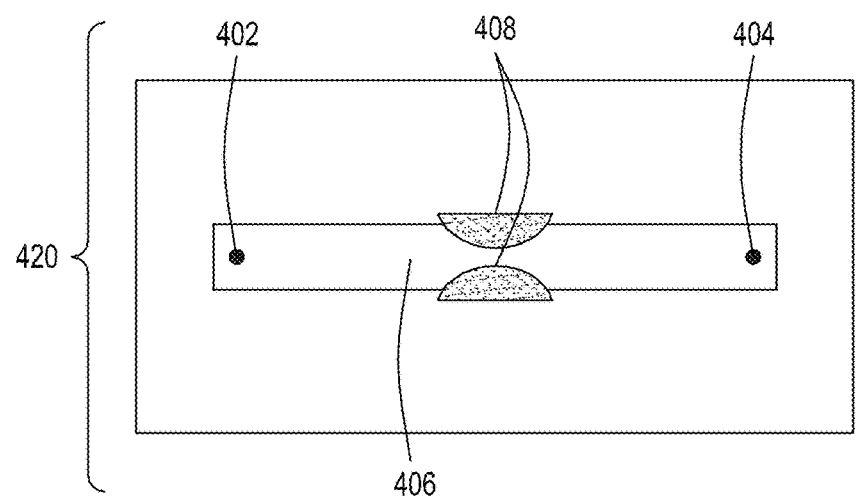
FIG. 4H is an illustration of the top view of a cross section of the embodiment of the device shown in FIG. 4G.
Figure 4I:
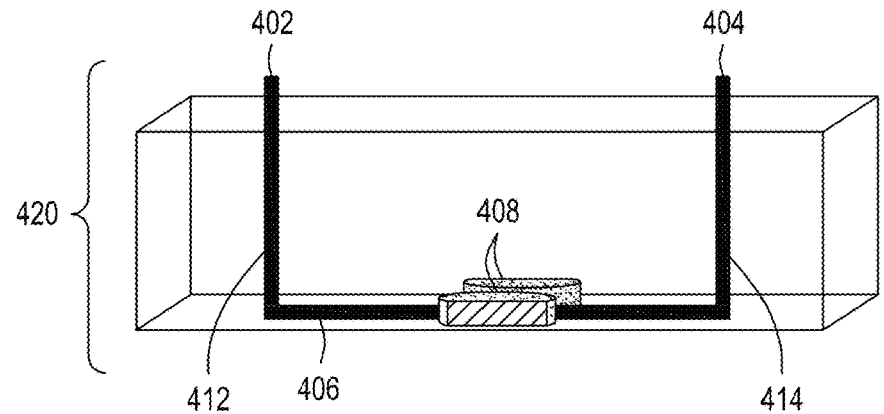
FIG. 4I is an illustration of a side view of a cross section of the embodiment of the device shown in FIGS. 4G and 4H.

Yet another embodiment of the FTEP devices of the disclosure is illustrated in FIGS. 4G-4I. FIG. 4G shows a top planar view of an FTEP device 420 having an inlet 402 for introducing a fluid containing cells and exogenous material into FTEP device 420, and an outlet 404 for removing the transformed cells following electroporation. The semi-cylindrical electrodes 408 are positioned so as to define a narrowed portion of a flow channel (not shown) where the channel narrows from both ends based on the curvature of the electrodes. FIG. 4H shows a cutaway view from the top of FTEP device 420, with the inlet 402, outlet 404, and electrodes 408 positioned with respect to a flow channel 406. FIG. 4I shows a side cutaway view of FTEP device 420 with inlet 402 and inlet channel 412, and outlet 404 and outlet channel 414. The semi-cylindrical electrodes 408 are positioned in the flow channel 406 so that they define a narrowed portion of the flow channel 406. It should be noted that the devices depicted in FIGS. 4A-4I show the electrodes positioned substantially mid-way along the flow channel; however, in other aspects of the devices, the electrodes may be positioned in narrowed regions of the flow channel more toward the inlet of the FTEP device or more toward the outlet of the FTEP device.

Figure 5A:
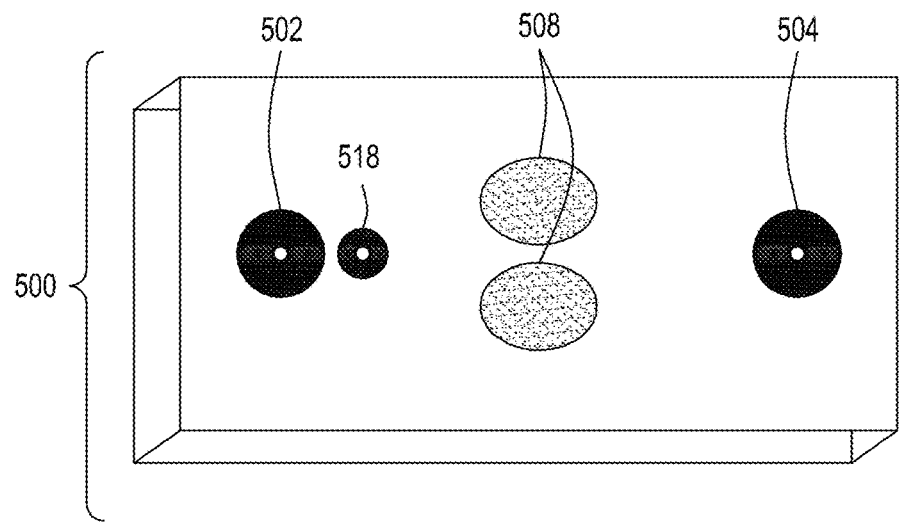
FIG. 5A is an illustration of the top view of a cross section of a further embodiment of the FTEP devices described herein with separate inlets for the cells and the exogenous materials.
Figure 5B:
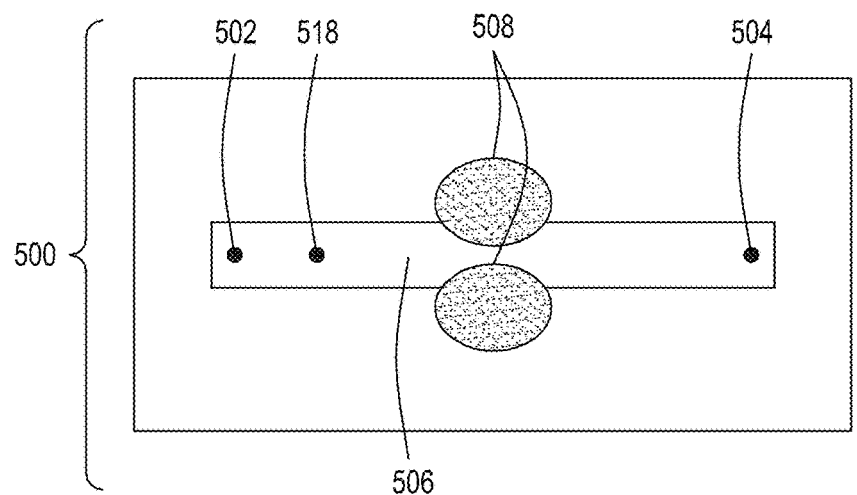
FIG. 5B is an illustration of the top view of a cross section of the embodiment of the device shown in FIG. 5A.

FIGS. 5A-5E show embodiments of the FTEP devices of the disclosure with separate inlets for the cells and the exogenous material. FIG. 5A shows a top planar view of an FTEP device 500 having a first inlet 502 for introducing a fluid containing cells into FTEP device 500; a second inlet 518 for introducing a fluid containing exogenous materials to be electroporated into the cells into FTEP device 500; electrodes 508; and an outlet 504 for removing the transformed cells following electroporation. Although these embodiments are illustrated with cylindrical electrodes, as shown in FIG. 5A, other shaped electrodes with a curved edge—e.g., oval, semi-cylindrical, and the like as shown in relation to FIGS. 4A-4I—may be used to define the flow channel. FIG. 5B shows a cutaway view from the top of FTEP device 500, with the first inlet 502, second inlet 518, outlet 504, and electrodes 508 positioned with respect to the flow channel 506.

Figure 5C:
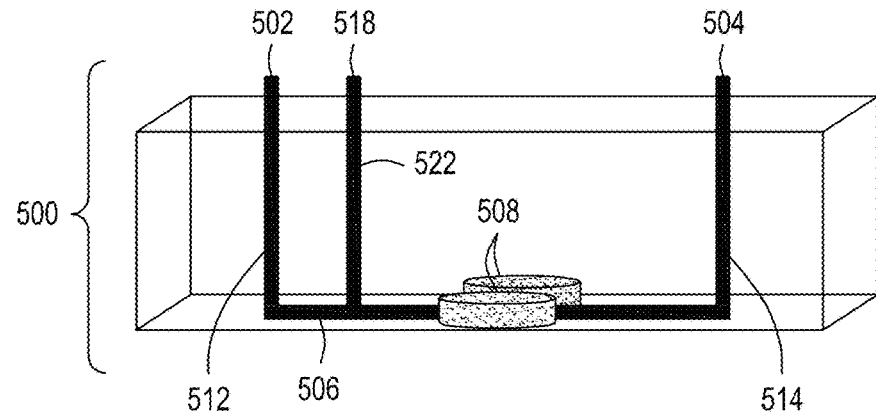
FIG. 5C is an illustration of a side view of a cross section of the embodiment of the device shown in FIG. 5B.
Figure 5D:
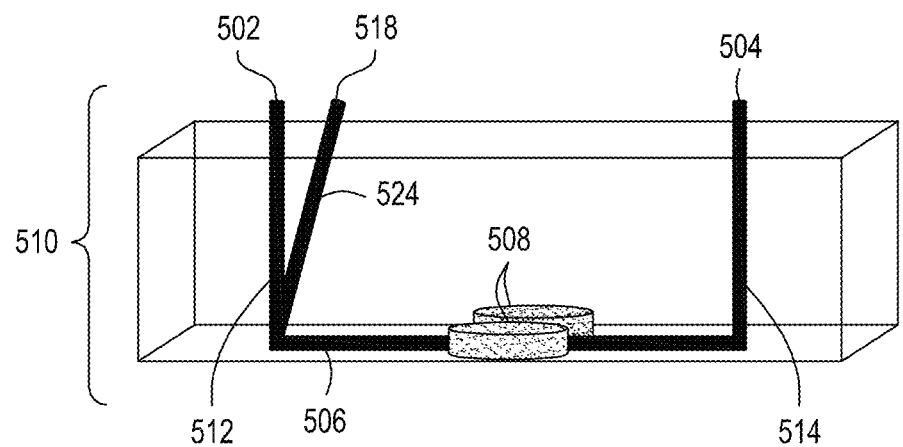
FIG. 5D is an illustration of a side view of a cross section of a variation on the embodiment of the device shown in FIGS. 5A and 5B.
Figure 5E:
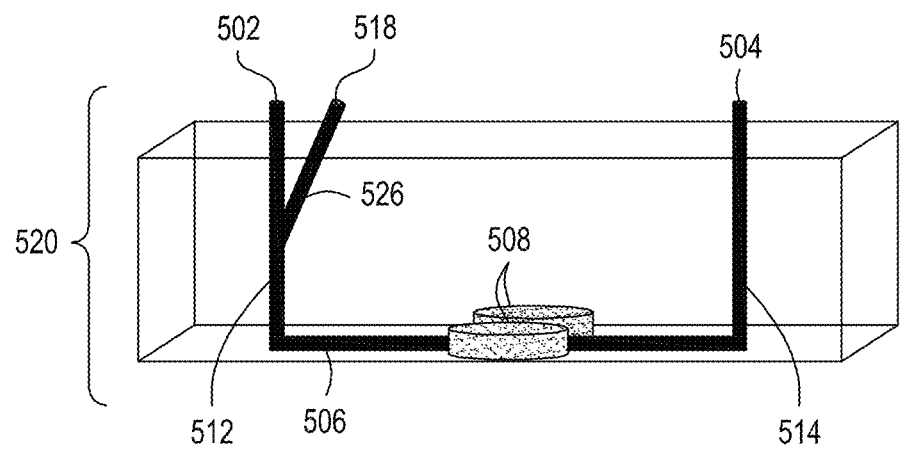
FIG. 5E is an illustration of a side view of a cross section of another variation on the embodiment of the device shown in FIGS. 5C and 5D.

FIG. 5C shows a cutaway view of the embodiment of FTEP device 500 with the first inlet 502 and second inlet 518 positioned as shown in FIGS. 5A and 5B. In FIG. 5C, the first inlet channel 512 and second inlet channel 522 meet independently with flow channel 506, and the liquid (cells and material to be porated or delivered to the cells) flows through the flow channel 506 to the outlet channel 514 and outlet 504 where the transformed cells are removed from the FTEP device. The electrodes 508 are positioned in the flow channel 506 so that they define a narrowed portion of the flow channel 506. FIG. 5D shows a side cutaway view of a variation 510 on the embodiment of the FTEP device 500 depicted in FIGS. 5A and 5B. Here, the first inlet channel 512 and second inlet channel 524 intersect with the flow channel 506 at a three-way junction, and the liquid (cells and material to be porated or delivered to the cells) flows through the flow channel 506 to the outlet channel 514 and outlet 504 where the transformed cells are removed from the FTEP device. The electrodes 508 are positioned in the flow channel 506 defining a narrowed portion of the flow channel 506. FIG. 5E shows a first side cutaway view 520 of a yet another variation of the FTEP device 500 shown in FIGS. 5A and 5B. Here, the first inlet channel 512 and second inlet channel 526 intersect at a junction where the cells and exogenous materials mix prior to introduction of the combined fluids to the flow channel 506. The fluids flow through the flow channel 506 to the outlet channel 514 and outlet 504 where the transformed cells are removed from the FTEP device. Electrodes 508 are positioned in the flow channel 506 so that they define a narrowed portion of the flow channel 506.

Figure 5F:
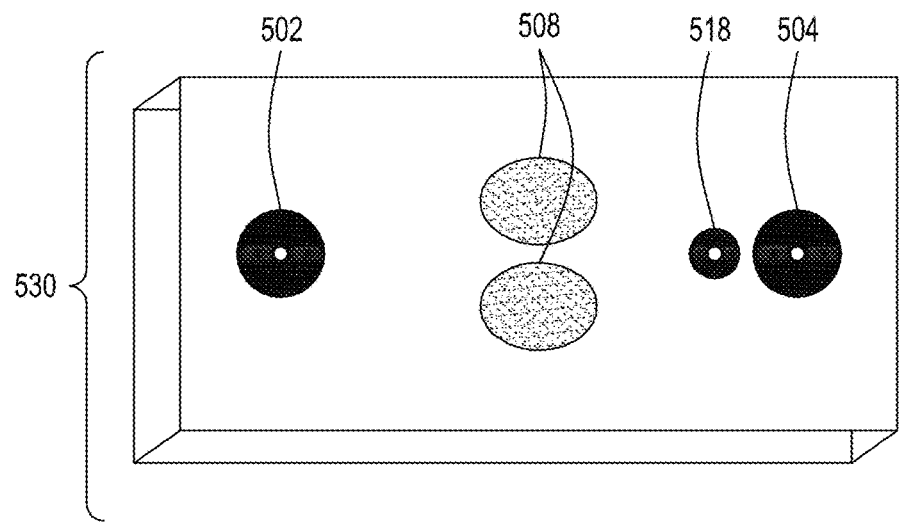
FIG. 5F is an illustration of the top view of a cross section of yet another embodiment of the FTEP devices of the disclosure where the FTEP comprises two separate inlets for the cells and the exogenous materials.
Figure 5G:
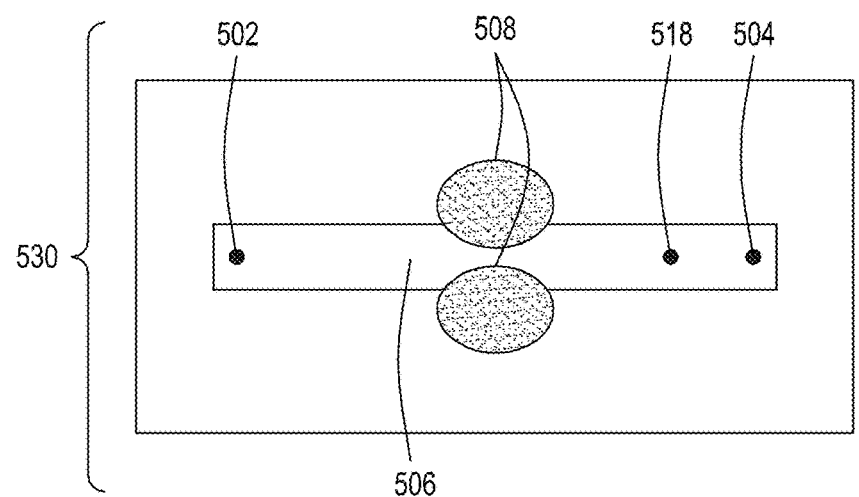
FIG. 5G is an illustration of a top view of a cross section of the embodiment of the device shown in FIG. 5F.
Figure 5H:
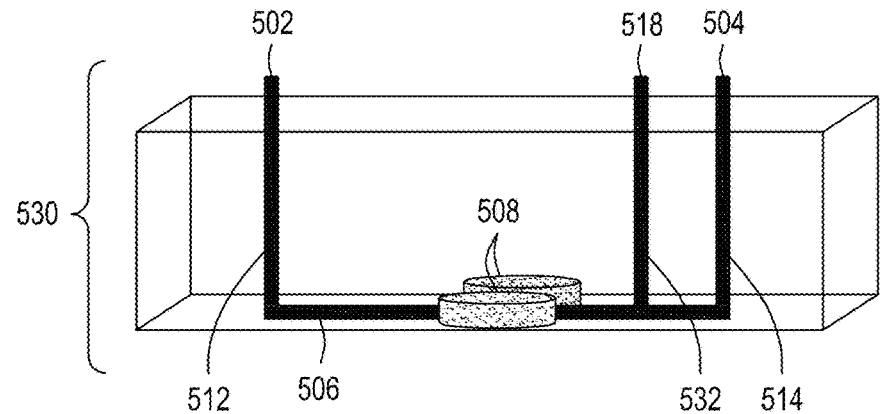
FIG. 5H is an illustration of a side view of a cross section of the embodiment of the device shown in FIGS. 5F and 5G.

FIGS. 5F-5H show another embodiment of the FTEP devices of the disclosure with separate inlets for the cells and the exogenous material. FIG. 5F shows a top planar view of an electroporation device 530 having a first inlet 502 for introducing a fluid containing cells, a second outlet 518 for introducing exogenous materials to be electroporated into the cells, and an outlet 504 for removing the transformed cells following electroporation. The electrodes 508 are positioned between the first inlet 502 where the cells are introduced into the FTEP device and the second inlet 518 where the exogenous materials are introduced into the FTEP device. FIG. 5G shows a cutaway view from the top of the FTEP device 530, with the first inlet 502, second inlet 518, and outlet 504, and with electrodes 508 positioned between the first inlet channel 502 and the second inlet channel 518, where the electrodes 508 form a narrowed portion of flow channel 506. FIG. 5H shows a side cutaway view of FTEP device 530 with the first inlet 502 where the cells are introduced into the FTEP device and first inlet channel 512, the second inlet 518 where the exogenous materials are introduced into the FTEP device and second inlet channel 532, and an outlet channel 514 and outlet 504 where the transformed cells are removed from the FTEP device. The electrodes 508 are positioned in the flow channel 506 defining a narrow portion of the flow channel 506 and are positioned between the first inlet channel 512 and the second inlet channel 532 such that the material to be introduced into the cells is added to the fluid comprising the cells after the cells have been electroporated.

Figure 6:
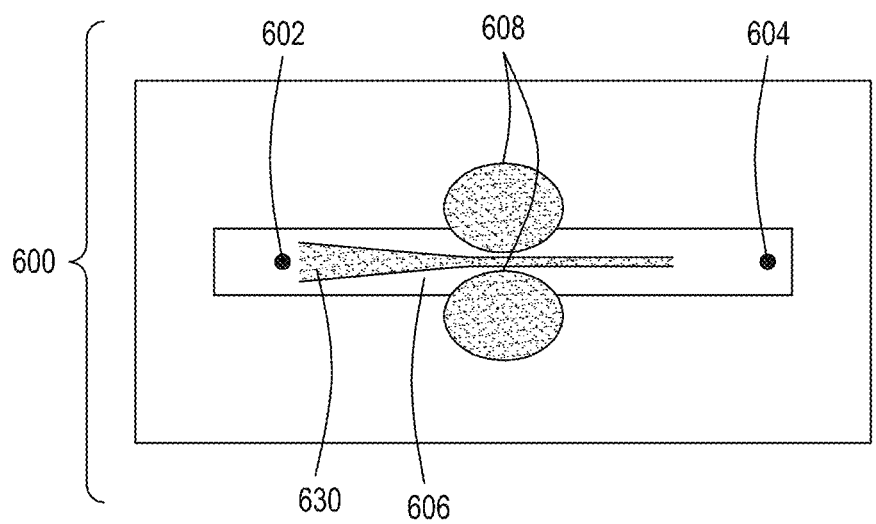
FIG. 6 is an illustration of a top view of a cross section of yet an additional embodiment of the FTEP devices of the disclosure, here including flow focusing of fluid from the input channels.

FIG. 6 illustrates an FTEP device in which the flow of the fluid introduced into the flow channel from the input channel(s) is focused, e.g., using an immiscible fluid such as an oil or a stream of air to narrow the stream of the fluid containing the cells and the exogenous materials as it passes by the electrodes. FIG. 6 shows a cutaway view from the top of the FTEP device 600, with the inlet 602, outlet 604, and the electrodes 608 positioned between the first inlet channel 602 and outlet 604. The flow focusing 630 is effected by an immiscible fluid, where the electrodes 608 form a narrowed portion of flow channel 606. (For methods and inlet configurations relevant to flow focusing, see, e.g., US Pub. Nol. 2010/0184928 to Kumacheva.)

Figure 7A:
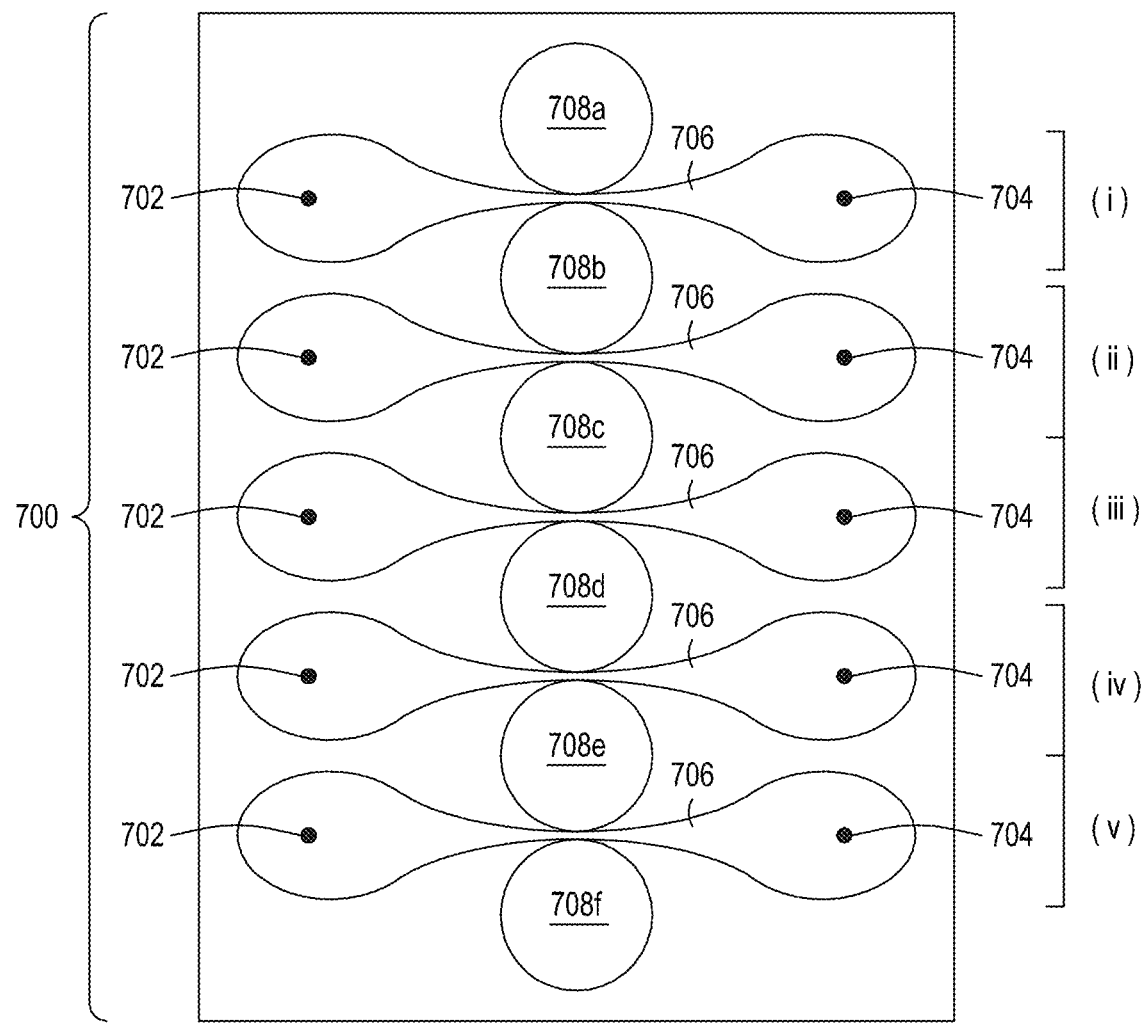
FIG. 7A is an illustration of a top view of a cross section of a first multiplexed embodiment of the FTEP devices of the disclosure.
Figure 7B:
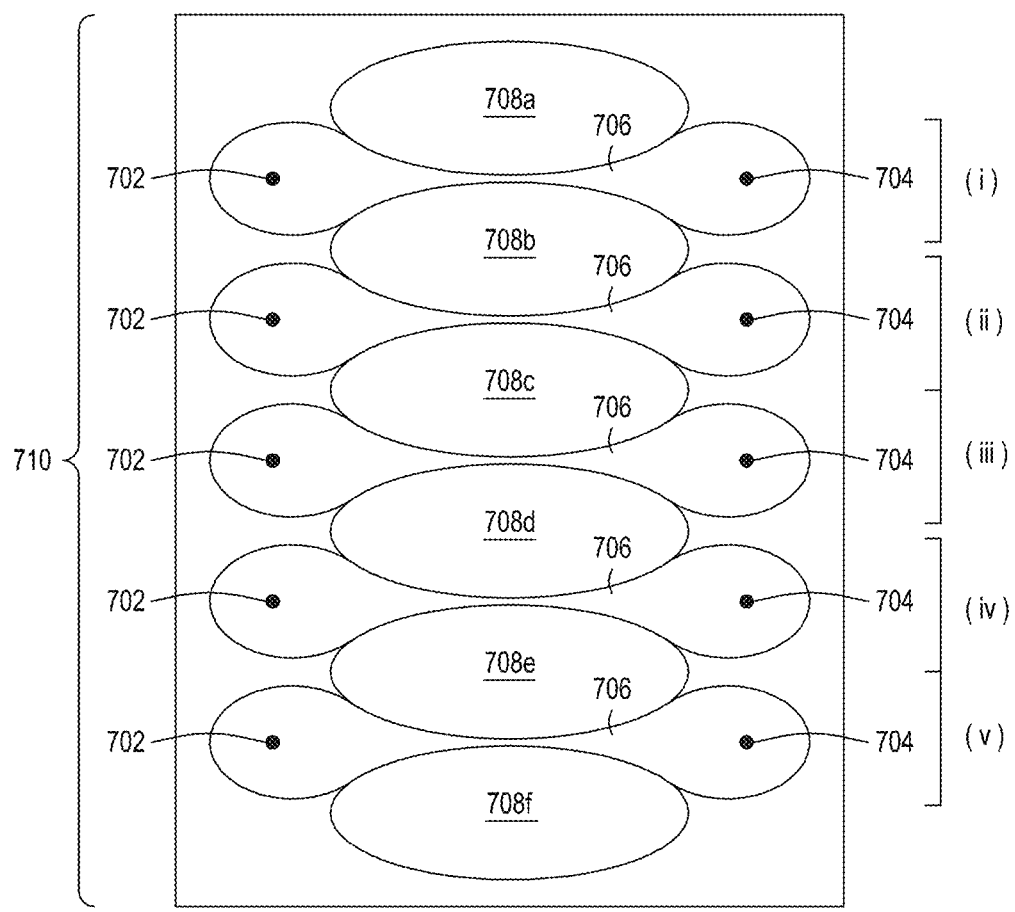
FIG. 7B is an illustration of a top view of a cross section of a second multiplexed embodiment of the devices of the disclosure.

Multiplexed embodiments of exemplary FTEP devices are illustrated in FIGS. 7A-7E. FIG. 7A illustrates a top view of a cross section of a first multiplexed aspect of the FTEP devices of the disclosure. The FTEP device in FIG. 7A is a multiplexed FTEP device 700 in which parallel flow channels 706 for each FTEP unit are defined in part by shared cylindrical electrodes 708a-708f forming devices (i), (ii), (iii), (iv), and (v). Each flow channel 706 has an inlet 702 for introducing different sets of cells and/or exogenous materials into the FTEP units and an outlet 704 for removing the transformed cells from the FTEP units. Adjacent units share electrodes, where the electrodes alternate charge, e.g., +/−/+/−/+ (that is, if electrode 708a is +, electrode 708b is −, electrode 708c is +, electrode 708d is −, and so on). FIG. 7B is an illustration of a top view of a cross section of a second multiplexed embodiment of the FTEP devices 710 of the disclosure. This is a multiplexed device 710 in which parallel flow channels 706 are defined in part by shared oval electrodes 708a-708f. Each flow channel 706 has an inlet 702 for introducing different sets of cells and/or exogenous materials into the flow channels 706, and an outlet for removing the transformed cells from FTEP units (i), (ii), (iii), (iv), and (v). Again, adjacent devices share electrodes, where the electrodes alternate charge, e.g., +/−/+/−/+.

Figure 7C:
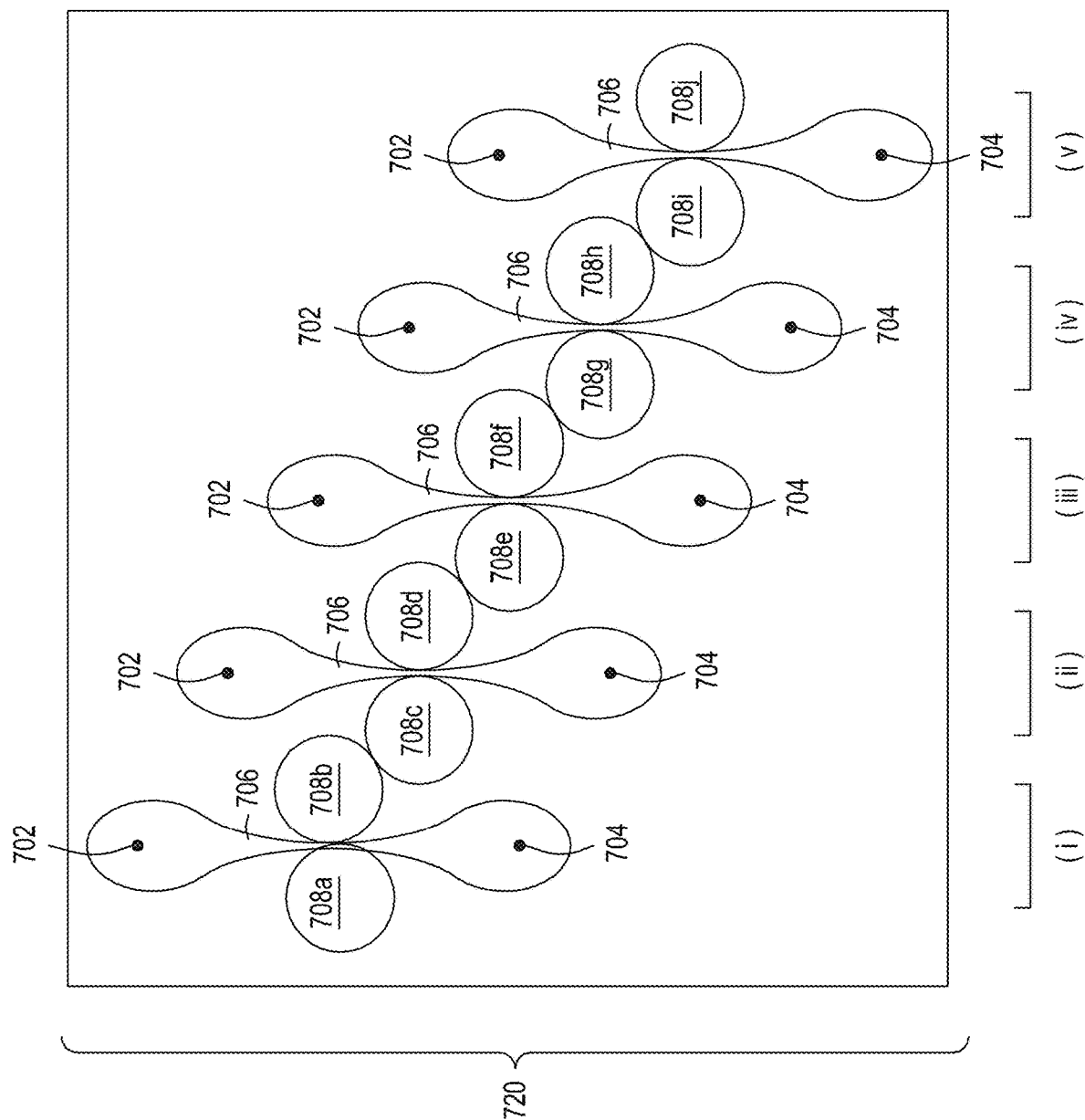
FIG. 7C is an illustration of a top view of a cross section of a third multiplexed embodiment of the devices of the disclosure.
Figure 7D:
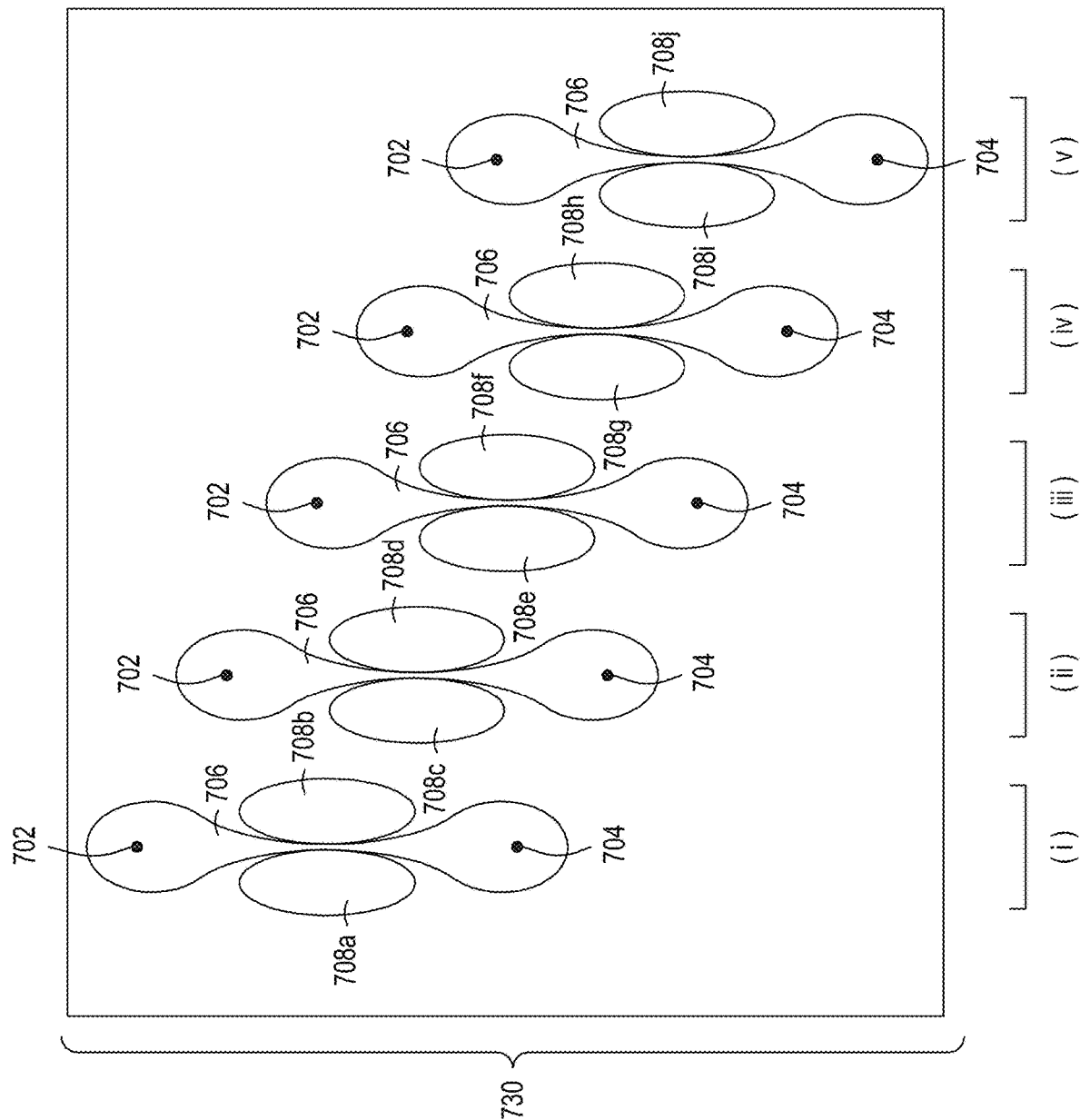
FIG. 7D is an illustration of a top view of a cross section of a fourth multiplexed embodiment of the devices of the disclosure.
Figure 7E:
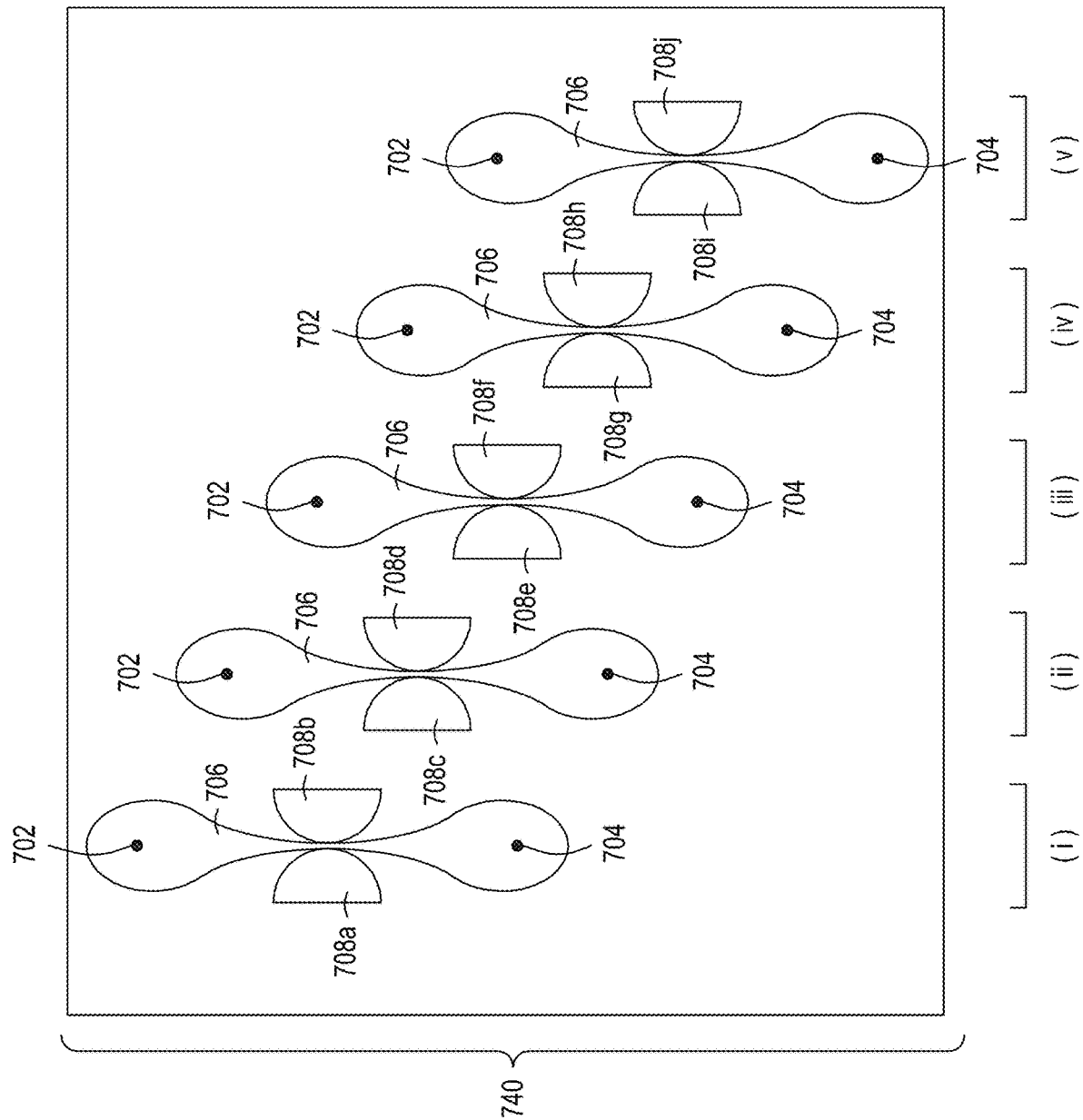
FIG. 7E is an illustration of a top view of a cross section of a fifth multiplexed embodiment of the devices of the disclosure.

FIG. 7C is an illustration of a top view of a cross section of a third multiplexed embodiment of the FTEP devices of the disclosure. In this exemplary multiplexed FTEP device 720, the individual FTEP units are staggered. The parallel flow channels 706 are defined in part by individual cylindrical electrodes 708a-708j that are not shared as shown in FIGS. 7A and 7B. Each flow channel 706 has its own pair of electrodes 708, an inlet 702 for introducing different sets of cells and/or exogenous materials into the FTEP device, and an outlet for removing transformed cells from the FTEP units (i), (ii), (iii), (iv), and (v). FIG. 7D is an illustration of a top view of a cross section of another exemplary multiplexed FTEP device. In this multiplexed FTEP device 730, staggered, parallel flow channels 706 are defined in part by individual oval electrodes 708a-708j. Each flow channel 706 has its own un-shared pair of electrodes 708 (e.g., 708a/708b, 708c/708d, 708e/708f, 708g/708h, and 708i/708j), an inlet 702 for introducing different sets of cells and/or exogenous materials into the FTEP units, and an outlet 704 for removing transformed cells from the FTEP units. FIG. 7E is an illustration of a top view of a cross section of another exemplary multiplexed FTEP device. In this exemplary multiplexed device 740, staggered, parallel flow channels 706 are defined in part by individual half-cylindrical electrodes 708a-708j. Each flow channel 706 has its own pair of electrodes 708, a separate inlet 702 for introducing different sets of cells and/or exogenous materials into the FTEP unit, and an outlet 704 for removing the transformed cells from the FTEP unit.

Figure 8A:
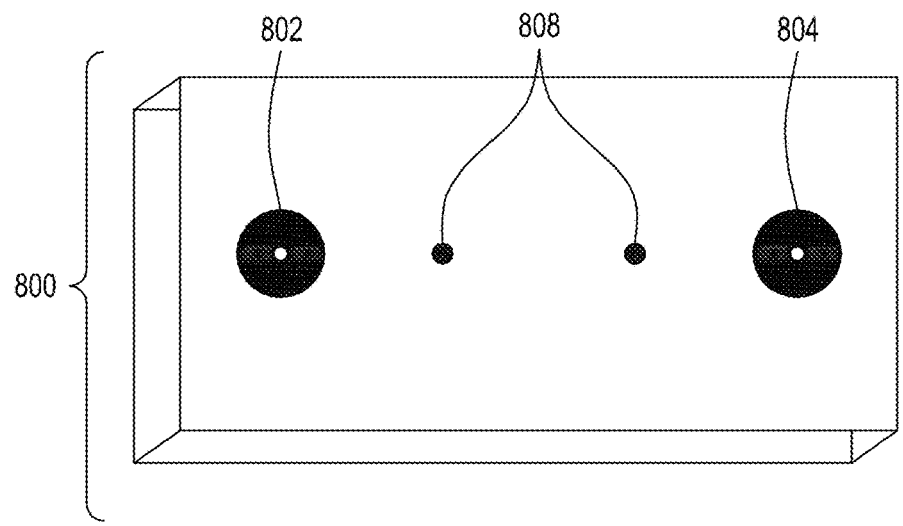
FIG. 8A is an illustration of a top view of yet another embodiment of the FTEP devices of the disclosure where the electrodes are placed on either end of the narrowed region of the flow channel rather than on either side and defining the narrowed region of the flow channel.
Figure 8B:
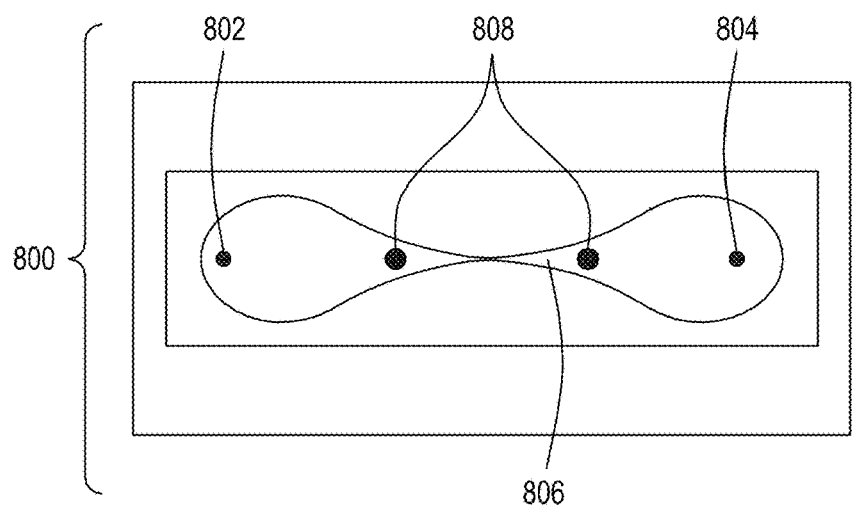
FIG. 8B is an illustration of the top view of a cross section of the embodiment of the device shown in FIG. 8A.
Figure 8C:
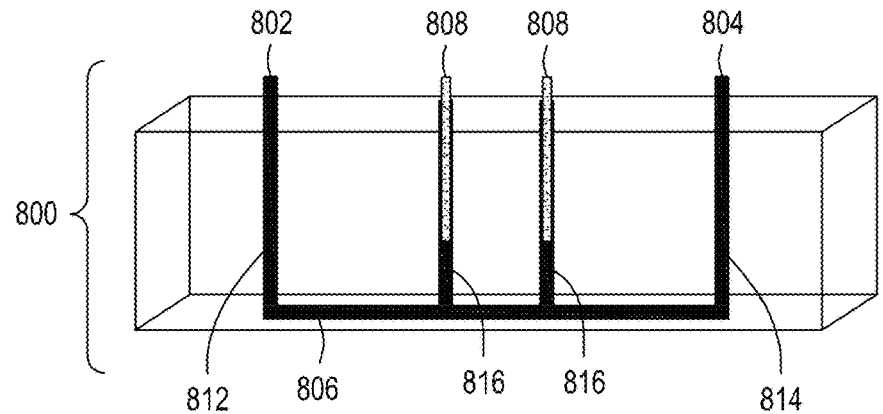
FIG. 8C is an illustration of a side view of a cross section of the embodiment of the device shown in FIGS. 8A and 8B.
Figure 8D:
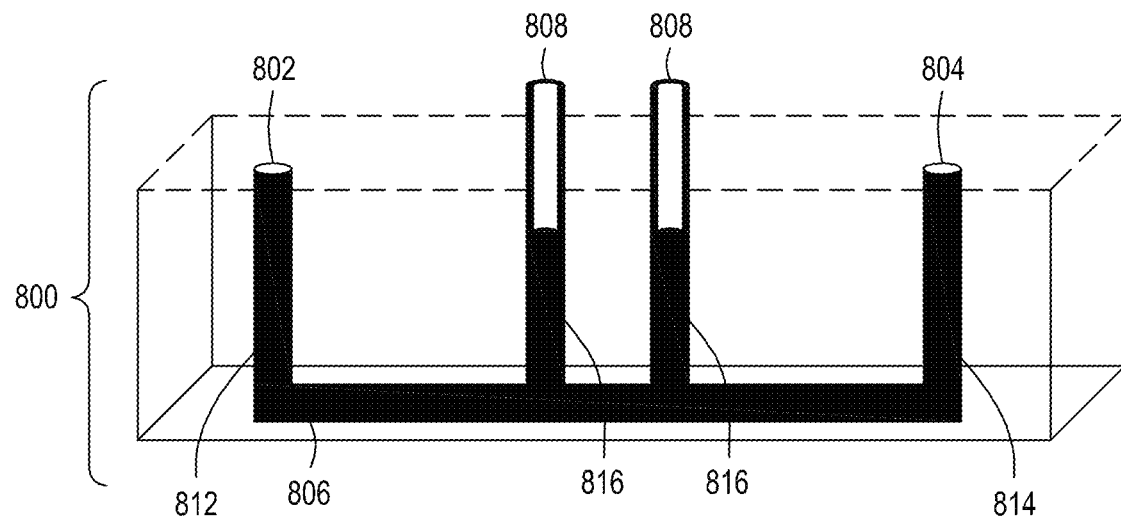
FIG. 8D is an illustration of a side view of a cross section of the bottom half of the embodiment of the devices shown in FIGS. 8A, 8B and 8C.
Figure 8E:
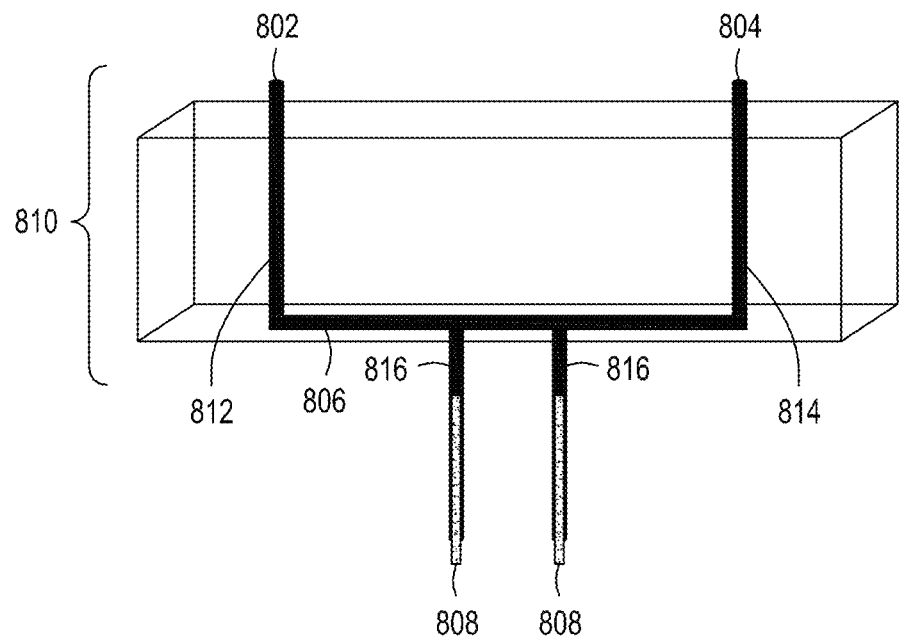
FIG. 8E is an illustration of a side view of a cross section of a variation of the embodiment of the devices shown in FIGS. 8A-8D where here the electrodes are positioned on the bottom of the FTEP device, on the opposite surface from the inlet and outlet.
Figure 8F:
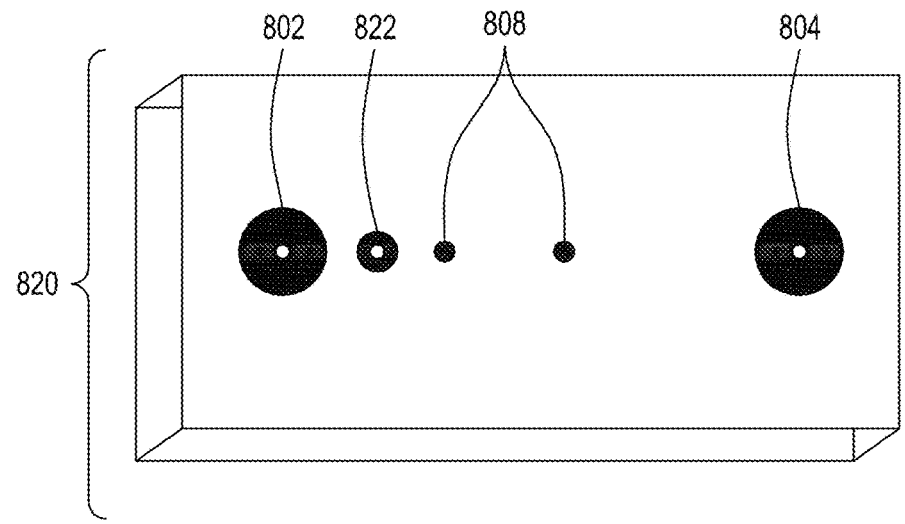
FIG. 8F is an illustration of a top view of yet another embodiment of the FTEP devices of the disclosure.
Figure 8G:
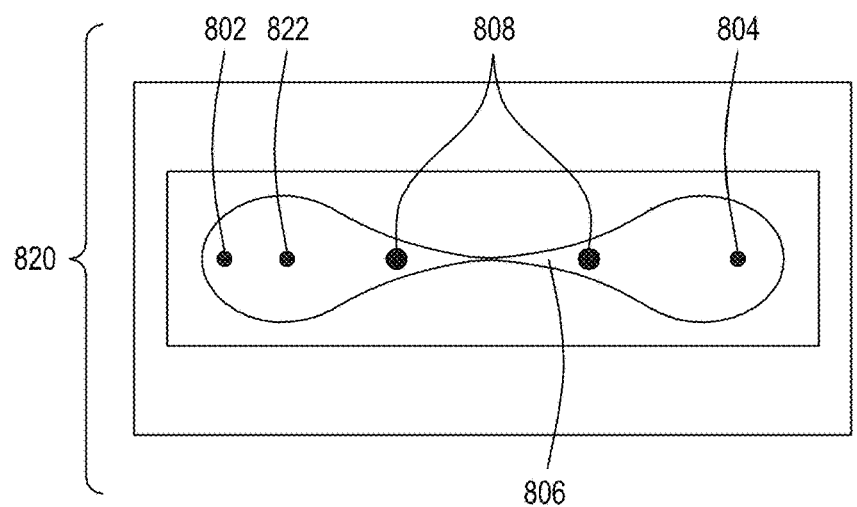
FIG. 8G an illustration of a top view of a cross section of the embodiment of the device shown in FIG. 8F.
Figure 8H:
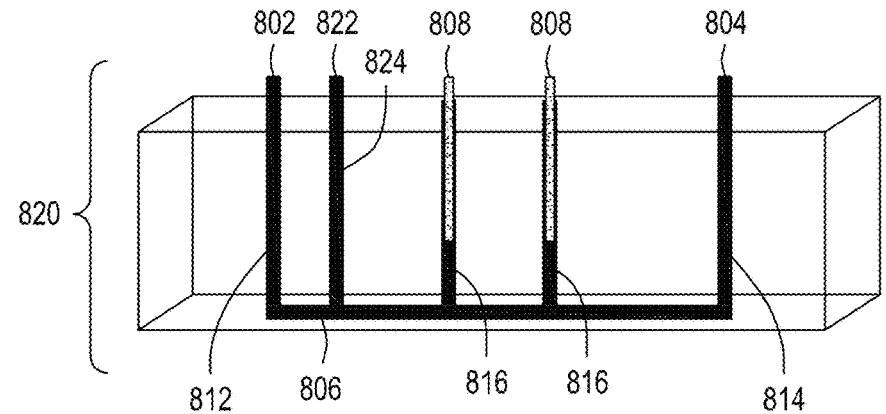
FIG. 8H is an illustration of a side view of a cross section of one variation of the embodiment of the device shown in FIGS. 8F and 8G.
Figure 8I:
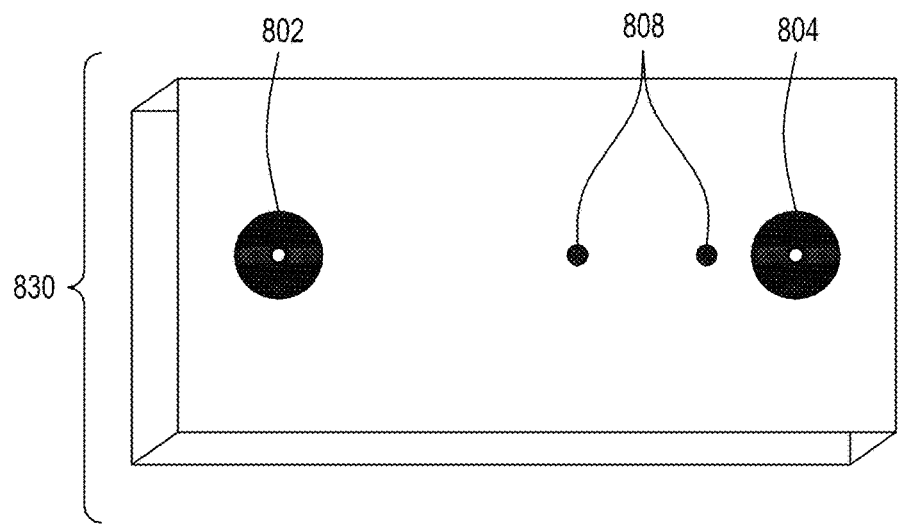
FIG. 8I is an illustration of a top view of an embodiment of the FTEP devices of the disclosure.
Figure 8J:
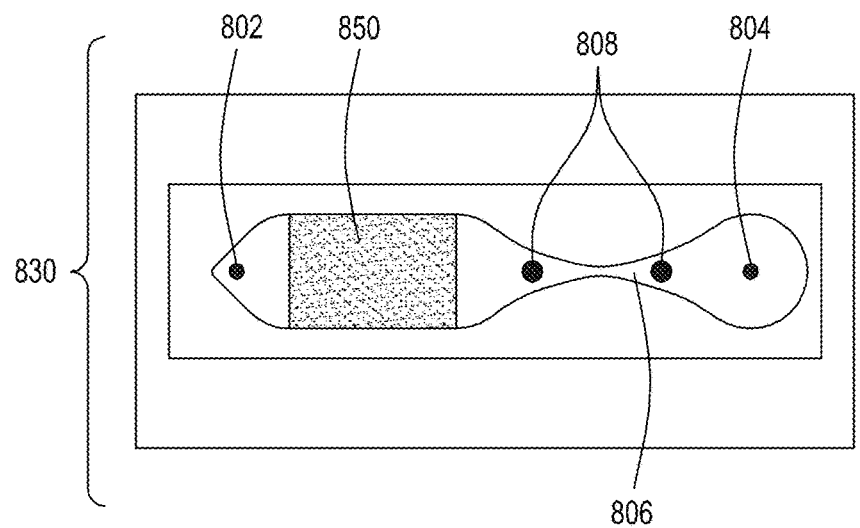
FIG. 8J is an illustration of the top view of a cross section of the embodiment of the device shown in FIG. 8I where in this embodiment the FTEP device comprises a filter.
Figure 8K:
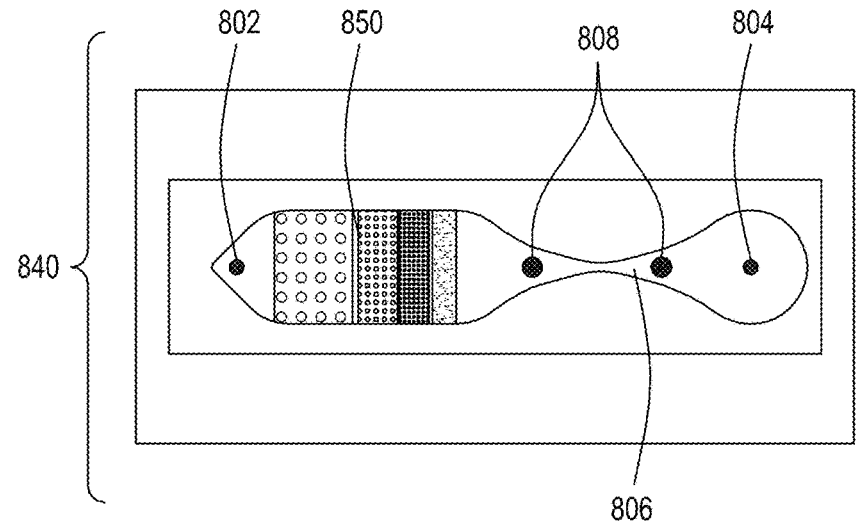
FIG. 8K is an illustration of the top view of a cross section of a variation of the embodiment of the device shown in FIGS. 8I and 8J.
Figure 8L:
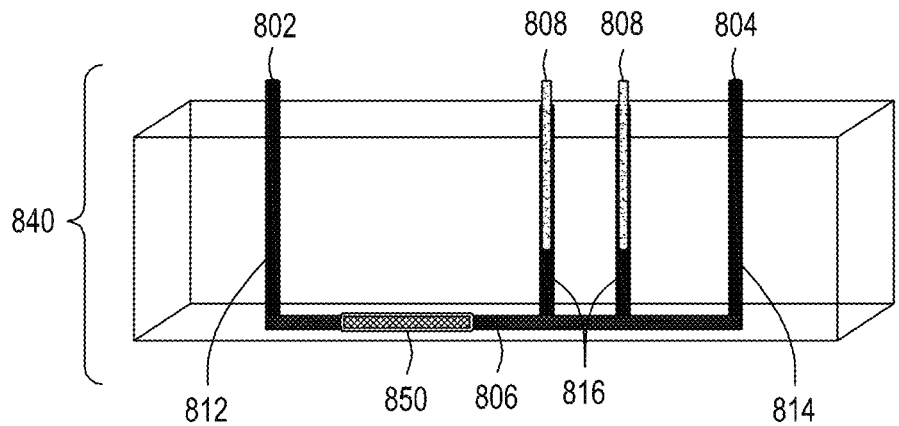
FIG. 8L is an illustration of a side view of a cross section of the embodiment of the devices shown in FIGS. 8I-8K.
Figure 8M:
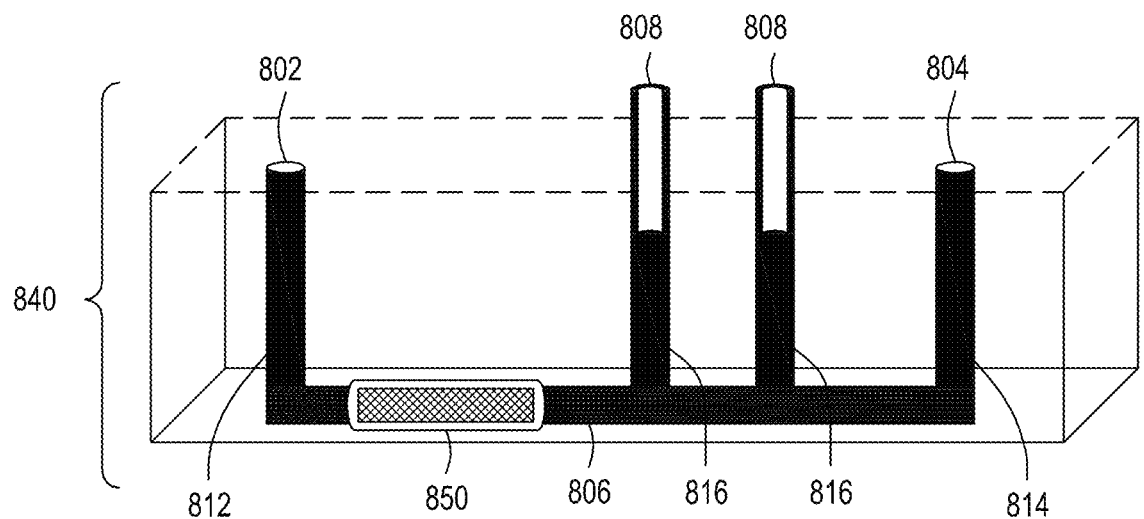
FIG. 8M is an illustration of a side view of a cross section of the bottom half of the embodiment of the devices shown in FIGS. 8I-8L.
Figure 8N:
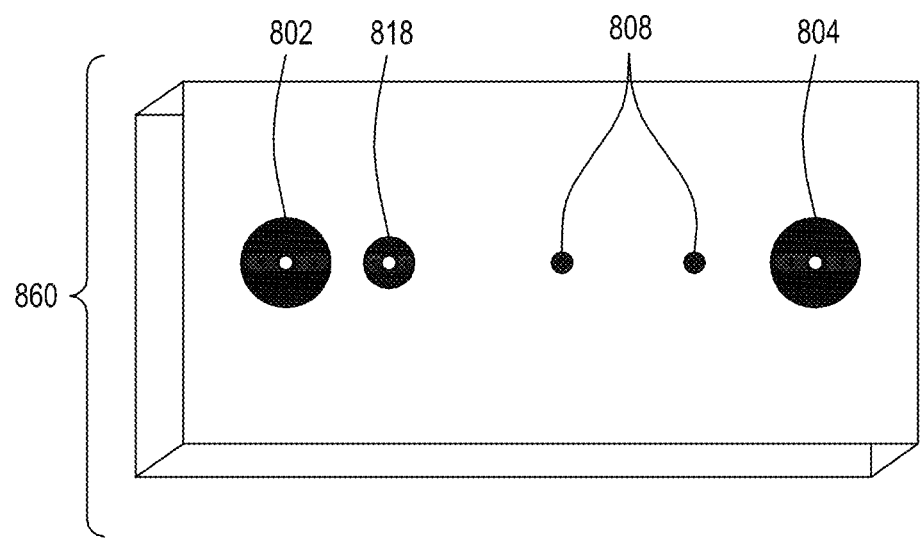
FIG. 8N is an illustration of a top view of yet another embodiment of the FTEP devices of the disclosure.
Figure 8O:
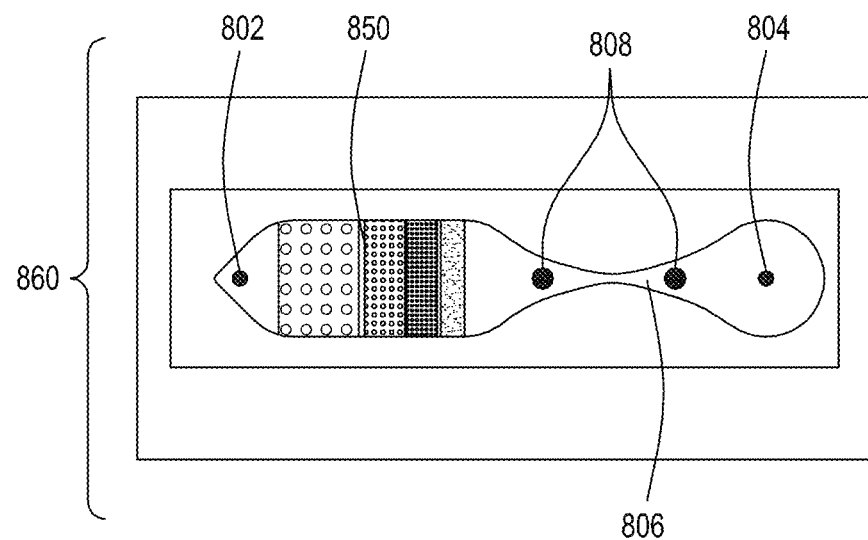
FIG. 8O is an illustration of the top view of a cross section of the embodiment of the device shown in FIG. 8N.
Figure 8P:
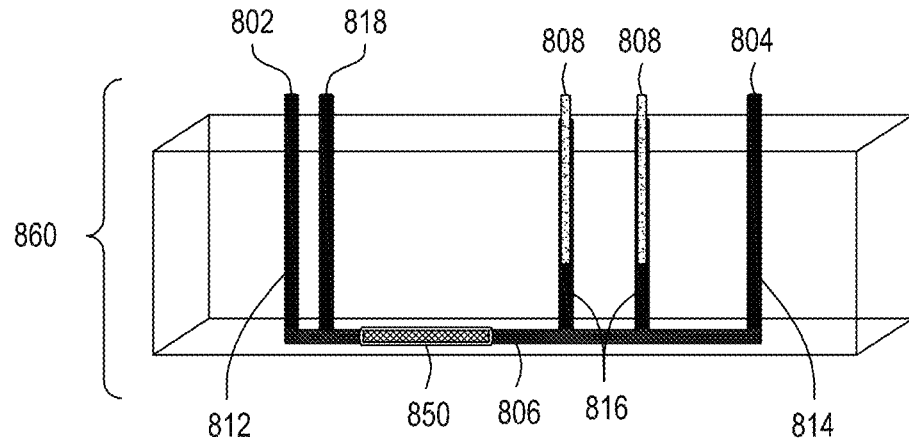
FIG. 8P is an illustration of a side view of a cross section of the embodiment of the device of the disclosure shown in FIGS. 8N-8O.
Figure 8Q:
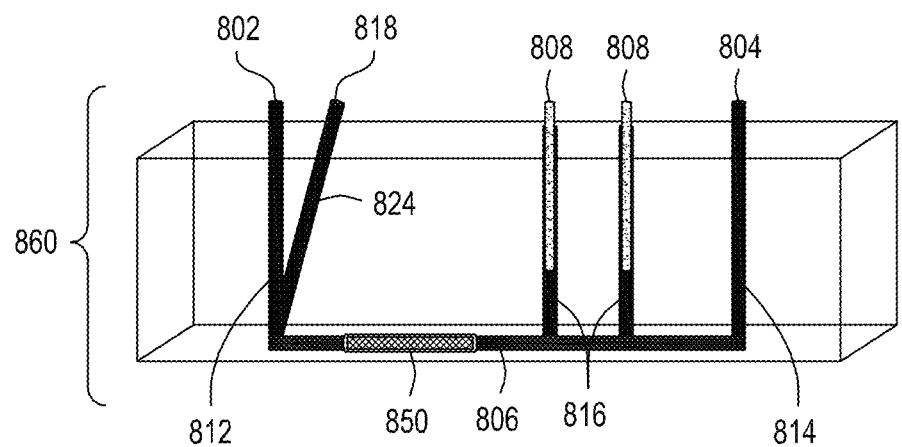
FIG. 8Q is an illustration of a side view of a cross section of a variation on the embodiment of the device shown in FIGS. 8N-8O.
Figure 8R:
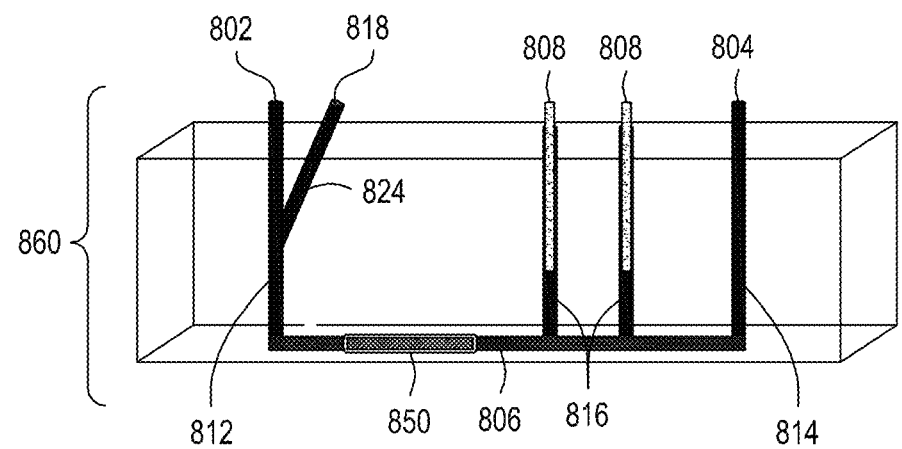
FIG. 8R is an illustration of a side view of a cross section of another variation on the embodiment of the device shown in FIGS. 8N-8Q.
Figure 8S:
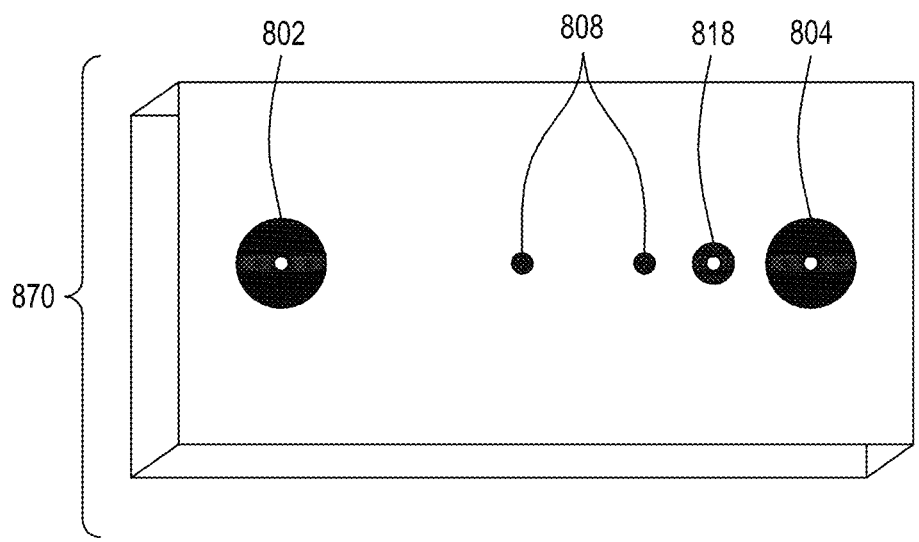
FIG. 8S is an illustration of the top view of a cross section of yet another embodiment of the FTEP devices of the disclosure.
Figure 8T:
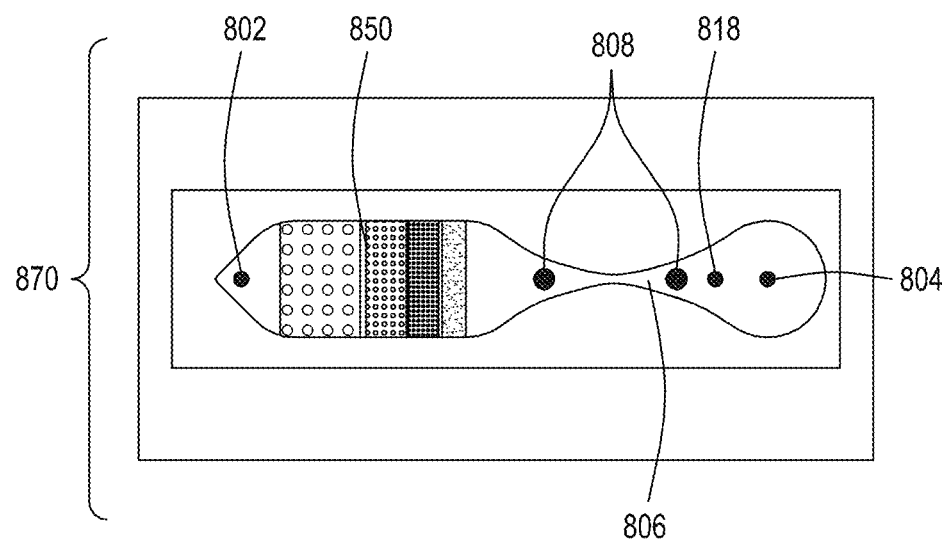
FIG. 8T is an illustration of the top view of a cross section of the embodiment of the device shown in FIG. 8S.
Figure 8U:
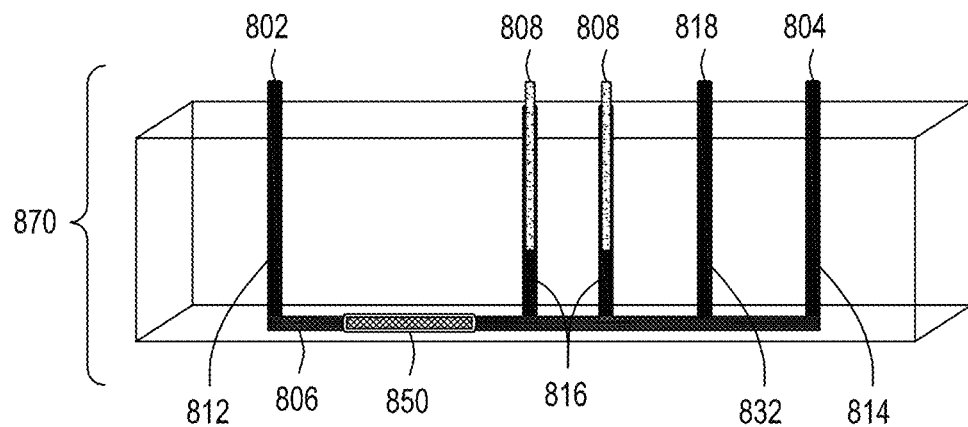
FIG. 8U is an illustration of a side view of a cross section of the embodiment of the device shown in FIGS. 8S and 8T.

Additional embodiments of the FTEP devices of the disclosure are illustrated in FIGS. 8A-8U. Note that in the FTEP devices in FIGS. 8A-8U the electrodes are not positioned on either side of the flow channel to narrow the flow channel; instead, the electrodes are placed such that a first electrode is placed between the inlet and the narrowed region of the flow channel, and the second electrode is placed between the narrowed region of the flow channel and the outlet. FIG. 8A shows a top planar view of an FTEP device 800 having an inlet 802 for introducing a fluid containing cells and exogenous material into FTEP device 800 and an outlet 804 for removing the transformed cells from the FTEP following electroporation. The electrodes 808 are introduced through channels (not shown) in the device. FIG. 8B shows a cutaway view from the top of the FTEP device 800, with the inlet 802, outlet 804, and electrodes 808 positioned with respect to a flow channel 806. FIG. 8C shows a side cutaway view of FTEP device 800 with the inlet 802 and inlet channel 812, and outlet 804 and outlet channel 814. The electrodes 808 are positioned in electrode channels 816 so that they are in fluid communication with the flow channel 806, but not directly in the path of the cells traveling through the flow channel 806. Again note that the first electrode is placed between the inlet and the narrowed region of the flow channel, and the second electrode is placed between the narrowed region of the flow channel and the outlet.

An expanded side cutaway view of the bottom portion of the device 800 in FIG. 8D shows that the electrodes 808 in this aspect of the device are positioned in the electrode channels 816 which are generally perpendicular to the flow channel 806 such that the fluid containing the cells and exogenous material flows from the inlet channel 812 through the flow channel 806 to the outlet channel 814, and in the process fluid flows into the electrode channels 816 to be in contact with the electrodes 808. In this aspect, the inlet channel, outlet channel and electrode channels all originate from the same planar side of the device, as shown in FIGS. 8C and 8D. In certain aspects, however, such as that shown in FIG. 8E, the electrodes are introduced from a different planar side of the FTEP device than the inlet and outlet channels. Here, the electrodes 808 in this alternative aspect of FTEP device 810 are positioned in the electrode channels 816 perpendicular to the flow channel 806 such that fluid containing the cells and exogenous material flow from the inlet channel 812 through the flow channel 806 to the outlet channel 814. The cells and exogenous material in buffer flow into the electrode channels 816 to be in contact with both electrodes 808; however, the electrodes 808 are not directly in flow channel 806. In this aspect, the inlet channel and outlet channel originate from a different planar side of the device than do the electrodes and electrode channels.

FIGS. 8F-8H illustrate yet another aspect of the FTEP devices of the disclosure. FIG. 8F shows a top planar view of an FTEP device 820 having a first inlet 802 for introducing a fluid containing cells into FTEP device 820 and an outlet 804 for removing the transformed cells from the FTEP device 820 following electroporation. However, in this FTEP device, there is a second inlet 822 for introducing exogenous material to be electroporated to the cells. The electrodes 808 are introduced through channels (not shown). FIG. 8G shows a cutaway view from the top of the FTEP device 820, with the first inlet 802, second inlet 822, outlet 804, and the electrodes 808 positioned with respect to the flow channel 806. FIG. 8H shows a side cutaway view of FTEP device 820 with inlets 802, 822 and inlet channels 812, 824 and outlet 804 and outlet channel 814. The electrodes 808 are positioned in the electrode channels 816 so that they are in fluid communication with the flow channel 806, but not substantially in the path of the cells traveling through the flow channel 806. The electrodes 808 in this aspect of the FTEP device 820 are positioned in the electrode channels 816 where the electrode channels 816 are generally perpendicular to the flow channel 806 such that fluid containing the cells and fluid containing the exogenous materials flow from the inlets 802, 822 through the inlet channels 812, 824 into the flow channel 806 and through to the outlet channel 814, and in the process the cells and exogenous material in medium flows into the electrode channels 816 to be in contact with the electrodes 808. One of the two electrodes 808 and electrode channels 816 is positioned between inlets 802 and 822 and inlet channels 812 and 824 and the narrowed region (not shown) of flow channel 806, and the other electrode 808 and electrode channel 816 is positioned between the narrowed region (not shown) of flow channel 806 and the outlet channel 814 and outlet 804. In FIG. 8H, the inlet channel, outlet channel and electrode channels all originate from the same planar side of the device, although the electrodes (and inlets and outlet) can also be configured to originate from a different planar sides of the FTEP device such as illustrated in FIG. 8E.

FIGS. 8I-8M illustrate yet another embodiment of the devices of the disclosure. FIG. 8I shows a top planar view of an electroporation device 830 having an inlet 802 for introducing a fluid containing cells and exogenous material into the FTEP device 830 and an outlet 804 for removal of the transformed cells from the FTEP device 8300 following electroporation. The electrodes 808 are introduced through channels (not shown) machined into the device. FIG. 8J shows a cutaway view from the top of the device 830, showing an inlet 802, an outlet 804, a filter 850 of substantially uniform density, and electrodes 808 positioned with respect to the flow channel 806. FIG. 8K shows a cutaway view from the top of an alternative configuration 840 of the device 830, with an inlet 802, an outlet 804, a filter 850 of increasing gradient density, and electrodes 808 positioned with respect to the flow channel 806. In FIGS. 8I-8M, like FIGS. 8F-8H, the first electrode is placed between the inlet and the narrowed region of the flow channel, and the second electrode is placed between the narrowed region of the flow channel and the outlet. In some embodiments such as those depicted in FIGS. 8I-8M, the FTEP devices comprise a filter disposed within the flow channel positioned in the flow channel after the inlet channel and before the first electrode channel. The filter may be substantially homogeneous in porosity (e.g., have a uniform density as in FIG. 8J); alternatively, the filter may increase in gradient density where the end of the filter proximal to the inlet is less dense, and the end of the filter proximal to the outlet is more dense (as shown in FIG. 8K). The filter may be fashioned from any suitable and preferably inexpensive material, including porous plastics, hydrophobic polyethylene, cotton, glass fibers, or the filter may be integral with and fabricated as part of the FTEP device body (see, e.g., FIG. 10E).

FIG. 8L shows a side cutaway view of the device 840 with an inlet 802 and an inlet channel 812, and an outlet 804 and an outlet channel 814. The electrodes 808 are positioned in the electrode channels 816 so that they are in fluid communication with the flow channel 806, but not directly in the path of the cells traveling through flow channel 806. Note that filter 850 is positioned between inlet 802 and inlet channel 812 and electrodes 808 and electrode channels 816. An expanded side cutaway view of the bottom portion of the FTEP device 840 in FIG. 8M shows that the electrodes 808 in this aspect of the FTEP device 840 are positioned in the electrode channels 816 and perpendicular to the flow channel 806 such that fluid containing the cells and exogenous material flows from the inlet channel 812 through the flow channel 806 to the outlet channel 814, and in the process fluid flows into the electrode channels 816 to be in contact with both electrodes 808. In FIGS. 8L and 8M, the inlet channel, outlet channel and electrode channels all originate from the same planar side of the device, although the electrodes (and the inlets and outlet) can also be configured to originate from a different planar side such as illustrated in FIG. 8E.

FIGS. 8N-8R illustrate other embodiments of the FTEP devices of the disclosure. FIG. 8N shows a top view of an FTEP device 860 having a first inlet 802 for introducing a fluid containing cells into the FTEP device and a second inlet 818 for introducing a fluid containing exogenous materials to be introduced to the cells into the FTEP device, electrodes 808 positioned in electrode channels (not shown), and an outlet 804 for removal of the transformed cells following electroporation. FIG. 8O shows a cutaway view from the top of the device 860, comprising a first inlet 802, second inlet 818, outlet 804, filter 850, and electrodes 808 positioned with respect to the flow channel 806. Again note that the electrodes 808 are positioned so that the first electrode is on the "inlet end" of the narrowed region in flow channel 806 and the second electrode is on the "outlet end" of the narrowed region in flow channel 806. FIG. 8P shows a first side cutaway view of an embodiment of the device 860 with the first inlet 802 and second inlet 818 positioned as shown in FIG. 8N. The first inlet channel 812 and second inlet channel 824 meet separately with the flow channel 806 prior to encountering filter 850, and the liquid flows from the inlet channels 812 and 824 through the flow channel 806 (and filter 850) to the outlet channel 814 and outlet 804. Note that in some embodiments, electrodes 808 may be positioned in electrode channels 816 such that electrodes 808 are flush with the walls of flow channel 806 (e.g., see FIG. 10F(iii)). Alternatively, electrodes 808 may extend a minimal distance into flow channel 806; however, in doing so electrodes 808 do not extend into flow channel 806 to the extent that the electrodes impede the flow of the cells through the flow channel.

FIG. 8Q shows a side cutaway view of a variation of the embodiment of the FTEP device 860 shown in FIGS. 8N-8P with the first inlet 802 and second inlet 818 positioned as shown in FIG. 8N. The first inlet channel 812 and second inlet channel 824 intersect with flow channel 806 at a three-way junction with flow channel 806 and prior to encountering filter 850. The liquid flows through the flow channel 806 to the outlet channel 824 and outlet 804. The electrodes 808 are positioned in the electrode channels 816 so that they are in fluid communication with the flow channel 806, but not directly in the path of the cells traveling through the flow channel 806. Again, the electrodes 808 are positioned so that the first electrode is on the "inlet end" of the narrowed region in flow channel 806 and the second electrode is on the "outlet end" of the narrowed region in flow channel 806. FIG. 8R shows a side cutaway view of yet another variation on the embodiment of the FTEP device 860 shown in FIGS. 8N-8P. The first inlet channel 812 and second inlet channel 826 intersect at a junction into a single channel prior to intersecting flow channel 806. The fluids flow from the inlets 802 and 818, through the inlet channels 812 and 826, into and through flow channel 806 and the filter 850, into electrode channels 816 (such that electrodes 808 are in fluid communication with flow channel 806) and continuing through flow channel 806 to the outlet channel 814 and finally to the outlet 804 where the transformed cells are removed from the FTEP device 860. Again in this embodiment, the electrodes 808 are positioned in the electrode channels 816 so that they are in fluid communication with the flow channel 806, but not directly in the flow path of the cells traveling through the flow channel 806. Although each of FIGS. 8P-8R show the inlet channels, outlet channel and electrode channels originating from the same planar side of the device, all of the inlets, outlet and electrodes in each of these aspects can also be configured to originate from different planar sides of the FTEP device.

FIGS. 8S-8U illustrate another embodiment of the FTEP devices of the disclosure. FIG. 8S shows a top view of an electroporation device 870 having a first inlet 802 for introducing a fluid containing cells into FTEP device 870, a second inlet 818 for introducing exogenous materials to be porated into the cells into FTEP device 870, and an outlet 804 for removing transformed cells from FTEP device 870 following electroporation. The electrodes 808 are introduced through channels (not shown) machined into the device and are positioned between the first inlet 802 and the second inlet 818. FIG. 8T shows a cutaway view from the top of the device 870, with the first inlet 802, second inlet 818, outlet 804, and the electrodes 808 positioned with respect to the flow channel 806. Additionally, the FTEP device depicted in FIG. 8T comprises a filter 850 disposed between the first inlet 802 and the first electrode 808 and before the narrowed region of flow channel 806. Filter 850 in this embodiment has a gradient of pore sizes, from large to small (moving from the inlet 802 toward the narrowed portion of flow channel 806. FIG. 8U shows a side cutaway view of FTEP device 870 comprising a first inlet 802 and first inlet channel 812, a filter 850, a second inlet 818 and second inlet channel 832, and an outlet 804 and outlet channel 814. The electrodes 808 are positioned in the electrode channels 816 perpendicular to flow channel 806 and between the first and second inlets. The electrodes 808 are in fluid communication with flow channel 806, but not in the flow channel and thus in the path of the cells traveling through flow channel 806. Exogenous materials are added to FTEP device 870 via the second inlet 818 and through the second inlet channel 832 and encounter the cells after the cells are electroporated. In FIG. 8U, the inlet channels, outlet channel and electrode channels all originate from the same planar side of the device, although these features can also be configured to originate from different planar sides of FTEP device 870.

Figure 9A:
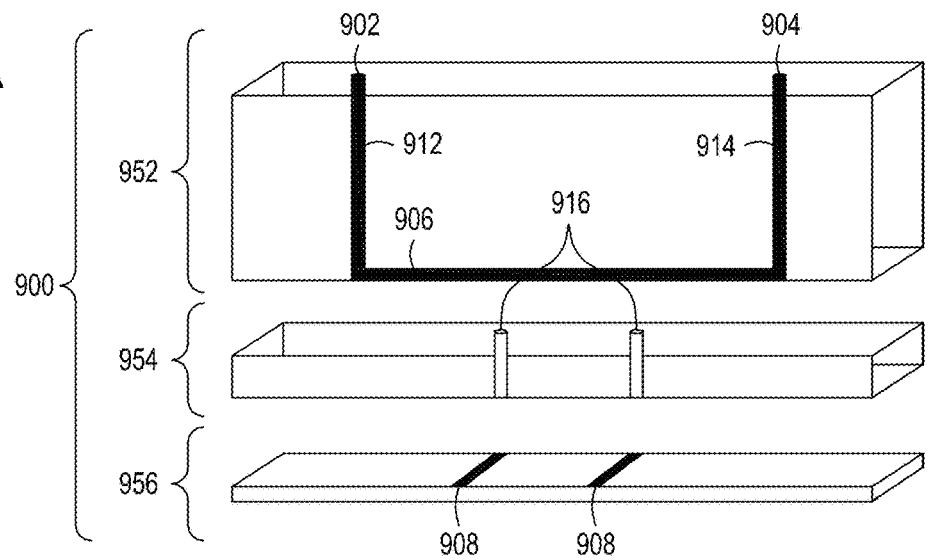
FIG. 9A is an illustration of a side view of a cross section of another embodiment of the FTEP devices of the disclosure.
Figure 9B:
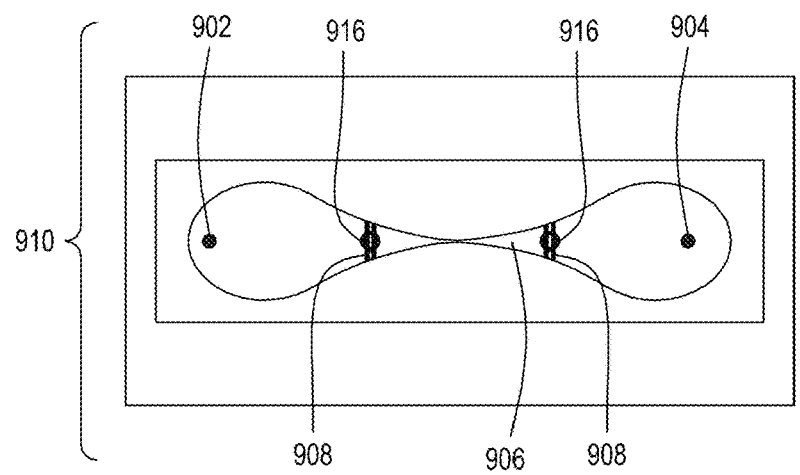
FIG. 9B is an illustration of the top view of a cross section of the embodiment of the device shown in FIG. 9A.

FIGS. 9A and 9B show the side and top cutaway views, respectively, of yet another embodiment of the invention. FIG. 9A shows a multilayer device 900 with a top layer 952 having an inlet 902 and an inlet channel 912, a flow channel 906, and outlet 904 and an outlet channel 914. The electrodes 908 are on bottom layer 956, e.g., provided as strips on a solid substrate. The middle layer 954 is a solid substrate with electrode channels 916 provided therein, and the electrode channels 916 in this aspect provide fluid communication between the electrodes 908 of bottom layer 956 and flow channel 906 of top layer 952. The cells and exogenous materials in fluid are introduced to the FTEP device 900 via inlet 902 and flow through inlet channel 912 and into flow channel 906, and then to the outlet channel 914. In the process, the fluid flows into electrode channels 916 so that electrodes 908 are in fluid contact with flow channel 906. The cells are porated as they pass through flow channel 906 between the two electrodes 908. FIG. 9B shows the top view of a cutaway 910 of the embodiment of the FTEP device 900 showing the position of the inlet 902, outlet 904, electrodes 908 and electrode channels 916 with respect to the flow channel 906. Although the electrodes are shown here as strips, they may also be configured to be other shapes, e.g., round, cylindrical, asymmetric, rectangular, or square.

Figure 9C:
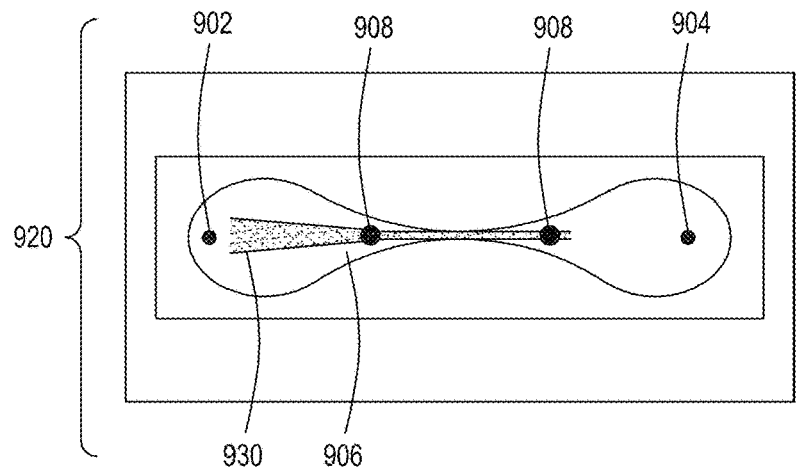
FIG. 9C is an illustration of a top view of a cross section of an embodiment of an FTEP device with a flow focusing feature.

FIG. 9C illustrates an FTEP device in which flow focusing 930 of the fluid introduced into the flow channel from the input channel(s) takes place, e.g., using an immiscible fluid such as an oil or using air to focus (narrow) the stream of the fluid containing the cells and exogenous materials as the fluid encounters the electrode channels, and the electrodes. FIG. 9C shows a cutaway view from the top of the device 920, with the first inlet 902, the flow focusing 930 of the fluid after it exits the inlet channel and enters the flow channel 906, and the electrodes 908 positioned between the inlet 902 and the outlet 904, where the electrodes 908 are positioned on either end of a narrowed portion of flow channel 906.

Figure 10A:
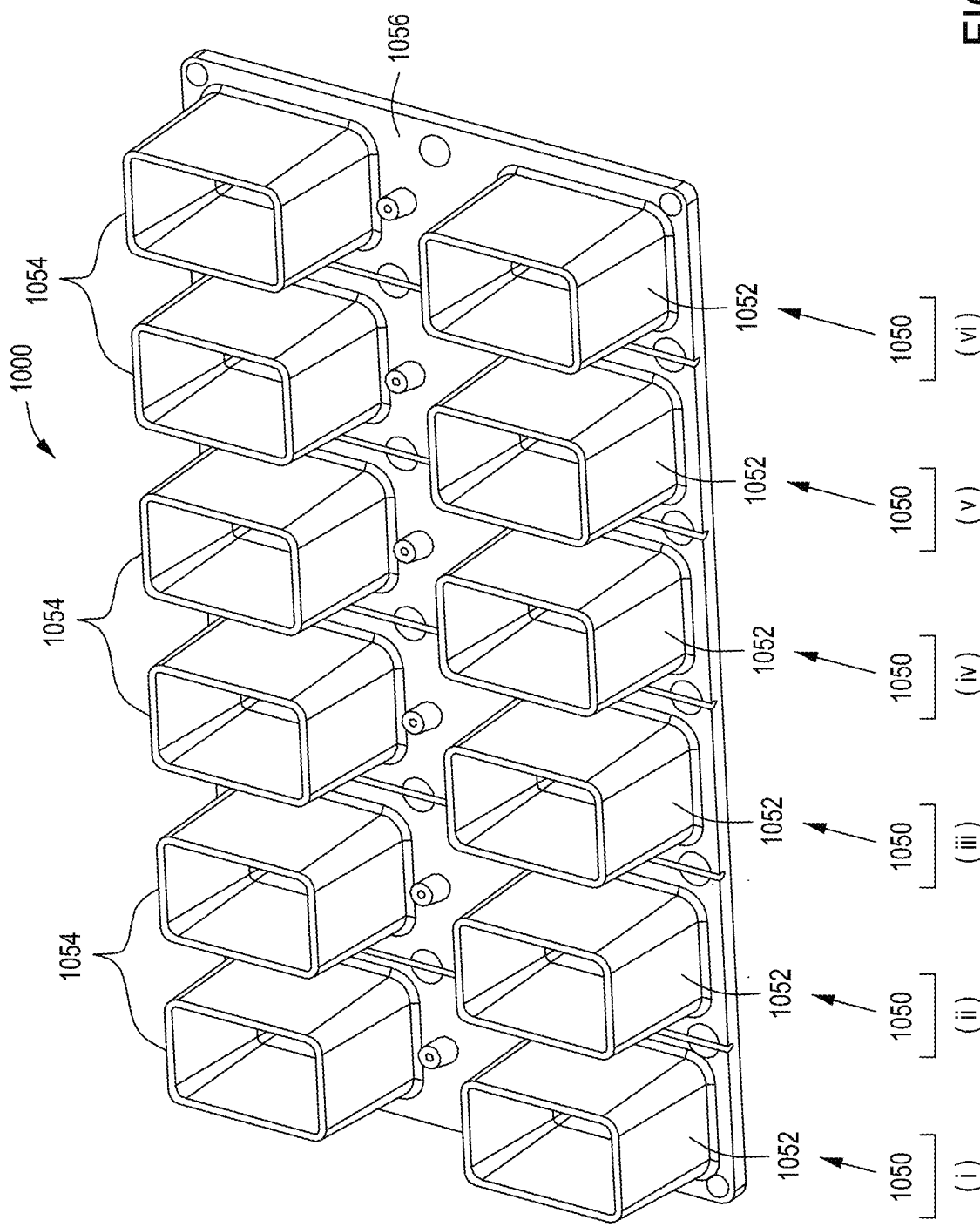
FIGS. 10A through 10C are top perspective, bottom perspective, and bottom views, respectively, of a flow-through electroporation device that may be part of a stand-alone FTEP module or as one module in an automated multi-module cell processing system.
Figure 10B:
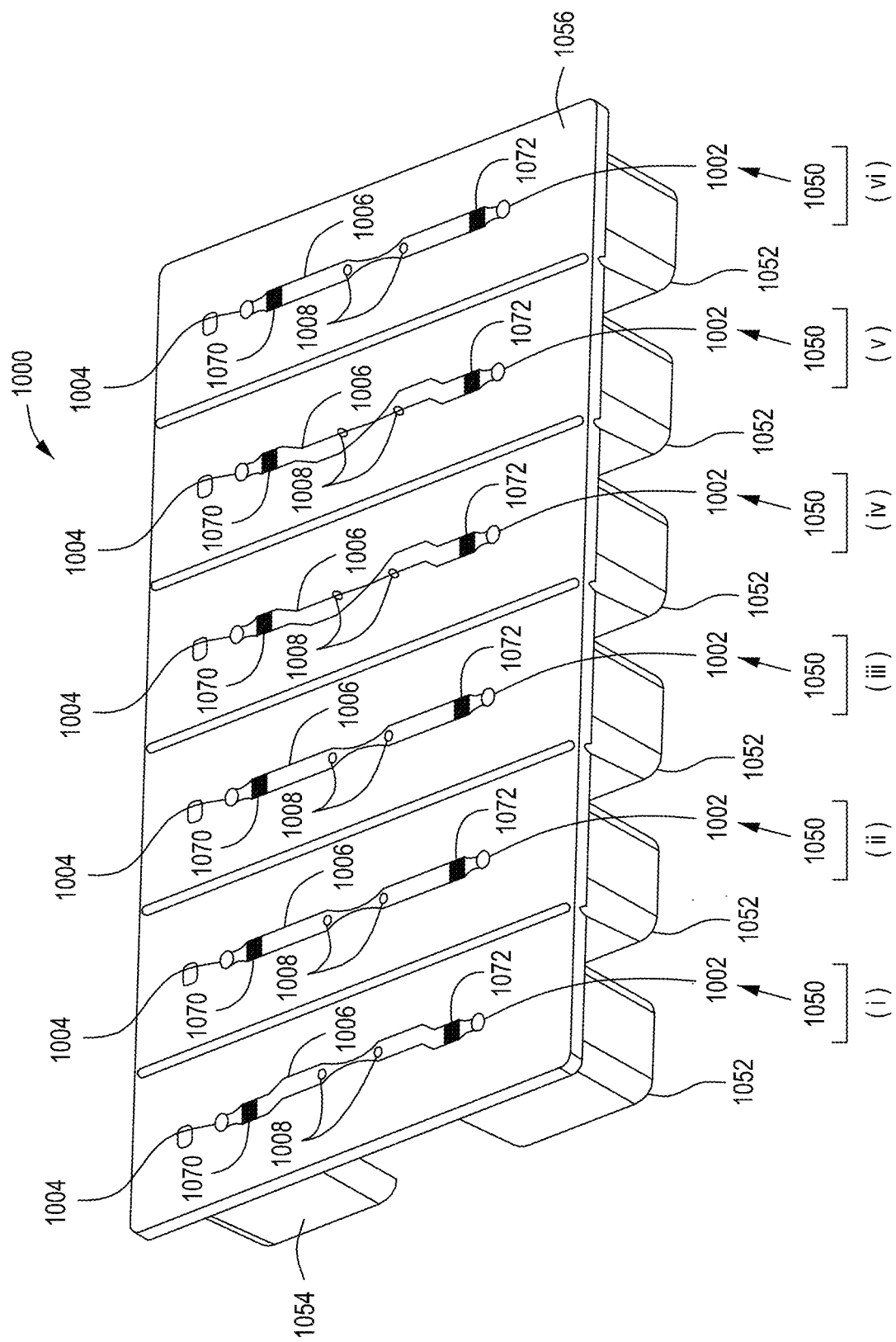
Figure 10C:
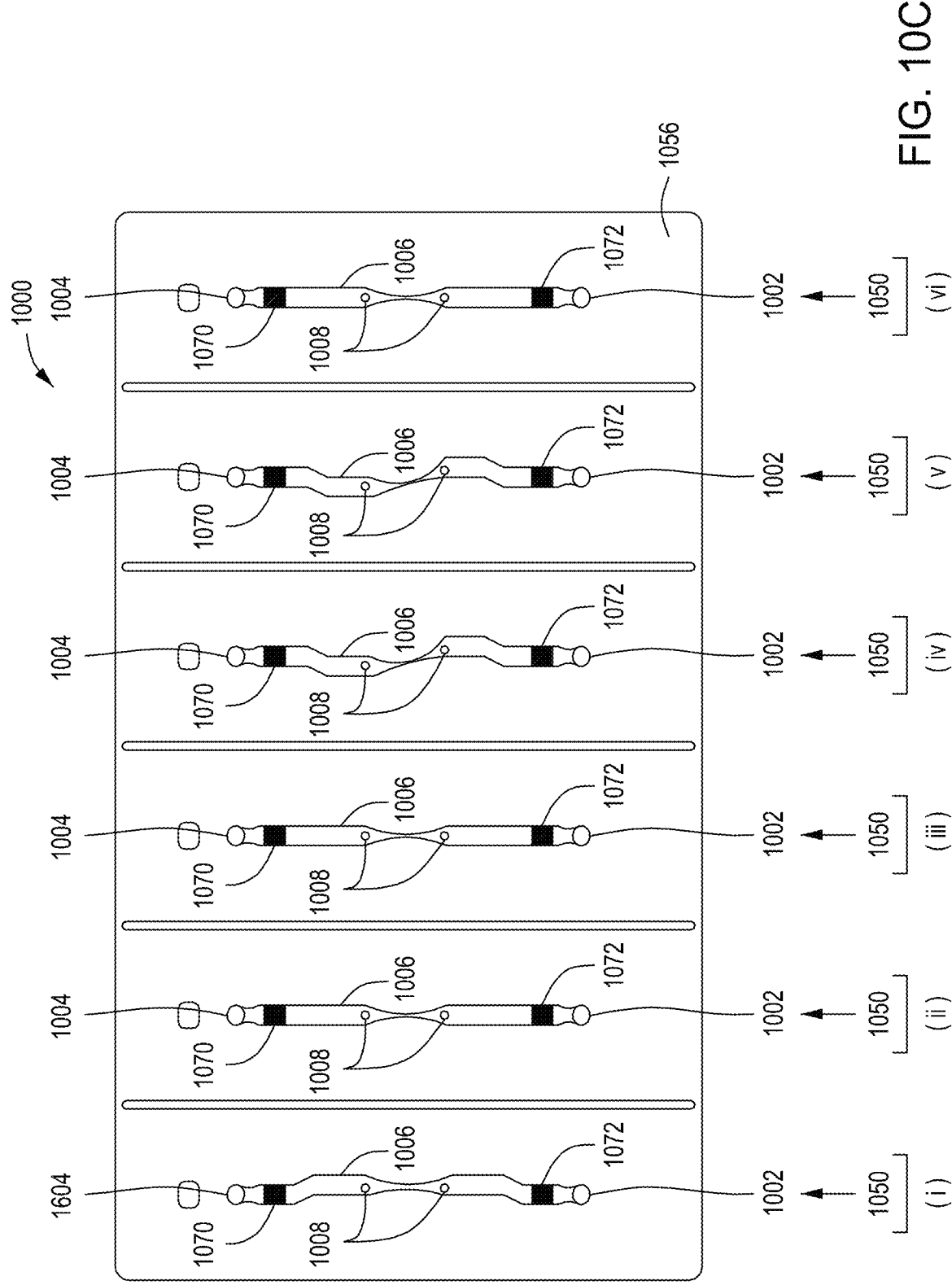
Figure 11E:
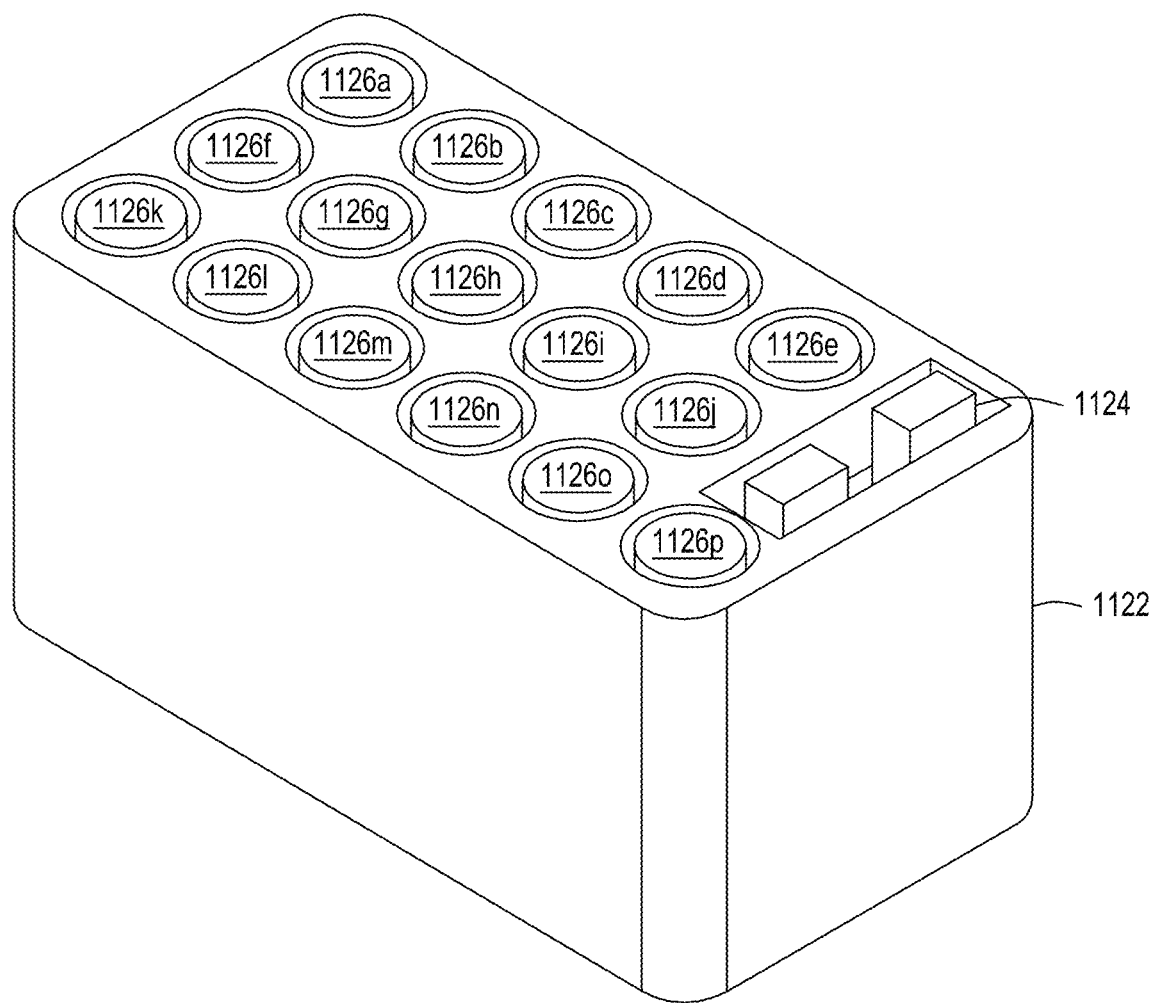

The reagent cartridges for use in the automated multi-module cell editing instruments (e.g., cartridge 104 of FIG. 1A), in some embodiments, include one or more FTEP devices (e.g., electroporation module 110c of FIG. 1A, also see 1124 of FIG. 11E). FIGS. 10A through 10C are top perspective, bottom perspective, and bottom views, respectively, of six co-joined FTEP devices 1050 that may be part of, e.g., reagent cartridge 1122 in FIG. 11E infra (i.e., serve as FTEP 1124 in reagent cartridge 1122). FIG. 10A depicts six FTEP units 1050 (i.e., (i), (ii), (iii), (iv), (v), and (vi)) arranged on a single, integrally-formed injection molded cyclic olefin copolymer (COC) substrate 1056. The channels 1006 shown in FIG. 10B are sealed with a COC film having a thickness of 50 microns to 1 mm (not shown). The COC film may be thermally bonded to the base of the assembly 1000 (the surface most prominently displayed in FIG. 10B). In FIGS. 10B and 10C, the co-joined FTEP devices have different channel architectures and electrode placements that may be advantageous in various applications. For instance, the curved channels of devices (i), (iv) and (v) take advantage of inertia to direct the cells in the fluid away from the electrodes. The electrodes may be positioned off center in the channel to further enhance cells flow and reduce the potential for damage to the cells. This may be particularly important for cells or materials that are particularly sensitive to electrolytic effects or local changes in pH proximate the electrodes. The electrodes may be at least partially embedded into the channel walls, as shown in embodiments (iii) and (iv), so as to further reduce these effects.

Each of the six FTEP units 1050 have wells or reservoirs 1052 that define cell sample inlets and wells 1054 that define cell sample outlets. FIG. 10B is a bottom perspective view of the six co-joined FTEP devices 1050 of FIG. 15A also depicting six FTEP units 1050 (i.e., (i)-(vi)) arranged on a single substrate 1056. Six inlet wells 1052 can be seen, one for each flow-through electroporation unit 1050, and one outlet well 1054 can be seen. Also seen in FIG. 10B for each FTEP unit 1050 are an inlet 1002, an outlet 1004, a flow channel 1006, and two electrodes 1008 on either end of a narrowed region in flow channel 1006. Filters 1070 and 1072 are included in the channels to prevent clogging of the channel, particularly at narrowed region of the flow channel. FIG. 10C is a bottom view of the six co-joined FTEP devices 1050 of FIGS. 10A and 10B. Depicted in FIG. 10C are six FTEP units 1050 (i.e., (i)-(vi)) arranged on a single substrate 1056, where each FTEP unit 1050 comprises an inlet 1002, outlet 1004, flow channel 1006 and two electrodes 1508 on either end of a narrowed region in flow channel 1006 in each FTEP unit 1050. Once the six FTEP units 1050 are fabricated, they can be separated from one another (e.g., "snapped apart") upon the depicted score lines and used one at a time as seen in the cartridge depicted in FIG. 11E; alternatively, the FTEP units may be used in embodiments where two or more FTEP units 1050 are used in parallel.

Figure 10D:
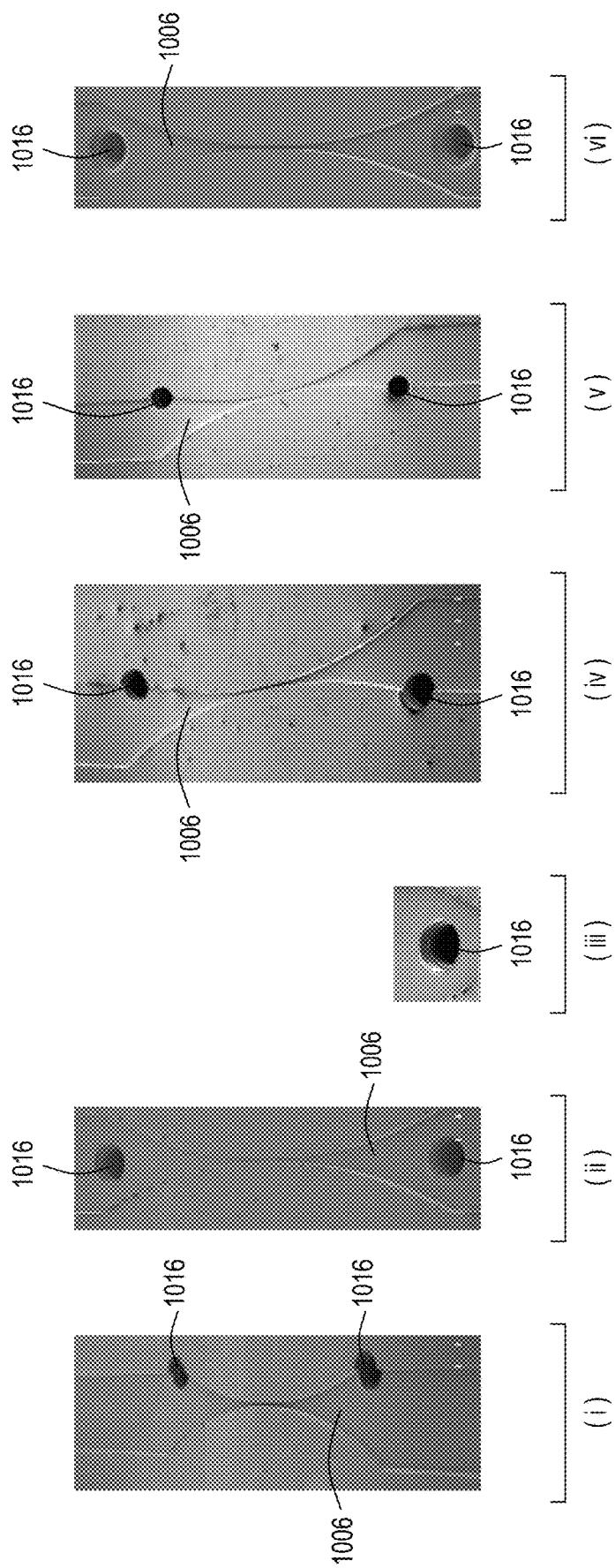
FIG. 10D shows scanning electromicrographs of the FTEP units depicted in FIG. 10C.

FIG. 10D shows scanning electromicrographs of the FTEP units depicted in FIG. 10C with the units (i), (ii), (iii), (iv), (v), and (vi) in FIG. 10D corresponding to units (i), (ii), (iii), (iv), (v), and (vi) in FIG. 10C. In FIG. 10D, for each unit both the electrode channels 1016 as well as the flow channel 1006 can be seen.

Figure 10E:
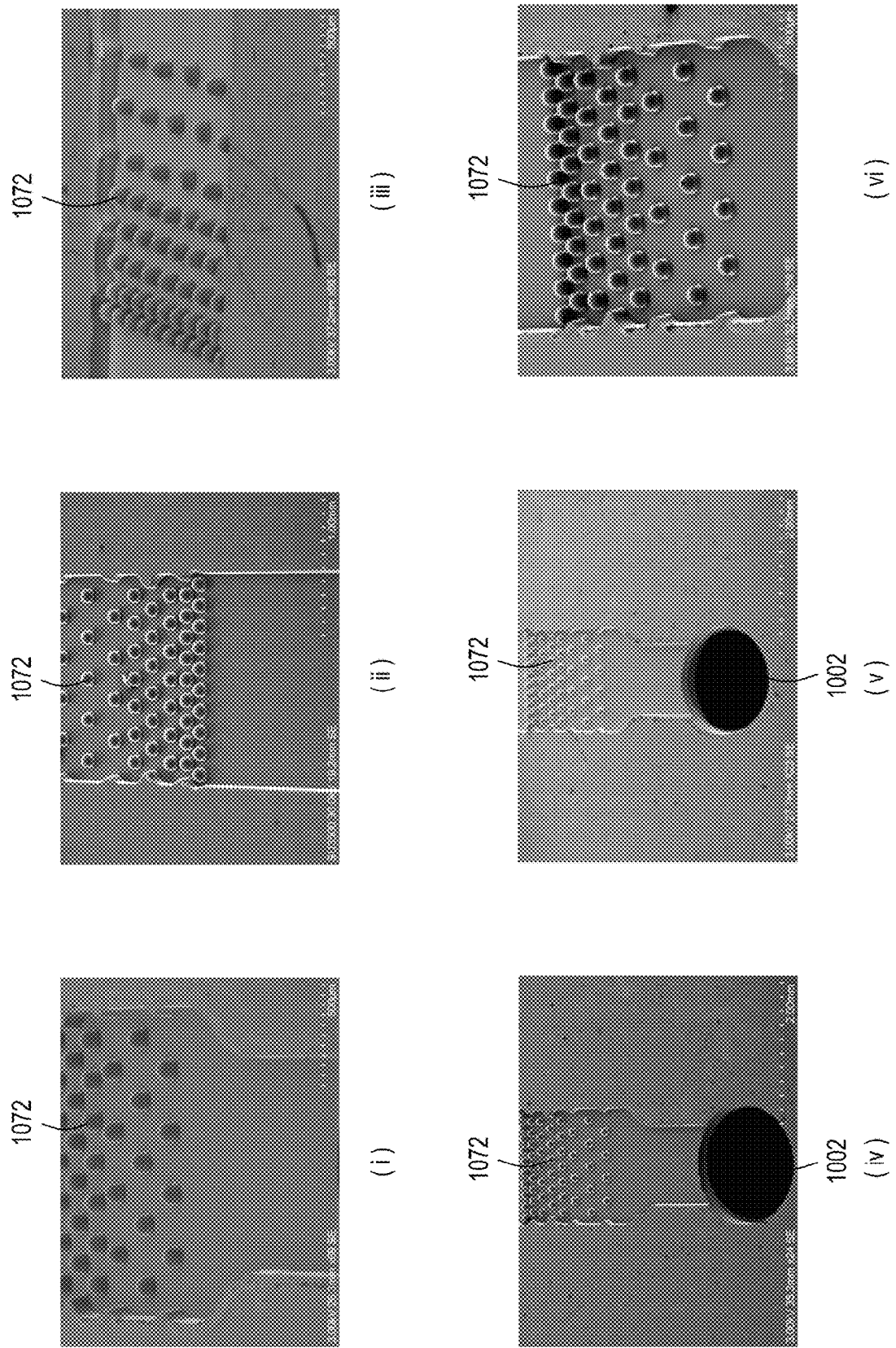
FIG. 10E shows scanning electromicrographs of filters 1070 and 1502 depicted as black bars in FIGS. 10B and 10C.

FIG. 10E shows scanning electromicrographs of the filters 1070 and 1072 depicted as black bars in FIGS. 10B and 10C. Note in this embodiment, the porosity of the filter 1072 varies from large pores (near the inlet 1002) to small pores toward the flow channel (not shown). In this embodiment, the channel optionally but not necessarily narrows. If a second filter is present, the second filter may also vary in porosity. In the case of a second filter between the second electrode and the outlet channel, the filter can vary from large pores (near the second electrode) to small pores toward the outlet channel. Scale information is shown in each micrograph.

In certain embodiments, the filter serves the purpose of filtering the fluid containing the cells and DNA before the fluid encounters the narrowed portion of the flow channel. The filter thus decreases the likelihood that cells or other matter do not clog the narrowed portion of the flow channel. Instead, if there is particulate matter that poses a threat to clogging the narrowed portion of the flow channel, the filter will catch the particulate matter leaving other pores through which the rest of the cell/DNA/fluid can move. The depicted construction (integral molding with the channel wall) is particularly advantageous because it reduces cost and complexity of the device while also reducing the risk that pieces of the filter itself may dislodge and clog the channel or otherwise interfere with device operation. Note that in this embodiment, the filter has a gradient pore size (from large pores proximate the inlet to smaller pores proximal the narrowed portion of the flow channel); however, in alternative embodiments the pores may be the same size or not gradient in size.

Further, in yet other embodiments the flow channel may not narrow. In these specific embodiments, the pores themselves can serve to provide such a narrowing function for enhancing electroporation, and the flow channel walls do not narrow or narrow minimally as the fluid flows through the channel. These embodiments can allow control of the rate of flow of cells through the device to optimize introduction of exogenous material into various cell types.

Moreover, though the scanning electromicrographs in FIG. 10E shown the filter elements as rounded "pegs", it should be understood that the filter elements may be triangular-, square-, rectangular-, pentagonal-, hexagonal-, oval-, elliptical- or other faceted-shaped pegs.

Figure 10F:
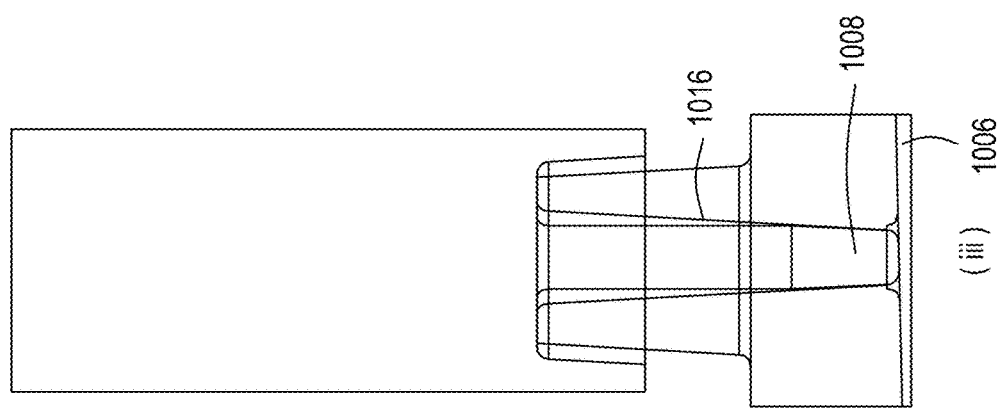
FIG. 10F depicts (i) the electrodes before insertion into the FTEP device; (ii) an electrode; and (iii) the electrode inserted into an electrode channel with the electrode and electrode channel adjacent to the flow channel.
Figure 10F:
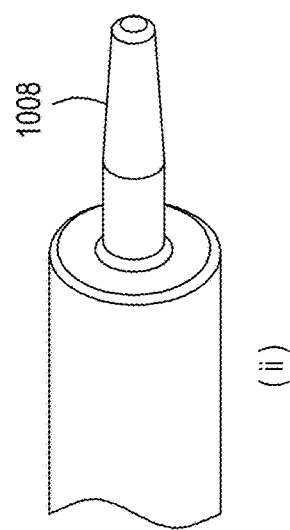
Figure 10F:
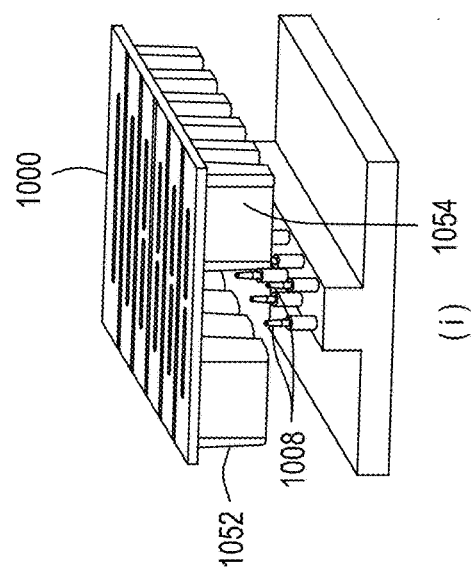

FIG. 10F depicts (i) the electrodes 1008 before insertion into the FTEP device 1000 (here, a six-unit FTEP device) having inlet reservoirs 1052 and outlet reservoirs 1054. In the preferred embodiment, the device 1000 is used in an orientation inverted relative to that shown in FIG. 10F (i). FIG. 10F (ii) depicts an electrode 1008 contained within and projecting from a sheath. FIG. 10F (iii) depicts the electrode 1008 inserted into an electrode channel 1016 with the electrode channel 1016 (and electrode 1008) adjacent to the flow channel 1006. In the embodiment shown in FIG. 10F (iii), the electrode is even with the walls of the flow channel; that is, the electrode is not in the path of the cells/DNA/fluid flowing through flow channel 1006, however, neither is the electrode recessed within the electrode channel 1016. Indeed, the electrode 1008 may be recessed within the electrode channel 1016, may be extend to the end of electrode channel 1016 and thus be even with the walls of flow channel 1006, or electrode 1008 may extend a minimal distance into flow channel 1006 so long as the electrode does not impede movement of the cells through the flow channel. The rounded or beveled edges of the aperture in the flow channel 1006 help prevent trapping air and reduce discontinuities in the electric field.

Figure 10G:
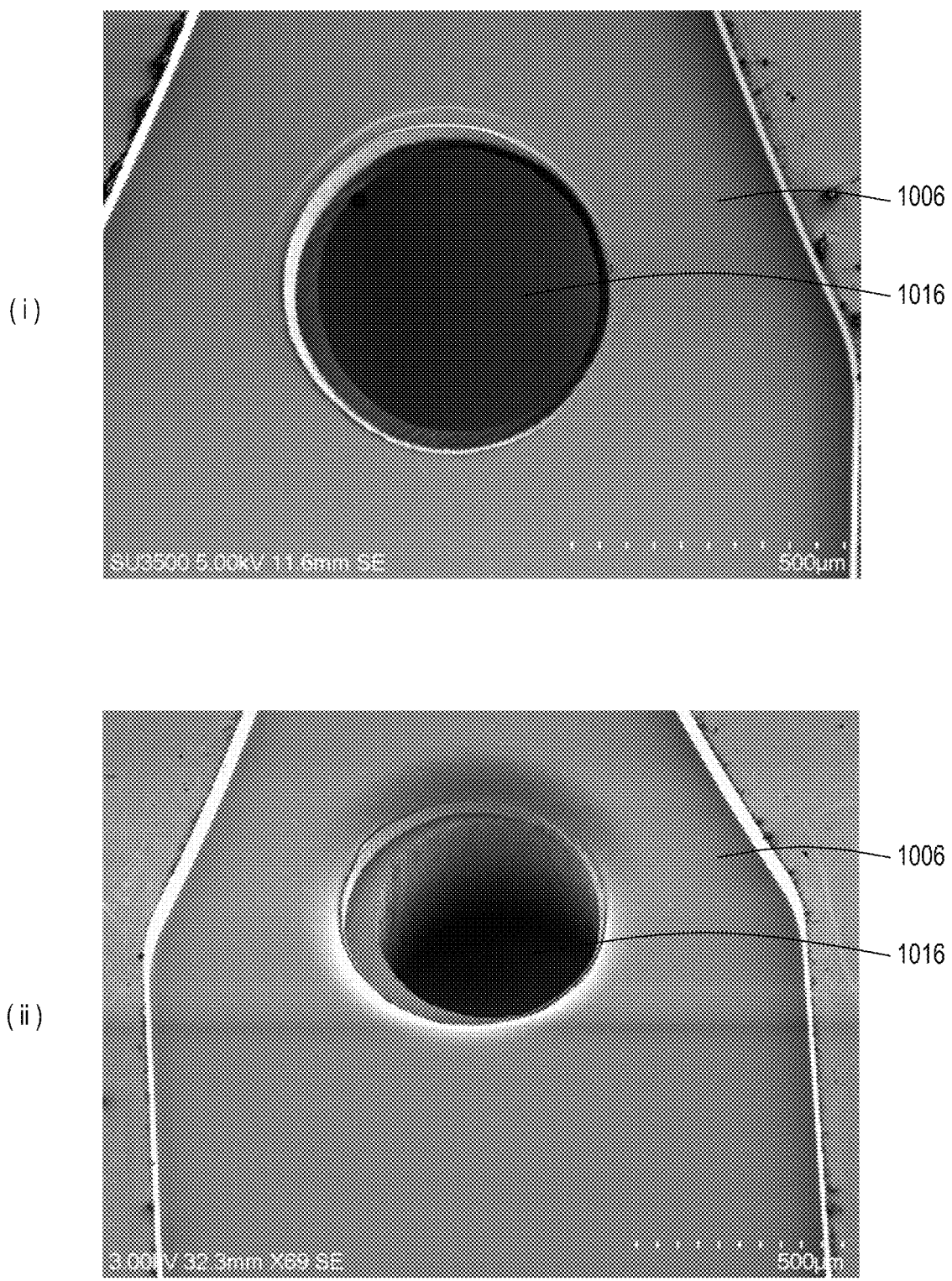
FIG. 10G shows two scanning electromicrographs of two different configurations of the aperture where the electrode channel meets the flow channel.

FIG. 10G presents two scanning electromicrographs of two different configurations of the aperture where electrode channel 1016 meets flow channel 1006. In FIG. 10G (i) (top), the edge of the junction of electrode channel 1016 and flow channel 1506 comprises a sharp edge. In contrast, in FIG. 10G (ii) (bottom), the edges of the junction of electrode channel 1016 and flow channel 1006 comprises a rounded edge. Both configurations were tested (data not shown), and it was found that the rounded-edge configuration decreases the likelihood that air will become trapped between flow channel 1006 and the electrode (not seen in this Figure) in electrode channel 1016. It can be seen that in this embodiment the inlet apertures have a rounded edge, the advantages of which include resistance to air trapping, promotion of laminar flow, and reduction of risk of cell damage. The rounded edges may have a radius of curvature of about 10, 20, 30, 40, 50, 60, 70, 80, 90, 100, 150, 200 or 250 microns. Indeed, the electrodes of the FTEP devices should be "wet"; that is, immersed in the fluid/cells/DNA.

After transformation, the cells are allowed to recover under conditions that promote the genome editing process that takes place as a result of the transformation and expression of the introduced nucleic acids in the cells.

Methods for Automated Multi-Module Cell Editing

Figure 14:
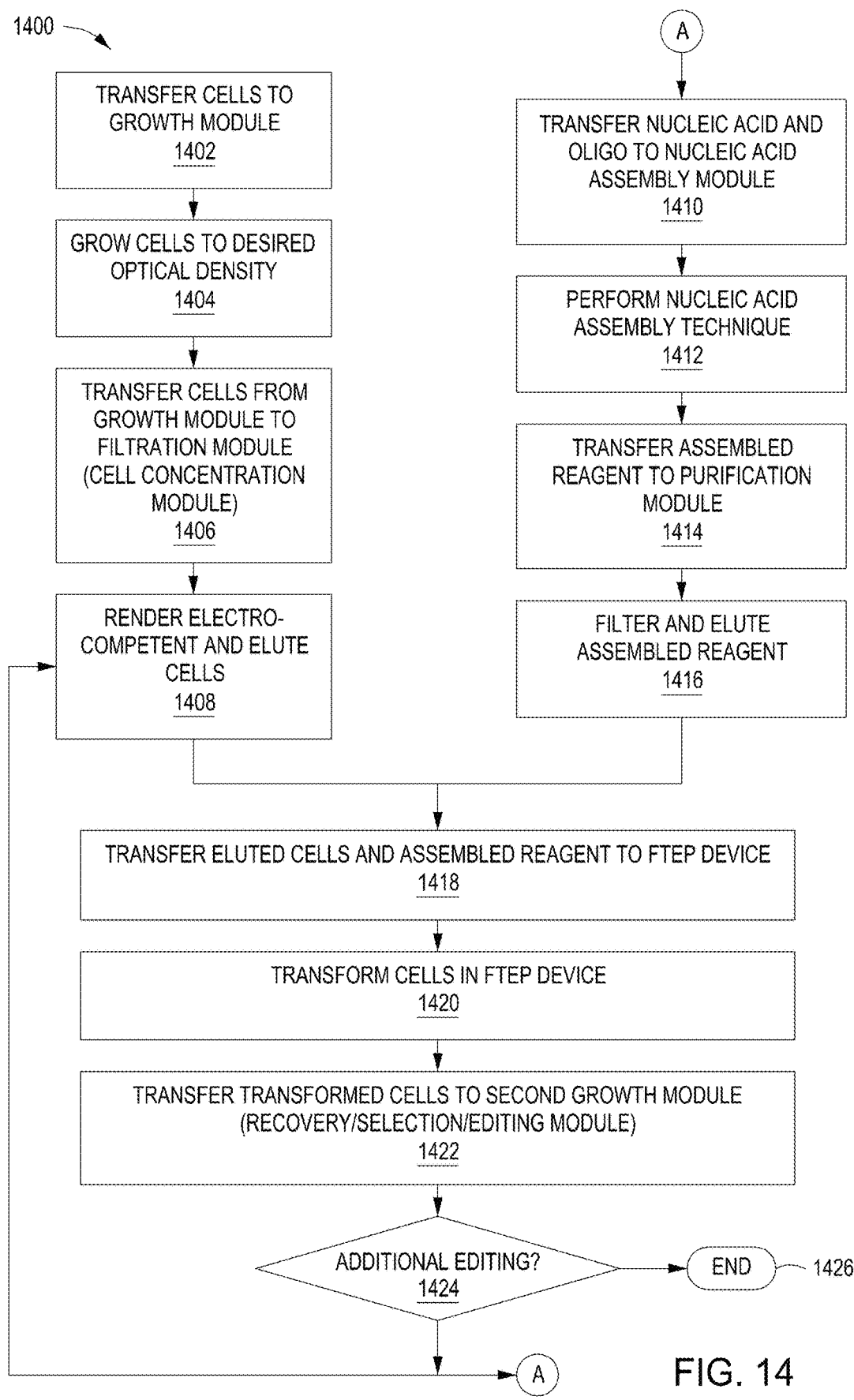
FIG. 14 is a flow chart of an example method for automated multi-module cell editing.

FIG. 14 is a flow chart of an example method 1400 for using an automated multi-module cell editing instrument such as the systems illustrated in FIGS. 1A-1B and 17A-17B. Further, the processing system of FIG. 18, for example, may direct the processing stage of the method 1400. For example, a software script may identify settings for each processing stage and instructions for movement of a robotic handling system to perform the actions of the method 1400. In some embodiments, a software instruction script may be identified by a cartridge supplied to the automated multi-module cell editing instrument. For example, the cartridge may include machine-readable indicia, such as a bar code or QR code, including identification of a script stored in a memory of the automated multi-module cell editing instrument (e.g., such as memory 1802 of FIG. 18). In another example, the cartridge may contain a downloadable script embedded in machine-readable indicia such as a radio frequency (RF) tag. In other embodiments, the user may identify a script, for example through downloading the script via a wired or wireless connection to the processing system of the automated multi-module cell editing instrument or through selecting a stored script through a user interface of the automated multi-module cell editing instrument. In a particular example, the automated multi-module cell editing instrument may include a touch screen interface for submitting user settings and activating cell processing.

In some implementations, the method 1400 begins with transferring cells to a growth module (1402). The growth module may be any growth module amendable to automation, for example, may be the growth module 1350 described in relation to FIGS. 13B and 13C. In a particular example, the processing system 1720 may direct the robotic handling system 1708 to transfer cells 1706 to the growth module 1710a, as described in relation to FIGS. 17A and 17B. In another example, as described in relation to FIG. 1A, the cells may be transferred from one of the cartridges 104, 106 to the growth modules 110a, 110b by the robotic handling system 108. In some embodiments, the growth vial may contain growth media and be supplied, e.g., as part of a kit. In other embodiments, the growth vial may be filled with medium transferred, e.g., via the liquid handling device, from a reagent container.

In some embodiments, prior to transferring the cells (e.g., from the reagent cartridge or from a vial added to the instrument), machine-readable indicia may be scanned upon the vial or other container situated in a position designated for cells to confirm that the vial or container is marked as containing cells. Further, the machine-readable indicia may indicate a type of cells provided to the instrument. The type of cells, in some embodiments, may cause the instrument to select a particular processing script (e.g., series of instructions for the robotic handling system and settings and activation of the various modules).

In some implementations, the cells are grown in the growth module to a desired optical density (1404). For example, the processing system 126 of FIGS. 1A-1B or processing system 1720 of FIGS. 17A-B may manage a temperature setting of the growth module 110a for incubating the cells during the growth cycle. The processing system 126, 1720 may further receive sensor signals from the growth module 110a, 110b, 1710a indicative of optical density and analyze the sensor signals to monitor growth of the cells. In some embodiments, a user may set growth parameters for managing growth of the cells. For example, temperature, and the degree of agitation of the cells. Further, in some embodiments, the user may be updated regarding growth process. The updates, in some examples, may include a message presented on a user interface of the automated multi-module cell editing instrument, a text message to a user's cell phone number, an email message to an email account, or a message transmitted to an app executing upon a portable electronic device (e.g., cell phone, tablet, etc.). Responsive to the messages, in some embodiments, the user may modify parameters, such as temperature, to adjust cell growth. For example, the user may submit updated parameters through a user interface of the automated multi-module cell editing instrument or through a portable computing device application in communication with the automated multi-module cell editing instrument, such as a user interface 1600 of FIG. 16.

Although described in relation to optical density, in other implementations cell growth within the growth module may be monitored using a different measure of cell density and physiological state such as, in some examples, pH, dissolved oxygen, released enzymes, acoustic properties, and electrical properties.

In some implementations, upon reaching the desired optical density (1404), the cells are transferred from the growth module to a filtration module or cell wash and concentration module (1406). The robotic handling system 108 of FIGS. 1A-1B or 1708 of FIGS. 17A-17B, for example, may transfer the cells from the growth module 1710a to the filtration module 1710b. The filtration module, for example, may be designed to render the cells electrocompetent. Further, the filtration module may be configured to reduce the volume of the cell sample to a volume appropriate for electroporation. In another example, the filtration module may be configured to remove unwanted components, such as salts, from the cell sample. In some examples, the filtration system performs two of the preceding tasks, and in certain preferred embodiments all three of the preceding tasks, rendering the cells electrocompetent, reducing the volume of the fluid containing the cells, and removing unwanted components. In some embodiments, the robotic handling system 1708 transfers a washing solution to the filtration module 1710b for washing the cells.

In some implementations, the cells are rendered electrocompetent and eluted in the filtration module or cell wash and concentration module (1408). The cells may be eluted using a wash solution. For example, the cells may be eluted using reagents from a reagent supply. The filtration module or cell wash and concentration module, for example, may be similar to the filtration module 1200 described in relation to in FIGS. 12A-12D. As discussed above, numerous different methods can be used to wash the cells, including density gradient purification, dialysis, ion exchange columns, filtration, centrifugation, dilution, and the use of beads for purification. In some aspects, the cell wash and concentration module utilizes a centrifugation device. In other aspects, the filtration module utilizes a filtration instrument. In yet other aspects, the beads are coupled to moieties that bind to the cell surface. These moieties include but are not limited to antibodies, lectins, wheat germ agglutinin, mutated lysozymes, and ligands. In other aspects, the cells are engineered to be magnetized, allowing magnets to pellet the cells after wash steps. Mechanism of cell magnetization can include but not limited to ferritin protein expression.

In some embodiments, the wash solution is transferred to the filtration module prior to eluting. The robotic handling system 1708 of FIGS. 17A-17B, for example, may transfer the wash solution from a vial or container situated in a position designated for wash solution. Prior to transferring the wash solution, machine-readable indicia may be scanned upon the vial or other container or reservoir situated in the position designated for the wash solution to confirm the contents of the vial, container, or reservoir. Further, the machine-readable indicia may indicate a type of wash solution provided to the instrument. The type of wash solution, in some embodiments, may cause the system to select a particular processing script (e.g., settings and activation of the filtration module appropriate for the particular wash solution).

In other embodiments, the cells are eluted in a cell wash module of a wash cartridge. For example, the eluted cells may be collected in an empty vessel of the wash cartridge 106 illustrated in FIG. 1A, and the robotic handling system 108 may transfer media from the reagent cartridge 104 (or a reagent well of the wash cartridge 106) to the eluted cells.

Once the cells have been rendered electrocompetent and suspended in an appropriate volume such as 50 µL to 10 mL, or 100 µL to 80 mL, or 150 µL to 8 mL, or 250 µL to 7 mL, or 500 µL to 6 mL, or 750 µL to 5 mL for transformation by the filtration module (1406), in some implementations, the cells are transferred to an FTEP module (1418). The robotic handling system 108 of FIGS. 1A-1B, for example, may transfer the cells from the filtration module to the FTEP device 110c. The filtration module may be physically coupled to the FTEP device, or these modules may be separate. In an embodiment such as the instrument 100 of FIG. 1A having cartridge-based supplies, the cells may be eluted to a reservoir within a cartridge, such as the reagent cartridge 104, prior to transferring to the transformation module.

In some implementations, nucleic acids are prepared outside of the automated multi-module cell editing instrument. For example, an assembled vector or other nucleic acid assembly may be included as a reagent by a user prior to running the transformation process and other processes in the method 1400.

However, in other implementations, nucleic acids are prepared by the automated multi-module cell editing instrument. A portion of the following steps 1410 through 1416, in some embodiments, are performed in parallel with a portion of steps 1402 through 1408. At least a portion of the following steps, in some embodiments, are performed before and/or after steps 1402 through 1408.

In some implementations nucleic acids such as an editing oligonucleotide and a vector backbone, as well as, in some examples, enzymes and other reaction components are transferred to a nucleic acid assembly module (1410). The nucleic acid assembly module may be configured to perform one or more of a wide variety of different nucleic acid assembly techniques in an automated fashion. Nucleic acid assembly techniques that can be performed in the nucleic acid assembly module may include, but are not limited to, those assembly methods that use restriction endonucleases, including PCR, BioBrick assembly, Type IIS cloning, GoldenGate assembly, and Ligase Cycling Reaction. In other examples, the nucleic acid assembly module may perform an assembly technique based on overlaps between adjacent parts of the nucleic acids, such as Gibson Assembly®, CPEC, SLIC, Ligase Cycling etc. Additional example assembly methods that may be performed by the nucleic acid assembly module include gap repair in yeast, gateway cloning and topoisomerase-mediated cloning. The nucleic acid assembly module, for example, may be the nucleic acid assembly module 300 described in relation to FIG. 3. In a particular example, the processing system 1720 may direct the robotic handling system 1708 to transfer nucleic acids 1704 to the nucleic acid assembly module 1710*g*, as described in relation to FIG. 17B. In another example, as described in relation to FIG. 1A, the nucleic acids may be transferred from one of the cartridges 104, 106 to a nucleic acid assembly module by the robotic handling system 108.

In some embodiments—prior to transferring each of the nucleic acid samples, the enzymes, and other reaction components—machine-readable indicia may be scanned upon the vials or other containers situated in positions designated for these materials to confirm that the vials or containers are marked as containing the anticipated material. Further, the machine-readable indicia may indicate a type of one or more of the nucleic acid samples, the enzymes, and other reaction components provided to the instrument. The type(s) of materials, in some embodiments, may cause the instrument to select a particular processing script (e.g., series of instructions for the robotic handling system to identify further materials and/or settings and activation of the nucleic acid assembly module).

In some embodiments, the nucleic acid assembly module is temperature controlled depending upon the type of nucleic acid assembly used. For example, when PCR is utilized in the nucleic acid assembly module, the module can have a thermocycling capability allowing the temperatures to cycle between denaturation, annealing and extension. When single temperature assembly methods are utilized in the nucleic acid assembly module, the module can have the ability to reach and hold at the temperature that optimizes the specific assembly process being performed.

Temperature control, in some embodiments, is managed by a processing system of the automated multi-module cell editing instrument, such as the processing system 1810 of FIG. 18. These temperatures and the duration of maintaining the temperatures can be determined by a preprogrammed set of parameters (e.g., identified within the processing script or in another memory space accessible by the processing system), or manually controlled by the user through interfacing with the processing system.

Once sufficient time has elapsed for the assembly reaction to take place, in some implementations, the nucleic acid assembly is transferred to a purification module (1414). The processing system, for example, may monitor timing of the assembly reaction based upon one or more of the type of reaction, the type of materials, and user settings provided to the automated multi-module cell editing instrument. The robotic handling system 108 of FIGS. 1A-1B or 1708 of FIGS. 17A-17B, for example, may transfer the nucleic acid assembly to the purification module through a sipper or pipettor interface. In another example, the robotic handling system 108 of FIGS. 1A-1B or 1708 of FIGS. 17A-17B may transfer a vial containing the nucleic acid assembly from a chamber of the nucleic acid assembly module to a chamber of the de-salt/purification module.

In some implementations, the nucleic acid assembly is de-salted and eluted at the purification module (1416). The purification module, for example, may remove unwanted components of the nucleic acid assembly mixture (e.g., salts, minerals, etc.). In some embodiments, the purification module concentrates the assembled nucleic acids into a smaller volume that the nucleic acid assembly volume. Examples of methods for exchanging liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc. For example, one or more micro-concentrators fitted with anisotropic, hydrophilic-generated cellulose membranes of varying porosities may be used. In another example, the de-salt/purification module may process a liquid sample including a nucleic acid and an ionic salt by contacting the mixture with an ion exchanger including an insoluble phosphate salt, removing the liquid, and eluting nucleic acid from the ion exchanger.

In an illustrative embodiment, the nucleic acid assembly may be combined with magnetic beads, such as SPRI beads, in a chamber of a purification module. The nucleic acid assembly may be incubated at a set temperature for sufficient time for the assembled nucleic acids to bind to the magnetic beads. After incubation, a magnet may be engaged proximate to the chamber so that the nucleic acid assembly can be washed and eluted. An illustrative example of this process is discussed in relation to the combination nucleic acid assembly and purification module of FIG. 3.

Once the nucleic acid assembly has been eluted, the nucleic acid assembly, in some implementations, is transferred to the transformation module (1418). The robotic handling system 108 of FIGS. 1A-1B or 1708 of FIGS. 17A-17B, for example, may transfer the assembled nucleic acids to the transformation module through a sipper or pipettor interface to the FTEP as described above. For example, the de-salted assembled nucleic acids, during the transfer, may be combined with the electrocompetent cells from step 1408. In other embodiments, the transformation module may accept each of the electrocompetent cells and the nucleic acid assembly separately and enable the mixing (e.g., open one or more channels to combine the materials in a shared chamber).

The cells are transformed in the FTEP module (1420). A buffer or medium may be transferred to the transformation module and added to the cells so that the cells may be suspended in a buffer or medium that is favorable for cell survival during electroporation. Prior to transferring the buffer or medium, machine-readable indicia may be scanned upon the vial or other container or reservoir situated in the position designated for the buffer or medium to confirm the contents of the vial, container, or reservoir. Further, the machine-readable indicia may indicate a type of buffer or medium provided to the instrument. The type of buffer or medium, in some embodiments, may cause the instrument to select a particular processing script (e.g., settings and activation of the transformation module appropriate for the particular buffer or medium). For bacterial cell electroporation, low conductance mediums, such as water or glycerol solutions, may be used to reduce the heat production by transient high current. For yeast cells a sorbitol solution may be used. For mammalian cell electroporation, cells may be suspended in a highly conductive medium or buffer, such as MEM, DMEM, IMDM, RPMI, Hanks', PBS, HBSS, HeBS and Ringer's solution. In a particular example, the robotic handling system 108 (FIG. 1A) may transfer a buffer solution to FTEP module 110*c* from one of the cartridges 104, 106. As described in relation to FIGS. 4A-4I, 5A-5H, 6, 7A-7E, 8A-8U, and 9A-9C, the FTEP device may be a disposable FTEP device and/or the FTEP device 110*c* may be provided with the cartridge 104 of FIG. 1A (or FTEP device 1124 of cartridge 1122 in FIG. 11E).

Once transformed, the cells are transferred to a second growth/recovery/editing module (1422). The robotic handling system 108 of FIGS. 1A-1B or 1708 of FIGS. 17A-17B, for example, may transfer the transformed cells to the second growth module through a sipper or pipettor interface. In another example, the robotic handling system 108 of 1A-1B or 1708 of FIGS. 17A-17B may transfer a vial containing the transformed cells from a chamber of the transformation module to a chamber of the second growth module.

The second growth module, in some embodiments, acts as a recovery module, allowing the cells to recover from the transformation process. In other embodiments, the cells may be provided to a separate recovery module prior to being transported to the second growth module. During recovery, the second growth module allows the transformed cells to uptake and, in certain aspects, integrate the introduced nucleic acids into the genome of the cell. The second growth module may be configured to incubate the cells at any user-defined temperature optimal for cell growth, preferably 25°, 30°, or 37° C.

In some embodiments, the second growth module behaves as a selection module, selecting the transformed cells based on an antibiotic or other reagent. In one example, the RNA-guided nuclease (RGN) protein system is used for selection to cleave the genomes of cells that have not received the desired edit. The RGN protein system used for selection can either be the same or different as the RGN used for editing. In the example of an antibiotic selection agent, the antibiotic may be added to the second growth module to enact selection. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, or chloramphenicol-resistance gene. The robotic handling system 108 of FIGS. 1A-1B or 1708 of FIGS. 17A-17B, for example, may transfer the antibiotic to the second growth module through a sipper or pipettor interface. In some embodiments, removing dead cell background is aided using lytic enhancers such as detergents, osmotic stress by hyponic wash, temperature, enzymes, proteases, bacteriophage, reducing agents, or chaotropes. The processing system 1810 of FIG. 18, for example, may alter environmental variables, such as temperature, to induce selection, while the robotic handling system 108 of FIGS. 1A-1B or 1708 of FIGS. 17A-17B may deliver additional materials (e.g., detergents, enzymes, reducing agents, etc.) to aid in selection. In other embodiments, cell removal and/or media exchange by filtration is used to reduce dead cell background.

In further embodiments, in addition to or as an alternative to applying selection, the second growth module serves as an editing module, allowing for genome editing in the transformed cells. Alternatively, in other embodiments the cells post-recovery and selection (if performed) are transferred to a separate editing module. As an editing module, the second growth module induces editing of the cells' genomes, e.g., through facilitating expression of the introduced nucleic acids. Expression of the nuclease and/or editing cassette nucleic acids may involve one or more of chemical, light, viral, or temperature induction methods. The second growth module, for example, may be configured to heat or cool the cells during a temperature induction process. In a particular illustration, the cells may be induced by heating at 42° C.-50° C. Further to the illustration, the cells may then be are cooled to 0-10° C. after induction. In the example of chemical or viral induction, an inducing agent may be transferred to the second growth module to induce editing. If an inducible nuclease and/or editing cassette was introduced to the cells during editing, it can be induced through introduction of an inducer molecule, such as the inducer molecule 1724 described in relation to FIG. 17A. The inducing agent or inducer molecule, in some implementations, is transferred to the second growth module by the robotic handling system 108 of FIGS. 1A-1B or 1708 of FIGS. 17A-17B (e.g., through a pipettor or sipper interface).

In some implementations, if no additional cell editing is desired (1424), the cells may be transferred from the cell growth module to a storage unit for later removal from the automated multi-module cell editing instrument (1426). The storage unit, for example, may include the storage unit 1714 of FIGS. 17A-17B. The robotic handling system 108 of FIGS. 1A-1B or 1708 of FIGS. 17A-17B, for example, may transfer the cells to the storage unit 114 through a sipper or pipettor interface. In another example, the robotic handling system 108 of FIGS. 1A-1B or 1708 of FIGS. 17A-17B may transfer a vial containing the cells from a chamber of the second growth module to a vial or tube within the storage unit.

In some implementations, if additional cell editing is desired (1424), the cells may be transferred to the same or a different filtration module and rendered electrocompetent (1408). Further, in some embodiments, a new assembled nucleic acid sample may be prepared by the nucleic acid assembly module at this time, or, alternatively, a second fully assembled nucleic acid may be directly introduced to the cells. Prior to recursive editing, in some embodiments, the automated multi-module cell editing instrument may require additional materials be supplied by the user, e.g., through the introduction of one or more separate reagents vials or cartridge.

The steps may be the same or different during the second round of editing. For example, in some embodiments, upon a subsequent execution of step 1404, a selective growth medium is transferred to the growth module to enable selection of edited cells from the first round of editing. The robotic handling system 108 of FIGS. 1A-B or 1708 of FIGS. 17A-17B, for example, may transfer the selective growth medium from a vial or container in a reagent cartridge situated in a position designated for selective growth medium. Prior to transferring the selective growth medium, machine-readable indicia may be scanned upon the vial or other container or reservoir situated in the position designated for the selective growth medium to confirm the contents of the vial, container, or reservoir. Further, the machine-readable indicia may indicate a type of selective growth medium provided to the instrument. The type of selective growth medium, in some embodiments, may cause the instrument to select a particular processing script (e.g., settings and activation of the growth module appropriate for the particular selective growth medium). Particular examples of recursive editing workflows are described in relation to FIGS. 15A through 15C.

In some implementations, the method 1400 can be timed to introduce materials and/or complete the editing cycle or growth cycle in coordination with a user's schedule. For example, the automated multi-module cell editing instrument may provide the user the ability to schedule completion of one or more cell processing cycles (e.g., one or more recursive edits) such that the method 1400 is enacted with a goal of completion at the user's preferred time. The time scheduling, for example, may be set through a user interface, such as the user interface 1816 of FIG. 18. For illustration only, a user may set completion of a first cycle to 4:00 PM so that the user can supply additional cartridges of materials to the automated multi-module cell editing instrument to enable overnight processing of another round of cell editing. Thus a user may time the programs so that two or more cycles may be programmed in a specific time period, e.g., a 24-hour period.

In some implementations, throughout the method 1400, the automated multi-module cell editing instrument may alert the user to its current status. For example, the user interface 1816 of FIG. 18 may present a graphical indication of the present stage of processing. In a particular example, a front face of the automated multi-module call processing instrument may be overlaid with a user interface (e.g., touch screen) that presents an animated graphic depicting present status of the cell processing. The user interface may further present any user and/or default settings associated with the current processing stage (e.g., temperature setting, time setting, etc.). In certain implementations, the status may be communicated to a user via wireless communications controller.

Although illustrated as a particular series of operations, in other embodiments, more or fewer steps may be included in the method 1400. For example, in some embodiments, prior to engaging in each round of editing, the contents of reservoirs, cartridges, and/or vials may be screened to confirm appropriate materials are available to proceed with processing. For example, in some embodiments, one or more imaging sensors (e.g., barcode scanners, cameras, etc.) may confirm contents at various locations within the housing of the automated multi-module cell editing instrument. In one example, multiple imaging sensors may be disposed within the housing of the automated multi-module cell editing instrument, each imaging sensor configured to detect one or more materials (e.g., machine-readable indicia such as barcodes or QR codes, shapes/sizes of materials, etc.). In another example, at least one imaging sensor may be moved by the robotic handling system to multiple locations to detect one or more materials. In further embodiments, one or more weight sensors may detect presence or absence of disposable or replaceable materials. In an illustrative example, the transfer tip supply holder may include a weight sensor to detect whether or not tips have been loaded into the region. In another illustrative example, an optical sensor may detect that a level of liquid waste has reached a threshold level, requiring disposal prior to continuation of cell processing or addition of liquid if the minimum level has not been reached to proceed. Requests for additional materials, removal of waste supplies, or other user interventions (e.g., manual cleaning of one or more elements, etc.), in some implementations, are presented on a graphical user interface of the automated multi-module cell editing instrument. The automated multi-module cell editing instrument, in some implementations, contacts the user with requests for new materials or other manual interventions, for example through a software app, email, or text message.

Workflows for Cell Processing in an Automated Multi-Module Cell Editing Instrument The automated multi-module cell editing instrument is designed to perform a variety of cell processing workflows using the same modules. For example, source materials, in individual containers or in cartridge form, may differ and the corresponding instructions (e.g., software script) may be selected accordingly, using the same basic instrumentation and robotic handling system; that is, the multi-module cell editing instrument can be configured to perform a number of different workflows for processing cell samples and different types of cell samples. In embodiments, a same workflow may be performed iteratively to recursively edit a cell sample. In other embodiments, a cell sample is recursively edited, but the workflow may change from iteration to iteration.

Figure 15A:
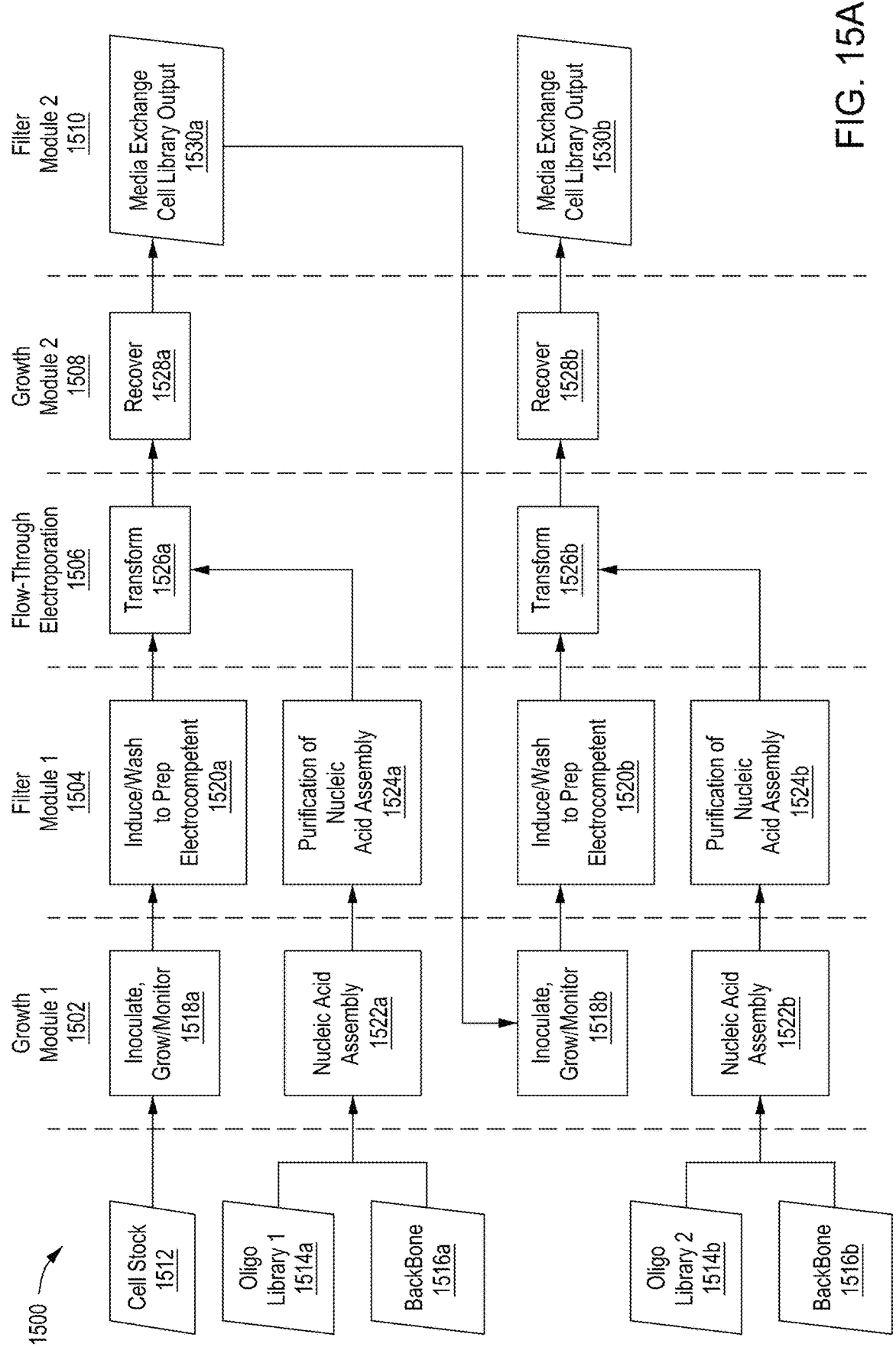
FIG. 15A is a flow diagram of a first example workflow for automated editing of bacterial cells by an automated multi-module cell editing instrument.
Figure 15B:
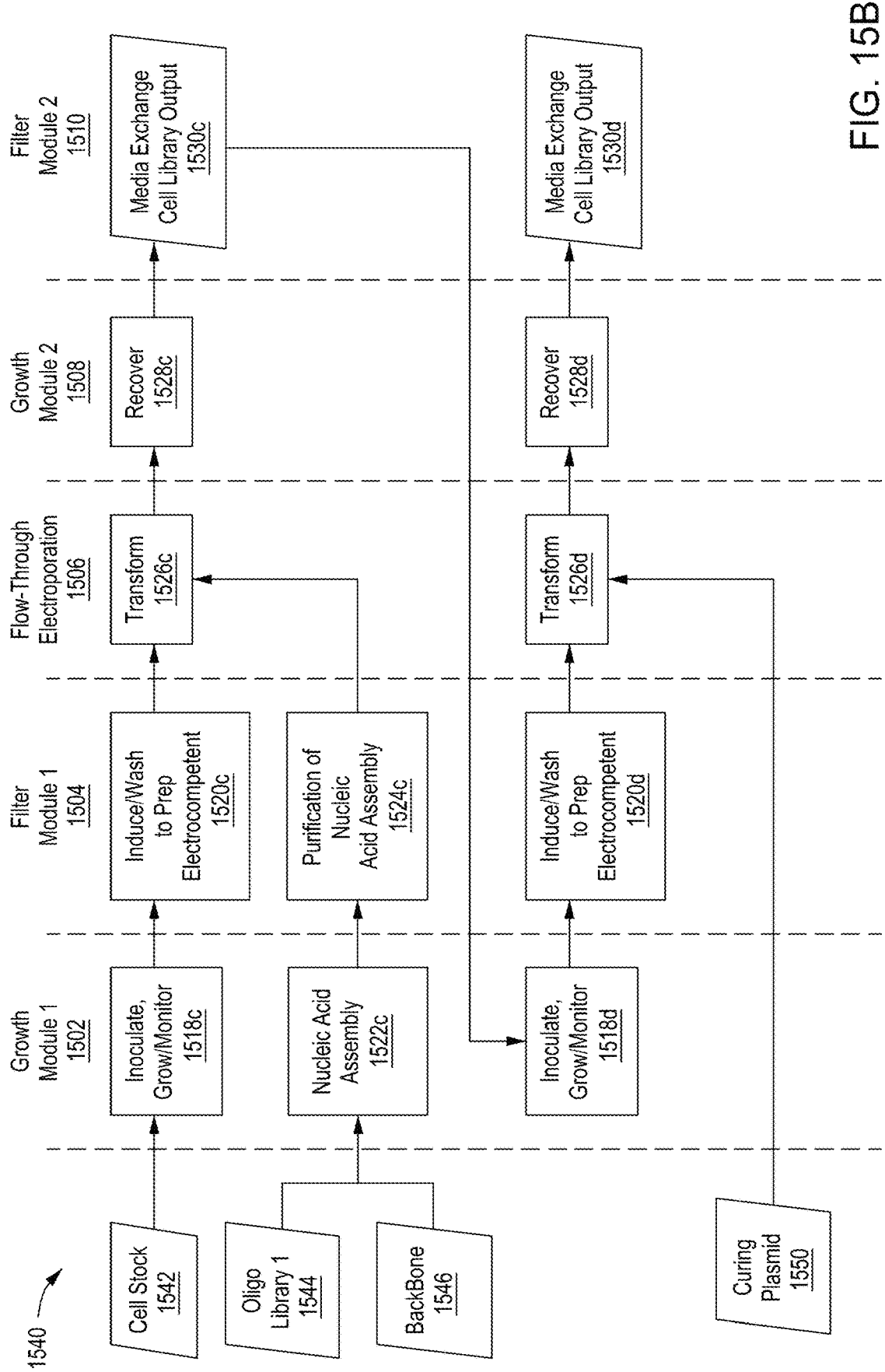
FIG. 15B is a flow diagram of a second example workflow for automated editing of a bacterial cells by an automated multi-module cell editing instrument.
Figure 15C:
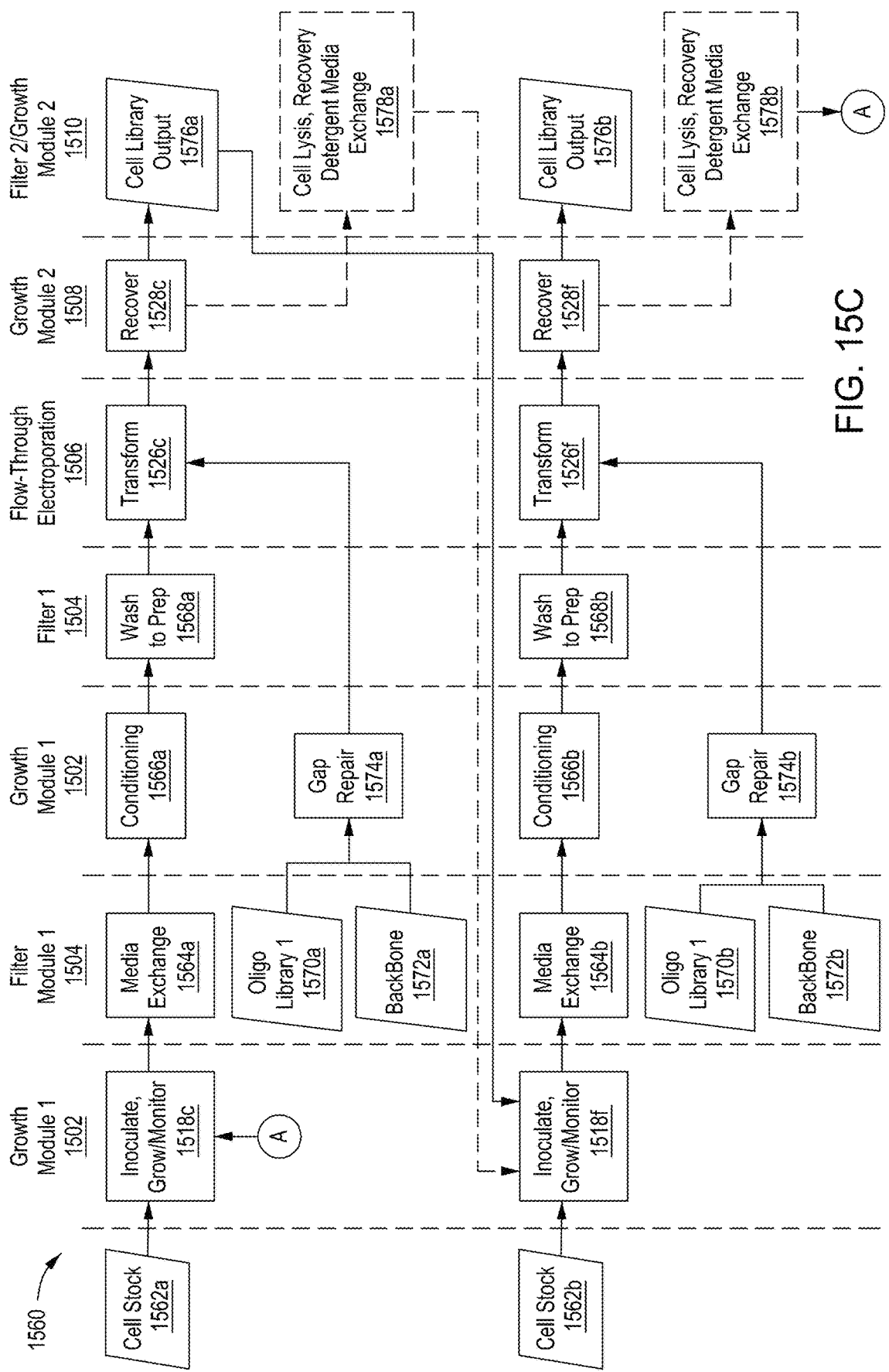
FIG. 15C is a flow diagram of an example workflow for automated cell editing of yeast cells by an automated multi-module cell editing instrument.

FIGS. 15A through 15C illustrate example workflows that may be performed using an automated multi-module cell editing instrument including two cell growth modules 1502, 1508, two filtration modules 1504 and 1510, and a flow-through electroporation module 1506. Although described as separate growth modules 1502, 1508 and filtration modules 1504, 1510, each may instead be designed as a dual or integrated module. For example, a dual growth module, including growth modules 1502 and 1508, may include dual rotating growth vials sharing some circuitry, controls, and a power source and disposed in a same housing. Similarly, a dual filtration module may include filtration modules 1504 and 1510, including two separate filters and liquid supply tubes but sharing circuitry, controls, a power source, and a housing. The modules 1502, 1504, 1506, 1508, and 1510, for example, may be part of the instrument 100 described in relation to FIGS. 1A and 1B.

Turning to FIG. 15A, a flow diagram illustrates a first bacteria genome editing workflow 1500 involving two stages of processing having identical processing steps, resulting in two edits to a cell stock 1512. Each stage may operate based upon a different cartridge of source materials. For example, a first cartridge may include a first oligo library 1514a and a first vector backbone, e.g., an expression plasmid 1516a. A second cartridge, introduced into the automated multi-module cell editing instrument between processing stages or prior to processing but in a different position than the first cartridge, may include a second oligo library 1514b and a second vector backbone 1516b. Each cartridge may be considered as a "library cartridge" for building a library of edited cells. The cell stock 1512, in some embodiments, is included in the first library cartridge. The cell stock 1512 may be supplied within a kit including the two cartridges. Alternatively, a user may add a container (e.g., vial or tube) of the cell stock 1512 to a purchased cartridge.

The workflow 1500, in some embodiments, is performed based upon a script executed by a processing system of the automated multi-module cell editing instrument, such as the processing system 1810 of FIG. 18. The script, in a first example, may be accessed via a machine-readable marker or tag added to the first cartridge. In some embodiments, each processing stage is performed using a separate script. For example, each cartridge may include an indication of a script or a script itself for processing the contents of the cartridge.

In some implementations, the first stage begins with introducing the cell stock 1512 into the first growth module 1502 for inoculation, growth, and monitoring (1518*a*). In one example, a robotic handling system adds a vial of the cell stock 1512 to medium contained in the rotating growth vial of the first growth module 1502. In another example, the robotic handling system pipettes cell stock 1512 from the first cartridge and adds the cell stock 1012 to the medium contained in the rotating growth vial. The cells may have been maintained at a temperature of 4° C. at this point. In a particular example, 20 ml of cell stock may be grown within a rotating growth vial of the first growth module 1002 at a temperature of 30° C. to an OD of 0.50. The cell stock 1012 added to the first growth module 1502 may be monitored over time until 0.50 OD is sensed via automated monitoring of the growth vial. Monitoring may be periodic or continuous. This may take, for example, around 900 minutes (estimated), although the exact time depends upon detection of the desired OD.

In some implementations, after growing the cells to the desired OD, an inducer is added to the first growth module 1502 for inducing the cells. In a particular example, 100 μl of inducer may be added, and the growth module 1502 may bring the temperature of the mixture up to 42° C. and hold for 15 minutes.

The cell stock 1512, after growth and induction, is transferred to the first filtration module 1504, in some implementations, for rendering the cells electrocompetent (1520*a*) and to reduce the volume of the cells for transformation. In one example, a robotic handling system moves the vial of the cell stock 1512 from the rotating growth vial of the first growth module 1502 to a vial holder of the first filtration module 1504. In another example, the robotic handling system pipettes cell stock 1512 from the rotating growth vial of the first growth module 1502 and delivers it to the first filtration module 1504. For example, the disposable pipetting tip used to transfer the cell stock 1512 to the first growth module 1502 may be used to transfer the cell stock 1512 from the first growth module 1502 to the first filtration module 1504. In some embodiments, prior to transferring the cell stock 1512 from the first growth module 1502 to the first filtration module 1504, the first growth module 1502 is cooled to 4° C. so that the cell stock 1512 is similarly reduced to this temperature. In a particular example, the temperature of the first growth module 1502 may be reduced to about 4° C. over the span of about 8 minutes, and the growth module 1502 may hold the temperature at 4° C. for about 15 minutes to ensure reduction in temperature of the cell stock 1512.

Prior to transferring the cell stock, in some implementations, a filter of the first filtration module 1504 is pre-washed using a wash solution. The wash solution, for example, may be supplied in a wash cartridge, such as the cartridge 106 described in relation to FIG. 1A.

The first filtration module 1504, for example, may be part of a dual filtration module such as the filtration module 1250 described in relation to FIGS. 12B and 12C. In a particular example, the first filtration module 1504 may be maintained at 4° C. during the washing and eluting process while transferring cell materials between an elution vial and the first filtration module 1504.

In some implementations, upon rendering the cells electrocompetent at the filtration module 1504, the cell stock 1512 is transferred to a transformation module 1506 (e.g., flow-through electroporation module) for transformation. In one example, a robotic handling system moves the vial of the cell stock 1512 from the vial holder of the first filtration module 1504 to a reservoir of the flow-through electroporation module 1506. In another example, the robotic handling system pipettes cell stock 1512 from the first filtration module 1502 or a temporary reservoir and delivers it to the first filtration module 1504. In a particular example, 400 μl of the concentrated cell stock 1512 from the first filtration module 1504 is transferred to a mixing reservoir prior to transfer to the transformation module 1506. For example, the cell stock 1512 may be transferred to a reservoir in a cartridge for mixing with the assembled nucleic acids, then transferred by the robotic handling system using a pipette tip. In a particular example, the transformation module is maintained at 4° C. The cell stock 1512 may be transformed, in an illustrative example, in about four minutes.

While the cells are growing and/or rendered electrocompetent, in some implementations, a first oligo library 1514*a* and the vector backbone 1516*a* are assembled using a nucleic acid assembly process to create assembled nucleic acids, e.g., using a thermal cycler and ligation process or in an nucleic acid assembly master mix (1522*a*). The assembled nucleic acids may be created at some point during the first processing steps 1518*a*, 1520*a* of the first stage of the workflow 1500. Alternatively, assembled nucleic acids may be created in advance of beginning the first processing step 1518.

In some embodiments, the nucleic acids are assembled using a nucleic acid assembly module of the automated multi-module cell editing instrument. For example, the robotic handling system may add the first oligo library 1514*a* and the vector backbone 1516*a* from a library vessel in the reagent cartridge in the automated multi-module cell editing instrument to a nucleic acid assembly module (not illustrated), such as the nucleic acid assembly module 1710*g* described in relation to FIG. 17B. In specific embodiments, the nucleic acid assembly performed in the nucleic acid assembly module is an isothermal nucleic acid assembly. The nucleic acid assembly mix, for example, may include in a particular example 50 μl Gibson Assembly® Master Mix, 25 μl vector backbone 1516*a*, and 25 μl oligo 1514*a*. The nucleic acid assembly module may be held at room temperature or at another desired temperature.

In other embodiments, the nucleic acids are assembled externally to the multi-module cell editing instrument and added as a functioning source material. For example, a vial or tube of assembled nucleic acids may be added to a reagent cartridge prior to activating the first step 1518*a* of inoculation, growth, and cell processing. In a particular example, 100 μl of assembled nucleic acids are provided.

In other embodiments, the nucleic acids are introduced to the cells in components, and the machinery of the transformed cells will perform the assembly within the cell, e.g., using gap repair mechanisms in yeast cells.

In some implementations, the assembled nucleic acids are purified (1524*a*) prior to further use. Following assembly, for example, nucleic acids, may be transferred by the robotic handling system from the nucleic acid assembly module to a purification module (not shown). In other embodiments, the nucleic acid assembly module may include purification features (e.g., a combination nucleic acid assembly and purification module). In further embodiments, the assembled or separate nucleic acids are purified externally to the multi-module cell editing instrument and added as a functional source material. For example, a vial or tube of purified assembled nucleic acids may be added to a reagent cartridge with the cell stock 1012 prior to activating the first step 1518*a* of cell processing.

In a particular example, 100 µl of assembled nucleic acids in nucleic acid assembly mix are assembled and subsequently purified. In some embodiments, magnetic beads are added to the nucleic acid assembly module, for example 180 µl of magnetic beads in a liquid suspension may be added to the nucleic acid assembly module by the robotic handling system. A magnet functionally coupled to the nucleic acid assembly module may be activated and the sample washed in 200 µl ethanol (e.g., the robotic handling system may transfer ethanol to the nucleic acid assembly module). Liquid waste from this operation, in some embodiments, is transferred to a waste receptacle of the cartridge (e.g., by the robotic handling system using a same pipette tip as used in transferring the ethanol). At this point, the de-salted assembled nucleic acids may be transferred to a holding container, such as a reservoir of the cartridge. The desalted assembled nucleic acids may be held, for example at a temperature of 4° C. until cells are ready for transformation. In a particular example, 100 µl of the assembled nucleic acids may be added to the 400 µl of the concentrated cell stock 1512 in the mixing reservoir prior to transfer to the transformation module 1506. In some embodiments, the purification process may take about 16 minutes.

In some implementations, the assembled nucleic acids and cell stock 1512 are added to the flow-through electroporation module 1506 and the cell stock 1512 is transformed (1526*a*). The robotic handling system, for example, may transfer the mixture of the cell stock 1512 and assembled nucleic acids to the flow-through electroporation module 1506 from a mixing reservoir, e.g., using a pipette tip or through transferring a vial or tube. In some embodiments, a built-in flow-through electroporation module such as the flow-through electroporation modules depicted in FIGS. 4A-4I, 5A-5H, 6, 8A-8U, and 9A-9C is used to transform the cell stock 1512. In other embodiments, a cartridge-based electroporation module such as shown in FIGS. 10A-10C and 10E is used to transform the cell stock 1512. The electroporation module 1506, for example, may be held at a temperature of 4° C. The electroporation process, in an illustrative example, may take about four minutes.

The transformed cell stock 1512 in some implementations is transferred to the second growth module 1508 for recovery (1528*a*). In a particular example, transformed cells undergo a recovery process in the second growth module 1508 at a temperature of 30° C. The transformed cells, for example, may be maintained in the second growth module 1508 for a predetermined period of time, e.g., about an hour for recovery.

In some implementations, a selective medium is transferred to the second growth vial (not illustrated), and the cells are left to incubate for a further period of time in a selection process. In an illustrative example, an antibiotic may be transferred to the second growth vial, and the cells may incubate for an additional two hours at a temperature of 30° C. to select for cells that have received the exogenous materials.

After recovery, the cells may be ready for either another round of editing or for storage in a vessel, e.g., for further experiments conducted outside of the automated cell processing environment. Alternatively, a portion of the cells may be transferred to a storage unit as cell library output, while another portion of the cells may be prepared for a second round of editing.

In some implementations, in preparation for a second round of editing the transformed cells are transferred to the second filtration module 1510 for media exchange and filtering (1530*a*). Prior to transferring the transformed cell stock, in some implementations, a filter of the second filtration module 1504 is pre-washed using a wash solution. The wash solution, for example, may be supplied in a wash cartridge, such as the cartridge 106 described in relation to FIG. 1A. The second filtration module 1510, for example, may be fluidly connected to the wash solution of the wash cartridge, as described in relation to FIG. 12A.

The second filtration module 1510, for example, may be part of a dual filtration module such as the filtration module 1250 described in relation to FIGS. 12B and 12C. In a particular example, the second filtration module 1510 may be maintained at a predetermined temperature (e.g., 4° C.) during the washing and eluting process while transferring cell materials between an elution vial and the second filtration module 1510. The output of this filtration process, in a particular example, is deposited in a vial or tube to await further processing, e.g., transfer to a transformation module. The vial or tube may be maintained in a storage unit at a temperature of 4° C.

The first stage of processing may take place during a single day. In one illustrative embodiment, the first stage of processing is estimated to take under 19 hours to complete (e.g., about 18.7 hours). At this point in the workflow 1500, in some implementations, new materials are manually added to the automated multi-module cell editing instrument. For example, a new reagent cartridge may be added. Further, a new wash cartridge, replacement filters, and/or replacement pipette tips may be added to the automated multi-module cell editing instrument at this point. Further, in some embodiments, the filter module may undergo a cleaning process and/or the solid and liquid waste units may be emptied in preparation for the next round of processing In yet other embodiments, the reagent cartridges may provide reagents for two or more cycles of editing, thus not requiring a change between two or more editing rounds.

In some implementations, the second round of editing involves the same modules 1502, 1504, 1506, 1508, and 1510, the same processing steps 1518, 1520, 1522, 1524, 1526, 1528, and 1530, and the same temperature and time ranges as the first processing stage described above. For example, the second oligo library 1514*b* and the second vector backbone 1516*b* may be used to edit the transformed cells in much the same manner as described above. Although illustrated as a two-stage process, in other embodiments, up to two, four, six, eight, or more recursions may be conducted to continue to edit the same cell stock 1512.

In other implementations, turning to FIG. 15B, a workflow 1540 involves the same modules 1502, 1504, 1506, 1508, and 1510 as well as the same processing steps 1518, 1520, 1522, 1524, 1526, 1528, and 1530 for the first stage of process. However, unlike the workflow 1500 of FIG. 15A, a second stage of the workflow 1540 of FIG. 15B involves a curing steps. "Curing" is a process in which a vector—for example the editing vector used in the prior round of editing, the "engine" vector comprising the expression sequence for the nuclease, or both—are eliminated from the transformed cells. Curing can be accomplished by, e.g., cleaving the editing vector using a curing plasmid thereby rendering the editing and/or engine vector nonfunctional (exemplified in the workflow of FIG. 15*b*); diluting the vector in the cell population via cell growth (that is, the more growth cycles the cells go through, the fewer daughter cells will retain the editing or engine vector(s)) (not shown), or by, e.g., utilizing a heat-sensitive origin of replication on the editing or engine vector (not shown). In one example, a "curing plasmid" may be contained within the reagent cartridge of the automated instrument, or added manually to the instrument prior to the second stage of processing. As with the workflow 1500, in some embodiments, the workflow 1540 is performed based upon a script executed by a processing system of the automated multi-module cell editing instrument, such as the processing system 1810 of FIG. 18. The script, in a first example, may be accessed via a machine-readable marker or tag added to the first cartridge. In some embodiments, each processing stage is performed using a separate script. For example, each cartridge may include an indication of a script or a script itself for processing the contents of the cartridge. In this manner, for example, the second stage, involving the curing cartridge, may be performed using a script designed for the settings (e.g., temperatures, times, material quantities, etc.) appropriate for curing. The conditions for curing will depend on the mechanism used for curing; that is, in this example, how the curing plasmid cleaves the editing and/or engine plasmid.

In some implementations, the second stage of the workflow 1540 begins by receiving first-edited cells from the first stage of the workflow 1540 at the first growth module 1502. For example, the first-edited cells may have been edited using a cell stock 1542, an oligo library 1544, and a vector backbone 1546 through applying the steps 1518, 1520, 1522, 1524, 1526, 1528, and 1530 as described in relation to the workflow 1500 of FIG. 15A. The first-edited cell stock 1542, for example, may be transferred to the first growth module 1502 by a robotic handling system. In one example, a robotic handling system adds a vial of the first-edited cell stock 1542 to a rotating growth vial of the first growth module 1502. In another example, the robotic handling system pipettes first-edited cell stock 1542 from a receptacle of a storage unit and adds the cell stock 1542 to the rotating growth vial. The cells may have been maintained at a temperature of 4° C. at this point.

In some implementations, the first-edited cells are inoculated, grown, and monitored in the first growth module 1502 (1518*d*). In a particular example, an aliquot of the first-edited cell stock 1542 may be transferred to a rotating growth vial containing, e.g., 20 mL of growth medium at a temperature of 30° C. to an OD of 0.50. The cell stock 1542 added to the first growth module 1502 may be monitored over time until 0.50 OD is sensed via the automated monitoring. Monitoring may be periodic or continuous. This may take, for example, around 900 minutes (estimated), although the exact time depends upon detection of the desired OD.

In some implementations, after growing to the desired OD, an inducer is added to the first growth module 1502 for inducing the cells. In a particular example, 100 µl of inducer may be added, and the growth module 1502 may bring the temperature of the mixture up to 42° C. and hold for 15 minutes.

The first-edited cell stock 1542, after growth and induction, is transferred to the first filtration module 1504, in some implementations, for rendering the first-edited cells electrocompetent (1520*d*). In one example, a robotic handling system moves the vial of the first-edited cell stock 1542 from the rotating growth vial of the first growth module 1502 to a vial holder of the first filtration module 1504. In another example, the robotic handling system pipettes first-edited cell stock 1542 from the rotating growth vial of the first growth module 1502 and delivers it to the first filtration module 1504. For example, the disposable pipetting tip used to transfer the first-edited cell stock 1542 to the first growth module 1502 may be used to transfer the cell stock 1542 from the first growth module 1502 to the first filtration module 1504. In some embodiments, prior to transferring the cell stock 1542 from the first growth module 1502 to the first filtration module 1504, the first growth module 1502 is cooled to 4° C. so that the cell stock 1542 is similarly reduced to this temperature. In a particular example, the temperature of the first growth module 1502 may be reduced to about 4° C. over the span of about 8 minutes, and the growth module 1502 may hold the temperature at 4° C. for about 15 minutes to ensure reduction in temperature of the cell stock 1512.

Prior to transferring the first-edited cell stock 1542 to the filtration module, in some implementations a filter of the first filtration module 1504 is pre-washed using a wash solution. The wash solution, for example, may be supplied in a wash cartridge, such as the cartridge 106 described in relation to FIG. 1A. The first filtration module 1504, for example, may be fluidly connected to the wash solution of the wash cartridge.

The first filtration module 1504, for example, may be part of a dual filtration module such as the filtration module 1250 described in relation to FIGS. 12B and 12C. In a particular example, the first filtration module 1504 may be maintained at a predetermined temperature (e.g., 4° C.) during the washing and eluting process while transferring cell materials between an elution vial and the first filtration module 1504.

In some implementations, upon rendering the first-edited cells electrocompetent at the filtration module 1504 (1520*d*), the first-edited cell stock 1542 is transferred to a transformation module 1506 (e.g., FTEP module) for transformation. In one example, a robotic handling system moves the vial of the cell stock 1542 from the vial holder of the first filtration module 1504 to a reservoir of the flow-through electroporation module 1506. In another example, the robotic handling system pipettes cell stock 1542 from the first filtration module 1502 or a temporary reservoir and delivers it to the first filtration module 1504. In a particular example, 400 µl of the concentrated cell stock 1542 from the first filtration module 1504 is transferred to a mixing reservoir prior to transfer to the transformation module 1506. For example, the cell stock 1542 may be transferred to a reservoir in a cartridge for mixing with a curing plasmid 1550, then mixed and transferred by the robotic handling system using a pipette tip. In a particular example, the transformation module 1506 is maintained at a predetermined temperature, e.g., 4° C. The cell stock 1542 may be transformed, in an illustrative example, in about four minutes.

The transformed cell stock 1542, in some implementations, is transferred to the second growth module 1508 for recovery/curing (1528*d*). In a particular example 20 ml of transformed cells undergo a recovery process in the second growth module 1508 at a temperature of 30° C. The transformed cells, for example, may be maintained in the second growth module 1508 for about an hour for recovery. If another round of editing is desired, the first editing plasmid or vector is cured. If another round of editing is not desired, the first editing plasmid and the engine plasmid may be cured.

After recovery and curing, the cells may be ready for either another round of editing or for storage to be used in further research outside the automated cell processing instrument. For example, a portion of the cells may be transferred to a storage unit as cell library output, while another portion of the cells may be prepared for a second round of editing.

In some implementations, in preparation for a second round of editing, the transformed cells are transferred to the second filtration module 1510 for media exchange and filtering (1530d) containing glycerol for rendering the cells electrocompetent. Prior to transferring the transformed cell stock, in some implementations, a filter of the second filtration module 1504 is pre-washed using a wash solution. The wash solution, for example, may be supplied in a wash cartridge, such as the cartridge 106 described in relation to FIG. 1A. The second filtration module 1510, for example, may be fluidly connected to the wash solution of the wash cartridge, as described in relation to FIG. 12A.

The second filtration module 1510, for example, may be part of a dual filtration module such as the filtration module 1250 described in relation to FIGS. 12B and 12C. In a particular example, the second filtration module 1510 may be maintained at 4° C. during the washing and eluting process while transferring cell materials between an elution vial and the second filtration module 1510. The output of this filtration process, in a particular example, are electrocompetent cells deposited in a vial or tube to await further processing. The vial or tube may be maintained in a storage unit at a temperature of 4° C.

Turning to FIG. 15C, a flow diagram illustrates a yeast workflow 1560 involving two stages of processing having identical processing steps, resulting in two edits to a cell stock 1562. Each stage may operate based upon a different cartridge of source materials. For example, a first cartridge may include a first oligo library 1570a and a first vector backbone 1572a. A second cartridge, introduced into the automated multi-module cell editing instrument between processing stages or prior to processing but in a different position than the first cartridge, may include a second oligo library 1570b and a second vector backbone 1572b. Each cartridge may be considered as a "library cartridge" for building a library of edited cells. Alternatively, a user may add a container (e.g., vial or tube of the cell stock 1562a to each of the purchased cartridges included in a yeast cell kit.

The workflow 1560, in some embodiments, is performed based upon a script executed by a processing system of the automated multi-module cell editing instrument, such as the processing system 1810 of FIG. 18. The script, in a first example, may be accessed via a machine-readable marker or tag added to the first cartridge. In some embodiments, each processing stage is performed using a separate script. For example, each cartridge may include an indication of a script or a script itself for processing the contents of the cartridge.

In some implementations, the first stage begins with introducing the cell stock 1562 into the first growth module 1502 for inoculation, growth, and monitoring (1518e). In one example, a robotic handling system adds a vial of the cell stock 1562 to a rotating growth vial of the first growth module 1502. In another example, the robotic handling system pipettes cell stock 1562 from the first cartridge and adds the cell stock 1562 to the rotating growth vial. The cells may have been maintained at a temperature of 4° C. at this point. In a particular example, 20 ml of cell stock may be grown within a rotating growth vial of the first growth module 1502 at a temperature of 30° C. to an OD of 0.75. The cell stock 1512 added to the first growth module 1502 may be automatically monitored over time within the growth module 1502 until 0.75 OD is sensed via the automated monitoring. Monitoring may be periodic or continuous.

In some implementations, an inducible expression system may be used. Thus, after growing to the desired OD, an inducer is added to the first growth module 1502 for inducing the cells. The inducer could be a small molecule or a media exchange to a medium with a different sugar like galactose.

The cell stock 1562, after growth and induction, is transferred to the first filtration module 1504, in some implementations, for exchanging media (1564a). In one example, a robotic handling system moves the vial of the cell stock 1562 from the rotating growth vial of the first growth module 1502 to a vial holder of the first filtration module 1504. In another example, the robotic handling system pipettes cell stock 1562 from the rotating growth vial of the first growth module 1502 and delivers it to the first filtration module 1504. For example, the disposable pipetting tip used to transfer the cell stock 1562a to the first growth module 1502 may be used to transfer the cell stock 1562 from the first growth module 1502 to the first filtration module 1504. In some embodiments, prior to transferring the cell stock 1562 from the first growth module 1502 to the first filtration module 1504, the first growth module 1502 is cooled to 4° C. so that the cell stock 1562 is similarly reduced to this temperature. In a particular example, the temperature of the first growth module 1502 may be reduced to about 4° C. over the span of about 8 minutes, and the growth module 1502 may hold the temperature at 4° C. for about 15 minutes to ensure reduction in temperature of the cell stock 1562. During media exchange, in an illustrative example, 0.4 ml of 1M sorbitol may be added to the cell stock 1562.

Prior to transferring the cell stock 1562, in some implementations, a filter of the first filtration module 1004 is pre-washed using a wash solution. The wash solution, for example, may be supplied in a wash cartridge, such as the cartridge 106 described in relation to FIG. 1A. The first filtration module 1504, for example, may be fluidly connected to the wash solution of the wash cartridge, as described in relation to FIG. 12A.

The first filtration module 1504, for example, may be part of a dual filtration module such as the filtration module 1250 described in relation to FIGS. 12B and 12C. In a particular example, the first filtration module 1504 may be maintained at 4° C. during the washing and eluting process while transferring cell materials between an elution vial and the first filtration module 1504.

After the media exchange operation, in some implementations, the cell stock 1562 is transferred back to the first growth module 1502 for conditioning (1566a). In one example, a robotic handling system moves the vial of the cell stock 1562 from the first filtration module 1504 to the first growth module 1502. In another example, the robotic handling system pipettes cell stock 1562 from the first filtration module 1504 and delivers it to the rotating growth vial of the first growth module 1502. During conditioning, for example, 5 ml DTT/LIAc and 80 mM of Sorbitol may be added to the cell stock 1562. For example, the robotic handling system may transfer the DTT/LIAc and Sorbitol, individually or concurrently, to the first growth module 1502. The cell stock 1562 may be mixed with the DTT/LIAc and Sorbitol, for example, via the rotation of the rotating growth vial of the first growth module 1502. During conditioning, the cell stock 1562 may be maintained at a temperature of 4° C.

In some implementations, after conditioning, the cell stock 1562 is transferred to the first filtration module 1504 for washing and preparing the cells (1568). For example, the cells may be rendered electrocompetent at this step. In one example, a robotic handling system moves the vial of the cell stock 1562 from the rotating growth vial of the first growth module 1502 to a vial holder of the first filtration module 1504. In another example, the robotic handling system pipettes cell stock 1562 from the rotating growth vial of the first growth module 1502 and delivers it to the first filtration module 1004.

Prior to transferring the cell stock, in some implementations, a filter of the first filtration module 1504 is pre-washed using a wash solution. The wash solution, for example, may be supplied in a wash cartridge, such as the cartridge 106 described in relation to FIG. 1A. The first filtration module 1504, for example, may be fluidly connected to the wash solution of the wash cartridge, as described in relation to FIG. 12A. In other embodiments, the same filter is used for rendering electrocompetent as the filter used for media exchange at step 1564*a*. In some embodiments, 1M sorbitol is used to render the yeast cells electrocompetent.

In some implementations, upon rendering electrocompetent at the filtration module 1504, the cell stock 1562 is transferred to a transformation module 1506 (e.g., flow-through electroporation module) for transformation. In one example, a robotic handling system moves the vial of the cell stock 1562 from the vial holder of the first filtration module 1504 to a reservoir of the flow-through electroporation module 1506. In another example, the robotic handling system pipettes cell stock 1562 from the filtration module 1504 or a temporary reservoir and delivers it to the first filtration module 1504. In a particular example, 400 µl of the concentrated cell stock 1562 from the first filtration module 1504 is transferred to a mixing reservoir prior to transfer to the transformation module 1506. For example, the cell stock 1562 may be transferred to a reservoir in a cartridge for mixing with the nucleic acid components (vector backbone and editing oligonucleotide), then mixed and transferred by the robotic handling system using a pipette tip. Because the vector backbone and editing oligonucleotide are assembled in the cells (in vivo), a nucleic acid assembly module is not a necessary component for yeast editing. In a particular example, the transformation module is maintained at 4° C.

In some implementations, the nucleic acids to be assembled and the cell stock 1562 is added to the FTEP module 1506 and the cell stock 1562 is transformed (1526*e*). The robotic handling system, for example, may transfer the mixture of the cell stock 1562*e* and nucleic acid assembly to the flow-through electroporation module 1506 from a mixing reservoir, e.g., using a pipette tip or through transferring a vial or tube. In some embodiments, a built-in FTEP module such as the flow-through electroporation modules FIGS. 4A-4I, 5A-5G, 6, 8A-8U, 9A-9C, and 10A-10C (that is, single unit FTEPs) is used to transform the cell stock 1562*e*. In other embodiments, a cartridge-based electroporation module is used to transform the cell stock 1562*e*. The FTEP module 1506, for example, may be held at a temperature of 4° C.

The transformed cell stock 1562*e*, in some implementations, is transferred to the second growth module 1508 for recovery (1528*a*). In a particular example, 20 ml of transformed cells undergo a recovery process in the second growth module 1508.

In some implementations, a selective medium, e.g. an auxotrophic growth medium or a medium containing a drug, is transferred to the second growth vial (not illustrated), and the cells are left to incubate for a further period of time in a selection process. In an illustrative example, an antibiotic may be transferred to the second growth vial, and the cells may incubate for an additional two hours at a temperature of 30° C.

After recovery, the cells may be ready for either another round of editing or for storage in a cell library. For example, a portion of the cells may be transferred to a storage unit as cell library output (1576*a*), while another portion of the cells may be prepared for a second round of editing (1578*a*). The cells may be stored, for example, at a temperature of 4° C.

In some implementations, in preparation for a second round of editing, the transformed cells are transferred to the second filtration module 1510 for media exchange (1578*a*). Prior to transferring the transformed cell stock 1562*a*, in some implementations, a filter of the second filtration module 1504 is pre-washed using a wash solution. The wash solution, for example, may be supplied in a wash cartridge, such as the cartridge 106 described in relation to FIG. 1A. The second filtration module 1510, for example, may be fluidly connected to the wash solution of the wash cartridge, as described in relation to FIG. 12A.

The second filtration module 1510, for example, may be part of a dual filtration module such as the filtration module 1250 described in relation to FIGS. 12B and 12C. In a particular example, the second filtration module 1510 may be maintained at 4° C. during the washing and eluting process while transferring cell materials between an elution vial and the second filtration module 1510.

In some implementations during the filtration process, an enzymatic preparation is added to lyse the cell walls of the cell stock 1562*a*. For example, a yeast lytic enzyme such as Zylomase® may be added to lyse the cell walls. The yeast lytic enzyme, in a particular example, may be incubated in the cell stock 1526*a* for between 5-60 minutes at a temperature of 30° C. The output of this filtration process, in a particular example, is deposited in a vial or tube to await further processing. The vial or tube may be maintained in a storage unit at a temperature of 4° C.

The first stage of processing may take place during a single day. At this point of the workflow 1560, in some implementations, new materials are manually added to the automated multi-module cell editing instrument. For example, new cell stock 1562*b* and a new reagent cartridge may be added. Further, a new wash cartridge, replacement filters, and/or replacement pipette tips may be added to the automated multi-module cell editing instrument at this point. Further, in some embodiments, the filter module may undergo a cleaning process and/or the solid and liquid waste units may be emptied in preparation for the next round of processing.

In some implementations, the second round of editing involves the same modules 1502, 1504, 1506, 1508, and 1510, the same processing steps 1518, 1564, 1566, 1526, 1528, and 1576 and/or 1578, and the same conditions (e.g., temperatures, time ranges, etc.) as the first processing stage described above. For example, the second oligo library 1570*b* and the second vector backbone 1572*b* may be used to edit a combination of the transformed cells in much the same manner as described above. Although illustrated as a two-stage process, in other embodiments, up to two, three, four, six, eight, or more recursions may be conducted to continue to edit the cell stock 1562.

Alternative Embodiments of Instrument Architecture

FIGS. 17A and 17B illustrate exemplary alternative embodiments of automated multi-module cell editing instruments for performing automated cell processing, e.g., editing in multiple cells in a single cycle. The automated multi-module cell editing instruments, for example, may be desktop instruments designed for use within a laboratory environment. The automated multi-module cell editing instruments may incorporate both reusable and disposable elements for performing various staged operations in conducting automated genome cleavage and/or editing in cells.

FIG. 17A is a block diagram of a first example instrument 1700 for performing automated cell processing, e.g., editing in multiple cells in a single cycle according to one embodiment of the disclosure. In some implementations, the instrument 1700 includes a deck, a reagent supply receptacle 1704 for introducing DNA sample components to the instrument 1700, a cell supply receptacle 1706 for introducing cells to the instrument 1700, and a robot handling system 1708 for moving materials between modules (for example, modules 1710a, 1710b, 1710c, 1710d) receptacles (for example, receptacles 1704, 1706, 1712a-c, 1722, 1724, and 1726), and storage units (e.g., units 1718, 1728, and 1714) of the instrument 1700 to perform the automated cell processing. Upon completion of editing of the cell supply 1706, in some embodiments, cell output 1712 may be transferred by the robot handling system 1708 to a storage unit 1714 for temporary storage and later retrieval.

The robotic handling system 1708, for example, may include an air displacement pump to transfer liquids from the various material sources to the various modules 1710a-d and storage unit 1714. In other embodiments, the robotic handling system 1708 may include a pick and place head to transfer containers of source materials (e.g., tubes) from a supply cartridge (not illustrated, discussed in relation to FIG. 1A) to the various modules 1710. In some embodiments, one or more cameras or other optical sensors (not shown), confirm proper gantry movement and position.

In some embodiments, the robotic handling system 1708 uses disposable transfer tips provided in a transfer tip supply 1716 to transfer source materials, reagents 1704 (e.g., for nucleic acid assembly), and cells 1706 within the instrument 1700. Used transfer tips, for example, may be discarded in a solid waste unit 1718. In some implementations, the solid waste unit 1718 contains a kicker to remove tubes from the pick and place head of robotic handling system 1708.

In some embodiments, the instrument 1700 includes electroporator cuvettes with sippers that connect to an air displacement pump. In some implementations, cells 1706 and reagent 1704 are aspirated into the electroporation cuvette through a sipper, and the cuvette is moved to one or more modules 1710a-d of the instrument 1700.

In some implementations, the instrument 1700 is controlled by a processing system 1720 such as the processing system 1810 of FIG. 18. The processing system 1720 may be configured to operate the instrument 1700 based on user input. The processing system 1720 may control the timing, duration, temperature and other operations of the various modules 1710 of the instrument 1700. The processing system 1720 may be connected to a power source (not shown) for the operation of the instrument 1700.

In some embodiments, instrument 1700 includes an FTEP device 1710c to introduce nucleic acid(s) into the cells 1706. For example, the robotic handling system 1708 may transfer the reagent 1704 and cells 1706 to the FTEP device 1710c. The FTEP device 1710 conducts cell transformation or transfection via electroporation. The processing system 1720 may control temperature and operation of the FTEP device 1710c. In some implementations, the processing system 1720 effects operation of the FTEP device 1710c according to one or more variable controls set by a user.

Following transformation, in some implementations, the cells may be transferred to a recovery module 1710d. In some embodiments, the recovery module 1710d is a combination recovery and induction of editing module. In the recovery module 1710d, the cells are allowed to recover, express the nucleic acids and, in an inducible nuclease system, a nuclease or guide RNA is induced in the cells, e.g., by means of temporally-controlled induction such as, in some examples, chemical, light, viral, or temperature induction or the introduction of an inducer molecule 1724 for expression of the nuclease.

Following editing, in some implementations the cells are transferred to the storage unit 1714, where the cells can be stored as cell output 1712a-d until the cells are removed for further study or retrieval of an edited cell population, e.g., an edited cell library.

In some implementations the instrument 1700 is designed for recursive genome editing, where multiple edits are sequentially introduced into genomes inside the cells of a cell population. In some implementations, the reagent supply 1704 is replenished prior to accessing cell output 1712a-d from the storage unit for recursive processing. In other implementations, multiple reagent supplies 1704 and/or large volumes thereof may be introduced into the instrument 1700 such that user interaction is not necessarily required prior to a subsequent processing cycle.

A portion of a cell output 1712a, in some embodiments, is transferred to an automated cell growth module 1710a. For example, all of the cell output 1712a may be transferred, or only an aliquot may be transferred such that the instrument retains incrementally modified samples. The cell growth module 1710a, in some implementations, measures the OD of the cells during growth to ensure they are at a desired concentration prior to induction of editing. Other measures of cell density and physiological state that can be used include but are not limited to, pH, dissolved oxygen, released enzymes, acoustic properties, and electrical properties.

To reduce the background of cells that have not received a genome edit, in some embodiments the growth module 1710a performs a selection process to enrich for the edited cells using a selective growth medium 1726. For example, the introduced nucleic acid can include a gene that confers antibiotic resistance or some other selectable marker. In some implementations, multiple selective genes or markers 1726 may be introduced into the cells during recursive editing. For example, alternating the introduction of selectable markers for sequential rounds of editing can eliminate the background of unedited cells and allow multiple cycles of the instrument 1700 to select for cells having sequential genome edits. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, and chloramphenicol-resistance gene.

From the growth module 1710a, the cells may be transferred to a filtration module 1710b. The filtration module 1710b or, alternatively, a cell wash and concentration module, may enable media exchange. In some embodiments, removing dead cell background is aided using lytic enhancers such as detergents, osmotic stress, temperature, enzymes, proteases, bacteriophage, reducing agents, or chaotropes. In other embodiments, cell removal and/or media exchange is used to reduce dead cell background. Waste product from the filtration module 1710b, in some embodiments, is collected in a liquid waste unit 1728.

After filtration, the cells may be presented to the FTEP device (transformation module) 1710*c*, and then to the recovery module 1710*d* and finally to the storage unit 1714 as detailed above.

Turning to FIG. 17B, similar to FIG. 17A, a second exemplary instrument 1740 for performing automated genome cleavage and/or editing in multiple cells in a single cycle includes the deck 1702, the reagent supply receptacle 1704 for introducing one or more nucleic acid components to the instrument 1740, the cell supply receptacle 1706 for introducing cells to the instrument 1740, and the robot handling system 1708 for moving materials between modules (for example, modules 1710*a*, 1710*b*, 1710*c*, 1710*f*, 1710*g*, 1710*m*, and 1710*h*), receptacles (for example, receptacles 1704 1706, 1712*a-c*, 1724, 1742, 1744, and 1746), and storage units (e.g., units 1714, 1718, and 1728) of the instrument 1740 to perform the automated cell processing. Upon completion of processing of the cell supply 1706, in some embodiments, cell output 1712*a-c* may be transferred by the robot handling system 1708 to the storage unit 1714 for temporary storage and later retrieval.

In some embodiments, the robotic handling system 1708 uses disposable transfer tips provided in the transfer tip supply 1716 to transfer source materials, a vector backbone 1742, editing oligos 1744, reagents 1704 (e.g., for nucleic acid assembly, nucleic acid purification, to render cells electrocompetent, etc.), and cells 1706 within the instrument 1740, as described in relation to FIG. 17A.

As described in relation to FIG. 17A, in some implementations, the instrument 1740 is controlled by the processing system 1720 such as the processing system 1810 of FIG. 18.

The instrument 1740, in some embodiments, includes a nucleic acid assembly module 1710*g*, and in certain exemplary automated multi-module cell editing instruments, the nucleic acid assembly module 1710*g* may perform in some embodiments nucleic acid assembly.

In some embodiments, after assembly of the nucleic acids, the nucleic acids (e.g., in the example of a nucleic acid assembly, the nucleic acid assembly mix (nucleic acids+ nucleic acid assembly reagents)) are transferred to a purification module 1710*h*. Here, unwanted components of the nucleic acid assembly mixture are removed (e.g., salts) and, in certain embodiments, the assembled nucleic acids are concentrated. For example, in an illustrative embodiment, in the purification module 1710*h*, the nucleic acid assembly mix may be combined with a no-salt buffer and magnetic beads, such as Solid Phase Reversible Immobilization (SPRI) magnetic beads or AMPure™ beads. The nucleic acid assembly mix may be incubated for sufficient time (e.g., 30 seconds to 10 minutes) for the assembled nucleic acids to bind to the magnetic beads. In some embodiments, the purification module includes a magnet configured to engage the magnetic beads. The magnet may be engaged so that the supernatant may be removed from the bound assembled nucleic acids and so that the bound assembled nucleic acids can be washed with, e.g., 80% ethanol. Again, the magnet may be engaged and the 80% ethanol wash solution removed. The magnetic bead/assembled nucleic acids may be allowed to dry, then the assembled nucleic acids may be eluted and the magnet may again be engaged, this time to sequester the beads and to remove the supernatant that contains the eluted assembled nucleic acids. The assembled nucleic acids may then be transferred to the transformation module (e.g., electroporator in a preferred embodiment). The transformation module may already contain the electrocompetent cells upon transfer.

Instrument 1740 includes an FTEP device 1710*c* for introduction of the nucleic acid(s) into the cells 1706, as described in relation to FIG. 17A. However, in this circumstance, the assembled nucleic acids 1704, output from the purification module 1710*h*, are transferred to the FTEP device 1710*c* to combine with the cells 1706.

Following transformation in the FTEP device 1710*c*, in some implementations, the cells may be transferred to a recovery module 1710*m*. In the recovery module 1710*e*, the cells are allowed to recover, express the exogenous nucleic acids, electroporated into the cells and, in an inducible system, the nuclease or other editing component such as the guide nucleic acid is induced, e.g., by means of temporally-controlled induction such as, in some examples, chemical, light, viral, or temperature induction or the introduction of the inducer molecule for expression of the editing component.

Following recovery, in some implementations the cells are transferred to an editing module 1710*f*. The editing module 1710*f* provides appropriate conditions to induce editing of the cells' genomes, e.g., through expression of the introduced nucleic acids and the induction of an inducible nuclease or guide nucleic acid. The editing components may be, in some examples, chemically induced, biologically induced (e.g., via inducible promoter) virally induced, light induced, temperature induced, and/or heat induced within the editing module 1710*f*.

Following editing, in some implementations, the cells are transferred to the storage unit 1714 as described in relation to FIG. 17A.

In some implementations, the instrument 1740 is designed for recursive genome editing, where multiple edits are sequentially introduced into genomes of cells in a cell population. In some implementations, the reagent supply 1704 is replenished prior to accessing cell output 1712 from the storage unit for recursive processing. For example, additional vector backbone 1742 and/or editing oligos 1744 may be introduced into the instrument 1740 for assembly and preparation via the nucleic acid assembly module 1710*g* and the purification module 1710*h*. In other implementations, multiple vector backbone volumes 1742 and/or editing oligos 1744 may be introduced into the instrument 1700 such that user interaction is not necessarily required prior to a subsequent processing cycle. For each subsequent cycle, the vector backbone 1742 and/or editing oligos 1744 may change. Upon preparation of the nucleic acid assembly, the nucleic acid assembly may be provided in the reagent supply 1704 or another storage region.

A portion of a cell output 1712*a*, in some embodiments, is transferred to the automated cell growth module 1710*a*, as discussed in relation to FIG. 17A.

To reduce background of cells that have not received a genome edit, in some embodiments, the growth module 1710*a* performs a selection process to enrich for the edited cells using a selective growth medium 1726, as discussed in relation to FIG. 17A.

From the growth module 1710*a*, the cells may be transferred to the filtration module 1710*b*, as discussed in relation to FIG. 17A. As illustrated, eluant from an eluting supply 1746 (e.g. buffer, glycerol) may be transferred into the filtration module 1710*b* for media exchange.

After filtration, the cells may be transferred to the FTEP device 1710*c* for transformation, and then to the recovery module 1710*m*, and the editing module 1710*f* and finally to the storage unit 1714 as detailed above.

In some embodiments, the automated multi-module cell editing instruments of FIGS. 17A and/or 17B contain one or more replaceable supply cartridges and a robotic handling system, as discussed in relation to FIGS. 1A and 1B. Each cartridge may contain one or more of a nucleic acid assembly mix, oligonucleotides, vector, growth media, selection agent (e.g., antibiotics), inducing agent, nucleic acid purification reagents such as Solid Phase Reversible Immobilization (SPRI) beads, ethanol, and 10% glycerol.

Although the exemplary instruments 1700, 1740 are illustrated as including a particular arrangement of modules 1710, these arrangements are for illustrative purposes only. For example, in other embodiments, more or fewer modules 1710 may be included within each of the instruments 1700, 1740. Also, different modules may be included in the instrument, such as, e.g., a module that facilitates cell fusion for providing, e.g., hybridomas, a module that amplifies nucleic acids before assembly, and/or a module that facilitates protein expression and/or secretion. Further, certain modules 1710 may be replicated within certain embodiments, such as the duplicate cell growth modules 110a, 110b of FIG. 1A. Each of the instruments 1700 and 1740, in another example, may be designed to accept a media cartridge such as the cartridges 104 and 106 of FIG. 1A. Further modifications are possible.

Control System for an Automated Multi-Module Cell Editing Instrument

Figure 16:
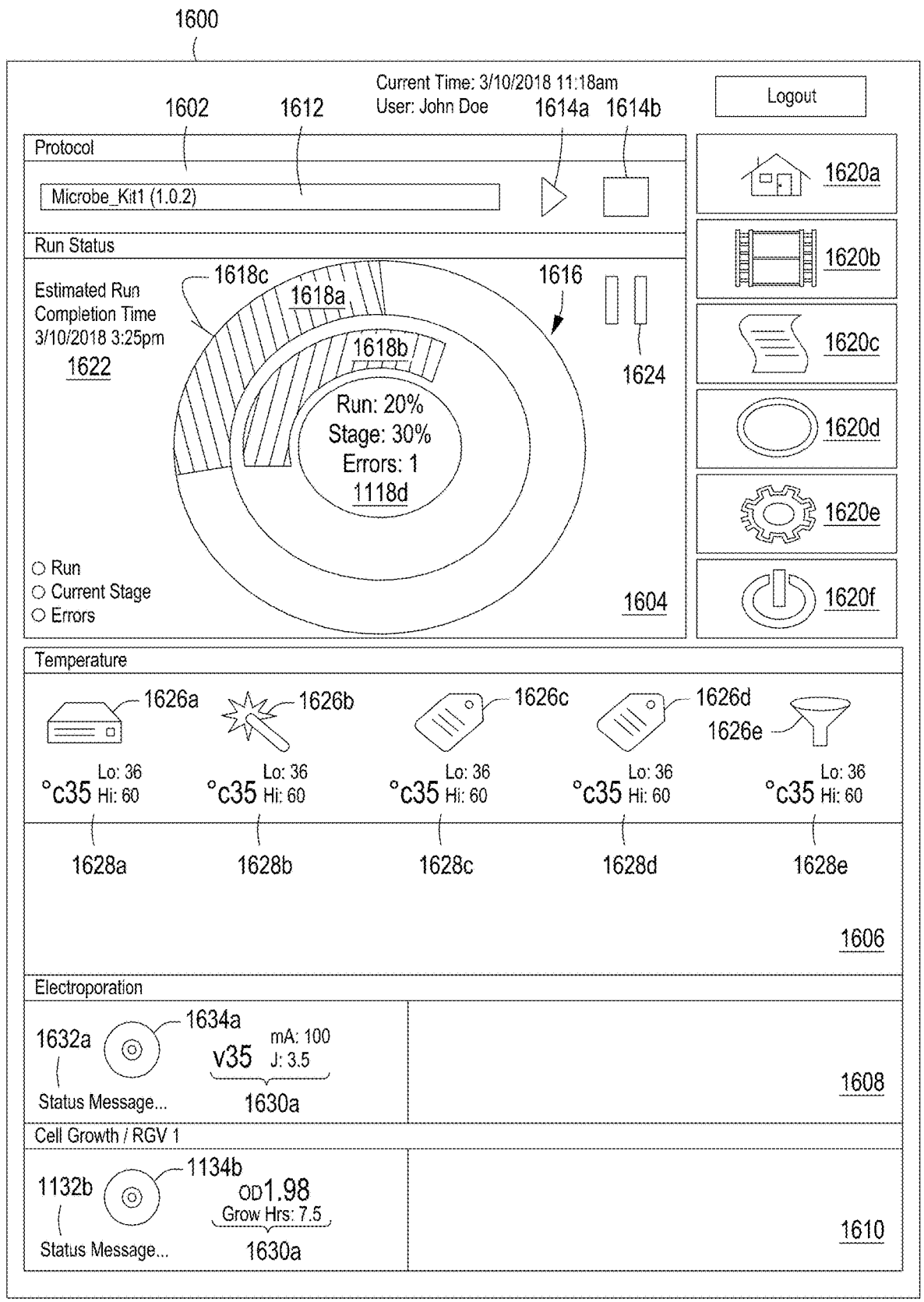
FIG. 16 illustrates an example graphical user interface for providing instructions to and receiving feedback from an automated multi-module cell editing instrument.

Turning to FIG. 16, a screen shot illustrates an example graphical user interface (GUI) 1600 for interfacing with an automated multi-module cell editing instrument. The interface, for example, may be presented on the display 236 of FIGS. 2C and 2D. In one example, the GUI 1600 may be presented by the processing system 1810 of FIG. 18 on the touch screen 1816.

In some implementations, the GUI 1600 is divided into a number of information and data entry panes, such as a protocol pane 1602, a temperature pane 1606, an electroporation pane 1608, and a cell growth pane 1610. Further panes are possible. For example, in some embodiments the GUI 1600 includes a pane for each module, such as, in some examples, one or more of each of a nucleic acid assembly module, a purification module, a cell growth module, a filtration module, a transformation module, an editing module, and a recovery module. The lower panes of the GUI 1600, in some embodiments, represent modules applicable to the present work flow (e.g., as selected in the protocol pane 1602 or as designated within a script loaded through a script interface (not illustrated)). In some embodiments, a scroll or paging feature may allow the user to access additional panes not illustrated within the screen shot of FIG. 16.

The GUI 1600, in some embodiments, includes a series of controls 1620 for accessing various screens such as the illustrated screen shot (e.g., through using a home control 1620a). For example, through selecting an editing control 1620b, the user may be provided the option to provide one, two or a series of cell editing steps. Through selecting a script control 1620c, the user may be provided the opportunity to add a new editing script or alter an existing editing script. The user in some embodiments, may select a help control 1620d to obtain further information regarding the features of the GUI 1600 and the automated multi-module cell editing instrument. In some implementations, the user selects a settings control 1620e to access settings options for desired processes and/or the GUI 1600 such as, in some examples, time zone, language, units, network access options. A power control 1620f, when selected, allows the user to power down the automated multi-module cell editing instrument.

Turning to the protocol pane 1602, in some implementations, a user selects a protocol (e.g., script or work flow) for execution by the automated multi-module cell editing instrument by entering the protocol in a protocol entry field 1612 (or, alternatively, drop-down menu). In other embodiments, the protocol may be selected through a separate user interface screen, accessed for example by selecting the script control 1620b. In another example, the automated multi-module cell editing instrument may select the protocol and present it in the protocol entry field 1612. For example, the processing system of the automated multi-module cell editing instrument may scan machine-readable indicia positioned on one or more cartridges loaded into the automated multi-module cell editing instrument to determine the appropriate protocol. As illustrated, the "Microbe_Kit1 (1.0.2)" protocol has been selected, which may correspond to a kit of cartridges and other disposable supplies purchased for use with the automated multi-module cell editing instrument.

In some implementations, the protocol pane 1602 further includes a start control 1614a and a stop control 1614b to control execution of the protocol presented in the protocol entry field 1612. The GUI 1600 may be provided on a touch screen interface, for example, where touch selection of the start control 1614a starts cell processing, and selection of the stop control 1614b stops cell processing.

Turning to the run status pane 1604, in some implementations a chart 1616 illustrates stages of the processing of the protocol identified in the protocol pane 1602. For example, a portion of run completion 1618a is illustrated in blue, while a portion of current stage 1618b is illustrated in green, and any errors 1618c are flagged with markers extending from the point in time along the course of the portion of the run completion 1618a where the error occurred. A message region 1618d presents a percentage of run completed, a percentage of stage completed, and a total number of errors. In some embodiments, upon selection of the chart 1616, the user may be presented with greater details regarding the run status such as, in some examples, identification of the type of error, a name of the current processing stage (e.g., nucleic acid assembly, purification, cell growth, filtration, transformation, recovery, editing, etc.), and a listing of processing stages within the run. Further, in some embodiments a run completion time message indicates a date and time at which the run is estimated to complete. The run, in some examples, may be indicative of a single cell editing process or a series of recursive cell editing processes scheduled for execution without user intervention. In some embodiments (not shown), the run status pane 1604 additionally illustrates an estimated time at which user intervention will be required (e.g., cartridge replacement, solid waste disposal, liquid waste disposal, etc.).

In some implementations, the run status pane 1604 includes a pause control 1624 for pausing cell processing. The user may select to pause the current run, for example, to correct for an identified error or to conduct manual intervention such as waste removal.

The temperature pane 1606, in some embodiments, illustrates a series of icons 1126 with corresponding messages 1628 indicating temperature settings for various apparatus of the automated multi-module cell editing instrument. The icons, from left to right, may represent an FTEP module 1626a (e.g., FTEP device associated with the reagent cartridge 110c of FIG. 1A), a purification module 1626b, a first growth module 1626c, a second growth module 1626d, and a filtration module 1626e. The corresponding messages 1628a-e identify a present temperature, low temperature, and high temperature of the corresponding module (e.g., for this stage or this run). In selecting one of the icons 1626, in some embodiments, a graphic display of temperature of time may be reviewed.

Beneath the temperature pane, in some implementations, a series of panes identify present status of a number of modules. For example, the electroporation pane 1608 represents status of a transformation module, while the cell growth pane 1610 represents the status of a growth module. In some embodiments, the panes presented here identify status of a presently operational module (e.g., the module involved in cell processing in the current stage) as well as the status of any modules which have already been utilized during the current run (as illustrated, for example, in the run status pane 1604). Past status information, for example, may present to the user information regarding the parameters used in the prior stage(s) of cell processing.

Turning to the electroporation pane 1608, in some implementations, operational parameters 1630*a* of volts, milliamps, and joules are presented. Additionally, a status message 1632*a* may identify additional information regarding the functioning of the transformation module such as, in some examples, an error status, a time remaining for processing, or contents of the module (e.g., materials added to the module). In some implementations, an icon 1634*a* above the status message 1632*a* will be presented in an active mode (e.g., colorful, "lit up", in bold, etc.) when the corresponding module is actively processing. Selection of the icon 1634*a*, in some embodiments, causes presentation of a graphic display of detailed information regarding the operational parameters 1630*a*.

Turning to the cell growth pane 1610, in some implementations, operational parameters 1630*b* of OD and hours of growth are presented. Additionally, a status message 1632*b* may identify additional information regarding the functioning of the growth module such as, in some examples, an error status, a time remaining for processing, or contents of the module (e.g., materials added to the module). In some implementations, an icon 1634*b* above the status message 1632*b* will be presented in an active mode (e.g., colorful, "lit up", in bold, etc.) when the corresponding module is actively processing. Selection of the icon 1634*b*, in some embodiments, causes presentation of a graphic display of detailed information regarding the operational parameters 1630*b*.

Next, a hardware description of an example processing system and processing environment according to exemplary embodiments is described with reference to FIG. 18. In FIG. 18, the processing system 1810 includes a CPU 1808 which performs a portion of the processes described above. For example, the CPU 1808 may manage the processing stages of the method 1400 of FIG. 14 and/or the workflows of FIGS. 15A-C. The process data and, scripts, instructions, and/or user settings may be stored in memory 1802. These process data and, scripts, instructions, and/or user settings may also be stored on a storage medium disk 1804 such as a portable storage medium (e.g., USB drive, optical disk drive, etc.) or may be stored remotely. For example, the process data and, scripts, instructions, and/or user settings may be stored in a location accessible to the processing system 1810 via a network 1828. Further, the claimed advancements are not limited by the form of the computer-readable media on which the instructions of the inventive process are stored. For example, the instructions may be stored in FLASH memory, RAM, ROM, or any other information processing device with which the processing system 1810 communicates, such as a server, computer, smart phone, or other hand-held computing device.

Further, components of the claimed advancements may be provided as a utility application, background daemon, or component of an operating system, or combination thereof, executing in conjunction with CPU 1808 and an operating system such as with other computing systems known to those skilled in the art.

CPU 1808 may be an ARM processor, system-on-a-chip (SOC), microprocessor, microcontroller, digital signal processor (DSP), or may be other processor types that would be recognized by one of ordinary skill in the art. Further, CPU 1808 may be implemented as multiple processors cooperatively working in parallel to perform the instructions of the inventive processes described above.

The processing system 1810 is part of a processing environment 1800. The processing system 1810 in FIG. 18 also includes a network controller 1806 for interfacing with the network 1828 to access additional elements within the processing environment 1800. As can be appreciated, the network 1828 can be a public network, such as the Internet, or a private network such as an LAN or WAN network, or any combination thereof and can also include PSTN or ISDN sub-networks. The network 1828 can be wireless such as a cellular network including EDGE, 3G and 4G wireless cellular systems. The wireless network can also be Wi-Fi, Bluetooth, or any other wireless form of communication that is known.

The processing system 1810 further includes a general purpose I/O interface 1812 interfacing with a user interface (e.g., touch screen) 1816, one or more sensors 1814, and one or more peripheral devices 1818. The peripheral I/O devices 1818 may include, in some examples, a video recording system, an audio recording system, microphone, external storage devices, and/or external speaker systems. The one or more sensors 1814 may include one or more of a gyroscope, an accelerometer, a gravity sensor, a linear accelerometer, a global positioning system, a bar code scanner, a QR code scanner, an RFID scanner, a temperature monitor, and a lighting system or lighting element.

The general purpose storage controller 1824 connects the storage medium disk 1804 with communication bus 1840, such as a parallel bus or a serial bus such as a Universal Serial Bus (USB), or similar, for interconnecting all of the components of the processing system. A description of the general features and functionality of the storage controller 1824, network controller 1806, and general purpose I/O interface 1812 is omitted herein for brevity as these features are known.

The processing system 1810, in some embodiments, includes one or more onboard and/or peripheral sensors 1814. The sensors 1814, for example, can be incorporated directly into the internal electronics and/or a housing of the automated multi-module processing instrument. A portion of the sensors 1814 can be in direct physical contact with the I/O interface 1812, e.g., via a wire; or in wireless contact e.g., via a Bluetooth, Wi-Fi or NFC connection. For example, a wireless communications controller 1826 may enable communications between one or more wireless sensors 1814 and the I/O interface 1812. Furthermore, one or more sensors 1814 may be in indirect contact e.g., via intermediary servers or storage devices that are based in the network 1828; or in (wired, wireless or indirect) contact with a signal accumulator somewhere within the automated multi-module cell editing instrument, which in turn is in (wired or wireless or indirect) contact with the I/O interface 1812.

A group of sensors 1814 communicating with the I/O interface 1812 may be used in combination to gather a given signal type from multiple places in order to generate a more complete map of signals. One or more sensors 1814 communicating with the I/O interface 1812 can be used as a comparator or verification element, for example to filter, cancel, or reject other signals.

In some embodiments, the processing environment 1800 includes a computing device 1838 communicating with the processing system 1810 via the wireless communications controller 1826. For example, the wireless communications controller 1826 may enable the exchange of email messages, text messages, and/or software application alerts designated to a smart phone or other personal computing device of a user.

The processing environment 1800, in some implementations, includes a robotic material handling system 1822. The processing system 1810 may include a robotics controller 1820 for issuing control signals to actuate elements of the robotic material handling system, such as manipulating a position of a gantry, lowering or raising a sipper or pipettor element, and/or actuating pumps and valves to cause liquid transfer between a sipper/pipettor and various vessels (e.g., chambers, vials, etc.) in the automated multi-module cell editing instrument. The robotics controller 1820, in some examples, may include a hardware driver, firmware element, and/or one or more algorithms or software packages for interfacing the processing system 1810 with the robotics material handling system 1822.

In some implementations, the processing environment 1810 includes one or more module interfaces 1832, such as, in some examples, one or more sensor interfaces, power control interfaces, valve and pump interfaces, and/or actuator interfaces for activating and controlling processing of each module of the automated multi-module processing system. For example, the module interfaces 1832 may include an actuator interface for the drive motor of rotating cell growth device 1350 (FIGS. 8C and 8D) and a sensor interface for the detector board 1372 that senses optical density of cell growth within rotating growth vial 1300. A module controller 1830, in some embodiments, is configured to interface with the module interfaces 1832. The module controller 1830 may include one or many controllers (e.g., possibly one controller per module, although some modules may share a single controller). The module controller 1830, in some examples, may include a hardware driver, firmware element, and/or one or more algorithms or software packages for interfacing the processing system 1810 with the module interfaces 1832.

The processing environment 1810, in some implementations, includes a thermal management system 1836 for controlling climate conditions within the housing of the automated multi-module processing system. The thermal management system 1836 may additional control climate conditions within one or more modules of the automated multi-module cell editing instrument. The processing system 1810, in some embodiments, includes a temperature controller 1834 for interfacing with the thermal management system 1836. The temperature controller 1834, in some examples, may include a hardware driver, firmware element, and/or one or more algorithms or software packages for interfacing the processing system 1810 with the thermal management system 1836.

Production of Cell Libraries Using Automated Editing Methods, Modules, Instruments and Systems In one aspect, the present disclosure provides automated editing methods, modules, instruments, and automated multi-module cell editing instruments for creating a library of cells that vary the expression, levels and/or activity of RNAs and/or proteins of interest in various cell types using various editing strategies, as described herein in more detail. Accordingly, the disclosure is intended to cover edited cell libraries created by the automated editing methods, automated multi-module cell editing instruments of the disclosure. These cell libraries may have different targeted edits, including but not limited to gene knockouts, gene knock-ins, insertions, deletions, single nucleotide edits, short tandem repeat edits, frameshifts, triplet codon expansion, and the like in cells of various organisms. These edits can be directed to coding or non-coding regions of the genome, and are preferably rationally designed.

In other aspects, the present disclosure provides automated editing methods, automated multi-module cell editing instruments for creating a library of cells that vary DNA-linked processes. For example, the cell library may include individual cells having edits in DNA binding sites to interfere with DNA binding of regulatory elements that modulate expression of selected genes. In addition, cell libraries may include edits in genomic DNA that impact on cellular processes such as heterochromatin formation, switch-class recombination and VDJ recombination.

In specific aspects, the cell libraries are created using multiplexed editing of individual cells within a cell population, with multiple cells within a cell population are edited in a single round of editing, i.e., multiple changes within the cells of the cell library are in a single automated operation. The libraries that can be created in a single multiplexed automated operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

In other specific aspects, the cell libraries are created using recursive editing of individual cells within a cell population, with edits being added to the individual cells in two or more rounds of editing. The use of recursive editing results in the amalgamation of two or more edits targeting two or more sites in the genome in individual cells of the library. The libraries that can be created in an automated recursive operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

Examples of non-automated editing strategies that can be modified based on the present specification to utilize the automated systems can be found, e.g., U.S. Pat. Nos. 8,110,360, 8,332,160, 9,988,624, 20170316353, and 20120277120.

In specific aspects, recursive editing can be used to first create a cell phenotype, and then later rounds of editing used to reverse the phenotype and/or accelerate other cell properties.

In some aspects, the cell library comprises edits for the creation of unnatural amino acids in a cell.

In specific aspects, the disclosure provides edited cell libraries having edits in one or more regulatory elements created using the automated editing methods, automated multi-module cell editing instruments of the disclosure. The term "regulatory element" refers to nucleic acid molecules that can influence the transcription and/or translation of an operably linked coding sequence in a particular environment and/or context. This term is intended to include all elements that promote or regulate transcription, and RNA stability including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include, but are not limited to, promoters, operator sequences and a ribosome binding sites. Regulatory elements that are used in eukaryotic cells may include, but are not limited to, promoters, enhancers, insulators, splicing signals and polyadenylation signals.

Preferably, the edited cell library includes rationally designed edits that are designed based on predictions of protein structure, expression and/or activity in a particular cell type. For example, rational design may be based on a system-wide biophysical model of genome editing with a particular nuclease and gene regulation to predict how different editing parameters including nuclease expression and/or binding, growth conditions, and other experimental conditions collectively control the dynamics of nuclease editing. See, e.g., Farasat and Salis, PLoS Comput Biol., 29:12(1):e1004724 (2016).

In one aspect, the present disclosure provides the creation of a library of edited cells with various rationally designed regulatory sequences created using the automated editing instrumentation, systems and methods of the invention. For example, the edited cell library can include prokaryotic cell populations created using set of constitutive and/or inducible promoters, enhancer sequences, operator sequences and/or ribosome binding sites. In another example, the edited cell library can include eukaryotic sequences created using a set of constitutive and/or inducible promoters, enhancer sequences, operator sequences, and/or different Kozak sequences for expression of proteins of interest.

In some aspects, the disclosure provides cell libraries including cells with rationally designed edits comprising one or more classes of edits in sequences of interest across the genome of an organism. In specific aspects, the disclosure provides cell libraries including cells with rationally designed edits comprising one or more classes of edits in sequences of interest across a subset of the genome. For example, the cell library may include cells with rationally designed edits comprising one or more classes of edits in sequences of interest across the exome, e.g., every or most open reading frames of the genome. For example, the cell library may include cells with rationally designed edits comprising one or more classes of edits in sequences of interest across the kinome. In yet another example, the cell library may include cells with rationally designed edits comprising one or more classes of edits in sequences of interest across the secretome. In yet other aspects, the cell library may include cells with rationally designed edits created to analyze various isoforms of proteins encoded within the exome, and the cell libraries can be designed to control expression of one or more specific isoforms, e.g., for transcriptome analysis.

Importantly, in certain aspects the cell libraries may comprise edits using randomized sequences, e.g., randomized promoter sequences, to reduce similarity between expression of one or more proteins in individual cells within the library. Additionally, the promoters in the cell library can be constitutive, inducible or both to enable strong and/or titratable expression.

In other aspects, the present disclosure provides automated editing methods, automated multi-module cell editing instruments for creating a library of cells comprising edits to identify optimum expression of a selected gene target. For example, production of biochemicals through metabolic engineering often requires the expression of pathway enzymes, and the best production yields are not always achieved by the highest amount of the target pathway enzymes in the cell, but rather by fine-tuning of the expression levels of the individual enzymes and related regulatory proteins and/or pathways. Similarly, expression levels of heterologous proteins sometimes can be experimentally adjusted for optimal yields.

The most obvious way that transcription impacts on gene expression levels is through the rate of Pol II initiation, which can be modulated by combinations of promoter or enhancer strength and trans-activating factors (Kadonaga, et al., Cell, 116(2):247-57 (2004)). In eukaryotes, elongation rate may also determine gene expression patterns by influencing alternative splicing (Cramer et al., PNAS USA, 94(21):11456-60 (1997)). Failed termination on a gene can impair the expression of downstream genes by reducing the accessibility of the promoter to Pol II (Greger, et al., PNAS USA, 97(15):8415-20 (2000)). This process, known as transcriptional interference, is particularly relevant in lower eukaryotes, as they often have closely spaced genes.

In some embodiments the present disclosure provides methods for optimizing cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination).

Site Directed Mutagenesis

Cell libraries can be created using the automated editing methods, modules, instruments, and systems employing site-directed mutagenesis, i.e., when the amino acid sequence of a protein or other genomic feature may be altered by deliberately and precisely by mutating the protein or genomic feature. These cell lines can be useful for various purposes, e.g., for determining protein function within cells, the identification of enzymatic active sites within cells, and the design of novel proteins. For example, site-directed mutagenesis can be used in a multiplexed fashion to exchange a single amino acid in the sequence of a protein for another amino acid with different chemical properties. This allows one to determine the effect of a rationally designed or randomly generated mutation in individual cells within a cell population. See, e.g., Berg, et al. Biochemistry, Sixth Ed. (New York: W.H. Freeman and Company) (2007).

In another example, edits can be made to individual cells within a cell library to substitute amino acids in binding sites, such as substitution of one or more amino acids in a protein binding site for interaction within a protein complex or substitution of one or more amino acids in enzymatic pockets that can accommodate a cofactor or ligand. This class of edits allows the creation of specific manipulations to a protein to measure certain properties of one or more proteins, including interaction with other cofactors, ligands, etc. within a protein complex.

In yet another examples, various edit types can be made to individual cells within a cell library using site specific mutagenesis for studying expression quantitative trait loci (eQTLs). An eQTL is a locus that explains a fraction of the genetic variance of a gene expression phenotype. The libraries of the invention would be useful to evaluate and link eQTLs to actual diseased states.

In specific aspects, the edits introduced into the cell libraries of the disclosure may be created using rational design based on known or predicted structures of proteins. See, e.g., Chronopoulou and Labrou, Curr Protoc Protein Sci.; Chapter 26:Unit 26.6 (2011). Such site-directed mutagenesis can provide individual cells within a library with one or more site-directed edits, and preferably two or more site-directed edits (e.g., combinatorial edits) within a cell population.

In other aspects, cell libraries of the disclosure are created using site-directed codon mutation "scanning" of all or substantially all of the codons in the coding region of a gene. In this fashion, individual edits of specific codons can be examined for loss-of-function or gain-of-function based on specific polymorphisms in one or more codons of the gene. These libraries can be a powerful tool for determining which genetic changes are silent or causal of a specific phenotype in a cell or cell population. The edits of the codons may be randomly generated or may be rationally designed based on known polymorphisms and/or mutations that have been identified in the gene to be analyzed. Moreover, using these techniques on two or more genes in a single in a pathway in a cell may determine potential protein:protein interactions or redundancies in cell functions or pathways.

For example, alanine scanning can be used to determine the contribution of a specific residue to the stability or function of given protein. See, e.g., Lefèvre, et al., Nucleic Acids Research, Volume 25(2):447-448 (1997). Alanine is often used in this codon scanning technique because of its non-bulky, chemically inert, methyl functional group that can mimic the secondary structure preferences that many of the other amino acids possess. Codon scanning can also be used to determine whether the side chain of a specific residue plays a significant role in cell function and/or activity. Sometimes other amino acids such as valine or leucine can be used in the creation of codon scanning cell libraries if conservation of the size of mutated residues is needed.

In other specific aspects, cell libraries can be created using the automated editing methods, automated multi-module cell editing instruments of the invention to determine the active site of a protein such as an enzyme or hormone, and to elucidate the mechanism of action of one or more of these proteins in a cell library. Site-directed mutagenesis associated with molecular modeling studies can be used to discover the active site structure of an enzyme and consequently its mechanism of action. Analysis of these cell libraries can provide an understanding of the role exerted by specific amino acid residues at the active sites of proteins, in the contacts between subunits of protein complexes, on intracellular trafficking and protein stability/half-life in various genetic backgrounds.

Saturation Mutagenesis

In some aspects, the cell libraries created using the automated editing methods and automated multi-module cell editing instruments of the disclosure may be saturation mutagenesis libraries, in which a single codon or set of codons is randomized to produce all possible amino acids at the position of a particular gene or genes of interest. These cell libraries can be particularly useful to generate variants, e.g., for directed evolution. See, e.g., Chica, et al., Current Opinion in Biotechnology 16 (4): 378-384 (2005); and Shivange, Current Opinion in Chemical Biology, 13 (1): 19-25 (2009).

In some aspects, edits comprising different degenerate codons can be used to encode sets of amino acids in the individual cells in the libraries. Because some amino acids are encoded by more codons than others, the exact ratio of amino acids cannot be equal. In certain aspects, more restricted degenerate codons are used. 'NNK' and 'NNS' have the benefit of encoding all 20 amino acids, but still encode a stop codon 3% of the time. Alternative codons such as 'NDT', 'DBK' avoid stop codons entirely, and encode a minimal set of amino acids that still encompass all the main biophysical types (anionic, cationic, aliphatic hydrophobic, aromatic hydrophobic, hydrophilic, small).

In specific aspects, the non-redundant saturation mutagenesis, in which the most commonly used codon for a particular organism is used in the saturation mutagenesis editing process.

Promoter Swaps and Ladders

One mechanism for analyzing and/or optimizing expression of one or more genes of interest is through the creation of a "promoter swap" cell library, in which the cells comprise genetic edits that have specific promoters linked to one or more genes of interest. Accordingly, the cell libraries created using the methods, automated multi-module cell editing instruments of the disclosure may be promoter swap cell libraries, which can be used, e.g., to increase or decrease expression of a gene of interest to optimize a metabolic or genetic pathway. In some aspects, the promoter swap cell library can be used to identify an increase or reduction in the expression of a gene that affects cell vitality or viability, e.g., a gene encoding a protein that impacts on the growth rate or overall health of the cells. In some aspects, the promoter swap cell library can be used to create cells having dependencies and logic between the promoters to create synthetic gene networks. In some aspects, the promoter swaps can be used to control cell to cell communication between cells of both homogeneous and heterogeneous (complex tissues) populations in nature.

The cell libraries can utilize any given number of promoters that have been grouped together based upon exhibition of a range of expression strengths and any given number of target genes. The ladder of promoter sequences vary expression of at least one locus under at least one condition. This ladder is then systematically applied to a group of genes in the organism using the automated editing methods, automated multi-module cell editing instruments of the disclosure.

In specific aspects, the cell library formed using the automated editing processes, modules and systems of the disclosure include individual cells that are representative of a given promoter operably linked to one or more target genes of interest in an otherwise identical genetic background. Examples of non-automated editing strategies that can be modified to utilize the automated systems can be found, e.g., in U.S. Pat. No. 9,988,624.

In specific aspects, the promoter swap cell library is produced by editing a set of target genes to be operably linked to a pre-selected set of promoters that act as a "promoter ladder" for expression of the genes of interest. For example, the cells are edited so that one or more individual genes of interest are edited to be operably linked with the different promoters in the promoter ladder. When an endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context.

The promoters are generally selected to result in variable expression across different loci, and may include inducible promoters, constitutive promoters, or both.

The set of target genes edited using the promoter ladder can include all or most open reading frames (ORFs) in a genome, or a selected subset of the genome, e.g., the ORFs of the kinome or a secretome. In some aspects, the target genes can include coding regions for various isoforms of the genes, and the cell libraries can be designed to expression of one or more specific isoforms, e.g., for transcriptome analysis using various promoters.

The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

Editing of other functional genetic elements, including insulator elements and other genomic organization elements, can also be used to systematically vary the expression level of a set of target genes, and can be introduced using the methods, automated multi-module cell editing instruments of the disclosure. In one aspect, a population of cells is edited using a ladder of enhancer sequences, either alone or in combination with selected promoters or a promoter ladder, to create a cell library having various edits in these enhancer elements. In another aspect, a population of cells is edited using a ladder of ribosome binding sequences, either alone or in combination with selected promoters or a promoter ladder, to create a cell library having various edits in these ribosome binding sequences.

In another aspect, a population of cells is edited to allow the attachment of various mRNA and/or protein stabilizing or destabilizing sequences to the 5' or 3' end, or at any other location, of a transcript or protein.

In certain aspects, a population of cells of a previously established cell line may be edited using the automated editing methods, modules, instruments, and systems of the disclosure to create a cell library to improve the function, health and/or viability of the cells. For example, many industrial strains currently used for large scale manufacturing have been developed using random mutagenesis processes iteratively over a period of many years, sometimes decades. Unwanted neutral and detrimental mutations were introduced into strains along with beneficial changes, and over time this resulted in strains with deficiencies in overall robustness and key traits such as growth rates. In another example, mammalian cell lines continue to mutate through the passage of the cells over periods of time, and likewise these cell lines can become unstable and acquire traits that are undesirable. The automated editing methods, automated multi-module cell editing instruments of the disclosure can use editing strategies such as SNP and/or STR swapping, indel creation, or other techniques to remove or change the undesirable genome sequences and/or introducing new genome sequences to address the deficiencies while retaining the desirable properties of the cells.

When recursive editing is used, the editing in the individual cells in the edited cell library can incorporate the inclusion of "landing pads" in an ectopic site in the genome (e.g., a CarT locus) to optimize expression, stability and/or control.

In some embodiments, each library produced having individual cells comprising one or more edits (either introducing or removing) is cultured and analyzed under one or more criteria (e.g., production of a chemical or product of interest). The cells possessing the specific criteria are then associated, or correlated, with one or more particular edits in the cell. In this manner, the effect of a given edit on any number of genetic or phenotypic traits of interest can be determined. The identification of multiple edits associated with particular criteria or enhanced functionality/robustness may lead to cells with highly desirable characteristics.

Knock-Out or Knock-in Libraries

In certain aspects, the present disclosure provides automated editing methods, modules, instruments and systems for creating a library of cells having "knock-out" (KO) or "knock-in" (KI) edits of various genes of interest. Thus, the disclosure is intended to cover edited cell libraries created by the automated editing methods, automated multi-module cell editing instruments of the disclosure that have one or more mutations that remove or reduce the expression of selected genes of interest to interrogate the effect of these edits on gene function in individual cells within the cell library.

The cell libraries can be created using targeted gene KO (e.g., via insertion/deletion) or KOs (e.g., via homologous directed repair). For example, double strand breaks are often repaired via the non-homologous end joining DNA repair pathway. The repair is known to be error prone, and thus insertions and deletions may be introduced that can disrupt gene function. Preferably the edits are rationally designed to specifically affect the genes of interest, and individual cells can be created having a KI or KI of one or more locus of interest. Cells having a KO or KI of two or more loci of interest can be created using automated recursive editing of the disclosure.

In specific aspects, the KO or KI cell libraries are created using simultaneous multiplexed editing of cells within a cell population, and multiple cells within a cell population are edited in a single round of editing, i.e., multiple changes within the cells of the cell library are in a single automated operation. In other specific aspects, the cell libraries are created using recursive editing of individual cells within a cell population, and results in the amalgamation of multiple edits of two or more sites in the genome into single cells.

SNP or Short Tandem Repeat Swaps

In one aspect, cell libraries are created using the automated editing methods, automated multi-module cell editing instruments of the disclosure by systematic introducing or substituting single nucleotide polymorphisms ("SNPs") into the genomes of the individual cells to create a "SNP swap" cell library. In some embodiments, the SNP swapping methods of the present disclosure include both the addition of beneficial SNPs, and removing detrimental and/or neutral SNPs. The SNP swaps may target coding sequences, non-coding sequences, or both.

In another aspect, a cell library is created using the automated editing methods, modules, instruments, instruments, and systems of the disclosure by systematic introducing or substituting short tandem repeats ("STR") into the genomes of the individual cells to create an "STR swap" cell library. In some embodiments, the STR swapping methods of the present disclosure include both the addition of beneficial STRs, and removing detrimental and/or neutral STRs. The STR swaps may target coding sequences, non-coding sequences, or both.

In some embodiments, the SNP and/or STR swapping used to create the cell library is multiplexed, and multiple cells within a cell population are edited in a single round of editing, i.e., multiple changes within the cells of the cell library are in a single automated operation. In other embodiments, the SNP and/or STR swapping used to create the cell library is recursive, and results in the amalgamation of multiple beneficial sequences and/or the removal of detrimental sequences into single cells. Multiple changes can be either a specific set of defined changes or a partly randomized, combinatorial library of mutations. Removal of detrimental mutations and consolidation of beneficial mutations can provide immediate improvements in various cellular processes. Removal of genetic burden or consolidation of beneficial changes into a strain with no genetic burden also provides a new, robust starting point for additional random mutagenesis that may enable further improvements.

SNP swapping overcomes fundamental limitations of random mutagenesis approaches as it is not a random approach, but rather the systematic introduction or removal of individual mutations across cells.

Splice Site Editing

RNA splicing is the process during which introns are excised and exons are spliced together to create the mRNA that is translated into a protein. The precise recognition of splicing signals by cellular machinery is critical to this process. Accordingly, in some aspects, a population of cells is edited using a systematic editing to known and/or predicted splice donor and/or acceptor sites in various loci to create a library of splice site variants of various genes. Such editing can help to elucidate the biological relevance of various isoforms of genes in a cellular context. Sequences for rational design of splicing sites of various coding regions, including actual or predicted mutations associated with various mammalian disorders, can be predicted using analysis techniques such as those found in Nalla and Rogan, Hum Mutat, 25:334-342 (2005); Divina, et al., Eur J Hum Genet, 17:759-765 (2009); Desmet, et el., Nucleic Acids Res, 37:e67 (2009); Faber, et al., BMC Bioinformatics, 12(suppl 4):S2 (2011).

Start/Stop Codon Exchanges and Incorporation of Nucleic Acid Analogs

In some aspects, the present disclosure provides for the creation of cell libraries using the automated editing methods, modules, instruments and systems of the disclosure, where the libraries are created by swapping start and stop codon variants throughout the genome of an organism or for a selected subset of coding regions in the genome, e.g., the kinome or secretome. In the cell library, individual cells will have one or more start or stop codons replacing the native start or stop codon for one or more gene of interest.

For example, typical start codons used by eukaryotes are ATG (AUG) and prokaryotes use ATG (AUG) the most, followed by GTG (GUG) and TTG (UUG). The cell library may include individual cells having substitutions for the native start codons for one or more genes of interest.

In some aspects, the present disclosure provides for automated creation of a cell library by replacing ATG start codons with TTG in front of selected genes of interest. In other aspects, the present disclosure provides for automated creation of a cell library by replacing ATG start codons with GTG. In other aspects, the present disclosure provides for automated creation of a cell library by replacing GTG start codons with ATG. In other aspects, the present disclosure provides for automated creation of a cell library by replacing GTG start codons with TTG. In other aspects, the present disclosure provides for automated creation of a cell library by replacing TTG start codons with ATG. In other aspects, the present disclosure provides for automated creation of a cell library by replacing TTG start codons with GTG.

In other examples, typical stop codons for *S. cerevisiae* and mammals are TAA (UAA) and TGA (UGA), respectively. The typical stop codon for monocotyledonous plants is TGA (UGA), whereas insects and *E. coli* commonly use TAA (UAA) as the stop codon (Dalphin. et al., Nucl. Acids Res., 24: 216-218 (1996)). The cell library may include individual cells having substitutions for the native stop codons for one or more genes of interest.

In some aspects, the present disclosure provides for automated creation of a cell library by replacing TAA stop codons with TAG. In other aspects, the present disclosure provides for automated creation of a cell library by replacing TAA stop codons with TGA. In other aspects, the present disclosure provides for automated creation of a cell library by replacing TGA stop codons with TAA. In other aspects, the present disclosure provides for automated creation of a cell library by replacing TGA stop codons with TAG. In other aspects, the present disclosure provides for automated creation of a cell library by replacing TAG stop codons with TAA. In other aspects, the present invention teaches automated creation of a cell library by replacing TAG stop codons with TGA.

Terminator Swaps and Ladders

One mechanism for identifying optimum termination of a pre-spliced mRNA of one or more genes of interest is through the creation of a "terminator swap" cell library, in which the cells comprise genetic edits that have specific terminator sequences linked to one or more genes of interest. Accordingly, the cell libraries created using the methods, modules, instruments and systems of the disclosure may be terminator swap cell libraries, which can be used, e.g., to affect mRNA stability by releasing transcripts from sites of synthesis. In other embodiments, the terminator swap cell library can be used to identify an increase or reduction in the efficiency of transcriptional termination and thus accumulation of unspliced pre-mRNA (e.g., West and Proudfoot, Mol Cell.; 33(3-9); 354-364 (2009)) and/or 3' end processing (e.g., West, et al., Mol Cell. 29(5):600-10 (2008)). In the case where a gene is linked to multiple termination sites, the edits may edit a combination of edits to multiple terminators that are associated with a gene. Additional amino acids may also be added to the ends of proteins to determine the effect on the protein length on terminators.

The cell libraries can utilize any given number of edits of terminators that have been selected for the terminator ladder based upon exhibition of a range of activity and any given number of target genes. The ladder of terminator sequences vary expression of at least one locus under at least one condition. This ladder is then systematically applied to a group of genes in the organism using the automated editing methods, modules, instruments and systems of the disclosure.

In some aspects, the present disclosure provides for the creation of cell libraries using the automated editing methods, modules, instruments and systems of disclosure, where the libraries are created to edit terminator signals in one or more regions in the genome in the individual cells of the library. Transcriptional termination in eukaryotes operates through terminator signals that are recognized by protein factors associated with the RNA polymerase II. For example, the cell library may contain individual eukaryotic cells with edits in genes encoding polyadenylation specificity factor (CPSF) and cleavage stimulation factor (CstF) and or gene encoding proteins recruited by CPSF and CstF factors to termination sites. In prokaryotes, two principal mechanisms, termed Rho-independent and Rho-dependent termination, mediate transcriptional termination. For example, the cell library may contain individual prokaryotic cells with edits in genes encoding proteins that affect the binding, efficiency and/or activity of these termination pathways.

In certain aspects, the present disclosure provides methods of selecting termination sequences ("terminators") with optimal properties. For example, in some embodiments, the present disclosure teaches provides methods for introducing and/or editing one or more terminators and/or generating variants of one or more terminators within a host cell, which exhibit a range of activity. A particular combination of terminators can be grouped together as a terminator ladder, and cell libraries of the disclosure include individual cells that are representative of terminators operably linked to one or more target genes of interest in an otherwise identical genetic background. Examples of non-automated editing strategies that can be modified to utilize the automated instruments can be found, e.g., in U.S. Pat. No. 9,988,624 to Serber et al., entitled "Microbial strain improvement by a HTP genomic engineering platform."

In specific aspects, the terminator swap cell library is produced by editing a set of target genes to be operably linked to a pre-selected set of terminators that act as a "terminator ladder" for expression of the genes of interest. For example, the cells are edited so that the endogenous promoter is operably linked to the individual genes of interest are edited with the different promoters in the promoter ladder. When the endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context. The terminator ladder in question is then associated with a given gene of interest.

The terminator ladder can be used to more generally affect termination of all or most ORFs in a genome, or a selected subset of the genome, e.g., the ORFs of a kinome or a secretome. The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Production and Transformation of Electrocompetent E. coli

For testing transformation of the FTEP device, such as the FTEP device configured as shown in FIGS. 10B-10D (vi), electrocompetent E. coli cells were created. To create a starter culture, 6 ml volumes of LB chlor-25 (LB with 25 µg/ml chloramphenicol) were transferred to 14 ml culture tubes. A 25 µl aliquot of E. coli was used to inoculate the LB chlor-25 tubes. Following inoculation, the tubes were placed at a 45° angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hr. When the OD600 of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells are aliquoted in 1:100 dilutions of cell suspension and ice-cold glycerol.

The comparative electroporation experiment was performed to determine the efficiency of transformation of the electrocompetent E. coli using the embodiment of the FTEP device shown at (ii), (iii), and (vi) of FIGS. 10B and 10C and (ii) and (vi) of FIG. 10D. The flow rate was controlled with a pressure control system. The suspension of cells with DNA was loaded into the FTEP inlet reservoir. The transformed cells flowed directly from the inlet and inlet channel, through the flow channel, through the outlet channel, and into the outlet containing recovery medium. The cells were transferred into a tube containing additional recovery medium, placed in an incubator shaker at 30° C. shaking at 250 rpm for 3 hours. The cells were plated to determine the colony forming units (CFUs) that survived electroporation and failed to take up a plasmid and the CFUs that survived electroporation and took up a plasmid. Plates were incubated at 30° C.; E. coli colonies were counted after 24 hrs.

Figure 19A:
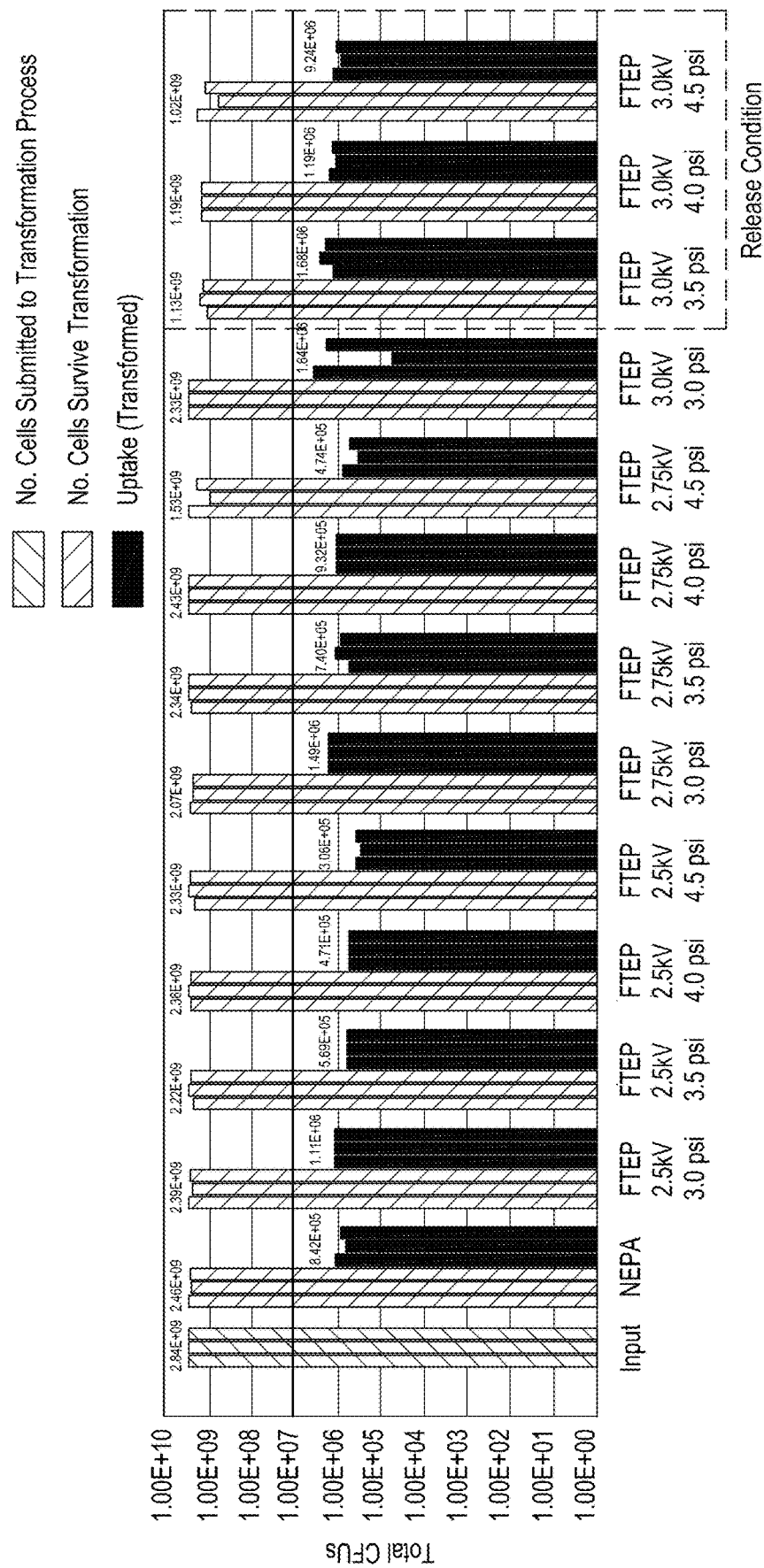
FIG. 19A is a bar graph showing the results of electroporation of *E. coli* using a device of the disclosure and a comparator electroporation device.

The flow-through electroporation experiments were benchmarked against 2 mm electroporation cuvettes (Bulldog Bio, Portsmouth, N.H.) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 19A. In FIG. 19A, the left-most bars hatched /// denote cell input, the bars to the left bars hatched \\\ denote the number of cells that survived transformation, and the right bars hatched /// denote the number of cells that were actually transformed. The FTEP device showed equivalent transformation of electrocompetent *E. coli* cells at various voltages as compared to the NEPAGENE™ electroporator. As can be seen, the transformation survival rate is at least 90% and in some embodiments is at least 95%, 96%, 97%, 98%, or 99%. The recovery ratio (the fraction of introduced cells which are successfully transformed and recovered) is in certain embodiments at least 0.001 and preferably between 0.00001 and 0.01. In FIG. 19A the recovery ratio is approximately 0.0001.

Figure 19B:
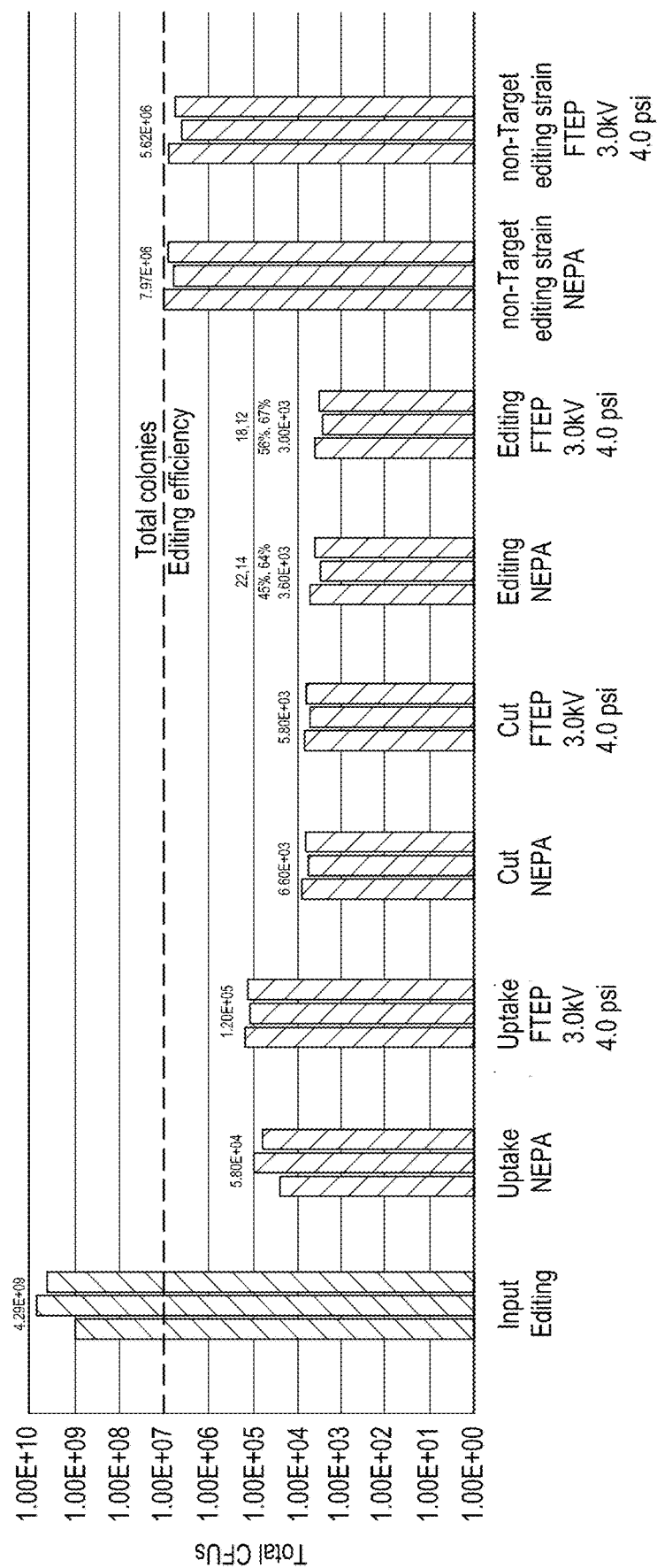
FIG. 19B is a bar graph showing uptake, cutting, and editing efficiencies of *E. coli* cells transformed via an FTEP as described herein benchmarked against a comparator electroporation device.

Additionally, a comparison of the NEPAGENE™ ELEPO21 and the FTEP device was made for efficiencies of transformation (uptake), cutting, and editing. In FIG. 19B, triplicate experiments were performed where the bars hatched /// denote the number of cells input for transformation, and the bars hatched \\\ denote the number of cells that were transformed (uptake), the number of cells where the genome of the cells was cut by a nuclease transcribed and translated from a vector transformed into the cells (cutting), and the number of cells where editing was effected (cutting and repair using a nuclease transcribed and translated from a vector transformed into the cells, and using a guide RNA and a donor DNA sequence both of which were transcribed from a vector transformed into the cells). In addition, note that in non-editing cell lines, the number of colonies for both the NEPAGENE™ electroporator and the FTEP showed equivalent transformation efficiencies. Moreover, it can be seen that the FTEP showed equivalent transformation, cutting, and editing efficiencies as the NEPAGENE™ electroporator.

Example 2: Production and Transformation of Electrocompetent S. *Cerevisiae*

For further testing transformation of the FTEP device, such as the FTEP device configured as shown in FIGS. 10B-10D (vi), S. *Cerevisiae* cells were prepared using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent S. *Cerevisiae* using the FTEP device. The flow rate was controlled with a syringe pump (Harvard apparatus PHD ULTRA™ 4400). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 20:
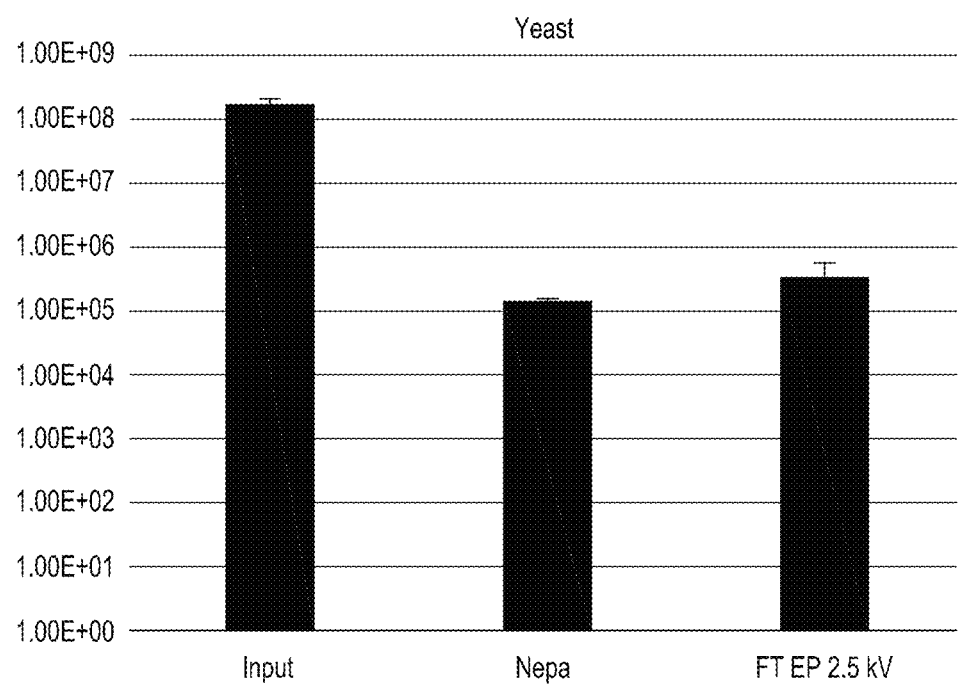
FIG. 20 is a bar graph showing the results of electroporation of *S. cerevisiae* using an FTEP device of the disclosure and a comparator electroporation method.

The flow-through electroporation experiments were benchmarked against 2 mm electroporation cuvettes (Bulldog Bio, Portsmouth, N.H.) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 20. The device showed better transformation and survival of electrocompetent S. *Cerevisiae* at 2.5 kV voltages as compared to the NEPAGENE™ method. Input is total number of cells that were processed.

Example 3: FTEP Pressure Sensing and Flow Rates

Figure 21:
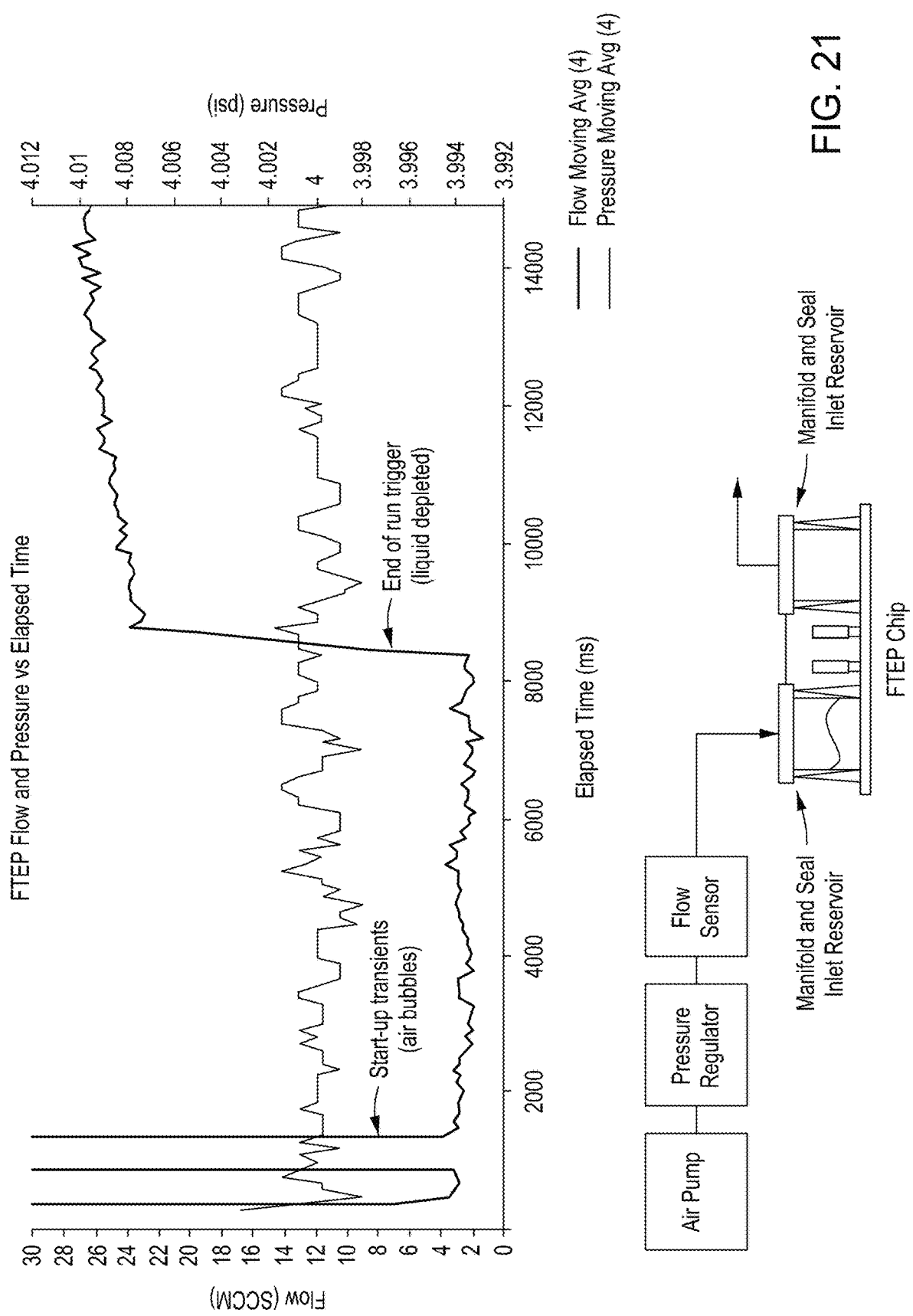
FIG. 21 shows a graph of FTEP flow and pressure versus elapsed time (top), as well as a simple depiction of the pressure system and FTEP (bottom).

The pressure and sensing was also tested using an FTEP device substantially as shown in FIGS. 1-B-10D (vi) as part of a cartridge device as illustrated in FIG. 1A. An inline flow sensor measurement was used to indicate when, after the liquid containing the cells and DNA flowed through the FTEP chip, where the inlet reservoir was emptied. Approximately 65 µL of liquid was loaded into the input reservoir and the automated FTEP module was powered on. Looking at the graph at the top of FIG. 21, it can be seen that after a few short startup transients, the flow rate shows about ~3 standard cubic centimeters per minute (SCCM) of flow for almost 8 seconds (8000 ms) until it jumps to 24 SCCM. This transition occurs at an end of run trigger, which is an indicator that the liquid containing the cells and DNA has been processed through the FTEP device and that air is not flowing through the FTEP device. That trigger may constitute detection of an increase flow rate or a sudden fluctuation (increase or decrease) in the pressure of the air (such as at a conduit leading from a syringe pump). In one preferred embodiment, the flow sensor in FIG. 27 detects an increase in air flow indicative of the fluid being completely drained from the input reservoir. At this point, pressure may be reversed to allow a multi-pass electroporation procedure; that is, cells to electroporated may be "pulled" from the inlet toward the outlet for one pass of electroporation, and once the inlet reservoir is emptied, the sensor may reverse the pressure where the liquid and cells/DNA is "pushed" from the outlet end of the flow-through FTEP device toward the inlet end to pass between the electrodes again for another pass of electroporation. This process may be repeated one to many times. Alternatively, the pressure may be stopped entirely and the transformed cells in the outlet retrieved.

The multi-cycle approach may be particularly advantageous in that it limits the dwell time of the cells and exogenous materials in the electric filed which may in turn prevent cell damage and increase survival rates. The back-and-forth process may be repeated 1, 2, 3, 4, 5, 6, 7, 8, 9, or 10 times. FIG. 27 at bottom shows a simple depiction of the pressure system and FTEP. The pressure manifold is mated to the upwardly-extending reservoirs via one or more complementary seals or gaskets disposed on the manifold or the reservoirs.

Example 4: Fully-Automated Singleplex RGN-Directed Editing Run

Singleplex automated genomic editing using MAD7 nuclease was successfully performed with an automated multi-module instrument of the disclosure. See U.S. Pat. No. 9,982,279.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. Coli cells were transferred into a transformation module for electroporation. The transformation module comprised an ADP-EPC cuvette. See, e.g., U.S. Pat No. 62/551,069. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on a petri dish containing a MacConkey agar base supplemented with lactose (as the sugar substrate), chloramphenicol and carbenicillin and the inoculates grown until visible colonies appeared. White colonies represented functionally edited cells, purple colonies represented un-edited cells. All liquid transfers were performed by the automated liquid handling device of the automated multi-module cell editing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example 5: Fully-Automated Recursive Editing Run

Recursive editing was successfully achieved using the automated multi-module cell editing instrument. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. Coli cells were transferred into a transformation module, such as FTEP device substantially as shown in FIGS. 1-B-10D (vi) as part of a cartridge device as illustrated in FIG. 1A, for electroporation. The transformation module comprised an ADP-EPC cuvette. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module, FTEP device substantially as shown in FIGS. 1-B-10D (vi) as part of a cartridge device as illustrated in FIG. 1A, for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell editing instrument.

In this recursive editing experiment, 41% of the colonies screened had both the lacZ and galK edits, the results of which were comparable to the double editing efficiencies obtained using a "benchtop" or manual approach.

While certain embodiments have been described, these embodiments have been presented by way of example only, and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

The invention claimed is:

1. A reagent cartridge comprising:
   a cartridge body;
   a plurality of receptacles disposed within the cartridge body configured to receive tubes and vials;
   a flow-through electroporation (FTEP) module disposed within the cartridge body configured to introduce nucleic acids into cells, wherein the FTEP module comprises:
      a. an inlet and an inlet channel for introducing a fluid comprising cells and exogenous material into the FTEP module;
      b. an outlet and an outlet channel for removing a fluid comprising transformed cells and exogenous material from the FTEP module;
      c. a flow channel intersecting and positioned between the inlet channel and the outlet channel; and
      d. two or more electrodes positioned in the flow channel between the intersection of the flow channel with the first inlet channel and the intersection of the flow channel with the outlet channel; wherein the electrodes are in fluid communication with fluid in the flow channel but are not in the direct flow path of the cells in the flow channel; and wherein the electrodes apply one or more electric pulses to the cells in the fluid as they pass through the flow channel, thereby introducing the exogenous material into the cells in the fluid;
   machine-readable indicia disposed upon the cartridge body for identifying contents of tubes and vials disposed in the receptacles and for operating the FTEP, wherein the machine-readable indicia is configured to be read by a processor;
   connection to a pressure control system, wherein the pressure control system pulls cells from the inlet toward the outlet and pushes cells from the outlet toward the inlet one to several times; and
   a cover for the cartridge body to secure tubes and vials disposed within the reagent cartridge.

2. The reagent cartridge of claim 1 wherein the FTEP module further comprises a reservoir connected to the inlet for introducing the cells in fluid into the FTEP module and a reservoir connected to the outlet for removing transformed cells from the FTEP module.

3. The reagent cartridge of claim 1 wherein the FTEP module further comprises a second inlet and a second inlet channel and further comprising a reservoir connected to the second inlet for introducing the exogenous material into the FTEP module.

4. The reagent cartridge of claim 3 wherein the second inlet and second inlet channel of the FTEP module are located between the inlet and inlet channel and the electrodes of the FTEP module.

5. The reagent cartridge of claim 3 wherein the second inlet and second inlet channel of the FTEP module are located between the electrodes and the outlet channel and outlet of the FTEP module.

6. The reagent cartridge of claim 1 wherein the electrodes in the FTEP module are spaced from 10 micrometers to 5 mm apart.

7. The reagent cartridge of claim 1 wherein the FTEP module further comprises a filter between the inlet channel and the electrodes.

8. The reagent cartridge of claim 1, wherein device is configured for use with bacterial, yeast and mammalian cells.

9. The reagent cartridge of claim 1, wherein one or more of the receptacles comprises a tube insert configured to accommodate small tubes.

10. The reagent cartridge of claim 1, comprising at least seven receptacles.

11. The reagent cartridge of claim 1, comprising at least seven receptacles.

12. The reagent cartridge of claim 11, comprising at least 15 receptacles.

13. The reagent cartridge of claim 1, wherein the reagent cartridge is part of a kit.

14. The reagent cartridge of claim 13, wherein the kit comprises reagents disposed within the receptacles.

15. The reagent cartridge of claim 14, wherein the reagents disposed within the receptacles are reagents to perform nucleic acid-guided nuclease editing.

16. A kit comprising the reagent cartridge of claim 1.

17. The kit of claim 16 wherein the reagents comprise three or more of a library of editing oligonucleotides in a vector backbone, cells, a wash solution, an enzyme, a cell culture medium and a buffer.

18. The kit of claim 16 wherein the reagents comprise four or more of a library of editing oligonucleotides in a vector backbone, cells, a wash solution, an enzyme, a cell culture medium and a buffer.

19. The kit of claim 16, wherein the machine-readable indicia disposed upon the cartridge body further provides instructions for movement of a robotic handling system.

20. The kit of claim 16, wherein each receptacle is separately labeled with machine-readable indicia.

* * * * *